United States Patent
Din Belle et al.

(10) Patent No.: US 11,098,032 B2
(45) Date of Patent: *Aug. 24, 2021

(54) PYRAN DERVATIVES AS CYP11A1 (CYTOCHROME P450 MONOOXYGENASE 11A1) INHIBITORS

(71) Applicant: ORION CORPORATION, Espoo (FI)

(72) Inventors: David Din Belle, Espoo (FI); Mikko Mäkelä, Espoo (FI); Mikko Passiniemi, Helsinki (FI); Pekka Pietikäinen, Espoo (FI); Petteri Rummakko, Siuntio (FI); Eija Tiainen, Espoo (FI); Matti Vaismaa, Espoo (FI); Gerd Wohlfahrt, Helsinki (FI)

(73) Assignee: ORION CORPORATION, Espoo (FI)

(*) Notice: Subject to any disclaimer, the term of this patent is extended or adjusted under 35 U.S.C. 154(b) by 0 days.

This patent is subject to a terminal disclaimer.

(21) Appl. No.: 16/895,221

(22) Filed: Jun. 8, 2020

(65) Prior Publication Data
US 2020/0299280 A1 Sep. 24, 2020

Related U.S. Application Data

(63) Continuation of application No. 16/472,377, filed as application No. PCT/FI2017/050926 on Dec. 21, 2017, now Pat. No. 10,717,726.

(30) Foreign Application Priority Data

Dec. 22, 2016 (FI) .................................... 20166024

(51) Int. Cl.
| C07D 405/06 | (2006.01) |
|---|---|
| C07D 405/14 | (2006.01) |
| C07D 409/14 | (2006.01) |
| C07D 413/14 | (2006.01) |
| C07D 417/14 | (2006.01) |
| C07D 451/02 | (2006.01) |
| C07D 491/056 | (2006.01) |
| A61K 45/06 | (2006.01) |

(52) U.S. Cl.
CPC ......... *C07D 405/06* (2013.01); *C07D 405/14* (2013.01); *C07D 409/14* (2013.01); *C07D 413/14* (2013.01); *C07D 417/14* (2013.01); *C07D 451/02* (2013.01); *C07D 491/056* (2013.01); *A61K 45/06* (2013.01)

(58) Field of Classification Search
None
See application file for complete search history.

(56) References Cited

U.S. PATENT DOCUMENTS 10,717,726 B2 * 7/2020 Din Belle ............ C07D 405/06
2014/0005181 A1    1/2014 Smith

FOREIGN PATENT DOCUMENTS

| WO | WO 03/074450 A2 | 9/2003 |
| WO | WO 2004/076445 A2 | 9/2004 |
| WO | WO 2014/202827 A1 | 12/2014 |

OTHER PUBLICATIONS

International Search Report, issued by the European Patent Office in International Application No. PCT/2017/050926, dated Mar. 6, 2018.

* cited by examiner

*Primary Examiner* — Zinna Northington Davis
(74) *Attorney, Agent, or Firm* — Finnegan, Henderson, Farabow, Garrett & Dunner, LLP

(57) ABSTRACT

Compounds of formula (I)

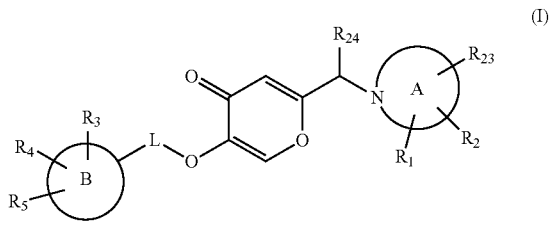

wherein $R_1$, $R_2$, $R_3$, $R_4$, $R_5$, $R_{23}$, $R_{24}$, L, A and B are as defined in claim 1, or pharmaceutically acceptable salts thereof are disclosed. The compounds of formula (I) possess utility as cytochrome P450 monooxygenase 11A1 (CYP11A1) inhibitors. The compounds are useful as medicaments in the treatment of steroid receptor, particularly androgen receptor, dependent diseases and conditions, such as prostate cancer.

11 Claims, No Drawings

PYRAN DERVATIVES AS CYP11A1 (CYTOCHROME P450 MONOOXYGENASE 11A1) INHIBITORS

This is a continuation of pending U.S. application Ser. No. 16/472,377, filed Jun. 21, 2019, which is a national stage application under 35 U.S.C. § 371 of International Patent Application No. PCT/FI2017/050926, filed Dec. 21, 2017, which claims the benefit of Finnish Patent Application No. 20166024, filed Dec. 22, 2016, all of which are incorporated herein by reference.

TECHNICAL FIELD

The present invention relates to therapeutically active compounds useful in the treatment of a steroid receptor, in particular androgen receptor (AR), dependent conditions and diseases, and to pharmaceutical compositions containing such compounds.

BACKGROUND OF THE INVENTION

Prostate cancer is worldwide the most common cancer in men. Even though the 5-year survival rate of patients with localized prostate cancer is high, the prognosis for those patients, who develop castration-resistant prostate cancer (CRPC) within that 5-year follow-up period, is poor.

The androgen receptor (AR) signalling axis is critical in all stages of prostate cancer. In the CPRC stage, disease is characterized by high AR expression, AR amplification and persistent activation of the AR signalling axis by residual tissue/tumor androgens and by other steroid hormones and intermediates of steroid biosynthesis. Thus, treatment of advanced prostate cancer involves androgen deprivation therapy (ADT) such as hormonal manipulation using gonadotropin-releasing hormone (GnRH) agonists/antagonists or surgical castration, AR antagonists or CYP17A1 inhibitors (such as abiraterone acetate in combination with prednisone).

Although therapies can initially lead to disease regression, eventually majority of the patients develop a disease that is refractory to currently available therapies. Increased progesterone levels in patients treated with abiraterone acetate has been hypothesized to be one of the resistance mechanisms. Several nonclinical and clinical studies have indicated upregulation of enzymes that catalyse steroid biosynthesis at the late stage of CRPC. Very recently it has been published that 11β-OH androstenedione can be metabolized into 11-ketotestosterone (11-K-T) and 11-ketodehydrotestosterone (11-K-DHT) which can bind and activate AR as efficiently as testosterone and dihydrotestosterone. It has been shown that these steroids are found in high levels in plasma and tissue in prostate cancer patients, suggesting their role as AR agonists in CRPC. Furthermore, it has been addressed that prostate cancer resistance to CYP17A1 inhibition may still remain steroid dependent and responsive to therapies that can further suppress de novo intratumoral steroid synthesis upstream of CYP17A1, such as by CYP11A1 inhibition therapy (Cai, C. et al, Cancer Res., 71(20), 6503-6513, 2011).

Cytochrome P450 monooxygenase 11A1 (CYP11A1), also called cholesterol side chain cleavage enzyme, is a mitochondrial monooxygenase which catalyses the conversion of cholesterol to pregnenolone, the precursor of all steroid hormones. By inhibiting CYP11A1, the key enzyme of steroid biosynthesis upstream of CYP17A1, the total block of the whole steroid biosynthesis can be achieved. CYP11A1 inhibitors may therefore have a great potential for treating steroid hormone dependent cancers, such as prostate cancer, even in advanced stages of the disease, and especially in those patients who appear to be hormone refractory. It has been recently shown that a compound having CYP11A1 inhibitory effect significantly inhibited tumor growth in vivo in a murine CRPC xenograft model (Oksala, R. et al, Annals of Oncology, (2017) 28 (suppl. 5): Abstract/Poster 28P).

SUMMARY OF THE INVENTION

It has been found that compounds of formula (I) are potent CYP11A1 inhibitors. The compounds of the invention are therefore useful as medicaments in the treatment of steroid hormone dependent conditions and diseases where CYP11A1 inhibition is desired. Such conditions and diseases include, but are not limited to, endocrine cancers and diseases, such as prostate cancer and breast cancer. In particular, the compounds of the invention are useful in the treatment of AR dependent conditions and diseases including prostate cancer.

The present invention relates to a compound of formula (I)

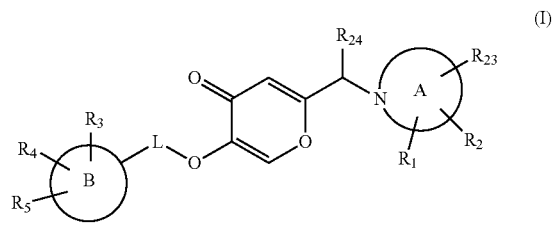

wherein
ring B is a 4-10 membered monocyclic or bicyclic ring containing 0-4 heteroatoms independently selected form N, O or S
ring A is any of the following groups

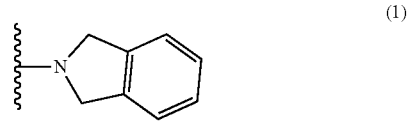

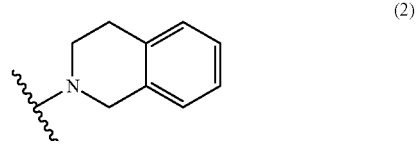

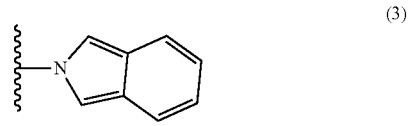

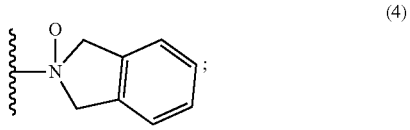

L is absent, —$CH_2$—, —$CH_2$—$CH_2$— or —$CH_2$—$CH_2$—$CH_2$—, or in case ring A is (1), L can also be —C(O)—$CH_2$—;

R₁ is hydrogen, C₁₋₇ alkyl, C₁₋₇ alkoxy, halogen, cyano, nitro, halo C₁₋₇ alkyl, halo C₁₋₇ alkoxy or C₁₋₇ alkylthio;

R₂ is hydrogen, C₁₋₇ alkyl, halogen, hydroxy, halo C₁₋₇ alkyl, nitro, halo C₁₋₇ alkoxy or thiol;

or R₁ and R₂ together with the carbon atoms to which they are attached form a fused 1,3 dioxole ring;

R₃ is hydrogen, halogen, nitro, cyano, oxo, C₁₋₇ alkyl, C₂₋₇ alkenyl, C₃₋₇ cycloalkyl, hydroxy C₃₋₇ cycloalkyl, C₁₋₇ alkoxy, hydroxy C₁₋₇ alkyl, halo C₁₋₇ alkyl, cyano C₁₋₇ alkyl, C₁₋₇ alkoxy C₁₋₇ alkyl, C₁₋₇ alkylthio, aminocarbonyl C₂₋₇ alkenyl, halo C₁₋₇ alkylthio, C₁₋₇ alkoxycarbonyl C₁₋₇ alkyl, C₁₋₇ alkoxycarbonyl C₂₋₇ alkenyl, =NSO₂R₂₀, —S(O)—C₁₋₇ alkyl, —S(O)(NR₁₄)(R₂₂), —S(NR₁₅)(C₁₋₇ alkyl), —C(S)NR₁₈R₁₉, -D-C(O)—NR₆R₇, —C(O)R₈, -D-NR₉R₁₀, —SO₂R₁, an optionally substituted 3-10 membered carbocyclyl, an optionally substituted 3-10 membered carbocyclyl C₁₋₇ alkyl, an optionally substituted 4-10 membered heterocyclyl or an optionally substituted 4-10 membered heterocyclyl C₁₋₇ alkyl;

R₄ is hydrogen, halogen, hydroxy, C₁₋₇ alkyl, halo C₁₋₇ alkyl or oxo;

R₅ is hydrogen, halogen or C₁₋₇ alkyl;

R₆ is hydrogen, C₁₋₇ alkyl, C₂₋₇ alkenyl, C₃₋₇ cycloalkyl, hydroxy C₁₋₇ alkyl, cyano C₁₋₇ alkyl, —C₁₋₇ alkyl-O—C(O) C₁₋₇ alkyl or an optionally substituted 4-10 membered heterocyclyl;

R₈ is hydrogen, C₁₋₇ alkyl, C₂₋₇ alkenyl, C₃₋₇ cycloalkyl, C₁₋₇ alkoxy, halo C₁₋₇ alkyl, C₁₋₇ alkoxy C₁₋₇ alkyl, C₁₋₇ alkylcarbonyl, C₁₋₇ alkoxycarbonyl, —C₁₋₇ alkyl-O—C(O)—C₁₋₇ alkyl, —C₁₋₇ alkyl-SO₂(C₁₋₇ alkyl), —N=S(O)(C₁₋₇ alkyl)(C₁₋₇ alkyl) or an optionally substituted 4-10 membered heterocyclyl;

R₉ is hydrogen, C₁₋₇ alkyl, C₃₋₇ cycloalkyl, C₁₋₇ alkylcarbonyl, —SO₂(C₁₋₇ alkyl) or —SO₂(C₃₋₇ cycloalkyl);

R₁₁ is C₁₋₇ alkyl, C₂₋₇ alkenyl, C₃₋₇ cycloalkyl, halo C₁₋₇ alkyl, cyano C₁₋₇ alkyl, C₁₋₇ alkoxy C₁₋₇ alkyl, —NR₁₂R₁₃, an optionally substituted 3-10 membered carbocyclic or an optionally substituted 4-10 membered heterocyclyl;

R₁₂ is hydrogen, C₁₋₇ alkyl, hydroxy C₁₋₇ alkyl, cyano C₁₋₇ alkyl, C₁₋₇ alkoxy, C₁₋₇ alkoxy C₁₋₇ alkyl or C₁₋₇ alkylcarbonyl;

R₇, R₁₀, R₁₃, R₁₈, and R₁₉ are, independently, hydrogen, C₁₋₇ alkyl or C₃₋₇ cycloalkyl;

R₁₄ is hydrogen, C₁₋₇ alkyl, C₁₋₇ alkylcarbonyl or —SO₂R₂₁;

R₁₅ is hydrogen, C₁₋₇ alkyl, C₃₋₇ cycloalkyl, C₁₋₇ alkylcarbonyl, —SO₂R₁₇;

R₁₇ is C₁₋₇ alkyl or an optionally substituted 3-10 membered carbocyclyl;

R₂₀ and R₂₁ are, independently, C₁₋₇ alkyl, C₃₋₇ cycloalkyl or an optionally substituted 3-10 membered carbocyclyl;

R₂₂ is C₁₋₇ alkyl or C₃₋₇ cycloalkyl;

R₂₃ is hydrogen or oxo;

R₂₄ is hydrogen or C₁₋₇ alkyl; D is absent, C₁₋₇ alkyl or C₂₋₇ alkenyl;

wherein the optional substitution in each occurrence is selected from 1-3 substituents independently selected from C₁₋₇ alkyl, halogen, hydroxy, C₁₋₇ alkoxy, C₁₋₇ alkoxy C₁₋₇ alkyl, C₁₋₇ alkoxycarbonyl or oxo; and wherein the heterocyclyl group in each occurrence has 1-4 heteroatoms independently selected from N, O and S;

or a pharmaceutically acceptable salt thereof;

with the proviso that the compound is not
2-[(3,4-Dihydro-2(1H)-isoquinolinyl)methyl]-5-[(2,5-dimethylphenyl)methoxy]-4H-pyran-4-one;
5-[(2,4-Dichlorophenyl)methoxy]-2-[(3,4-dihydro-2(1H)-isoquinolinyl)methyl]-4H-pyran-4-one;
5-[(3-Chlorophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(4-methylphenyl)methoxy]-4H-pyran-4-one;
5-[(3,4-Dichlorophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(3-fluorophenyl)methoxy]-4H-pyran-4-one;
2-[(3,4-Dihydro-2(1H)-isoquinolinyl)methyl]-5-(1-naphthalenylmethoxy)-4H-pyran-4-one;
2-[(3,4-Dihydro-2(1H)-isoquinolinyl)methyl]-5-[[3-(trifluoromethyl)phenyl]methoxy]-4H-pyran-4-one;
5-[(2-Chlorophenyl)methoxy]-2-[(3,4-dihydro-2(1H)-isoquinolinyl)methyl]-4H-pyran-4-one;
5-[(2-Chloro-6-fluorophenyl)methoxy]-2-[(3,4-dihydro-2(1H)-isoquinolinyl) methyl]-4H-pyran-4-one;
5-[(4-Chlorophenyl)methoxy]-2-[(3,4-dihydro-2(1H)-isoquinolinyl)methyl]-4H-pyran-4-one;
5-[(4-Bromophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(2-fluorophenyl)methoxy]-4H-pyran-4-one;
2-[(3,4-Dihydro-2(1H)-isoquinolinyl)methyl]-5-[(2-methylphenyl)methoxy]-4H-pyran-4-one;
2-[(3,4-Dihydro-2(1H)-isoquinolinyl)methyl]-5-(phenylmethoxy)-4H-pyran-4-one;
2-[(3,4-Dihydro-2(1H)-isoquinolinyl)methyl]-5-[[4-(trifluoromethyl)phenyl]methoxy]-4H-pyran-4-one;
Methyl 4-(((6-((3,4-dihydroisoquinolin-2(1H)-yl)methyl)-4-oxo-4H-pyran-3-yl)oxy)methyl)benzoate;
2-[(3,4-Dihydro-2(1H)-isoquinolinyl)methyl]-5-[(4-fluorophenyl)methoxy]-4H-pyran-4-one;
2-[(3,4-Dihydro-2(1H)-isoquinolinyl)methyl]-5-[(3,5-dimethoxyphenyl)methoxy]-4H-pyran-4-one;
2-[(3,4-Dihydro-2(1H)-isoquinolinyl)methyl]-5-[(3-nitrophenyl)methoxy]-4H-pyran-4-one;
Methyl 5-(((6-((3,4-dihydroisoquinolin-2(1H)-yl)methyl)-4-oxo-4H-pyran-3-yl)oxy)methyl)furan-2-carboxylate;
2-[(3,4-Dihydro-2(1H)-isoquinolinyl)methyl]-5-(2-phenylethoxy)-4H-pyran-4-one;
2-[(3,4-Dihydro-2(1H)-isoquinolinyl)methyl]-5-[(3-methylphenyl)methoxy]-4H-pyran-4-one; or
2-[(3,4-Dihydro-2(1H)-isoquinolinyl)methyl]-5-[(4-nitrophenyl)methoxy]-4H-pyran-4-one.

According to one embodiment, the invention provides a method for the treatment or prevention of a steroid receptor, particularly androgen receptor (AR), dependent conditions and diseases, comprising administering to a subject in need thereof a therapeutically effective amount of a compound of formula (I)

(I)

wherein
ring B is a 4-10 membered monocyclic or bicyclic ring containing 0-4 heteroatoms independently selected form N, O or S
ring A is any of the following groups (1)

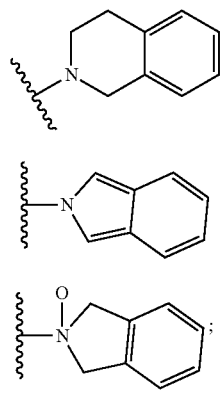

(2)

(3)

(4)

L is absent, —CH₂—, —CH₂—CH₂— or —CH₂—CH₂—CH₂—, or in case ring A is (1), L can also be —C(O)—CH₂—;

R₁ is hydrogen, C₁₋₇ alkyl, C₁₋₇ alkoxy, halogen, cyano, nitro, halo C₁₋₇ alkyl, halo C₁₋₇ alkoxy or C₁₋₇ alkylthio;

R₂ is hydrogen, C₁₋₇ alkyl, halogen, hydroxy, halo C₁₋₇ alkyl, nitro, halo C₁₋₇ alkoxy or thiol;

or R₁ and R₂ together with the carbon atoms to which they are attached form a fused 1,3 dioxole ring;

R₃ is hydrogen, halogen, nitro, cyano, oxo, C₁₋₇ alkyl, C₂₋₇ alkenyl, C₃₋₇ cycloalkyl, ydroxyl C₃₋₇ cycloalkyl, C₁₋₇ alkoxy, ydroxyl C₁₋₇ alkyl, halo C₁₋₇ alkyl, cyano C₁₋₇ alkyl, C₁₋₇ alkoxy C₁₋₇ alkyl, C₁₋₇ alkylthio, aminocarbonyl C₂₋₇ alkenyl, halo C₁₋₇ alkylthio, C₁₋₇ alkoxycarbonyl C₁₋₇ alkyl, C₁₋₇ alkoxycarbonyl C₂₋₇ alkenyl, =NSO₂R₂₀, —S(O)—C₁₋₇ alkyl, —S(O)(NR₁₄)(R₂₂), —S(NR₁₅)(C₁₋₇ alkyl), —C(S)NR₁₈R₁₉, -D-C(O)—NR₆R₇, —C(O)R₈, -D-NR₉R₁₀, —SO₂R₁₁, an optionally substituted 3-10 membered carbocyclyl, an optionally substituted 3-10 membered carbocyclyl C₁₋₇ alkyl, an optionally substituted 4-10 membered heterocyclyl or an optionally substituted 4-10 membered heterocyclyl C₁₋₇ alkyl;

R₄ is hydrogen, halogen, hydroxy, C₁₋₇ alkyl, halo C₁₋₇ alkyl or oxo;

R₅ is hydrogen, halogen or C₁₋₇ alkyl;

R₆ is hydrogen, C₁₋₇ alkyl, C₂₋₇ alkenyl, C₃₋₇ cycloalkyl, hydroxy C₁₋₇ alkyl, cyano C₁₋₇ alkyl, —C₁₋₇ alkyl-O—C(O) C₁₋₇ alkyl or an optionally substituted 4-10 membered heterocyclyl;

R₈ is hydrogen, C₁₋₇ alkyl, C₂₋₇ alkenyl, C₃₋₇ cycloalkyl, C₁₋₇ alkoxy, halo C₁₋₇ alkyl, C₁₋₇ alkoxy C₁₋₇ alkyl, C₁₋₇ alkylcarbonyl, C₁₋₇ alkoxycarbonyl, —C₁₋₇ alkyl-O—C(O)—C₁₋₇ alkyl, —C₁₋₇ alkyl-SO₂(C₁₋₇ alkyl), —N=S(O)(C₁₋₇ alkyl)(C₁₋₇ alkyl) or an optionally substituted 4-10 membered heterocyclyl;

R₉ is hydrogen, C₁₋₇ alkyl, C₃₋₇ cycloalkyl, C₁₋₇ alkylcarbonyl, —SO₂(C₁₋₇ alkyl) or —SO₂(C₃₋₇ cycloalkyl);

R₁₁ is C₁₋₇ alkyl, C₂₋₇ alkenyl, C₃₋₇ cycloalkyl, halo C₁₋₇ alkyl, cyano C₁₋₇ alkyl, C₁₋₇ alkoxy C₁₋₇ alkyl, —NR₁₂R₁₃, an optionally substituted 3-10 membered carbocyclyl or an optionally substituted 4-10 membered heterocyclyl;

R₁₂ is hydrogen, C₁₋₇ alkyl, hydroxy C₁₋₇ alkyl, cyano C₁₋₇ alkyl, C₁₋₇ alkoxy, C₁₋₇ alkoxy C₁₋₇ alkyl or C₁₋₇ alkylcarbonyl;

R₇, R₁₀, R₁₃, R₁₈, and R₁₉ are, independently, hydrogen, C₁₋₇ alkyl or C₃₋₇ cycloalkyl;

R₁₄ is hydrogen, C₁₋₇ alkyl, C₁₋₇ alkylcarbonyl or —SO₂R₂₁;

R₁₅ is hydrogen, C₁₋₇ alkyl, C₃₋₇ cycloalkyl, C₁₋₇ alkylcarbonyl, —SO₂R₁₇;

R₁₇ is C₁₋₇ alkyl or an optionally substituted 3-10 membered carbocyclyl;

R₂₀ and R₂₁ are, independently, C₁₋₇ alkyl, C₃₋₇ cycloalkyl or an optionally substituted 3-10 membered carbocyclyl;

R₂₂ is C₁₋₇ alkyl or C₃₋₇ cycloalkyl;

R₂₃ is hydrogen or oxo;

R₂₄ is hydrogen or C₁₋₇ alkyl;

D is absent, C₁₋₇ alkyl or C₂₋₇ alkenyl;

wherein the optional substitution in each occurrence is selected from 1-3 substituents independently selected from C₁₋₇ alkyl, halogen, hydroxy, C₁₋₇ alkoxy, C₁₋₇ alkoxy C₁₋₇ alkyl, C₁₋₇ alkoxycarbonyl or oxo; and wherein the heterocyclyl group in each occurrence has 1-4 heteroatoms independently selected from N, O and S;

or a pharmaceutically acceptable salt thereof.

According to one embodiment, the invention provides a pharmaceutical composition comprising a compound of formula (I) as defined in any of the above embodiments together with a pharmaceutically acceptable carrier.

According to one embodiment, the invention provides a method for the treatment or prevention of a steroid receptor, in particular androgen receptor (AR), dependent conditions and diseases. Such conditions and diseases include, but are not limited to, endocrine cancers and diseases, such as prostate cancer and breast cancer. The method comprises administering to a subject in need thereof a therapeutically effective amount of a compound of formula (I) as defined in any of the above embodiments.

DETAILED DESCRIPTION OF THE INVENTION

The present application provides novel 4H-pyran-4-one derivatives of formula (I) or pharmaceutically acceptable salts thereof which are useful as CYP11A1 inhibitors.

One of the embodiments of the present invention provides a compound of formula (I)

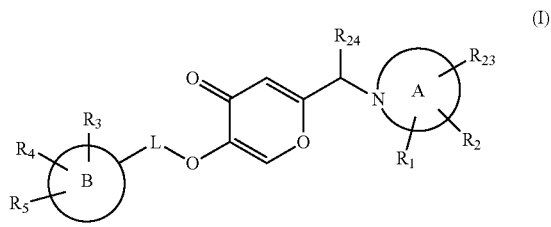

(I)

wherein
ring B is a 4-10 membered monocyclic or bicyclic ring containing 0-4 heteroatoms independently selected form N, O or S ring A is any of the following groups

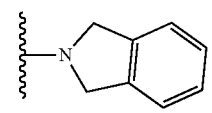

(1)

-continued

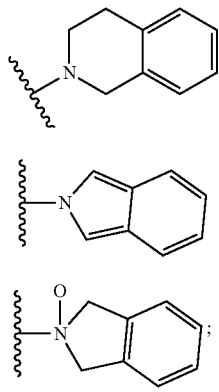

(2)

(3)

(4)

L is absent, —CH$_2$—, —CH$_2$—CH$_2$— or —CH$_2$—CH$_2$—CH$_2$—, or in case ring A is (1), L can also be —C(O)—CH$_2$—;

R$_1$ is hydrogen, C$_{1-7}$ alkyl, C$_{1-7}$ alkoxy, halogen, cyano, nitro, halo C$_{1-7}$ alkyl, halo C$_{1-7}$ alkoxy or C$_{1-7}$ alkylthio;

R$_2$ is hydrogen, C$_{1-7}$ alkyl, halogen, hydroxy, halo C$_{1-7}$ alkyl, nitro, halo C$_{1-7}$ alkoxy or thiol;

or R$_1$ and R$_2$ together with the carbon atoms to which they are attached form a fused 1,3 dioxole ring;

R$_3$ is hydrogen, halogen, nitro, cyano, oxo, C$_{1-7}$ alkyl, C$_{2-7}$ alkenyl, C$_{3-7}$ cycloalkyl, hydroxy C$_{3-7}$ cycloalkyl, C$_{1-7}$ alkoxy, hydroxy C$_{1-7}$ alkyl, halo C$_{1-7}$ alkyl, cyano C$_{1-7}$ alkyl, C$_{1-7}$ alkoxy C$_{1-7}$ alkyl, C$_{1-7}$ alkylthio, aminocarbonyl C$_{2-7}$ alkenyl, halo C$_{1-7}$ alkylthio, C$_{1-7}$ alkoxycarbonyl C$_{1-7}$ alkyl, C$_{1-7}$ alkoxycarbonyl C$_{2-7}$ alkenyl, =NSO$_2$R$_{20}$, —S(O)—C$_{1-7}$ alkyl, —S(O)(NR$_{14}$)(R$_{22}$), —S(NR$_{15}$)(C$_{1-7}$ alkyl), —C(S)NR$_{18}$R$_{19}$, -D-C(O)—NR$_6$R$_7$, —C(O)R$_8$, -D-NR$_9$R$_{10}$, —SO$_2$R$_{11}$, an optionally substituted 3-10 membered carbocyclyl, an optionally substituted 3-10 membered carbocyclyl C$_{1-7}$ alkyl, an optionally substituted 4-10 membered heterocyclyl or an optionally substituted 4-10 membered heterocyclyl C$_{1-7}$ alkyl;

R$_4$ is hydrogen, halogen, hydroxy, C$_{1-7}$ alkyl, halo C$_{1-7}$ alkyl or oxo;

R$_5$ is hydrogen, halogen or C$_{1-7}$ alkyl;

R$_6$ is hydrogen, C$_{1-7}$ alkyl, C$_{2-7}$ alkenyl, C$_{3-7}$ cycloalkyl, hydroxy C$_{1-7}$ alkyl, cyano C$_{1-7}$ alkyl, —C$_{1-7}$ alkyl-O—C(O) C$_{1-7}$ alkyl or an optionally substituted 4-10 membered heterocyclyl;

R$_8$ is hydrogen, C$_{1-7}$ alkyl, C$_{2-7}$ alkenyl, C$_{3-7}$ cycloalkyl, C$_{1-7}$ alkoxy, halo C$_{1-7}$ alkyl, C$_{1-7}$ alkoxy C$_{1-7}$ alkyl, C$_{1-7}$ alkylcarbonyl, C$_{1-7}$ alkoxycarbonyl, —C$_{1-7}$ alkyl-O—C(O)—C$_{1-7}$ alkyl, —C$_{1-7}$ alkyl-SO$_2$(C$_{1-7}$ alkyl), —N=S(O)(C$_{1-7}$ alkyl)(C$_{1-7}$ alkyl) or an optionally substituted 4-10 membered heterocyclyl;

R$_9$ is hydrogen, C$_{1-7}$ alkyl, C$_{3-7}$ cycloalkyl, C$_{1-7}$ alkylcarbonyl, —SO$_2$(C$_{1-7}$ alkyl) or —SO$_2$(C$_{3-7}$ cycloalkyl);

R$_{11}$ is C$_{1-7}$ alkyl, C$_{2-7}$ alkenyl, C$_{3-7}$ cycloalkyl, halo C$_{1-7}$ alkyl, cyano C$_{1-7}$ alkyl, C$_{1-7}$ alkoxy C$_{1-7}$ alkyl, —NR$_{12}$R$_{13}$, an optionally substituted 3-10 membered carbocyclyl or an optionally substituted 4-10 membered heterocyclyl;

R$_{12}$ is hydrogen, C$_{1-7}$ alkyl, hydroxy C$_{1-7}$ alkyl, cyano C$_{1-7}$ alkyl, C$_{1-7}$ alkoxy, C$_{1-7}$ alkoxy C$_{1-7}$ alkyl or C$_{1-7}$ alkylcarbonyl;

R$_7$, R$_{10}$, R$_{13}$, R$_{18}$, and R$_{19}$ are, independently, hydrogen, C$_{1-7}$ alkyl or C$_{3-7}$ cycloalkyl;

R$_{14}$ is hydrogen, C$_{1-7}$ alkyl, C$_{1-7}$ alkylcarbonyl or —SO$_2$R$_{21}$;

R$_{15}$ is hydrogen, C$_{1-7}$ alkyl, C$_{3-7}$ cycloalkyl, C$_{1-7}$ alkylcarbonyl, —SO$_2$R$_{17}$;

R$_{17}$ is C$_{1-7}$ alkyl or an optionally substituted 3-10 membered carbocyclyl;

R$_{20}$ and R$_{21}$ are, independently, C$_{1-7}$ alkyl, C$_{3-7}$ cycloalkyl or an optionally substituted 3-10 membered carbocyclyl;

R$_{22}$ is C$_{1-7}$ alkyl or C$_{3-7}$ cycloalkyl;

R$_{23}$ is hydrogen or oxo;

R$_{24}$ is hydrogen or C$_{1-7}$ alkyl;

D is absent, C$_{1-7}$ alkyl or C$_{2-7}$ alkenyl;

wherein the optional substitution in each occurrence is selected from 1-3 substituents independently selected from C$_{1-7}$ alkyl, halogen, hydroxy, C$_{1-7}$ alkoxy, C$_{1-7}$ alkoxy C$_{1-7}$ alkyl, C$_{1-7}$ alkoxycarbonyl or oxo; and wherein the heterocyclyl group in each occurrence has 1-4 heteroatoms independently selected from N, O and S;

or a pharmaceutically acceptable salt thereof;

with the proviso that the compound is not
2-[(3,4-Dihydro-2(1H)-isoquinolinyl)methyl]-5-[(2,5-dimethylphenyl)methoxy]-4H-pyran-4-one;
5-[(2,4-Dichlorophenyl)methoxy]-2-[(3,4-dihydro-2(1H)-isoquinolinyl)methyl]-4H-pyran-4-one;
5-[(3-Chlorophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(4-methylphenyl)methoxy]-4H-pyran-4-one;
5-[(3,4-Dichlorophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(3-fluorophenyl)methoxy]-4H-pyran-4-one;
2-[(3,4-Dihydro-2(1H)-isoquinolinyl)methyl]-5-(1-naphthalenylmethoxy)-4H-pyran-4-one;
2-[(3,4-Dihydro-2(1H)-isoquinolinyl)methyl]-5-[[3-(trifluoromethyl)phenyl]methoxy]-4H-pyran-4-one;
5-[(2-Chlorophenyl)methoxy]-2-[(3,4-dihydro-2(1H)-isoquinolinyl)methyl]-4H-pyran-4-one;
5-[(2-Chloro-6-fluorophenyl)methoxy]-2-[(3,4-dihydro-2(1H)-isoquinolinyl) methyl]-4H-pyran-4-one;
5-[(4-Chlorophenyl)methoxy]-2-[(3,4-dihydro-2(1H)-isoquinolinyl)methyl]-4H-pyran-4-one;
5-[(4-Bromophenyl)methoxy]-2-[(3,4-dihydro-2(1H)-isoquinolinyl)methyl]-4H-pyran-4-one;
2-[(3,4-Dihydro-2(1H)-isoquinolinyl)methyl]-5-[(2-fluorophenyl)methoxy]-4H-pyran-4-one;
2-[(3,4-Dihydro-2(1H)-isoquinolinyl)methyl]-5-[(2-methylphenyl)methoxy]-4H-pyran-4-one;
2-[(3,4-Dihydro-2(1H)-isoquinolinyl)methyl]-5-(phenylmethoxy)-4H-pyran-4-one;
2-[(3,4-Dihydro-2(1H)-isoquinolinyl)methyl]-5-[[4-(trifluoromethyl)phenyl]methoxy]-4H-pyran-4-one;
Methyl 4-(((6-((3,4-dihydroisoquinolin-2(1H)-yl)methyl)-4-oxo-4H-pyran-3-yl)oxy)methyl)benzoate;
2-[(3,4-Dihydro-2(1H)-isoquinolinyl)methyl]-5-[(4-fluorophenyl)methoxy]-4H-pyran-4-one;
2-[(3,4-Dihydro-2(1H)-isoquinolinyl)methyl]-5-[(3,5-dimethoxyphenyl)methoxy]-4H-pyran-4-one;
2-[(3,4-Dihydro-2(1H)-isoquinolinyl)methyl]-5-[(3-nitrophenyl)methoxy]-4H-pyran-4-one;
Methyl 5-(((6-((3,4-dihydroisoquinolin-2(1H)-yl)methyl)-4-oxo-4H-pyran-3-yl)oxy)methyl)furan-2-carboxylate;
2-[(3,4-Dihydro-2(1H)-isoquinolinyl)methyl]-5-(2-phenylethoxy)-4H-pyran-4-one;
2-[(3,4-Dihydro-2(1H)-isoquinolinyl)methyl]-5-[(3-methylphenyl)methoxy]-4H-pyran-4-one; or
2-[(3,4-Dihydro-2(1H)-isoquinolinyl)methyl]-5-[(4-nitrophenyl)methoxy]-4H-pyran-4-one.

It is to be understood that the left bond in linker L is attached to the ring B of formula (I).

According to one embodiment, the compound according to the present invention is represented by formula (IA):

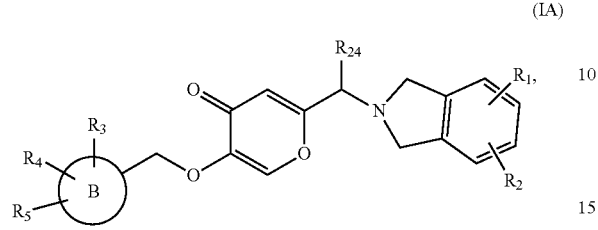
(IA)

wherein $R_1$, $R_2$, $R_3$, $R_4$, $R_5$, $R_{23}$, $R_{24}$, L and B are as defined in any of the above embodiments for formula (I), or a pharmaceutically acceptable salt thereof.

According to one embodiment, the compound according to the present invention is represented by formula (IB):

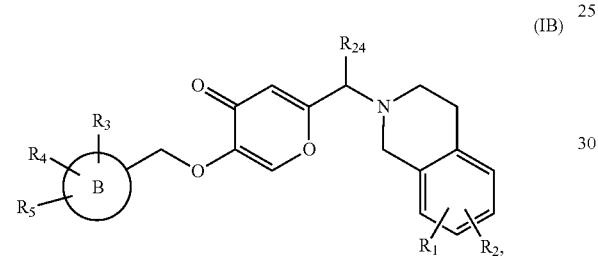
(IB)

wherein $R_1$, $R_2$, $R_3$, $R_4$, $R_5$, $R_{24}$, L and B are as defined in any of the above embodiments for formula (I), or a pharmaceutically acceptable salt thereof.

According to one embodiment, specifically provided is a compound of formula (I) wherein L is —CH$_2$— or —CH$_2$—CH$_2$—, for example L is —CH$_2$— or as another example L is —CH$_2$—CH$_2$—.

According to one embodiment, specifically provided is a compound of formula (I), wherein ring B is any one of the following groups

 (1')

 (2')

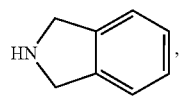 (3')

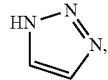 (4')

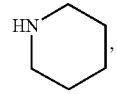 (5')

 (6')

 (7')

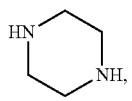 (8')

 (9')

 (10')

 (11')

 (12')

 (13')

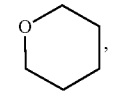 (14')

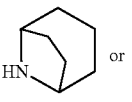 or (15')

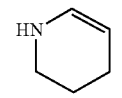 (16')

wherein $R_3$, $R_4$ and $R_5$, as defined in any of the above embodiments for formula (I), are attached to the above B-rings.

In a subclass of the above embodiment are compounds wherein ring B is any one of the following groups

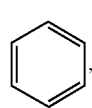 (1')

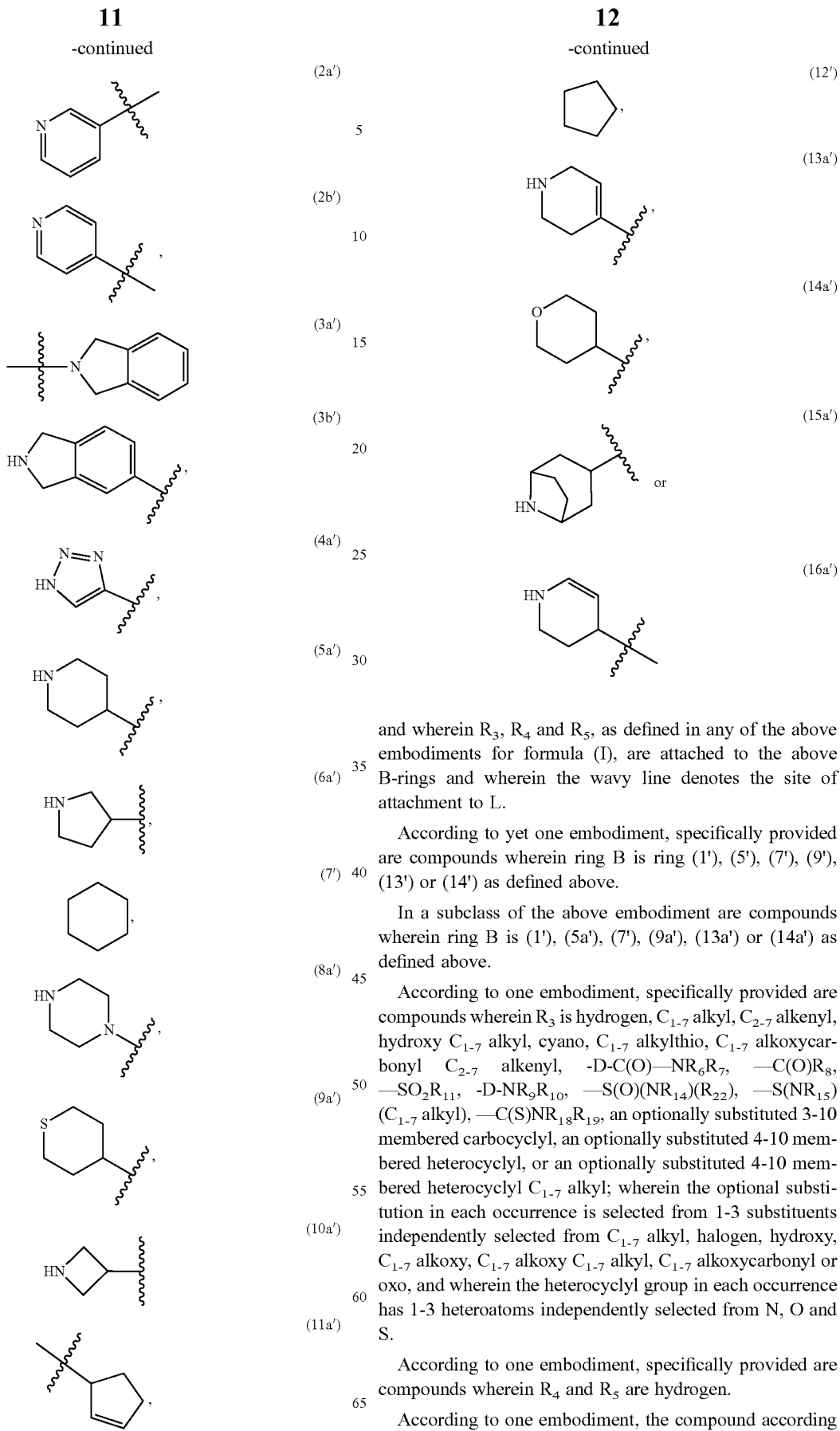

and wherein $R_3$, $R_4$ and $R_5$, as defined in any of the above embodiments for formula (I), are attached to the above B-rings and wherein the wavy line denotes the site of attachment to L.

According to yet one embodiment, specifically provided are compounds wherein ring B is ring (1'), (5'), (7'), (9'), (13') or (14') as defined above.

In a subclass of the above embodiment are compounds wherein ring B is (1'), (5a'), (7'), (9a'), (13a') or (14a') as defined above.

According to one embodiment, specifically provided are compounds wherein $R_3$ is hydrogen, $C_{1-7}$ alkyl, $C_{2-7}$ alkenyl, hydroxy $C_{1-7}$ alkyl, cyano, $C_{1-7}$ alkylthio, $C_{1-7}$ alkoxycarbonyl $C_{2-7}$ alkenyl, -D-C(O)—$NR_6R_7$, —C(O)$R_8$, —$SO_2R_{11}$, -D-$NR_9R_{10}$, —S(O)($NR_{14}$)($R_{22}$), —S($NR_{15}$)($C_{1-7}$ alkyl), —C(S)$NR_{18}R_{19}$, an optionally substituted 3-10 membered carbocyclyl, an optionally substituted 4-10 membered heterocyclyl, or an optionally substituted 4-10 membered heterocyclyl $C_{1-7}$ alkyl; wherein the optional substitution in each occurrence is selected from 1-3 substituents independently selected from $C_{1-7}$ alkyl, halogen, hydroxy, $C_{1-7}$ alkoxy, $C_{1-7}$ alkoxy $C_{1-7}$ alkyl, $C_{1-7}$ alkoxycarbonyl or oxo, and wherein the heterocyclyl group in each occurrence has 1-3 heteroatoms independently selected from N, O and S.

According to one embodiment, specifically provided are compounds wherein $R_4$ and $R_5$ are hydrogen.

According to one embodiment, the compound according to the present invention is represented by formula (IC):

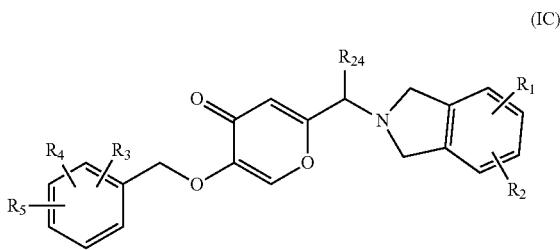

(IC)

wherein $R_1$, $R_2$, $R_3$, $R_4$, $R_5$ and $R_{24}$ are as defined in any of the above embodiments for formula (I), or a pharmaceutically acceptable salt thereof.

According to one embodiment, the compound according to the present invention is represented by formula (ID):

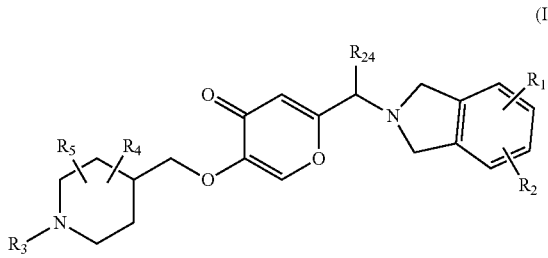

(ID)

wherein $R_1$, $R_2$, $R_3$, $R_4$, $R_5$ and $R_{24}$ are as defined in any of the above embodiments for formula (I), or a pharmaceutically acceptable salt thereof.

According to one embodiment, the compound according to the present invention is represented by formula (IE):

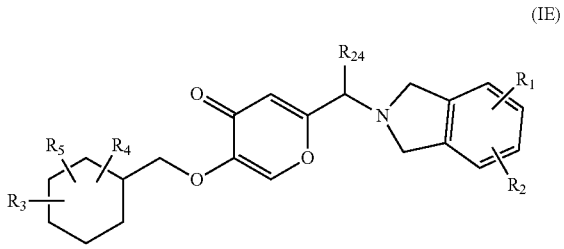

(IE)

wherein $R_1$, $R_2$, $R_3$, $R_4$, $R_5$ and $R_{24}$ are as defined in any of the above embodiments for formula (I), or a pharmaceutically acceptable salt thereof.

According to one embodiment, specifically provided are compounds as defined in any of the above embodiments wherein $R_1$ is hydrogen, $C_{1-7}$ alkyl, $C_{1-7}$ alkoxy, halogen, cyano, nitro, halo $C_{1-7}$ alkyl, halo $C_{1-7}$ alkoxy or $C_{1-7}$ alkylthio;

$R_2$ is hydrogen or halogen;

$R_3$ is hydrogen, $C_{1-7}$ alkyl, $C_{2-7}$ alkenyl, hydroxy $C_{1-7}$ alkyl, cyano, thio, $C_{1-7}$ alkoxycarbonyl $C_{2-7}$ alkenyl, -D-C(O)—$NR_6R_7$, —C(O)$R_8$, —$SO_2R_{11}$, -D-$NR_9R_{10}$, —S(O)($NR_{14}$)($R_{22}$), —S($NR_{15}$)($C_{1-7}$ alkyl), —C(S)$NR_{18}R_{19}$, a 3-6 membered carbocyclyl which is optionally substituted with 1-2 hydroxyl substituents, a 4-6 membered heterocyclyl which is optionally substituted with 1-2 substituents selected from halogen, hydroxyl, $C_{1-7}$ alkoxycarbonyl or oxo, or a 4-6 membered heterocyclyl $C_{1-7}$ alkyl optionally substituted with 1-2 oxo substituents;

$R_4$ is hydrogen, $C_{1-7}$ alkyl, hydroxy or halogen;

$R_5$ is hydrogen or halogen;

$R_6$ is $C_{1-7}$ alkyl, $C_{3-7}$ cycloalkyl, hydroxy $C_{1-7}$ alkyl, —$C_{1-7}$ alkyl-O—C(O)$C_{1-7}$ alkyl;

$R_7$ is hydrogen or $C_{1-7}$ alkyl;

$R_8$ is hydrogen, $C_{1-7}$ alkyl, $C_{2-7}$ alkenyl, $C_{3-7}$ cycloalkyl, $C_{1-7}$ alkoxy, halo $C_{1-7}$ alkyl, $C_{1-7}$ alkoxy $C_{1-7}$ alkyl, $C_{1-7}$ alkylcarbonyl, $C_{1-7}$ alkoxycarbonyl, —$C_{1-7}$ alkyl-O—C(O)—$C_{1-7}$ alkyl, —$C_{1-7}$ alkyl-$SO_2$($C_{1-7}$ alkyl), —N=S(O)($C_{1-7}$ alkyl)($C_{1-7}$ alkyl) or a 4-6 membered heterocyclyl which is optionally substituted with 1-2 halogen substituents;

$R_9$ is $C_{1-7}$ alkylcarbonyl, —$SO_2$($C_{1-7}$ alkyl) or —$SO_2$($C_{3-7}$ cycloalkyl);

$R_{10}$ is hydrogen, $C_{1-7}$ alkyl or $C_{3-7}$ cycloalkyl;

$R_{11}$ is $C_{1-7}$ alkyl, $C_{3-7}$ cycloalkyl, halo $C_{1-7}$ alkyl, cyano $C_{1-7}$ alkyl, $C_{1-7}$ alkoxy $C_{1-7}$ alkyl, —$NR_{12}R_{13}$, a 3-6 membered carbocyclyl which is optionally substituted with 1-2 substituents selected from halogen or $C_{1-7}$ alkyl, or a 4-6 membered heterocyclyl which is optionally substituted with 1-2 substituents selected from halogen or $C_{1-7}$ alkyl;

$R_{12}$ is $C_{1-7}$ alkyl, hydroxy $C_{1-7}$ alkyl, cyano $C_{1-7}$ alkyl, $C_{1-7}$ alkoxy $C_{1-7}$ alkyl or $C_{1-7}$ alkylcarbonyl;

$R_{13}$ is hydrogen or $C_{1-7}$ alkyl;

$R_{14}$ is hydrogen, $C_{1-7}$ alkyl, $C_{1-7}$ alkylcarbonyl or —$SO_2R_{21}$;

$R_{15}$ is hydrogen, $C_{1-7}$ alkyl, —$SO_2R_{17}$;

$R_{17}$ is $C_{1-7}$ alkyl or a 3-6 membered carbocyclyl which is optionally substituted by 1-2 $C_{1-7}$ alkyl substituent;

$R_{18}$, and $R_{19}$ are, independently, hydrogen or $C_{1-7}$ alkyl;

$R_{21}$ is a 3-6 membered carbocyclyl optionally substituted with 1-2 $C_{1-7}$ alkyl substituents;

$R_{22}$ is $C_{1-7}$ alkyl or $C_{3-7}$ cycloalkyl;

$R_{24}$ is hydrogen or $C_{1-7}$ alkyl;

wherein the heterocyclyl group in each occurrence has 1-3 heteroatoms independently selected from N, O and S;

or a pharmaceutically acceptable salt thereof.

In one subclass are compounds represented by formula (IC) wherein $R_1$ is hydrogen, $C_{1-7}$ alkoxy, halogen, nitro, halo $C_{1-7}$ alkyl, halo $C_{1-7}$ alkoxy or $C_{1-7}$ alkylthio;

$R_2$ is hydrogen or halogen;

$R_3$ is $C_{2-7}$ alkenyl, hydroxy $C_{1-7}$ alkyl, cyano, $C_{1-7}$ alkoxycarbonyl $C_{2-7}$ alkenyl, -D-C(O)—$NR_6R_7$, —C(O)$R_8$, —$SO_2R_{11}$, -D-$NR_9R_{10}$, —S(O)($NR_{14}$)($R_{22}$), —S($NR_{15}$)($C_{1-7}$ alkyl), a 3-6 membered carbocyclyl which is optionally substituted with 1-2 hydroxy substituents, or a 4-6 membered heterocyclyl which is optionally substituted with 1-2 substituents selected from halogen or hydroxy;

$R_4$ is hydrogen, hydroxy or halogen;

$R_5$ is hydrogen or halogen;

$R_6$ is $C_{1-7}$ alkyl, hydroxy $C_{1-7}$ alkyl or —$C_{1-7}$ alkyl-O—C(O)$C_{1-7}$ alkyl;

$R_7$ is hydrogen or $C_{1-7}$ alkyl;

$R_8$ is $C_{1-7}$ alkyl, halo $C_{1-7}$ alkyl, —N=S(O)($C_{1-7}$ alkyl)($C_{1-7}$ alkyl) or a 4-6 membered heterocyclyl which is optionally substituted with 1-2 halogen substituents;

$R_9$ is $C_{1-7}$ alkylcarbonyl or —$SO_2$($C_{1-7}$ alkyl);

$R_{10}$ is hydrogen or $C_{1-7}$ alkyl;

$R_{11}$ is $C_{1-7}$ alkyl, $C_{3-7}$ cycloalkyl, halo $C_{1-7}$ alkyl, $C_{1-7}$ alkoxy $C_{1-7}$ alkyl, —$NR_{12}R_{13}$ or a 4-6 membered heterocyclyl;

$R_{12}$ is $C_{1-7}$ alkyl, hydroxy $C_{1-7}$ alkyl, cyano $C_{1-7}$ alkyl, $C_{1-7}$ alkoxy $C_{1-7}$ alkyl or $C_{1-7}$ alkylcarbonyl;

$R_{13}$ is hydrogen or $C_{1-7}$ alkyl;

$R_{14}$ is hydrogen, $C_{1-7}$ alkyl or $C_{1-7}$ alkylcarbonyl;

$R_{15}$ is hydrogen or —$SO_2R_{17}$;

$R_{17}$ is a 3-6 membered carbocyclyl which is optionally substituted by 1-2 $C_{1-7}$ alkyl substituents;

$R_{22}$ is $C_{1-7}$ alkyl or $C_{3-7}$ cycloalkyl;

$R_{24}$ is hydrogen or $C_{1-7}$ alkyl;

D is absent, $C_{1-7}$ alkyl or $C_{2-7}$ alkenyl;

wherein the heterocyclyl group in each occurrence has 1-3 heteroatoms independently selected from N, O and S;

or a pharmaceutically acceptable salt thereof.

In a subclass of the above embodiment are compounds wherein $R_1$ is hydrogen, $C_{1-7}$ alkoxy, halogen, nitro, halo $C_{1-7}$ alkyl or halo $C_{1-7}$ alkoxy;

$R_2$ and $R_{10}$ are hydrogen;

$R_3$ is $C_{2-7}$ alkenyl, hydroxy $C_{1-7}$ alkyl, cyano, $C_{1-7}$ alkoxycarbonyl $C_{2-7}$ alkenyl, -D-C(O)—$NR_6R_7$, —C(O)$R_8$, —$SO_2R_1$, -D-$NR_9R_{10}$, —S(O)($NR_{14}$)($R_{22}$), —S($NR_{15}$)($C_{1-7}$ alkyl), oxazolyl, cyclobutyl optionally substituted with a hydroxy substituent, or oxetanyl optionally substituted with a hydroxy substituent;

$R_4$ and $R_5$ are hydrogen or halogen;

$R_6$ is $C_{1-7}$ alkyl or hydroxy $C_{1-7}$ alkyl;

$R_7$, $R_{13}$, $R_{14}$ and $R_{24}$ are hydrogen or $C_{1-7}$ alkyl;

$R_8$ is $C_{1-7}$ alkyl, pyrrolidinyl, oxetanyl, or azetidinyl optionally substituted with 1-2 halogen substituents, —N=S(O)($C_{1-7}$ alkyl)($C_{1-7}$ alkyl);

$R_9$ is —$SO_2$($C_{1-7}$ alkyl);

$R_{11}$ is $C_{1-7}$ alkyl, $C_{3-7}$ cycloalkyl, halo $C_{1-7}$ alkyl, $C_{1-7}$ alkoxy $C_{1-7}$ alkyl, —$NR_{12}R_{13}$, pyrrolidinyl, piperidinyl, azetidinyl or morpholinyl;

$R_{12}$ is $C_{1-7}$ alkyl, hydroxy $C_{1-7}$ alkyl, cyano $C_{1-7}$ alkyl, $C_{1-7}$ alkoxy $C_{1-7}$ alkyl or $C_{1-7}$ alkylcarbonyl;

$R_{15}$ is hydrogen or —$SO_2R_{17}$;

$R_{17}$ is phenyl optionally substituted by a $C_{1-7}$ alkyl substituent;

$R_{22}$ is $C_{1-7}$ alkyl or $C_{3-7}$ cycloalkyl;

D is absent, $C_{1-7}$ alkyl or $C_{2-7}$ alkenyl;

or a pharmaceutically acceptable salt thereof.

In still another subclass of the above embodiment are compounds wherein $R_1$ is hydrogen, $C_{1-7}$ alkoxy, halogen, halo $C_{1-7}$ alkyl or halo $C_{1-7}$ alkoxy;

$R_2$ and $R_{10}$ are hydrogen;

$R_3$ is hydroxy $C_{1-7}$ alkyl, cyano, $C_{1-7}$ alkoxycarbonyl $C_{2-7}$ alkenyl, -D-C(O)—$NR_6R_7$, —C(O)$R_8$, —$SO_2R_{11}$, -D-$NR_9R_{10}$, —S(O)($NR_{14}$)($R_{22}$), —S($NR_{15}$)($C_{1-7}$ alkyl), oxazolyl, cyclobutyl optionally substituted with a hydroxy substituent, or oxetanyl optionally substituted with a hydroxy substituent;

$R_4$ and $R_5$ are hydrogen or halogen;

$R_6$ is $C_{1-7}$ alkyl;

$R_7$, $R_{13}$, $R_{14}$ and $R_{24}$ are hydrogen or $C_{1-7}$ alkyl;

$R_8$ is pyrrolidinyl, azetidinyl or —N=S(O)($C_{1-7}$ alkyl)($C_{1-7}$ alkyl);

$R_9$ is —$SO_2$($C_{1-7}$ alkyl);

$R_{11}$ is $C_{1-7}$ alkyl, halo $C_{1-7}$ alkyl, —$NR_{12}R_{13}$ or pyrrolidinyl;

$R_{12}$ is $C_{1-7}$ alkyl, hydroxy $C_{1-7}$ alkyl, cyano $C_{1-7}$ alkyl, $C_{1-7}$ alkoxy $C_{1-7}$ alkyl or $C_{1-7}$ alkylcarbonyl;

$R_{15}$ is —$SO_2R_{17}$;

$R_{17}$ is phenyl optionally substituted by a $C_{1-7}$ alkyl substituent;

$R_{22}$ is $C_{1-7}$ alkyl or $C_{3-7}$ cycloalkyl;

D is absent, $C_{1-7}$ alkyl or $C_{2-7}$ alkenyl;

or a pharmaceutically acceptable salt thereof.

In still another subclass of the above embodiment are compounds wherein $R_1$ is hydrogen, halogen, halo $C_{1-7}$ alkyl or halo $C_{1-7}$ alkoxy;

$R_2$, $R_4$, $R_5$ and $R_{10}$ are hydrogen;

$R_3$ is hydroxy $C_{1-7}$ alkyl, -D-C(O)—$NR_6R_7$, —C(O)$R_8$, —$SO_2R_{11}$, -D-$NR_9R_{10}$, —S(O)($NR_{14}$)($R_{22}$) or oxetanyl optionally substituted with a hydroxy substituent;

$R_6$ and $R_7$ is $C_{1-7}$ alkyl;

$R_8$ is pyrrolidinyl, or —N=S(O)($C_{1-7}$ alkyl)($C_{1-7}$ alkyl);

$R_9$ is —$SO_2$($C_{1-7}$ alkyl);

$R_{11}$ is $C_{1-7}$ alkyl, —$NR_{12}R_{13}$ or pyrrolidinyl;

$R_{12}$ is $C_{1-7}$ alkyl, hydroxy $C_{1-7}$ alkyl, or $C_{1-7}$ alkoxy $C_{1-7}$ alkyl;

$R_{13}$ and $R_{14}$ is hydrogen or $C_{1-7}$ alkyl;

$R_{22}$ is $C_{1-7}$ alkyl or $C_{3-7}$ cycloalkyl; D is $C_{1-7}$ alkyl or $C_{2-7}$ alkenyl;

or a pharmaceutically acceptable salt thereof.

In one subclass are compounds represented by formula (ID) wherein $R_1$ is hydrogen, $C_{1-7}$ alkyl, cyano, halogen, nitro, halo $C_{1-7}$ alkyl, halo $C_{1-7}$ alkoxy or $C_{1-7}$ alkylthio;

$R_2$ is hydrogen or halogen;

$R_3$ is -D-C(O)—$NR_6R_7$, —C(O)$R_8$, —$SO_2R_{11}$ or —C(S)$NR_{18}R_{19}$;

$R_4$ is hydrogen, $C_{1-7}$ alkyl, hydroxy or halogen;

$R_5$ is hydrogen;

$R_6$ is $C_{1-7}$ alkyl or $C_{3-7}$ cycloalkyl;

$R_7$ and $R_{24}$ are hydrogen or $C_{1-7}$ alkyl;

$R_8$ is hydrogen, $C_{1-7}$ alkyl, $C_{2-7}$ alkenyl, $C_{3-7}$ cycloalkyl, halo $C_{1-7}$ alkyl, $C_{1-7}$ alkylcarbonyl, $C_{1-7}$ alkoxycarbonyl, $C_{1-7}$ alkoxy $C_{1-7}$ alkyl, —$C_{1-7}$ alkyl-O—C(O)—$C_{1-7}$ alkyl, —$C_{1-7}$ alkyl-$SO_2$($C_{1-7}$ alkyl) or a 4-10 membered heterocyclyl;

$R_{11}$ is $C_{1-7}$ alkyl, $C_{3-7}$ cycloalkyl, halo $C_{1-7}$ alkyl, cyano $C_{1-7}$ alkyl, $C_{1-7}$ alkoxy $C_{1-7}$ alkyl, —$NR_{12}R_{13}$, a 3-6 membered carbocyclyl which is optionally substituted with 1-2 halogen substituents, or a 4-6 membered heterocyclyl which is optionally substituted with 1-2 substituents selected from halogen or $C_{1-7}$ alkyl;

$R_{12}$ and $R_{13}$ are $C_{1-7}$ alkyl;

$R_{18}$, and $R_{19}$ are, independently, hydrogen or $C_{1-7}$ alkyl;

D is absent;

wherein the heterocyclyl group in each occurrence has 1-3 heteroatoms independently selected from N, O and S. or a pharmaceutically acceptable salt thereof.

In a subclass of the above embodiment are compounds wherein $R_1$ is hydrogen, $C_{1-7}$ alkyl, halogen, halo $C_{1-7}$ alkyl or halo $C_{1-7}$ alkoxy;

$R_2$ and $R_5$ are hydrogen;

$R_3$ is -D-C(O)—$NR_6R_7$, —C(O)$R_8$, —$SO_2R_{11}$, or —C(S)$NR_{18}R_{19}$, or oxetanyl optionally substituted by a hydroxy substituent;

$R_4$ is hydrogen, $C_{1-7}$ alkyl or halogen;

$R_6$ is $C_{1-7}$ alkyl;

$R_7$ is hydrogen or $C_{1-7}$ alkyl;

$R_8$ is $C_{1-7}$ alkyl, $C_{2-7}$ alkenyl, $C_{3-7}$ cycloalkyl, halo $C_{1-7}$ alkyl, $C_{1-7}$ alkylcarbonyl, $C_{1-7}$ alkoxycarbonyl, $C_{1-7}$ alkoxy $C_{1-7}$ alkyl, —$C_{1-7}$ alkyl-O—C(O)—$C_{1-7}$ alkyl, —$C_{1-7}$ alkyl-$SO_2$($C_{1-7}$ alkyl), azetidinyl, morpholinyl, furanyl or pyrrolidinyl;

$R_{11}$ is $C_{1-7}$ alkyl, $C_{3-7}$ cycloalkyl, halo $C_{1-7}$ alkyl, cyano $C_{1-7}$ alkyl, $C_{1-7}$ alkoxy $C_{1-7}$ alkyl, —$NR_{12}R_{13}$, pyrrolidinyl, phenyl optionally substituted with a halogen substituent, oxetanyl, or pyrazolyl optionally substituted with a $C_{1-7}$ alkyl substituent;

$R_{12}$ and $R_{13}$ are $C_{1-7}$ alkyl;
$R_{18}$ and $R_{19}$ are, independently, hydrogen or $C_{1-7}$ alkyl;
$R_{24}$ is hydrogen or $C_{1-7}$ alkyl;
D is absent;
or a pharmaceutically acceptable salt thereof.

In still another subclass of the above embodiment are compounds wherein
$R_1$ is hydrogen, $C_{1-7}$ alkyl, halogen, halo $C_{1-7}$ alkyl or halo $C_{1-7}$ alkoxy;
$R_2$, $R_5$ and $R_7$ are hydrogen;
$R_3$ is -D-C(O)—NR$_6$R$_7$, —C(O)R$_8$ or —SO$_2$R$_{11}$;
$R_4$ is hydrogen or $C_{1-7}$ alkyl;
$R_6$ is $C_{1-7}$ alkyl;
$R_8$ is $C_{1-7}$ alkyl, $C_{3-7}$ cycloalkyl, halo $C_{1-7}$ alkyl, $C_{1-7}$ alkylcarbonyl, —$C_{1-7}$ alkyl-O—C(O)—$C_{1-7}$ alkyl, —$C_{1-7}$ alkyl-SO$_2$($C_{1-7}$ alkyl), morpholinyl or pyrrolidinyl;
$R_{11}$ is $C_{1-7}$ alkyl, $C_{3-7}$ cycloalkyl, cyano $C_{1-7}$ alkyl, $C_{1-7}$ alkoxy $C_{1-7}$ alkyl, —NR$_{12}$R$_{13}$, oxetanyl, or pyrazolyl optionally substituted with a $C_{1-7}$ alkyl substituent;
$R_{12}$ and $R_{13}$ are $C_{1-7}$ alkyl;
$R_{24}$ is hydrogen or $C_{1-7}$ alkyl;
D is absent;
or a pharmaceutically acceptable salt thereof.

In still another subclass of the above embodiment are compounds wherein
$R_1$ is hydrogen, halogen, halo $C_{1-7}$ alkyl or halo $C_{1-7}$ alkoxy;
$R_2$, $R_4$, $R_5$ and $R_7$ are hydrogen;
$R_3$ is -D-C(O)—NR$_6$R$_7$, —C(O)R$_8$ or —SO$_2$R$_{11}$;
$R_6$, $R_{12}$ and $R_{13}$ are $C_{1-7}$ alkyl;
$R_8$ is $C_{1-7}$ alkyl or halo $C_{1-7}$ alkyl;
$R_{11}$ is $C_{1-7}$ alkyl, $C_{3-7}$ cycloalkyl, $C_{1-7}$ alkoxy $C_{1-7}$ alkyl, —NR$_{12}$R$_{13}$ or oxetanyl;
$R_{24}$ is hydrogen;
D is absent;
or a pharmaceutically acceptable salt thereof.

In one subclass are compounds represented by formula (IE) wherein
$R_1$, $R_2$, $R_4$, $R_5$ and $R_{24}$ are hydrogen;
$R_3$ is hydrogen, -D-C(O)—NR$_6$R$_7$, —C(O)R$_8$, —SO$_2$R$_{11}$, -D-NR$_9$R$_{10}$, —S(O)(NR$_{14}$)(R$_{22}$), a 4-6 membered heterocyclyl which is optionally substituted with 1-2 oxo substituents, or a 4-6 membered heterocyclyl $C_{1-7}$ alkyl optionally substituted with 1-2 oxo substituents;
$R_6$, $R_{11}$ and $R_{22}$ are $C_{1-7}$ alkyl;
$R_7$ is hydrogen or $C_{1-7}$ alkyl;
$R_8$ is $C_{1-7}$ alkyl, $C_{1-7}$ alkoxy, or a 4-6 membered heterocyclyl;
$R_9$ is —SO$_2$($C_{1-7}$ alkyl);
$R_{10}$ is hydrogen, $C_{1-7}$ alkyl or $C_{3-7}$ cycloalkyl;
$R_{14}$ is hydrogen or —SO$_2$R$_{21}$;
$R_{21}$ is 3-6 membered carbocyclyl optionally substituted with 1-2 $C_{1-7}$ alkyl;
D is absent or $C_{1-7}$ alkyl;
wherein the heterocyclyl group in each occurrence has 1-3 heteroatoms independently selected from N, O and S;
or a pharmaceutically acceptable salt thereof.

In still another subclass of the above embodiment are compounds wherein
$R_1$, $R_2$, $R_4$, $R_5$ and $R_{24}$ are hydrogen;
$R_3$ is -D-C(O)—NR$_6$R$_7$, —C(O)R$_8$, —SO$_2$R$_{11}$, -D-NR$_9$R$_{10}$, —S(O)(NR$_{14}$)(R$_{22}$), 1,1-dioxidoisothiazolidinyl or 1,1-dioxidoisothiazolidinyl $C_{1-7}$ alkyl;
$R_6$, $R_{11}$ and $R_{22}$ are $C_{1-7}$ alkyl;
$R_7$ is $C_{1-7}$ alkyl;
$R_8$ is $C_{1-7}$ alkyl or azetidinyl;
$R_9$ is —SO$_2$($C_{1-7}$ alkyl);

$R_{10}$ is hydrogen, $C_{1-7}$ alkyl or $C_{3-7}$ cycloalkyl;
$R_{14}$ is —SO$_2$R$_{21}$;
$R_{21}$ is phenyl optionally substituted with a $C_{1-7}$ alkyl substituent;
D is absent or $C_{1-7}$ alkyl;
or a pharmaceutically acceptable salt thereof.

According to one embodiment, the invention provides a pharmaceutical composition comprising a compound of formula (I) as defined in any of the above embodiments together with a pharmaceutically acceptable carrier.

According to still one embodiment, the present invention provides a method for the treatment of a steroid receptor, in particular androgen receptor (AR), dependent conditions and diseases, comprising administering to a subject in need thereof a therapeutically effective amount of a compound of formula (I)

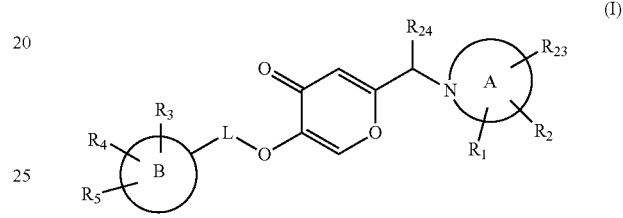

wherein
ring B is a 4-10 membered monocyclic or bicyclic ring containing 0-4 heteroatoms independently selected form N, O or S;
ring A is any of the following groups

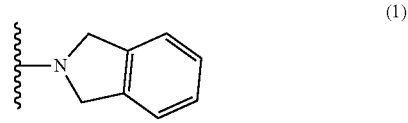

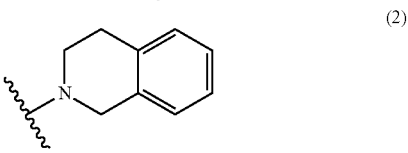

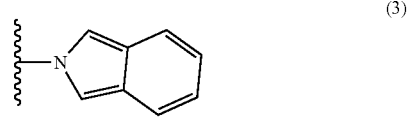

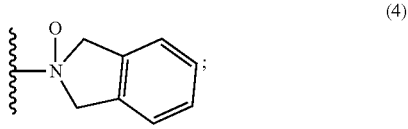

L is absent, —CH$_2$—, —CH$_2$—CH$_2$— or —CH$_2$—CH$_2$—CH$_2$—, or in case ring A is (1), L can also be —C(O)—CH$_2$—;
$R_1$ is hydrogen, $C_{1-7}$ alkyl, $C_{1-7}$ alkoxy, halogen, cyano, nitro, halo $C_{1-7}$ alkyl, halo $C_{1-7}$ alkoxy or $C_{1-7}$ alkylthio;
$R_2$ is hydrogen, $C_{1-7}$ alkyl, halogen, hydroxy, halo $C_{1-7}$ alkyl, nitro, halo $C_{1-7}$ alkoxy or thiol;
or $R_1$ and $R_2$ together with the carbon atoms to which they are attached form a fused 1,3 dioxole ring;
$R_3$ is hydrogen, halogen, nitro, cyano, oxo, $C_{1-7}$ alkyl, $C_{2-7}$ alkenyl, $C_{3-7}$ cycloalkyl, hydroxy $C_{3-7}$ cycloalkyl, $C_{1-7}$ alkoxy, hydroxy $C_{1-7}$ alkyl, halo $C_{1-7}$ alkyl, cyano $C_{1-7}$ alkyl, $C_{1-7}$ alkoxy $C_{1-7}$ alkyl, $C_{1-7}$ alkylthio, aminocarbonyl $C_{2-7}$ alkenyl, halo $C_{1-7}$ alkylthio, $C_{1-7}$ alkoxycarbonyl $C_{1-7}$ alkyl, $C_{1-7}$ alkoxycarbonyl $C_{2-7}$ alkenyl, =NSO$_2$R$_{20}$, —S(O)—$C_{1-7}$ alkyl, —S(O)(NR$_{14}$)(R$_{22}$), —S(NR$_{15}$)($C_{1-7}$ alkyl), —C(S)NR$_{18}$R$_{19}$, -D-C(O)NR$_6$R$_7$, —C(O)R$_8$, -D-NR$_9$R$_{10}$, —SO$_2$R$_{11}$, an optionally substituted 3-10 membered carbocyclyl, an optionally substituted 3-10 membered carbocyclyl $C_{1-7}$ alkyl, an optionally substituted 4-10 membered heterocyclyl or an optionally substituted 4-10 membered heterocyclyl $C_{1-7}$ alkyl;

$R_4$ is hydrogen, halogen, hydroxy, $C_{1-7}$ alkyl, halo $C_{1-7}$ alkyl or oxo;

$R_5$ is hydrogen, halogen or $C_{1-7}$ alkyl;

$R_6$ is hydrogen, $C_{1-7}$ alkyl, $C_{2-7}$ alkenyl, $C_{3-7}$ cycloalkyl, hydroxy $C_{1-7}$ alkyl, cyano $C_{1-7}$ alkyl, —$C_{1-7}$ alkyl-O—C(O) $C_{1-7}$ alkyl or an optionally substituted 4-10 membered heterocyclyl;

$R_8$ is hydrogen, $C_{1-7}$ alkyl, $C_{2-7}$ alkenyl, $C_{3-7}$ cycloalkyl, $C_{1-7}$ alkoxy, halo $C_{1-7}$ alkyl, $C_{1-7}$ alkoxy $C_{1-7}$ alkyl, $C_{1-7}$ alkylcarbonyl, $C_{1-7}$ alkoxycarbonyl, —$C_{1-7}$ alkyl-O—C(O)—$C_{1-7}$ alkyl, —$C_{1-7}$ alkyl-SO$_2$($C_{1-7}$ alkyl), —N=S(O)($C_{1-7}$ alkyl)($C_{1-7}$ alkyl) or an optionally substituted 4-10 membered heterocyclyl;

$R_9$ is hydrogen, $C_{1-7}$ alkyl, $C_{3-7}$ cycloalkyl, $C_{1-7}$ alkylcarbonyl, —SO$_2$($C_{1-7}$ alkyl) or —SO$_2$($C_{3-7}$ cycloalkyl);

$R_{11}$ is $C_{1-7}$ alkyl, $C_{2-7}$ alkenyl, $C_{3-7}$ cycloalkyl, halo $C_{1-7}$ alkyl, cyano $C_{1-7}$ alkyl, $C_{1-7}$ alkoxy $C_{1-7}$ alkyl, —NR$_{12}$R$_{13}$, an optionally substituted 3-10 membered carbocyclyl or an optionally substituted 4-10 membered heterocyclyl;

$R_{12}$ is hydrogen, $C_{1-7}$ alkyl, hydroxy $C_{1-7}$ alkyl, cyano $C_{1-7}$ alkyl, $C_{1-7}$ alkoxy, $C_{1-7}$ alkoxy $C_{1-7}$ alkyl or $C_{1-7}$ alkylcarbonyl;

$R_7$, $R_{10}$, $R_{13}$, $R_{18}$, and $R_{19}$ are, independently, hydrogen, $C_{1-7}$ alkyl or $C_{3-7}$ cycloalkyl;

$R_{14}$ is hydrogen, $C_{1-7}$ alkyl, $C_{1-7}$ alkylcarbonyl or —SO$_2$R$_{21}$;

$R_{15}$ is hydrogen, $C_{1-7}$ alkyl, $C_{3-7}$ cycloalkyl, $C_{1-7}$ alkylcarbonyl, —SO$_2$R$_{17}$;

$R_{17}$ is $C_{1-7}$ alkyl or an optionally substituted 3-10 membered carbocyclyl;

$R_{20}$ and $R_{21}$ are, independently, $C_{1-7}$ alkyl, $C_{3-7}$ cycloalkyl or an optionally substituted 3-10 membered carbocyclyl;

$R_{22}$ is $C_{1-7}$ alkyl or $C_{3-7}$ cycloalkyl;

$R_{23}$ is hydrogen or oxo;

$R_{24}$ is hydrogen or $C_{1-7}$ alkyl;

D is absent, $C_{1-7}$ alkyl or $C_{2-7}$ alkenyl;

wherein the optional substitution in each occurrence is selected from 1-3 substituents independently selected from $C_{1-7}$ alkyl, halogen, hydroxy, $C_{1-7}$ alkoxy, $C_{1-7}$ alkoxy $C_{1-7}$ alkyl, $C_{1-7}$ alkoxycarbonyl or oxo; and wherein the heterocyclyl group in each occurrence has 1-4 heteroatoms independently selected from N, O and S;

or a pharmaceutically acceptable salt thereof.

According to one embodiment, the steroid receptor dependent disease or condition is androgen receptor dependent disease or condition including endocrine cancers and diseases, for example prostate cancer or breast cancer, particularly castration-resistant prostate cancer (CRPC). According to one embodiment of the invention, the CRPC to be treated is refractory to CYP17A1 inhibitor treatment. According to another embodiment, the androgen receptor dependent disease or condition is endocrine cancer which is dependent upon CYP11A1 activation.

The compounds of the invention can be prepared by a variety of synthetic routes analogously to the methods known in the literature using suitable starting materials. The compounds according to formula (I) can be prepared e.g. analogously or according to the following reaction Schemes.

Some compounds included in the formula (I) can be obtained by converting the functional groups of the other compounds of formula (I) obtained in accordance with the following Schemes, by well known reaction steps such as oxidation, reduction, hydrolysis, acylation, alkylation, amidation, amination, sulfonation and others. It should be noted that any appropriate leaving groups, e.g. N-protecting groups, such as a t-butoxycarbonyl (t-BOC) group or a phenylsulfonyl group, can be used in well known manner during the syntheses in order to improve the selectivity of the reaction steps.

Compounds of formula (I) can be prepared, for example, according to Scheme 1, wherein $R_1$, $R_2$, $R_3$, $R_4$, $R_5$, $R_{23}$, $R_{24}$, L, A and B, are as defined above, and X is a halogen. In the method of Scheme 1, the 5-hydroxy-4H-pyran-4-one derivative [1] is coupled with ring B derivative [2] where halogen is acting as the leaving group in a suitable solvent in the presence of a base at elevated temperature, for example using K$_2$CO$_3$ in DMF, K$_2$CO$_3$ in DMSO, NaOH/KOH in MeOH/EtOH, NaH in DMF or K$_2$CO$_3$ in THF/1,4-dioxane, to produce a compound of formula (I).

SCHEME 1.

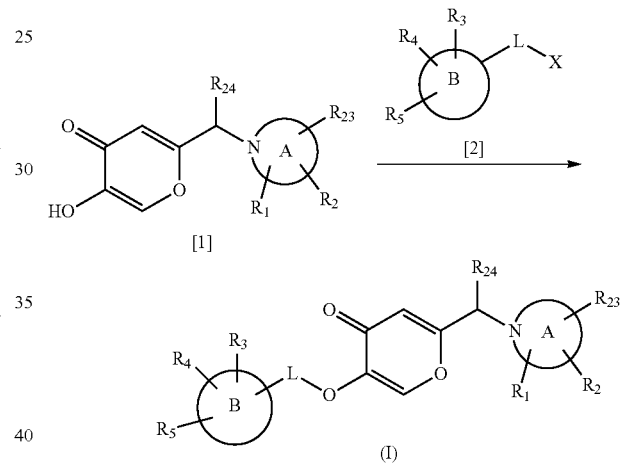

Alternatively, compounds of formula (I) can be prepared according to Scheme 2, wherein $R_1$, $R_2$, $R_3$, $R_4$, $R_5$, $R_{23}$, $R_{24}$, L, A and B, are as defined above, and Z is mesyl or tosyl group. In the method of Scheme 2, the 5-hydroxy-4H-pyran-4-one derivative [1] is coupled with ring B derivative [3], where mesylate or tosylate is acting as the leaving group, in a suitable solvent in the presence of a base at elevated temperature, for example using K$_2$CO$_3$ in DMF, K$_2$CO$_3$ in DMSO, NaOH/KOH in MeOH/EtOH, NaH in DMF or K$_2$CO$_3$ in THF/1,4-dioxane, to produce a compound of formula (I).

SCHEME 2.

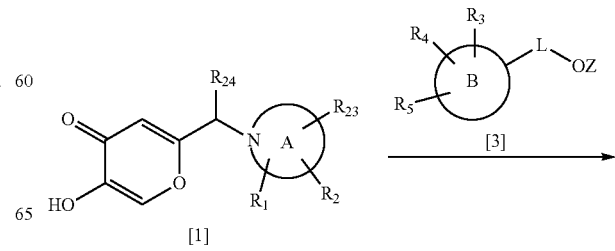

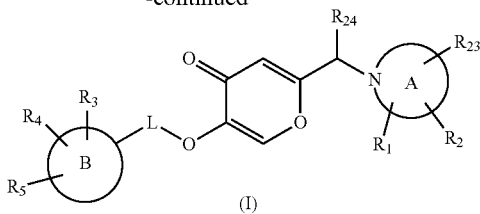

(I)

Compounds of formula (ID) where $R_3$ is coupled to the piperidine ring via acyl or sulfonyl group, can be prepared, for example, according to Scheme 3, wherein $R_1$, $R_2$, $R_3$, $R_4$, $R_5$ and $R_{24}$ are as defined above, and X is a halogen. In the method of Scheme 3, the compound of formula (ID') is coupled with a halogen compound [4] in a suitable solvent such as $CH_2Cl_2$ in the presence of suitable base such as triethylamine to produce a compound of formula (ID).

SCHEME 3.

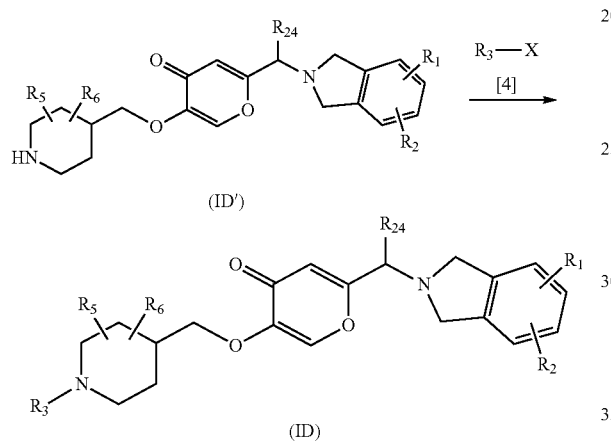

Compounds of formula (ID) where $R_3$ is —C(O)—$NHR_6$, can be prepared, for example, according to Scheme 4, wherein $R_1$, $R_2$, $R_4$, $R_5$, $R_7$ and $R_{24}$ are as defined above. In the method of Scheme 4, the compound of formula (ID') is coupled with a isocyanate compound [5] in a suitable solvent such as $CH_2Cl_2$ or DMF in the presence of suitable base such as triethylamine or DIPEA to produce a compound of formula (IDa). Compounds of formula (ID) where $R_3$ is —C(S)$NHR_{19}$ can be prepared in similar manner using $R_{19}$—N=C=S as a reagent.

SCHEME 4.

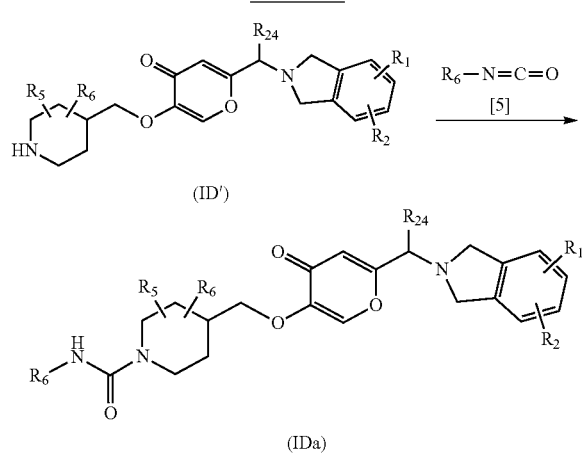

Compounds of formula (I) can also be prepared according to Scheme 5, wherein $R_1$, $R_2$, $R_3$, $R_4$, $R_5$, $R_{23}$, $R_{24}$, L, A and B, are as defined above, and X is a halogen. In the method of Scheme 5, the compound of formula [6] is coupled with a compound of formula [7] in a suitable solvent such as DMF in the presence of a base such as $K_2CO_3$ at elevated temperature to produce a compound of formula [8]. The compound of formula [8] can be then reacted with methanesulfonyl chloride in a suitable solvent such as DCM under cooling in the presence of suitable base such as triethylamine to produce a compound of formula [9]. Compounds of formula (I) can be obtained by coupling the compound of formula [9] with a compound of formula [10] in a suitable solvent such as DMSO or DMF in the presence of a base such as $K_2CO_3$ at elevated temperature.

SCHEME 5.

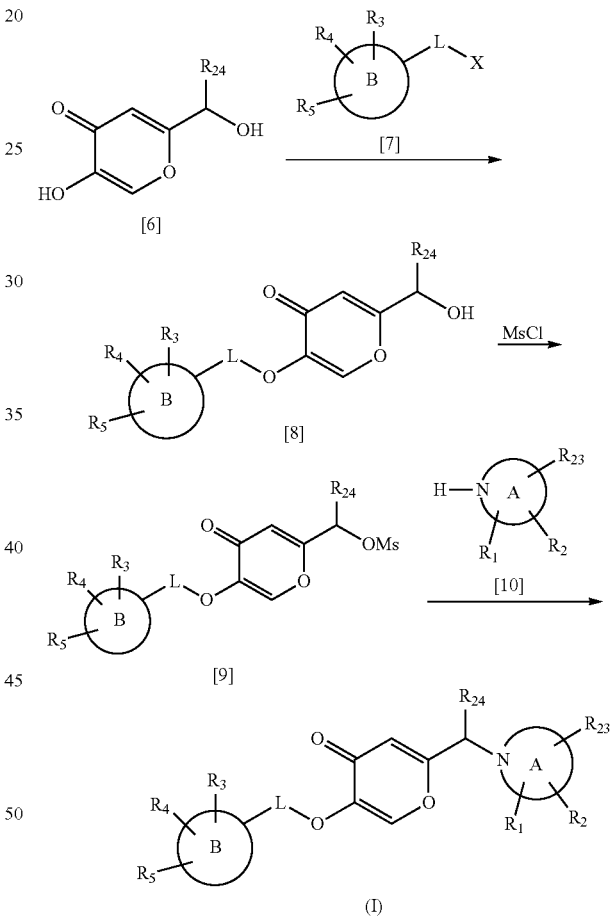

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "subject", as employed herein, refers to humans and animals.

The term "steroid receptor" refers to receptor which binds to and is activated by a steroid hormone. Examples of steroid receptors include, but are not limited to, androgen, glucocorticoid, and progesterone receptors.

The term "endocrine cancer" refers to partially or completely unregulated growth of one or more cellular components of the endocrine system, including, but not limited to, cancers of one or more of the adrenal glands.

The term "halo" or "halogen", as employed herein as such or as part of another group, refers to chlorine, bromine, fluorine or iodine.

The term "$C_{1-7}$ alkyl", as employed herein as such or as part of another group, refers to a straight or branched chain saturated hydrocarbon group having 1, 2, 3, 4, 5, 6 or 7 carbon atom(s). Representative examples of $C_{1-7}$ alkyl include, but are not limited to, methyl, ethyl, n-propyl, iso-propyl, n-butyl, iso-butyl, sec-butyl, tert-butyl, n-pentyl, iso-pentyl and n-hexyl. One preferred embodiment of "$C_{1-7}$ alkyl" is $C_{1-3}$ alkyl. The term "$C_{1-3}$ alkyl" refers to a preferred embodiment of "$C_{1-7}$ alkyl" having 1, 2 or 3 carbon atoms.

The term "$C_{2-7}$ alkenyl", as employed herein as such or as part of another group, refers to an aliphatic hydrocarbon group having 2, 3, 4, 5, 6 or 7 carbon atoms and containing one or several double bonds. Representative examples include, but are not limited to, ethenyl, propenyl and cyclohexenyl.

The term "$C_{3-7}$ cycloalkyl", as employed herein as such or as part of another group, refers to a saturated cyclic hydrocarbon group containing 3, 4, 5, 6 or 7 carbon atoms. Representative examples of cycloalkyl include, but are not limited to, cyclopropyl, cyclobutyl, cyclopentyl and cyclohexyl.

The term "$C_{3-7}$ cycloalkyl $C_{1-7}$ alkyl", as employed herein refers to a $C_{3-7}$ cycloalkyl group, as defined herein, appended to the parent molecular moiety through a $C_{1-7}$ alkyl group, as defined herein.

The term "hydroxy", as employed herein as such or as part of another group, refers to an —OH group.

The term "cyano", as employed herein as such or as part of another group, refers to a —CN group.

The term "carboxy", as employed herein as such or as part of another group, refers to —COOH group.

The term "carbonyl", as employed herein as such or as part of another group, refers to a carbon atom double-bonded to an oxygen atom (C=O).

The term "oxo", as employed herein as such or as part of another group, refers to oxygen atom linked to another atom by a double bond (=O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tert-butoxy.

The term "hydroxy $C_{1-7}$ alkyl", as employed herein, refers to at least one hydroxy group, as defined herein, appended to the parent molecular moiety through a $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl and 3-bromopropyl.

The term "cyano $C_{1-7}$ alkyl", as employed herein, refers to a cyano group, as defined herein, appended to the parent molecular moiety through a $C_{1-7}$ alkyl group, as defined herein. Representative examples of cyano $C_{1-7}$ alkyl include, but are not limited to, cyanomethyl, 1-cyanoethyl, 1-cyanopropyl and 2-cyanopropyl.

The term "halo $C_{1-7}$ alkoxy", as employed herein, refers to at least one halogen, as defined herein, appended to the parent molecular moiety through a $C_{1-7}$ alkoxy group, as defined herein.

The term "phenyl $C_{1-7}$ alkyl", as employed herein, refers to at least one phenyl group appended to the parent molecular moiety through a $C_{1-7}$ alkyl group, as defined herein.

The term "$C_{1-7}$ alkyl carbonyl", as employed herein as such or as part of another group, refers to a $C_{1-7}$ alkyl group, as defined herein, appended to the parent molecular moiety through a carbonyl group, as defined herein.

The term "$C_{1-7}$ alkoxy $C_{1-7}$ alkyl", as employed herein as such or as part of another group, refers to at least one $C_{1-7}$ alkoxy group, as defined herein, appended to the parent molecular moiety through an $C_{1-7}$ alkyl group, as defined herein.

The term "hydroxy $C_{1-7}$ alkoxy", as employed herein such or as part of another group, refers to at least one hydroxy group, as defined herein, appended to the parent molecular moiety through an $C_{1-7}$ alkoxy group, as defined herein.

The term "hydroxy $C_{1-7}$ alkoxy $C_{1-7}$ alkyl", as employed herein, refers to a hydroxy $C_{1-7}$ alkoxy group, as defined herein, appended to the parent molecular moiety through an $C_{1-7}$ alkyl group, as defined herein.

The term "4-10 membered heterocyclyl" as employed herein, refers to a saturated, partially saturated or aromatic ring with 4-10 ring atoms, of which 1-4 atoms are heteroatoms selected from a group consisting of N, O and S. One embodiment of a "4-10 membered heterocyclyl" is a "4-6 membered heterocyclyl" which refers to a saturated, partially saturated or aromatic ring with 4-6 ring atoms, of which 1-4 atoms are heteroatoms selected from a group consisting of N, O and S. Representative examples of a 4-10 membered heterocyclic ring include, but are not limited to, oxetanyl, azetidinyl, pyrazolyl, 1,2,4-triazol-1-yl, 1,2,3-triazol-1-yl, pyrimidinyl, pyridinyl, piperidinyl, tetrazolyl, piperazinyl, furanyl, morpholinyl, piperidinyl, pyrrolidinyl, thiazolyl, isoxazolyl, pyrazinyl tetrahydropyranyl, 1,2,4-oxadiazolyl, oxazolyl, imidazolyl, indolyl and 4,5-dihydroimidazolyl rings.

The term "3-10 membered carbocyclyl" as employed herein, refers to a saturated, partially saturated or aromatic ring with 3 to 10 ring atoms consisting of carbon atoms only. One embodiment of a "3-10 membered carbocyclyl" is a "3-6 membered carbocyclyl" which refers to a saturated, partially saturated or aromatic ring with 3 to 6 ring atoms consisting of carbon atoms only. Representative examples of a 3-10 membered carbocyclic ring include, but are not limited to, phenyl, cyclohexyl, cyclohexenyl, cyclopentyl, cyclopentenyl and cyclobutyl rings.

The term "4-10 membered heterocyclyl $C_{1-7}$ alkyl" as employed herein, refers to a "4-10 membered heterocyclyl" group, as defined herein, appended to the parent molecular moiety through an $C_{1-7}$ alkyl group, as defined herein.

The term "3-10 membered carbocyclyl $C_{1-7}$ alkyl" as employed herein, refers to a "3-10 membered carbocyclyl" group, as defined herein, appended to the parent molecular moiety through an $C_{1-7}$ alkyl group, as defined herein.

The term "substituted" as used herein in connection with various residues refers to, if not otherwise defined, to halogen substituents, such as fluorine, chlorine, bromine, iodine, or $C_{1-7}$ alkyl, $C_{3-7}$ cycloalkyl, hydroxy, amino, nitro, cyano, thiol $C_{1-7}$ alkyl, methylsulfonyl, $C_{1-7}$ alkoxy, halo $C_{1-7}$ alkyl, hydroxy $C_{1-7}$ alkyl or amino $C_{1-7}$ alkyl substituents. Preferred are halogen, $C_{1-7}$ alkyl, hydroxy, amino, halo $C_{1-7}$ alkyl, $C_{1-7}$ alkoxy and methylsulfonyl substituents. In one group of preferred substituents are 1-2 substituents selected from $C_{1-7}$ alkyl or halogen substituents, particularly $C_{1-3}$ alkyl or halogen substituents, particularly methyl, ethyl, chloro, fluoro or bromo substituents.

The "substituted" groups may contain 1 to 3, preferably 1 or 2, of the above mentioned substituents, if not otherwise defined.

Optically active enantiomers or diastereomers of compounds of formula (I) can be prepared e.g. by resolution of the racemic end product by known methods or by using suitable optically active starting materials. Similarly, racemic compounds of formula (I) can be prepared by using racemic starting materials. Resolution of racemic compounds of formula (I) or a racemic starting material thereof can be carried out, for example, by converting the racemic compound into its diastereromeric salt mixture by reaction with an optically active acid and subsequent separation of the diastereomers by crystallization.

Representative examples of said optically active acids include, but are not limited to, D-tartaric acid and dibenzoyl-D-tartaric acid. Alternatively, preparative chiral chromatography may be used for resolution of the racemic mixture.

Pharmaceutically acceptable salts are well known in the field of pharmaceuticals. Non-limiting examples of suitable salts include metal salts, ammonium salts, salts with an organic base, salts with an inorganic acid, salts with organic acid, and salts with basic or acidic amino acid. Non-limiting examples of metal salts include alkali metal salts such as sodium salt and potassium salt; alkaline earth metal salts such as calcium salt, and magnesium salt. Non-limiting examples of salts with inorganic or organic acids include chlorides, bromides, sulfates, nitrates, phosphates, sulfonates, methane sulfonates, formates, tartrates, maleates, citrates, benzoates, salicylates, ascorbates, acetates, oxalates, fumarates, hemifumarates, and succinates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) above is inclusive of all the possible isotopes and isomers, such as stereoisomers, of the compounds, including geometric isomers, for example Z and E isomers (cis and trans isomers), and optical isomers, e.g. diastereomers and enantiomers, and prodrug esters, e.g. phosphate esters and carbonate esters.

It will be appreciated by those skilled in the art that the present compounds may contain at least one chiral center. Accordingly, the compounds may exist in optically active or racemic forms. It is to be understood that the formula (I) includes any racemic or optically active form, or mixtures thereof. In one embodiment, the compounds are the pure (R)-isomers. In another embodiment, the compounds are the pure (S)-isomers. In another embodiment, the compounds are a mixture of the (R) and the (S) isomers. In another embodiment, the compounds are a racemic mixture comprising an equal amount of the (R) and the (S) isomers. The compounds may contain two chiral centers. In such case, according to one embodiment, the compounds are a mixture of diastereomers. According to another embodiment, the compounds of the invention are a mixture of enantiomers. According to still another embodiment, the compounds are pure enantiomers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The present compounds may also exist as tautomers or equilibrium mixtures thereof wherein a proton of a compound shifts from one atom to another. Examples of tautomerism include, but are not limited to, amido-imido, keto-enol, phenol-keto, oxime-nitroso, nitro-aci, imine-enamine, annular tautomerism of heterocyclic rings, and the like. Tautomeric forms are intended to be encompassed by compounds of formula (I), even though only one tautomeric form may be depicted.

Examples of preferred compounds of one group of formula (I) include

Methyl (E)-3-(4-(((6-(isoindolin-2-ylmethyl)-4-oxo-4H-pyran-3-yl)oxy)-methyl)phenyl)acrylate (Compound 2);

2-(Isoindolin-2-ylmethyl)-5-((4-(pyrrolidin-1-ylsulfonyl) benzyl)oxy)-4H-pyran-4-one (Compound 5);

4-(((6-(Isoindolin-2-ylmethyl)-4-oxo-4H-pyran-3-yl)oxy) methyl)-N-methylbenzenesulfonamide (Compound 8);

4-(((6-(Isoindolin-2-ylmethyl)-4-oxo-4H-pyran-3-yl)oxy) methyl)-N,N-di-methylbenzenesulfonamide (Compound 10);

4-(((6-(Isoindolin-2-ylmethyl)-4-oxo-4H-pyran-3-yl)oxy) methyl)-N-(2-methoxyethyl)benzenesulfonamide (Compound 11);

N-(2-Hydroxyethyl)-4-(((6-(isoindolin-2-ylmethyl)-4-oxo-4H-pyran-3-yl)-oxy)methyl)-N-methylbenzenesulfonamide (Compound 12);

N-(2-Hydroxyethyl)-4-(((6-(isoindolin-2-ylmethyl)-4-oxo-4H-pyran-3-yl)-oxy)methyl)benzenesulfonamide (Compound 15);

N-Ethyl-N-(2-hydroxyethyl)-4-(((6-(isoindolin-2-ylmethyl)-4-oxo-4H-pyran-3-yl)oxy)methyl)benzenesulfonamide (Compound 21);

5-((4-((Difluoromethyl)sulfonyl)benzyl)oxy)-2-(isoindolin-2-ylmethyl)-4H-pyran-4-one (Compound 22);

N-(2-Cyanoethyl)-4-(((6-(isoindolin-2-ylmethyl)-4-oxo-4H-pyran-3-yl)oxy)-methyl)-N-methylbenzenesulfonamide (Compound 23);

2-(Isoindolin-2-ylmethyl)-5-((1-(oxetan-3-ylsulfonyl)piperidin-4-yl)methoxy)-4H-pyran-4-one (Compound 36);

5-((4-(Methylsulfonyl)benzyl)oxy)-2-((5-(trifluoromethoxy)isoindolin-2-yl)-methyl)-4H-pyran-4-one (Compound 37);

2-((3,4-dihydroisoquinolin-2(1H)-yl)methyl)-5-((4-(2-hydroxypropan-2-yl)-benzyl)oxy)-4H-pyran-4-one (Compound 44);

2-Isoindolin-2-ylmethyl)-5-((4-(prop-1-en-2-yl)benzyl) oxy)-4H-pyran-4-one (Compound 47);

5-((4-(2-Hydroxypropan-2-yl)benzyl)oxy)-2-(isoindolin-2-ylmethyl)-4H-pyran-4-one (Compound 49);

5-(Cyclohexylmethoxy)-2-(isoindolin-2-ylmethyl)-4H-pyran-4-one (Compound 65);

5-((1-(Oxetan-3-ylsulfonyl)piperidin-4-yl)methoxy)-2-((5-(trifluoromethyl)-isoindolin-2-yl)methyl)-4H-pyran-4-one (Compound 69a);

N-((4-(((6-(Isoindolin-2-ylmethyl)-4-oxo-4H-pyran-3-yl) oxy)methyl)phenyl)-sulfonyl)-N-methylacetamide (Compound 70);

5-((4-(Cyclobutanesulfonimidoyl)benzyl)oxy)-2-(isoindolin-2-ylmethyl)-4H-pyran-4-one (Compound 71);

5-((4-(Cyclopropylsulfonyl)benzyl)oxy)-2-(isoindolin-2-ylmethyl)-4H-pyran-4-one (Compound 72);

5-((4-(Isobutylsulfonyl)benzyl)oxy)-2-(isoindolin-2-ylmethyl)-4H-pyran-4-one (Compound 73);

5-((4-(S-methylsulfinimidoyl)benzyl)oxy)-2-((5-(trifluoromethyl)isoindolin-2-yl)methyl)-4H-pyran-4-one (Compound 74);

4-({[6-(1,3-Dihydro-2H-isoindol-2-ylmethyl)-4-oxo-4H-pyran-3-yl]oxy}methyl)-N-[dimethyl(oxido)-λ$^6$-sulfanylidene]benzamide (Compound 83);

N-[Dimethyl(oxido)-λ$^6$-sulfanylidene]-4-[({6-[(5-fluoro-1,3-dihydro-2H-iso-indol-2-yl)methyl]-4-oxo-4H-pyran-3-yl}oxy)methyl]benzamide (Compound 84);

5-((4-(S-Methylsulfonimidoyl)benzyl)oxy)-2-((5-(trifluoromethyl)isoindolin-2-yl)methyl)-4H-pyran-4-one (Compound 89);

5-((4-(S-Methylsulfonimidoyl)benzyl)oxy)-2-((5-(trifluoromethoxy)isoindolin-2-yl)methyl)-4H-pyran-4-one (Compound 90);

2-(1-(Isoindolin-2-yl)ethyl)-5-((4-(S-methylsulfonimidoyl)benzyl)oxy)-4H-pyran-4-one (Compound 91);

5-((4-(N,S-Dimethylsulfonimidoyl)benzyl)oxy)-2-(isoindolin-2-ylmethyl)-4H-pyran-4-one (Compound 92);

N-{[4-({[6-(1,3-dihydro-2H-isoindol-2-ylmethyl)-4-oxo-4H-pyran-3-yl]oxy}-methyl)phenyl](methyl)-λ$^4$-sulfanylidene}-4-methylbenzenesulfonamide (Compound 93);

5-((4-(Azetidine-1-carbonyl)-2-fluorobenzyl)oxy)-2-(isoindolin-2-ylmethyl)-4H-pyran-4-one (Compound 95);

2-Isoindolin-2-ylmethyl)-5-((4-(propan-2-ylsulfonimidoyl)benzyl)oxy)-4H-pyran-4-one (Compound 103);

5-((5-Fluoro-1-(methylsulfonyl)-1,2,3,6-tetrahydropyridin-4-yl)methoxy)-2-(isoindolin-2-ylmethyl)-4H-pyran-4-one (Compound 104);

2-(Isoindolin-2-ylmethyl)-5-((4-(oxazol-2-yl)benzyl)oxy)-4H-pyran-4-one (Compound 109);

5-((4-(1-Hydroxycyclobutyl)benzyl)oxy)-2-(isoindolin-2-ylmethyl)-4H-pyran-4-one (Compound 111);

N-(4-(((6-(Isoindolin-2-ylmethyl)-4-oxo-4H-pyran-3-yl)oxy)methyl)benzyl)-methanesulfonamide (Compound 113);

5-((4-(3-Hydroxyoxetan-3-yl)benzyl)oxy)-2-(isoindolin-2-ylmethyl)-4H-pyran-4-one (Compound 114);

2-((5-Fluoroisoindolin-2-yl)methyl)-5-((4-(3-hydroxyoxetan-3-yl)benzyl)oxy)-4H-pyran-4-one (Compound 115);

5-((4-(3-Hydroxyoxetan-3-yl)benzyl)oxy)-2-((5-(trifluoromethyl)isoindolin-2-yl)methyl)-4H-pyran-4-one (Compound 116);

2-(Isoindolin-2-ylmethyl)-5-((4-(pyrrolidine-1-carbonyl)benzyl)oxy)-4H-pyran-4-one (Compound 122);

5-((4-(Azetidine-1-carbonyl)benzyl)oxy)-2-(isoindolin-2-ylmethyl)-4H-pyran-4-one (Compound 129);

2-((5-Bromoisoindolin-2-yl)methyl)-5-((4-(pyrrolidine-1-carbonyl)benzyl)oxy)-4H-pyran-4-one (Compound 130);

N-(tert-Butyl)-4-(((6-(isoindolin-2-ylmethyl)-4-oxo-4H-pyran-3-yl)oxy)methyl)-benzamide (Compound 131);

4-(((6-Isoindolin-2-ylmethyl)-4-oxo-4H-pyran-3-yl)oxy)methyl)-N,N-diiso-propylbenzamide (Compound 134);

4-(((6-((5-Chloroisoindolin-2-yl)methyl)-4-oxo-4H-pyran-3-yl)oxy)methyl)-N,N-dimethylbenzamide (Compound 137);

4-(((6-((5-Methoxyisoindolin-2-yl)methyl)-4-oxo-4H-pyran-3-yl)oxy)methyl)-N,N-dimethylbenzamide (Compound 138);

N,N-Dimethyl-4-(((4-oxo-6-((5-(trifluoromethyl)isoindolin-2-yl)methyl)-4H-pyran-3-yl)oxy)methyl)benzamide (Compound 139);

(E)-3-(4-(((6-(Isoindolin-2-ylmethyl)-4-oxo-4H-pyran-3-yl)oxy)methyl)phenyl)-N,N-dimethylacrylamide (Compound 146);

5-((4-(3,3-Difluoroazetidine-1-carbonyl)benzyl)oxy)-2-((5-methoxyisoindolin-2-yl)methyl)-4H-pyran-4-one (Compound 162);

3,5-Difluoro-4-(((6-(isoindolin-2-ylmethyl)-4-oxo-4H-pyran-3-yl)oxy)methyl)-N,N-dimethylbenzamide (Compound 172);

N-((4-(((6-(Isoindolin-2-ylmethyl)-4-oxo-4H-pyran-3-yl)oxy)methyl)cyclohexyl)-methyl)methanesulfonamide (Compound 173);

5-((4-((1,1-Dioxidoisothiazolidin-2-yl)methyl)cyclohexyl)methoxy)-2-(isoindolin-2-ylmethyl)-4H-pyran-4-one (Compound 176);

5-((1-(Methylsulfonyl)piperidin-4-yl)methoxy)-2-((5-(trifluoromethyl)isoindolin-2-yl)methyl)-4H-pyran-4-one (Compound 184);

2-(Isoindolin-2-ylmethyl)-5-((1-(methylsulfonyl)piperidin-4-yl)methoxy)-4H-pyran-4-one (Compound 185);

2-((5-Fluoroisoindolin-2-yl)methyl)-5-((1-(methylsulfonyl)piperidin-4-yl)-methoxy)-4H-pyran-4-one (Compound 186);

5-((1-(Cyclopropylsulfonyl)piperidin-4-yl)methoxy)-2-(isoindolin-2-ylmethyl)-4H-pyran-4-one (Compound 187);

5-((1-(Ethylsulfonyl)piperidin-4-yl)methoxy)-2-(isoindolin-2-ylmethyl)-4H-pyran-4-one (Compound 188);

5-((1-(Ethylsulfonyl)piperidin-4-yl)methoxy)-2-((5-fluoroisoindolin-2-yl)methyl)-4H-pyran-4-one (Compound 189);

5-((1-(Cyclopropylsulfonyl)piperidin-4-yl)methoxy)-2-((5-fluoroisoindolin-2-yl)methyl)-4H-pyran-4-one (Compound 190);

5-((1-(Ethylsulfonyl)-4-methylpiperidin-4-yl)methoxy)-2-(isoindolin-2-ylmethyl)-4H-pyran-4-one (Compound 192);

2-(1-Isoindolin-2-yl)ethyl)-5-((1-(methylsulfonyl)piperidin-4-yl)methoxy)-4H-pyran-4-one (Compound 195);

2-(Isoindolin-2-ylmethyl)-5-((tetrahydro-2H-thiopyran-4-yl)methoxy)-4H-pyran-4-one (Compound 196);

5-((1-(Methylsulfonyl)piperidin-4-yl)methoxy)-2-((5-(trifluoromethoxy)-isoindolin-2-yl)methyl)-4H-pyran-4-one (Compound 205);

2-((5-Methylisoindolin-2-yl)methyl)-5-((1-(methylsulfonyl)piperidin-4-yl)-methoxy)-4H-pyran-4-one (Compound 211);

2-(Isoindolin-2-ylmethyl)-5-(3-(1-(methylsulfonyl)piperidin-4-yl)propoxy)-4H-pyran-4-one (Compound 213);

2-(Isoindolin-2-ylmethyl)-5-((1-(pyrrolidine-1-carbonyl)piperidin-4-yl)methoxy)-4H-pyran-4-one (Compound 215);

5-(((1r,4r)-4-(1,1-Dioxidoisothiazolidin-2-yl)cyclohexyl)methoxy)-2-(isoindolin-2-ylmethyl)-4H-pyran-4-one (Compound 216);

4-(((6-(Isoindolin-2-ylmethyl)-4-oxo-4H-pyran-3-yl)oxy)methyl)-N,N-dimethylcyclohexane-1-carboxamide (Compound 217);

N-Cyclopropyl-N-(4-(((6-(isoindolin-2-ylmethyl)-4-oxo-4H-pyran-3-yl)oxy)-methyl)cyclohexyl)methanesulfonamide (Compound 219);

5-((1-Butyrylpiperidin-4-yl)methoxy)-2-(isoindolin-2-ylmethyl)-4H-pyran-4-one (Compound 221);

5-((1-(2,2-Difluoropropanoyl)piperidin-4-yl)methoxy)-2-(isoindolin-2-ylmethyl)-4H-pyran-4-one (Compound 222);
2-((5-Fluoroisoindolin-2-yl)methyl)-5-((1-propionylpiperidin-4-yl)methoxy)-4H-pyran-4-one (Compound 224);
4-(((6-(Isoindolin-2-ylmethyl)-4-oxo-4H-pyran-3-yl)oxy)methyl)-N,N-di-methylpiperidine-1-sulfonamide (Compound 225);
5-((1-(Cyclopropanecarbonyl)piperidin-4-yl)methoxy)-2-(isoindolin-2-ylmethyl)-4H-pyran-4-one (Compound 226);
4-(((6-(Isoindolin-2-ylmethyl)-4-oxo-4H-pyran-3-yl)oxy)methyl)-N-isopropyl-piperidine-1-carboxamide (Compound 229);
4-(((6-((5-Fluoroisoindolin-2-yl)methyl)-4-oxo-4H-pyran-3-yl)oxy)methyl)-N,N-dimethylpiperidine-1-sulfonamide (Compound 230);
2-(Isoindolin-2-ylmethyl)-5-((1-(morpholine-4-carbonyl)piperidin-4-yl)methoxy)-4H-pyran-4-one (Compound 232);
5-((4-(Azetidine-1-carbonyl)cyclohexyl)methoxy)-2-(isoindolin-2-ylmethyl)-4H-pyran-4-one (Compound 234);
2-(Isoindolin-2-ylmethyl)-5-((1-(2-(methylsulfonyl)acetyl)piperidin-4-yl)-methoxy)-4H-pyran-4-one (Compound 238);
5-(((1r,4r)-4-Acetylcyclohexyl)methoxy)-2-(isoindolin-2-ylmethyl)-4H-pyran-4-one (Compound 244);
5-((1-Propionylpiperidin-4-yl)methoxy)-2-((5-(trifluoromethyl)isoindolin-2-yl)-methyl)-4H-pyran-4-one (Compound 244a);
2-((5-((1-(methylsulfonyl)piperidin-4-yl)methoxy)-4-oxo-4H-pyran-2-yl)methyl)-isoindoline-5-carbonitrile (Compound 245a);
1-(4-(((6-(Isoindolin-2-ylmethyl)-4-oxo-4H-pyran-3-yl)oxy)methyl)piperidin-1-yl)-4-methylpentane-1,2-dione (Compound 249);
2-(Isoindolin-2-ylmethyl)-5-((1-pivaloylpiperidin-4-yl)methoxy)-4H-pyran-4-one (Compound 251);
2-((4-(((6-(Isoindolin-2-ylmethyl)-4-oxo-4H-pyran-3-yl)oxy)methyl)piperidin-1-yl)sulfonyl)acetonitrile (Compound 254);
2-(Isoindolin-2-ylmethyl)-5-((1-((1-methyl-1H-pyrazol-5-yl)sulfonyl)piperidin-4-yl)methoxy)-4H-pyran-4-one (Compound 255);
2-(4-(((6-(Isoindolin-2-ylmethyl)-4-oxo-4H-pyran-3-yl)oxy)methyl)piperidin-1-yl)-2-oxoethyl acetate (Compound 257);
2-(Isoindolin-2-ylmethyl)-5-((1-propionylpiperidin-4-yl)methoxy)-4H-pyran-4-one (Compound 261);
2-(Isoindolin-2-ylmethyl)-5-((1-((2-methoxyethyl)sulfonyl)piperidin-4-yl)-methoxy)-4H-pyran-4-one (Compound 262);
5-((1-(Isobutylsulfonyl)piperidin-4-yl)methoxy)-2-(isoindolin-2-ylmethyl)-4H-pyran-4-one (Compound 271);
5-((1-Isobutyrylpiperidin-4-yl)methoxy)-2-(isoindolin-2-ylmethyl)-4H-pyran-4-one (Compound 272);
4-((6-((5-Bromoisoindolin-2-yl)methyl)-4-oxo-4H-pyran-3-yloxy)methyl)benzonitrile (Compound 278);
5-((4-(S-Methylsulfonimidoyl)benzyl)oxy)-2-((5-(trifluoromethyl)isoindolin-2-yl)methyl)-4H-pyran-4-one (Compound 285);
5-((4-(R-Methylsulfonimidoyl)benzyl)oxy)-2-((5-(trifluoromethyl)isoindolin-2-yl)methyl)-4H-pyran-4-one (Compound 286);
and tautomers and pharmaceutically acceptable salts thereof.

Examples of preferred compounds of another group of formula (I) include 2-(Isoindolin-2-ylmethyl)-5-((4-(methylsulfonyl)benzyl)oxy)-4H-pyran-4-one (Compound 1);
N,N-Diethyl-4-(((6-(isoindolin-2-ylmethyl)-4-oxo-4H-pyran-3-yl)oxy)methyl)-benzenesulfonamide (Compound 4);
2-(Isoindolin-2-ylmethyl)-5-((4-(morpholinosulfonyl)benzyl)oxy)-4H-pyran-4-one (Compound 6);
2-(Isoindolin-2-ylmethyl)-5-((4-(piperidin-1-ylsulfonyl)benzyl)oxy)-4H-pyran-4-one (Compound 7);
5-((4-(Azetidin-1-ylsulfonyl)benzyl)oxy)-2-(isoindolin-2-ylmethyl)-4H-pyran-4-one (Compound 9);
4-(((6-(Isoindolin-2-ylmethyl)-4-oxo-4H-pyran-3-yl)oxy)methyl)-N-(2-methoxyethyl)-N-methylbenzenesulfonamide (Compound 20);
5-((4-(Ethylsulfonyl)benzyl)oxy)-2-(isoindolin-2-ylmethyl)-4H-pyran-4-one (Compound 24);
2-(Isoindolin-2-ylmethyl)-5-((4-(isopropylsulfonyl)benzyl)oxy)-4H-pyran-4-one (Compound 25);
2-((5,6-Difluoroisoindolin-2-yl)methyl)-5-((4-(methylsulfonyl)benzyl)oxy)-4H-pyran-4-one (Compound 26);
2-(Isoindolin-2-ylmethyl)-5-((4-((2-methoxyethyl)sulfonyl)benzyl)oxy)-4H-pyran-4-one (Compound 28);
2-((5-Fluoroisoindolin-2-yl)methyl)-5-((4-((2-methoxyethyl)sulfonyl)benzyl)oxy)-4H-pyran-4-one (Compound 29);
5-((1-((5-Chlorothiophen-3-yl)sulfonyl)azetidin-3-yl)methoxy)-2-(isoindolin-2-ylmethyl)-4H-pyran-4-one (Compound 30);
5-((4-Acetylbenzyl)oxy)-2-(isoindolin-2-ylmethyl)-4H-pyran-4-one (Compound 31);
5-((2-Fluoro-4-(methylsulfonyl)benzyl)oxy)-2-(isoindolin-2-ylmethyl)-4H-pyran-4-one (Compound 34);
5-((4-(4-Bromo-1H-pyrazol-1-yl)benzyl)oxy)-2-(isoindolin-2-ylmethyl)-4H-pyran-4-one (Compound 39);
2-((3,4-Dihydroisoquinolin-2(1H)-yl)methyl)-5-((4-(2-hydroxy-2-methyl-propyl)benzyl)oxy)-4H-pyran-4-one (Compound 46);
4-(((6-((6-Methoxy-3,4-dihydroisoquinolin-2(1H)-yl)methyl)-4-oxo-4H-pyran-3-yl)oxy)methyl)benzonitrile (Compound 53);
3-Fluoro-4-(((6-(isoindolin-2-ylmethyl)-4-oxo-4H-pyran-3-yl)oxy)methyl)-benzamide (Compound 56);
3-Fluoro-4-(((6-(isoindolin-2-ylmethyl)-4-oxo-4H-pyran-3-yl)oxy)methyl)-N,N-dimethylbenzamide (Compound 61);
2-((5-Fluoroisoindolin-2-yl)methyl)-5-((4-(methylsulfonyl)benzyl)oxy)-4H-pyran-4-one (Compound 63);
2-((5-Chloroisoindolin-2-yl)methyl)-5-((4-(methylsulfonyl)benzyl)oxy)-4H-pyran-4-one (Compound 64);
2-(Isoindolin-2-ylmethyl)-5-((tetrahydro-2H-pyran-4-yl)methoxy)-4H-pyran-4-one (Compound 67);
5-((4-(Methylsulfonyl)benzyl)oxy)-2-((5-nitroisoindolin-2-yl)methyl)-4H-pyran-4-one (Compound 68);
N-(2-(4-(((6-(Isoindolin-2-ylmethyl)-4-oxo-4H-pyran-3-yl)oxy)methyl)phenyl)-propan-2-yl)acetamide (Compound 69);
2-(Isoindolin-2-ylmethyl)-5-((4-(methylsulfinyl)benzyl)oxy)-4H-pyran-4-one (Compound 81);
2-(Isoindolin-2-ylmethyl)-5-((4-(methylthio)benzyl)oxy)-4H-pyran-4-one (Compound 82);
4-(((6-((5,6-Difluoroisoindolin-2-yl)methyl)-4-oxo-4H-pyran-3-yl)oxy)methyl)-N,N-dimethylbenzamide (Compound 82a);
2-(Isoindolin-2-ylmethyl)-5-((4-(S-methylsulfinimidoyl)benzyl)oxy)-4H-pyran-4-one (Compound 85);
2-(Isoindolin-2-ylmethyl)-5-((4-(S-methylsulfonimidoyl)benzyl)oxy)-4H-pyran-4-one (Compound 86);

2-((5-Fluoroisoindolin-2-yl)methyl)-5-((4-(S-methylsulfonimidoyl)benzyl)oxy)-4H-pyran-4-one (Compound 88);

N-{[4-({[6-(1,3-dihydro-2H-isoindol-2-ylmethyl)-4-oxo-4H-pyran-3-yl]oxy}-methyl)phenyl](methyl)oxido-λ⁶-sulfanylidene} (Compound 94);

5-((4-(N-Ethyl-S-methylsulfonimidoyl)benzyl)oxy)-2-(isoindolin-2-ylmethyl)-4H-pyran-4-one (Compound 97);

2-(Isoindolin-2-ylmethyl)-5-((1-(methylsulfonyl)-1,2,3,6-tetrahydropyridin-4-yl)methoxy)-4H-pyran-4-one (Compound 98);

5-((1-(Ethylsulfonyl)-1,2,3,6-tetrahydropyridin-4-yl)methoxy)-2-(isoindolin-2-ylmethyl)-4H-pyran-4-one (Compound 99);

2-(Isoindolin-2-ylmethyl)-5-((1-(isopropylsulfonyl)-1,2,3,6-tetrahydropyridin-4-yl)methoxy)-4H-pyran-4-one (Compound 100);

5-((4-(Ethylsulfonimidoyl)benzyl)oxy)-2-(isoindolin-2-ylmethyl)-4H-pyran-4-one (Compound 101);

5-((4-(Ethylsulfonimidoyl)benzyl)oxy)-2-((5-fluoroisoindolin-2-yl)methyl)-4H-pyran-4-one (Compound 102);

5-((4-(1H-1,2,3-triazol-1-yl)benzyl)oxy)-2-(isoindolin-2-ylmethyl)-4H-pyran-4-one (Compound 107);

5-((4-(1H-Pyrazol-1-yl)benzyl)oxy)-2-(isoindolin-2-ylmethyl)-4H-pyran-4-one (Compound 108);

4-(((6-(Isoindolin-2-ylmethyl)-4-oxo-4H-pyran-3-yl)oxy)methyl)-N,N-dimethylbenzamide (Compound 120);

2-((3,4-Dihydroisoquinolin-2(1H)-yl)methyl)-5-((4-methoxybenzyl)oxy)-4H-pyran-4-one (Compound 121);

4-(((6-((6-Fluoro-3,4-dihydroisoquinolin-2(1H)-yl)methyl)-4-oxo-4H-pyran-3-yl)oxy)methyl)-N,N-dimethylbenzamide (Compound 124);

N,N-Diethyl-4-(((6-(isoindolin-2-ylmethyl)-4-oxo-4H-pyran-3-yl)oxy)methyl)-benzamide (Compound 126);

4-(((6-((5-Fluoroisoindolin-2-yl)methyl)-4-oxo-4H-pyran-3-yl)oxy)methyl)-N,N-dimethylbenzamide (Compound 127);

2-(Isoindolin-2-ylmethyl)-5-((4-(piperidine-1-carbonyl)benzyl)oxy)-4H-pyran-4-one (Compound 128);

N-(tert-Butyl)-4-(((6-((3,4-dihydroisoquinolin-2(1H)-yl)methyl)-4-oxo-4H-pyran-3-yl)oxy)methyl)benzamide (Compound 135);

2-(4-(((6-(Isoindolin-2-ylmethyl)-4-oxo-4H-pyran-3-yl)oxy)methyl)phenyl)-N,N-dimethylacetamide (Compound 136);

4-(((6-(Isoindolin-2-ylmethyl)-4-oxo-4H-pyran-3-yl)oxy)methyl)-N-isopropylbenzamide (Compound 140);

N-Hexyl-4-(((6-(isoindolin-2-ylmethyl)-4-oxo-4H-pyran-3-yl)oxy)methyl)-benzamide (Compound 142);

2-(4-(((6-(Isoindolin-2-ylmethyl)-4-oxo-4H-pyran-3-yl)oxy)methyl)benzamido)-2-methylpropyl acetate (Compound 143);

N-(2-Hydroxyethyl)-4-(((6-(isoindolin-2-ylmethyl)-4-oxo-4H-pyran-3-yl)oxy)-methyl)-N-methylbenzamide (Compound 147);

5-((4-(3,3-Difluoroazetidine-1-carbonyl)benzyl)oxy)-2-(isoindolin-2-ylmethyl)-4H-pyran-4-one (Compound 158);

5-((4-(3,3-Difluoroazetidine-1-carbonyl)benzyl)oxy)-2-((5-fluoroisoindolin-2-yl)methyl)-4H-pyran-4-one (Compound 161);

2-((5-Chloroisoindolin-2-yl)methyl)-5-((4-(3,3-difluoroazetidine-1-carbonyl)-benzyl)oxy)-4H-pyran-4-one (Compound 163);

5-([1,1'-Biphenyl]-4-ylmethoxy)-2-(isoindolin-2-ylmethyl)-4H-pyran-4-one (Compound 164);

2-(Isoindolin-2-ylmethyl)-5-((4-(pyridin-2-yl)benzyl)oxy)-4H-pyran-4-one (Compound 165);

5-((4-(Ethylsulfonimidoyl)benzyl)oxy)-2-((5-nitroisoindolin-2-yl)methyl)-4H-pyran-4-one (Compound 168);

N-Butyl-4-(((6-(isoindolin-2-ylmethyl)-4-oxo-4H-pyran-3-yl)oxy)methyl)-benzamide (Compound 169);

2,6-Difluoro-4-(((6-(isoindolin-2-ylmethyl)-4-oxo-4H-pyran-3-yl)oxy)methyl)-N,N-dimethylbenzamide (Compound 174);

2-(Isoindolin-2-ylmethyl)-5-(((1R,5S)-8-(methylsulfonyl)-8-azabicyclo[3.2.1]octan-3-yl)methoxy)-4H-pyran-4-one (Compound 177);

5-(((6-(Isoindolin-2-ylmethyl)-4-oxo-4H-pyran-3-yl)oxy)methyl)isoindolin-1-one (Compound 180);

4-(((6-((5-Fluoroisoindolin-2-yl)methyl)-4-oxo-4H-pyran-3-yl)oxy)methyl)-N,N-dimethylpiperidine-1-carboxamide (Compound 181);

2-(Isoindolin-2-ylmethyl)-5-((4-methyl-1-(methylsulfonyl)piperidin-4-yl)-methoxy)-4H-pyran-4-one (Compound 191);

N-(4-(((6-(Isoindolin-2-ylmethyl)-4-oxo-4H-pyran-3-yl)oxy)methyl)-1-oxido-tetrahydro-2H-thiopyran-1-ylidene)-4-methylbenzenesulfonamide (Compound 194);

2-(Isoindolin-2-ylmethyl)-5-(2-(1-(methylsulfonyl)piperidin-4-yl)ethoxy)-4H-pyran-4-one (Compound 198);

(R)-tert-Butyl 3-(((6-(isoindolin-2-ylmethyl)-4-oxo-4H-pyran-3-yl)oxy)methyl)-pyrrolidine-1-carboxylate (Compound 199);

(S)-tert-Butyl 3-(((6-(isoindolin-2-ylmethyl)-4-oxo-4H-pyran-3-yl)oxy)methyl)-pyrrolidine-1-carboxylate (Compound 200);

5-((1-(Methylsulfonyl)piperidin-4-yl)methoxy)-2-((5-(methylthio)isoindolin-2-yl)methyl)-4H-pyran-4-one (Compound 208);

2-((5,7-Dihydro-6H-[1,3]dioxolo[4,5-f]isoindol-6-yl)methyl)-5-((1-(methyl-sulfonyl)piperidin-4-yl)methoxy)-4H-pyran-4-one (Compound 209);

2-((5,6-Difluoroisoindolin-2-yl)methyl)-5-((1-(methylsulfonyl)piperidin-4-yl)methoxy)-4H-pyran-4-one (Compound 210);

2-(Isoindolin-2-ylmethyl)-5-(3-(pyridin-4-yl)propoxy)-4H-pyran-4-one (Compound 214);

N-(4-(((6-(Isoindolin-2-ylmethyl)-4-oxo-4H-pyran-3-yl)oxy)methyl)cyclohexyl)-N-methylmethanesulfonamide (Compound 218);

2-(Isoindolin-2-ylmethyl)-5-((4-(methylsulfonyl)cyclohexyl)methoxy)-4H-pyran-4-one (Compound 220);

5-((1-(2,2-Difluoropropanoyl)piperidin-4-yl)methoxy)-2-((5-fluoroisoindolin-2-yl)methyl)-4H-pyran-4-one (Compound 223);

4-(((6-(Isoindolin-2-ylmethyl)-4-oxo-4H-pyran-3-yl)oxy)methyl)-N-methylcyclo-hexanecarboxamide (Compound 227);

4-(((6-(Isoindolin-2-ylmethyl)-4-oxo-4H-pyran-3-yl)oxy)methyl)-N-methyl-piperidine-1-carboxamide (Compound 228);

5-((1-(Azetidine-1-carbonyl)piperidin-4-yl)methoxy)-2-(isoindolin-2-ylmethyl)-4H-pyran-4-one (Compound 231);

2-(Isoindolin-2-ylmethyl)-5-((4-(oxetan-3-ylsulfonyl)benzyl)oxy)-4H-pyran-4-one (Compound 233);

5-((4-Fluoro-1-(methylsulfonyl)piperidin-4-yl)methoxy)-2-(isoindolin-2-yl-methyl)-4H-pyran-4-one (Compound 235);

5-((4-Fluoro-1-(isopropylsulfonyl)piperidin-4-yl)methoxy)-2-(isoindolin-2-ylmethyl)-4H-pyran-4-one (Compound 236);

5-((4-Fluoro-1-(methylsulfonyl)piperidin-4-yl)methoxy)-2-((5-fluoroisoindolin-2-yl)methyl)-4H-pyran-4-one (Compound 237);

N-{[4-({[6-(1,3-Dihydro-2H-isoindol-2-ylmethyl)-4-oxo-4H-pyran-3-yl]oxy}-methyl)cyclohexyl](methyl)oxido-λ⁶-sulfanylidene}-4-methylbenzenesulfonamide (Compound 239);

2-((5-Chloroisoindolin-2-yl)methyl)-5-((1-(methylsulfonyl)piperidin-4-yl)-methoxy)-4H-pyran-4-one (Compound 241);

N-Cyclopropyl-4-(((6-(isoindolin-2-ylmethyl)-4-oxo-4H-pyran-3-yl)oxy)-methyl)piperidine-1-carboxamide (Compound 247);

N-(tert-Butyl)-4-(((6-(isoindolin-2-ylmethyl)-4-oxo-4H-pyran-3-yl)oxy)-methyl)piperidine-1-carboxamide (Compound 248);

4-(((6-(Isoindolin-2-ylmethyl)-4-oxo-4H-pyran-3-yl)oxy)methyl)-N-methyl-piperidine-1-carbothioamide (Compound 250);

5-((1-Acetylpiperidin-4-yl)methoxy)-2-(isoindolin-2-ylmethyl)-4H-pyran-4-one (Compound 252);

5-((1-((4-Fluorophenyl)sulfonyl)piperidin-4-yl)methoxy)-2-(isoindolin-2-yl-methyl)-4H-pyran-4-one (Compound 256);

5-((1-Acryloylpiperidin-4-yl)methoxy)-2-(isoindolin-2-yl-methyl)-4H-pyran-4-one (Compound 258);

5-((1-(Furan-2-carbonyl)piperidin-4-yl)methoxy)-2-(isoindolin-2-ylmethyl)-4H-pyran-4-one (Compound 260);

2-(Isoindolin-2-ylmethyl)-5-((1-(pyrrolidin-1-ylsulfonyl)piperidin-4-yl)methoxy)-4H-pyran-4-one (Compound 267);

5-((1-(Azetidin-1-ylsulfonyl)piperidin-4-yl)methoxy)-2-(isoindolin-2-ylmethyl)-4H-pyran-4-one (Compound 268);

Ethyl 2-(4-(((6-(isoindolin-2-ylmethyl)-4-oxo-4H-pyran-3-yl)oxy)methyl)-piperidin-1-yl)-2-oxoacetate (Compound 269);

2-(Isoindolin-2-ylmethyl)-5-((1-(isopropylsulfonyl)piperidin-4-yl)methoxy)-4H-pyran-4-one (Compound 270);

2-(Isoindolin-2-ylmethyl)-5-((1-(2,2,2-trifluoroacetyl)piperidin-4-yl)methoxy)-4H-pyran-4-one (Compound 273);

Cis-N-(3-(((6-(Isoindolin-2-ylmethyl)-4-oxo-4H-pyran-3-yl)oxy)methyl)-cyclo-pentyl)-methanesulfonamide (Compound 276);

2-((5-Methylisoindolin-2-yl)methyl)-5-((4-(methylsulfonyl)benzyl)oxy)-4H-pyran-4-one (Compound 279);

5-((4-(Methylsulfonyl)benzyl)oxy)-2-((5-(methylthio)isoindolin-2-yl)methyl)-4H-pyran-4-one (Compound 280);

N-(1-Hydroxy-2-methylpropan-2-yl)-4-(((6-(isoindolin-2-ylmethyl)-4-oxo-4H-pyran-3-yl)oxy)methyl)benzamide (Compound 283);

4-(((6-(Isoindolin-2-ylmethyl)-4-oxo-4H-pyran-3-yl)oxy)methyl)piperidine-1-carbaldehyde (Compound 284);

5-((1-(Methylsulfonyl)-1,2,3,4-tetrahydropyridin-4-yl)methoxy)-2-((5-(trifluoro-methyl)isoindolin-2-yl)methyl)-4H-pyran-4-one (Compound 291);

and tautomers and pharmaceutically acceptable salts thereof.

Examples of preferred compounds of still another group of formula (I) include 2-(Isoindolin-2-ylmethyl)-5-((4-((trifluoromethyl)thio)benzyl)oxy)-4H-pyran-4-one (Compound 3);

4-(((6-(Isoindolin-2-ylmethyl)-4-oxo-4H-pyran-3-yl)oxy)methyl)benzenesulfonamide (Compound 13);

2-((3,4-Dihydroisoquinolin-2(1H)-yl)methyl)-5-((4-(methylsulfonyl)benzyl)oxy)-4H-pyran-4-one (Compound 14);

5-((2-Chloro-4-(methylsulfonyl)benzyl)oxy)-2-(isoindolin-2-ylmethyl)-4H-pyran-4-one (Compound 16);

5-((3-Fluoro-4-(methylsulfonyl)benzyl)oxy)-2-(isoindolin-2-ylmethyl)-4H-pyran-4-one (Compound 17);

5-((2-Chloro-4-(methylsulfonyl)benzyl)oxy)-2-((3,4-dihydroisoquinolin-2(1H)-yl)methyl)-4H-pyran-4-one (Compound 18);

2-(Isoindolin-2-ylmethyl)-5-((4-(methylsulfonyl)-2-(trifluoromethyl)benzyl)oxy)-4H-pyran-4-one (Compound 19);

2-((4-Fluoroisoindolin-2-yl)methyl)-5-((4-(methylsulfonyl)benzyl)oxy)-4H-pyran-4-one (Compound 27);

4-(((6-((4-Fluoroisoindolin-2-yl)methyl)-4-oxo-4H-pyran-3-yl)oxy)methyl)-N,N-dimethylbenzamide (Compound 32);

2-((4-Fluoroisoindolin-2-yl)methyl)-5-((4-(2-hydroxypropan-2-yl)benzyl)oxy)-4H-pyran-4-one (Compound 33);

5-((1,1-Dioxidotetrahydro-2H-thiopyran-4-yl)methoxy)-2-(isoindolin-2-yl-methyl)-4H-pyran-4-one (Compound 35);

2-(Isoindolin-2-ylmethyl)-5-((4-nitrobenzyl)oxy)-4H-pyran-4-one (Compound 38);

Ethyl 1-(4-(((6-(isoindolin-2-ylmethyl)-4-oxo-4H-pyran-3-yl)oxy)methyl)phenyl)-1H-pyrazole-4-carboxylate (Compound 40);

4-(((6-((3,4-Dihydroisoquinolin-2(1H)-yl)methyl)-4-oxo-4H-pyran-3-yl)oxy)-methyl)benzonitrile (Compound 41);

2-((3,4-Dihydroisoquinolin-2(1H)-yl)methyl)-5-((4-methylbenzyl)oxy)-4H-pyran-4-one (Compound 42);

4-(((6-((3,4-Dihydroisoquinolin-2(1H)-yl)methyl)-4-oxo-4H-pyran-3-yl)oxy)-methyl)benzamide (Compound 43);

4-(((6-(Isoindolin-2-ylmethyl)-4-oxo-4H-pyran-3-yl)oxy)methyl)benzonitrile (Compound 45);

4-(((6-((3,4-Dihydroisoquinolin-2(1H)-yl)methyl)-4-oxo-4H-pyran-3-yl)oxy)-methyl)-N-methylbenzamide (Compound 48);

3-(((6-((3,4-Dihydroisoquinolin-2(1H)-yl)methyl)-4-oxo-4H-pyran-3-yl)oxy)-methyl)benzonitrile (Compound 50);

4-(((6-((3,4-Dihydroisoquinolin-2(1H)-yl)methyl)-4-oxo-4H-pyran-3-yl)oxy)-methyl)-3-fluorobenzonitrile (Compound 51);

5-((4-(2-Hydroxypropan-2-yl)benzyl)oxy)-2-((6-methoxy-3,4-dihydroisoquinolin-2(1H)-yl)methyl)-4H-pyran-4-one (Compound 52);

4-(((6-((3,4-Dihydroisoquinolin-2(1H)-yl)methyl)-4-oxo-4H-pyran-3-yl)oxy)-methyl)-3-fluorobenzamide (Compound 55);

4-(((6-(Isoindolin-2-ylmethyl)-4-oxo-4H-pyran-3-yl)oxy)methyl)benzamide (Compound 57);

5-((4-Bromobenzyl)oxy)-2-(isoindolin-2-ylmethyl)-4H-pyran-4-one (Compound 58);

5-((4-(2-Hydroxypropan-2-yl)benzyl)oxy)-2-((1-methyl-3,4-dihydroisoquinolin-2(1H)-yl)methyl)-4H-pyran-4-one (Compound 59);

Methyl 4-(((6-(isoindolin-2-ylmethyl)-4-oxo-4H-pyran-3-yl)oxy)methyl)benzoate (Compound 60);

4-(((6-(Isoindolin-2-ylmethyl)-4-oxo-4H-pyran-3-yl)oxy)methyl)-N-methylbenzamide (Compound 62);

2-((5,7-Dihydro-6H-[1,3]dioxolo[4,5-f]isoindol-6-yl)methyl)-5-((4-(methyl-sulfonyl)benzyl)oxy)-4H-pyran-4-one (Compound 66);

2-(Isoindolin-2-ylmethyl)-5-((6-(trifluoromethyl)pyridin-3-yl)methoxy)-4H-pyran-4-one (Compound 75);

2-(Isoindolin-2-ylmethyl)-5-((6-methoxypyridin-3-yl)methoxy)-4H-pyran-4-one (Compound 76);

N,N-Dimethyl-4-(((6-((1-methylisoindolin-2-yl)methyl)-4-oxo-4H-pyran-3-yl)oxy)methyl)benzamide (Compound 77);

4-(((6-((3,4-Dihydroisoquinolin-2(1H)-yl)methyl)-4-oxo-4H-pyran-3-yl)oxy)-methyl)-2-fluoro-N,N-dimethylbenzamide (Compound 78);

2-Fluoro-4-(((6-(isoindolin-2-ylmethyl)-4-oxo-4H-pyran-3-yl)oxy)methyl)-N-methylbenzamide (Compound 79);

4-(((6-((3,4-Dihydroisoquinolin-2(1H)-yl)methyl)-4-oxo-4H-pyran-3-yl)oxy)-methyl)-2-fluoro-N-methylbenzamide (Compound 80);

2-((3,4-Dihydroisoquinolin-2(1H)-yl)methyl)-5-((4-(S-methylsulfonimidoyl)-benzyl)oxy)-4H-pyran-4-one (Compound 87);

4-(((6-(Isoindolin-2-ylmethyl)-4-oxo-4H-pyran-3-yl)oxy)methyl)-N-(2-oxotetra-hydrothiophen-3-yl)benzamide (Compound 96);

2-(Isoindolin-2-ylmethyl)-5-((3-nitrobenzyl)oxy)-4H-pyran-4-one (Compound 105);

5-(((6-(Isoindolin-2-ylmethyl)-4-oxo-4H-pyran-3-yl)oxy)methyl)-2-methyl-isoindolin-1-one (Compound 106);

2-(Isoindolin-2-ylmethyl)-5-((2-methoxypyridin-4-yl)methoxy)-4H-pyran-4-one (Compound 110);

4-(2-((6-(Isoindolin-2-ylmethyl)-4-oxo-4H-pyran-3-yl)oxy)ethyl)-N,N-dimethylbenzamide (Compound 112);

2-((3,4-Dihydroisoquinolin-2(1H)-yl)methyl)-5-((4-(3-hydroxyoxetan-3-yl)-benzyl)oxy)-4H-pyran-4-one (Compound 117);

2-Chloro-4-(((6-((3,4-dihydroisoquinolin-2(1H)-yl)methyl)-4-oxo-4H-pyran-3-yl)oxy)methyl)benzonitrile (Compound 118);

4-(((6-((3,4-Dihydroisoquinolin-2(1H)-yl)methyl)-4-oxo-4H-pyran-3-yl)oxy)-methyl)-N,N-dimethylbenzamide (Compound 119);

5-((4-(Hydroxymethyl)benzyl)oxy)-2-(isoindolin-2-ylmethyl)-4H-pyran-4-one (Compound 123);

2-((1-Methyl-3,4-dihydroisoquinolin-2(1H)-yl)methyl)-5-((4-(pyrrolidine-1-carbonyl)benzyl)oxy)-4H-pyran-4-one (Compound 125);

(S)—N,N-Dimethyl-4-(((6-((1-methylisoindolin-2-yl)methyl)-4-oxo-4H-pyran-3-yl)oxy)methyl)benzamide (Compound 132);

(R)—N,N-Dimethyl-4-(((6-((1-methylisoindolin-2-yl)methyl)-4-oxo-4H-pyran-3-yl)oxy)methyl)benzamide (Compound 133);

4-(((6-(Isoindolin-2-ylmethyl)-4-oxo-4H-pyran-3-yl)oxy)methyl)-N-(prop-2-yn-1-yl)benzamide (Compound 141);

2-(Isoindolin-2-ylmethyl)-5-((4-vinylbenzyl)oxy)-4H-pyran-4-one (Compound 144);

N-(4-Hydroxybutyl)-4-(((6-(isoindolin-2-ylmethyl)-4-oxo-4H-pyran-3-yl)oxy)-methyl)benzamide (Compound 145);

(E)-3-(4-(((6-((3,4-Dihydroisoquinolin-2(1H)-yl)methyl)-4-oxo-4H-pyran-3-yl)oxy)methyl)phenyl)-N-methylacrylamide (Compound 148);

2-((3,4-Dihydroisoquinolin-2(1H)-yl)methyl)-5-((4-(3-hydroxypiperidine-1-carbonyl)benzyl)oxy)-4H-pyran-4-one (Compound 149);

5-((4-(Azetidine-1-carbonyl)benzyl)oxy)-2-((5-fluoroisoindolin-2-yl)methyl)-4H-pyran-4-one (Compound 150);

N-(3-Hydroxy-2,2-dimethylpropyl)-4-(((6-(isoindolin-2-ylmethyl)-4-oxo-4H-pyran-3-yl)oxy)methyl)benzamide (Compound 151);

5-((4-(4-Hydroxypiperidine-1-carbonyl)benzyl)oxy)-2-(isoindolin-2-ylmethyl)-4H-pyran-4-one (Compound 152);

5-(2-(4-Benzylpiperazin-1-yl)-2-oxoethoxy)-2-(isoindolin-2-ylmethyl)-4H-pyran-4-one (Compound 153);

5-(2-(4-(4-Chlorophenyl)piperazin-1-yl)-2-oxoethoxy)-2-(isoindolin-2-ylmethyl)-4H-pyran-4-one (Compound 154);

5-(2-(4-Benzylpiperidin-1-yl)-2-oxoethoxy)-2-(isoindolin-2-ylmethyl)-4H-pyran-4-one (Compound 155);

2-(Isoindolin-2-ylmethyl)-5-(2-oxo-2-(4-(phenylsulfonyl)piperazin-1-yl)ethoxy)-4H-pyran-4-one (Compound 156);

2-(Isoindolin-2-ylmethyl)-5-(2-oxo-2-(4-tosylpiperazin-1-yl)ethoxy)-4H-pyran-4-one (Compound 157);

2-(Isoindolin-2-ylmethyl)-5-(2-(4-(3-(methoxymethyl)pyridin-2-yl)piperazin-1-yl)-2-oxoethoxy)-4H-pyran-4-one (Compound 159);

5-((4-(3-Hydroxypiperidine-1-carbonyl)benzyl)oxy)-2-(isoindolin-2-ylmethyl)-4H-pyran-4-one (Compound 160);

2-((3,4-Dihydroisoquinolin-2(1H)-yl)methyl)-5-((4-(ethylsulfonimidoyl)-benzyl)oxy)-4H-pyran-4-one (Compound 166);

6-(((6-(Isoindolin-2-ylmethyl)-4-oxo-4H-pyran-3-yl)oxy)methyl)-N,N-dimethyl-nicotinamide (Compound 170);

2-Fluoro-4-(((6-(isoindolin-2-ylmethyl)-4-oxo-4H-pyran-3-yl)oxy)methyl)-benzamide (Compound 171);

Methyl (1r,4r)-4-(((6-(isoindolin-2-ylmethyl)-4-oxo-4H-pyran-3-yl)oxy)methyl)-cyclohexane-1-carboxylate (Compound 178);

2-((3,4-Dihydroisoquinolin-2(1H)-yl)methyl)-5-((1-(methylsulfonyl)piperidin-4-yl)methoxy)-4H-pyran-4-one (Compound 179);

tert-Butyl 3-(((6-(isoindolin-2-ylmethyl)-4-oxo-4H-pyran-3-yl)oxy)methyl)-pyrrolidine-1-carboxylate (Compound 182);

3-(((6-(Isoindolin-2-ylmethyl)-4-oxo-4H-pyran-3-yl)oxy)methyl)-N,N-dimethyl-pyrrolidine-1-carboxamide (Compound 183);

5-((3-Hydroxy-1-(methylsulfonyl)piperidin-4-yl)methoxy)-2-(isoindolin-2-yl-methyl)-4H-pyran-4-one (Compound 193);

tert-Butyl 4-(2-((6-(isoindolin-2-ylmethyl)-4-oxo-4H-pyran-3-yl)oxy)ethyl)-piperidine-1-carboxylate (Compound 197);

(S)-tert-Butyl 3-(((6-(isoindolin-2-ylmethyl)-4-oxo-4H-pyran-3-yl)oxy)methyl)-piperidine-1-carboxylate (Compound 201);

(R)-tert-Butyl 3-(((6-(isoindolin-2-ylmethyl)-4-oxo-4H-pyran-3-yl)oxy)methyl)-piperidine-1-carboxylate (Compound 202);

tert-Butyl 4-((6-(isoindolin-2-ylmethyl)-4-oxo-4H-pyran-3-yl)oxy)piperidine-1-carboxylate (Compound 203);

5-(2-(1-Acetylpiperidin-4-yl)ethoxy)-2-(isoindolin-2-ylmethyl)-4H-pyran-4-one (Compound 206);

5-((1-(Methylsulfonyl)piperidin-4-yl)methoxy)-2-((5-nitroisoindolin-2-yl)methyl)-4H-pyran-4-one (Compound 207);

2-((1,1-Dimethylisoindolin-2-yl)methyl)-5-((1-(methylsulfonyl)piperidin-4-yl)-methoxy)-4H-pyran-4-one (Compound 212);

2-(Isoindolin-2-ylmethyl)-5-((4-(S-methylsulfonimidoyl)cyclohexyl)methoxy)-4H-pyran-4-one (Compound 240);

5-((1-Imino-1-oxidohexahydro-1$\lambda^6$-thiopyran-4-yl)methoxy)-2-(isoindolin-2-ylmethyl)-4H-pyran-4-one (Compound 242);

N-(4-(((6-(Isoindolin-2-ylmethyl)-4-oxo-4H-pyran-3-yl)oxy)methyl)-1-oxido-tetrahydro-2H-1$\lambda^6$-thiopyran-1-ylidene)acetamide (Compound 243);

2-((4,5-Difluoroisoindolin-2-yl)methyl)-5-((1-(methylsulfonyl)piperidin-4-yl)-methoxy)-4H-pyran-4-one (Compound 245);

2-Isoindolin-2-ylmethyl)-5-((1-((2,2,2-trifluoroethyl)sulfonyl)piperidin-4-yl)-methoxy)-4H-pyran-4-one (Compound 253);
5-((3-Aminobenzyl)oxy)-2-(isoindolin-2-ylmethyl)-4H-pyran-4-one (Compound 263);
4/5-(((6-(Isoindolin-2-ylmethyl)-4-oxo-4H-pyran-3-yl)oxy)methyl)-N,N-dimethyl-1H-1,2,3-triazole-1-carboxamide (Compound 264);
4/5-(((6-((3,4-Dihydroisoquinolin-2(1H)-yl)methyl)-4-oxo-4H-pyran-3-yl)-oxy)methyl)-N,N-dimethyl-1H-1,2,3-triazole-1-carboxamide (Compound 265);
Cis-N-(4-(((6-(Isoindolin-2-ylmethyl)-4-oxo-4H-pyran-3-yl)oxy)methyl)cyclo-pent-2-en-1-yl)cyclopropanesulfonamide (Compound 274);
Cis-N-(4-(((6-(Isoindolin-2-ylmethyl)-4-oxo-4H-pyran-3-yl)oxy)methyl)cyclo-pent-2-en-1-yl)-3-methylbutanamide (Compound 275);
(R)-2-(Isoindolin-2-ylmethyl)-5-((1-(methylsulfonyl)pyrrolidin-3-yl)methoxy)-4H-pyran-4-one (Compound 277);
2-((4-Chloroisoindolin-2-yl)methyl)-5-((4-(methylsulfonyl)benzyl)oxy)-4H-pyran-4-one (Compound 281);
N-(3-Hydroxypropyl)-4-(((6-(isoindolin-2-ylmethyl)-4-oxo-4H-pyran-3-yl)oxy)-methyl)benzamide (Compound 282);
5-((1-(Methylsulfonyl)piperidin-4-yl)methoxy)-2-((5-(trifluoromethyl)-2H-isoindol-2-yl)methyl)-4H-pyran-4-one (Compound 287);
2-((5-((1-(Methylsulfonyl)piperidin-4-yl)methoxy)-4-oxo-4H-pyran-2-yl)-methyl)isoindoline 2-oxide (Compound 289);
2-((5-((1-(Methylsulfonyl)piperidin-4-yl)methoxy)-4-oxo-4H-pyran-2-yl)methyl)-5-(trifluoromethyl)isoindoline 2-oxide (Compound 290);
and tautomers and pharmaceutically acceptable salts thereof.

Examples of compounds in one particularly preferred group of compounds of formula (I) include
N-Ethyl-N-(2-hydroxyethyl)-4-(((6-(isoindolin-2-ylmethyl)-4-oxo-4H-pyran-3-yl)oxy)methyl)benzenesulfonamide (Compound 21);
5-((4-(2-Hydroxypropan-2-yl)benzyl)oxy)-2-(isoindolin-2-ylmethyl)-4H-pyran-4-one (Compound 49);
4-({[6-(1,3-Dihydro-2H-isoindol-2-ylmethyl)-4-oxo-4H-pyran-3-yl]oxy}methyl)-N-[dimethyl(oxido)-λ$^6$-sulfanylidene]benzamide (Compound 83);
5-((4-(S-Methylsulfonimidoyl)benzyl)oxy)-2-((5-(trifluoromethoxy)isoindolin-2-yl)methyl)-4H-pyran-4-one (Compound 90);
2-(1-(Isoindolin-2-yl)ethyl)-5-((4-(S-methylsulfonimidoyl)benzyl)oxy)-4H-pyran-4-one (Compound 91);
2-(Isoindolin-2-ylmethyl)-5-((4-(pyrrolidine-1-carbonyl)benzyl)oxy)-4H-pyran-4-one (Compound 122);
5-((4-((1,1-Dioxidoisothiazolidin-2-yl)methyl)cyclohexyl)methoxy)-2-(isoindolin-2-ylmethyl)-4H-pyran-4-one (Compound 176);
5-((1-(Methylsulfonyl)piperidin-4-yl)methoxy)-2-((5-(trifluoromethyl)isoindolin-2-yl)methyl)-4H-pyran-4-one (Compound 184);
2-(Isoindolin-2-ylmethyl)-5-((1-(methylsulfonyl)piperidin-4-yl)methoxy)-4H-pyran-4-one (Compound 185);
5-((1-(Cyclopropylsulfonyl)piperidin-4-yl)methoxy)-2-(isoindolin-2-ylmethyl)-4H-pyran-4-one (Compound 187);
5-((1-(Ethylsulfonyl)piperidin-4-yl)methoxy)-2-(isoindolin-2-ylmethyl)-4H-pyran-4-one (Compound 188);
5-((1-(Ethylsulfonyl)piperidin-4-yl)methoxy)-2-((5-fluoroisoindolin-2-yl)methyl)-4H-pyran-4-one (Compound 189);
2-(1-Isoindolin-2-yl)ethyl)-5-((1-(methylsulfonyl)piperidin-4-yl)methoxy)-4H-pyran-4-one (Compound 195);
2-(Isoindolin-2-ylmethyl)-5-(3-(1-(methylsulfonyl)piperidin-4-yl)propoxy)-4H-pyran-4-one (Compound 213);
5-(((1r,4r)-4-(1,1-Dioxidoisothiazolidin-2-yl)cyclohexyl)methoxy)-2-(isoindolin-2-ylmethyl)-4H-pyran-4-one (Compound 216);
4-(((6-(Isoindolin-2-ylmethyl)-4-oxo-4H-pyran-3-yl)oxy)methyl)-N,N-dimethyl-cyclohexane-1-carboxamide (Compound 217);
4-(((6-(Isoindolin-2-ylmethyl)-4-oxo-4H-pyran-3-yl)oxy)methyl)-N,N-dimethyl-piperidine-1-sulfonamide (Compound 225);
5-(((1r,4r)-4-Acetylcyclohexyl)methoxy)-2-(isoindolin-2-ylmethyl)-4H-pyran-4-one (Compound 244);
5-((1-Propionylpiperidin-4-yl)methoxy)-2-((5-(trifluoromethyl)isoindolin-2-yl)methyl)-4H-pyran-4-one (Compound 244a);
2-(Isoindolin-2-ylmethyl)-5-((1-propionylpiperidin-4-yl)methoxy)-4H-pyran-4-one (Compound 261);
4-((6-((5-Bromoisoindolin-2-yl)methyl)-4-oxo-4H-pyran-3-yloxy)methyl)benzonitrile (Compound 278);
and tautomers and pharmaceutically acceptable salts thereof.

Compounds of the invention may be administered to a patient in therapeutically effective amounts which range usually from about 1 to about 2000 mg, more typically form about 10 to about 1500 mg, daily depending on the age, sex, weight, ethnic group, condition of the patient, condition to be treated, administration route and the active ingredient used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel forming ingredients, dispersion forming ingredients, antioxidants, colours, sweeteners, wetting compounds and other ingredients normally used in this field of technology may also be used. The compositions containing the active compound can be given enterally or parenterally, the oral route being the preferred way. The contents of the active compound in the composition is from about 0.5 to 100%, preferably from about 0.5 to about 20%, per weight of the total composition.

The compounds of the invention can be given to the subject as the sole active ingredient or in combination with one of more other active ingredients for treatment of a particular disease.

In the treatment of a steroid receptor dependent disease or condition, such as endocrine cancers and disorders including prostate cancer and breast cancer, a combination of therapeutic agents and/or other treatments (e.g., radiation therapy) is often advantageous. The second (or third) agent to be administered may have the same or different mechanism of action than the primary therapeutic agent.

Accordingly, a compound of the invention may be administered in combination with other anti-cancer treatments useful in the treatment of cancers such as prostate cancer or breast cancer. For example, a compound of the invention can be packaged together with instructions that the compound is to be used in combination with other anti-cancer agents and treatments for the treatment of cancer. The present invention further comprises combinations of a compound of the invention and one or more additional agents in kit form, for example, where they are packaged together or placed in separate packages to be sold together as a kit, or where they are packaged to be formulated together.

According to one embodiment of the invention, the therapeutically effective amount of a compound of formula (I) is co-administered with a glucocorticoid and/or a mineralocorticoid and, optionally, with one or more anti-cancer agents.

Examples of suitable glucocorticoids include, but are not limited to, hydrocortisone, prednisone, prednisolone, methylprednisolone and dexamethasone. Examples of suitable mineralocorticoids include, but are not limited to, fludrocortisone, deoxycorticosterone, 11-desoxycortisone and deoxycorticosterone acetate.

The optional other anti-cancer agents which can be administered in addition to a compound of formula (I) include, but are not limited to,
non-steroidal androgen receptor antagonists (e.g. enzalutamide, apalutamide and darolutamide);
steroidogenesis inhibitors (e.g. CYP17A1 inhibitors such as abiraterone acetate and seviteronel);
chemotherapeutic agents (e.g. docetaxel and paclitaxel);
antiestrogens (e.g. tamoxifen and fulvestrant);
epigenetic modulators (e.g. BET inhibitors and HDAC inhibitors);
mTOR inhibitors (e.g. everolimus);
AKT inhibitors (e.g. AZ5363);
radiopharmaceuticals (e.g. alpharadin);
GnRH/LHRH analogues (such as leuprorelin);
PI3K inhibitors (e.g. idelalisib); and
CDK4/6 inhibitors (e.g. ribocyclib).

According to one embodiment of the invention, the therapeutically effective amount of a compound of formula (I) is administered to a subject in need thereof in addition to a therapeutically effective amount of one or more anti-cancer agents selected from the list consisting of
non-steroidal androgen receptor antagonists (e.g. enzalutamide, apalutamide and darolutamide);
steroidogenesis inhibitors (e.g. CYP17A1 inhibitors such as abiraterone acetate and seviteronel);
chemotherapeutic agents (e.g. docetaxel and paclitaxel);
antiestrogens (e.g. tamoxifen and fulvestrant);
epigenetic modulators (e.g. BET inhibitors and HDAC inhibitors);
mTOR inhibitors (e.g. everolimus);
AKT inhibitors (e.g. AZ5363);
radiopharmaceuticals (e.g. alpharadin);
GnRH/LHRH analogues (such as leuprorelin);
PI3K inhibitors (e.g. idelalisib); and
CDK4/6 inhibitors (e.g. ribocyclib).

According to one embodiment of the invention, the therapeutically effective amount of a compound of formula (I) is administered to a subject in need thereof in addition to a therapeutically effective amount of a steroidogenesis inhibitor (e.g. a CYP17A1 inhibitor). Examples of suitable CYP17A1 inhibitors include, but are not limited to, abiraterone acetate and seviteronel.

According to another embodiment of the invention, the therapeutically effective amount of a compound of formula (I) is administered to a subject in need thereof in addition to a therapeutically effective amount of a non-steroidal androgen receptor antagonist. Examples of suitable non-steroidal androgen receptor (AR) antagonists include, but are not limited to, enzalutamide, apalutamide and darolutamide.

According to still another embodiment, the present invention provides a pharmaceutical combination comprising a compound of formula (I) and at least one additional active ingredient selected from the list consisting of
a glucocorticoid,
a mineralocorticoid,
a steroidogenesis inhibitor (e.g. a CYP17A1 inhibitor),
a non-steroidal androgen receptor antagonist,
chemotherapeutic agents (e.g. docetaxel and paclitaxel),
antiestrogens (e.g. tamoxifen and fulvestrant),
epigenetic modulators (e.g. BET inhibitors and HDAC inhibitors),
mTOR inhibitors (e.g. everolimus);
AKT inhibitors (e.g. AZ5363);
radiopharmaceuticals (e.g. alpharadin);
GnRH/LHRH analogues (such as leuprorelin);
PI3K inhibitors (e.g. idelalisib); and
CDK4/6 inhibitors (e.g. ribocyclib)
for simultaneous, separate or sequential administration.

The above other therapeutic agents, when employed in combination with a compound of the invention can be used, for example, in those amounts indicated in the Physicians' Desk Reference (PDR) or as otherwise determined by one of ordinary skill in the art.

The compounds of the invention can be prepared by a variety of synthetic routes analogously to the methods known in the literature using suitable starting materials. The present invention will be explained in more detail by the following experiments and examples. The experiments and examples are meant only for illustrating purposes and do not limit the scope of the invention defined in claims.

EXAMPLES

Intermediate-1: Methyl 4-((2-methoxyethyl)thio)benzoate

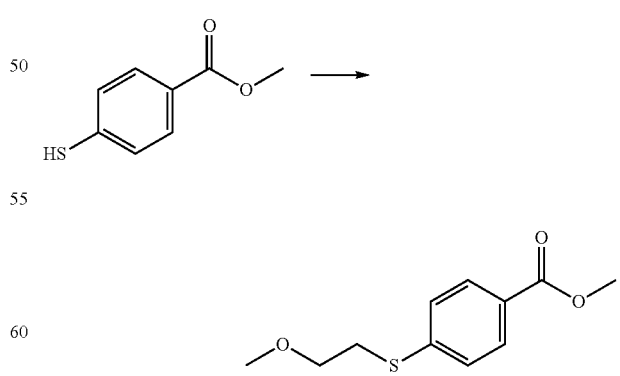

To a solution of methyl 4-mercaptobenzoate (2 g, 10.98 mmol) in MeOH (35 ml) was added $K_2CO_3$ (2.27 g, 16.48 mmol) followed by addition of 1-bromo-2-methoxy-ethane (1.54 g, 16.48 mmol) at RT. The mixture was refluxed for 16 h. The reaction mixture was quenched with water and extracted with EtOAc. The organic layer was washed with water, dried with anhydrous Na$_2$SO$_4$, filtered and concentrated under reduced pressure to give 2.19 g of the title compound as colorless oil. $^1$H-NMR (400 MHz; CDCl$_3$): δ 7.95 (d, 2H), 7.33 (d, 2H), 3.89 (s, 3H), 3.64 (t, 2H), 3.37 (s, 3H), 3.18 (t, 2H).

Intermediate-2: Methyl 4-((2-methoxyethyl)sulfonyl)benzoate

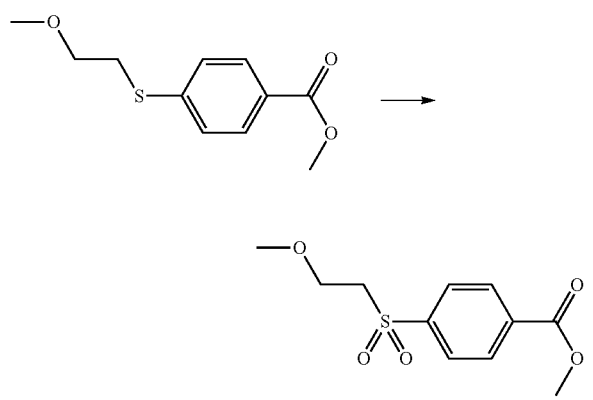

To a solution of methyl 4-((2-methoxyethyl)thio)benzoate (2.19 g, 9.15 mmol) in DCM (30 ml) was added m-CPBA (~70% assay, 7.89 g, 32.1 mmol) at 0° C. followed by stirring at RT for 16 h. The reaction mixture was quenched with 10% aqueous NaOH solution and extracted with DCM. The organic layer was washed with water, dried with anhydrous Na$_2$SO$_4$, filtered and concentrated under reduced pressure to give 1.86 g of the title compound as a white solid. $^1$H-NMR (400 MHz; CDCl$_3$): δ 8.22 (d, 2H), 8.02 (d, 2H), 3.97 (s, 3H), 3.75 (t, 2H), 3.42 (t, 2H), 3.20 (t, 3H).

Intermediate-3: 4-(Cyclopropylsulfonyl)benzaldehyde

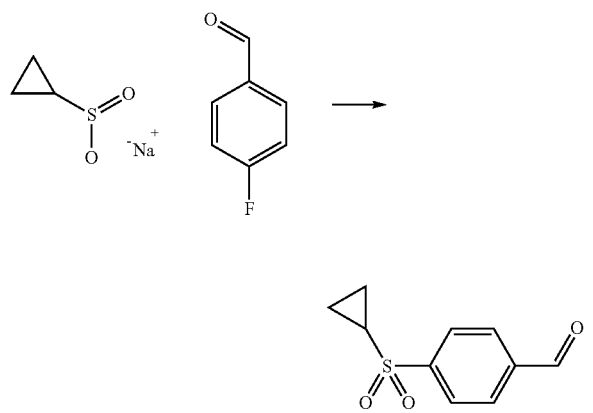

To a solution of 4-fluorobenzaldehyde (0.09 ml, 0.8 mmol) in DMSO (5 ml) was added cyclopropanesulfinic acid sodium salt (0.13 g, 1.0 mmol). The reaction mixture was heated in microwave oven at 140° C. for 1 h. Water was added to the mixture and the product was extracted with EtOAc. The organic layer was washed with water, dried with anhydrous Na$_2$SO$_4$, filtered and concentrated under reduced pressure to give 0.15 g of the title compound. LC-MS: m/z 211.1 [M+H]$^+$.

The following intermediates were prepared according to the procedure described for Intermediate-3 from the starting material indicated on the table.

| No | Structure | LC-MS | Starting material |
|----|-----------|-------|-------------------|
| 4 | 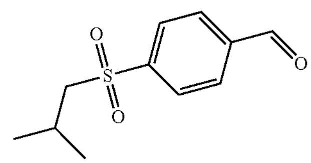 | LC-MS: m/z 227.2 (M + H)$^+$. | iso-Butyl-sulfinic acid sodium salt |
| 5 | 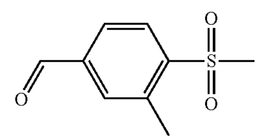 | LC-MS: m/z 199.2 (M + H)$^+$ | Methane-sulfinic acid sodium salt |

Intermediate-6: Methyl 4-(dimethylcarbamoyl)cyclohexane-1-carboxylate

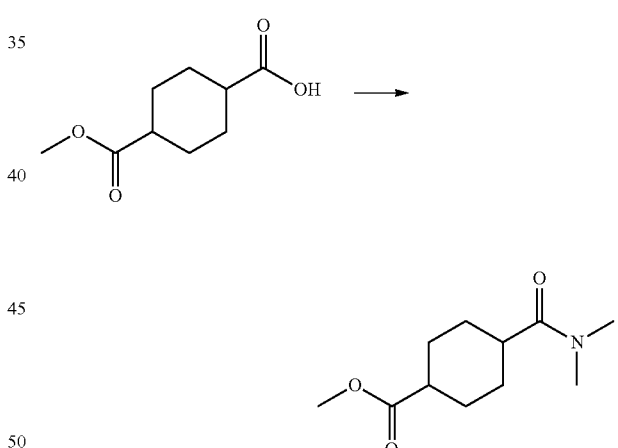

To a solution of 4-(methoxycarbonyl)cyclohexane-1-carboxylic acid (2.0 g, 10.7 mmol) in DCM (25 ml) were added DMF (1 drop) and oxalyl chloride (2.32 ml, 26.8 mmol) at 0° C. followed by stirring at RT for 3 h. The reaction mixture was concentrated under reduced pressure. The crude residue was dissolved in DCM (25 ml) and cooled to 0° C. Dimethyl amine (30 ml) was added to the above solution followed by stirring at RT for 2 h. The reaction mixture was concentrated under reduced pressure. The crude product was purified by column chromatography to give the title compound. MS: m/z 213 [M+H]$^+$.

The following intermediates were prepared according to the procedure described for Intermediate 6 from the starting material indicated on the table.

| No | Structure | LC-MS | Starting material |
|---|---|---|---|
| 7 | 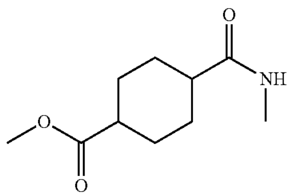 | LC-MS: m/z 200.1 [M + H]⁺ | 4-(Methoxycarbonyl) cyclohexane-1-carboxylic acid and methylamine |
| 8 | 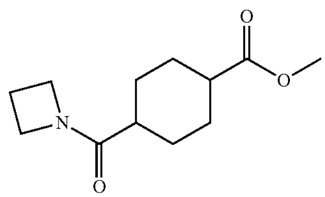 [SMILES: COC(=O)C1CCC(C(=O)N2CCC2)CC1] | LC-MS: m/z 226.1 [M + H]⁺ | 4-(Methoxycarbonyl) cyclohexane-1-carboxylic acid and azetidine |

Intermediate-9:
(4-((2-Methoxyethyl)sulfonyl)phenyl)methanol

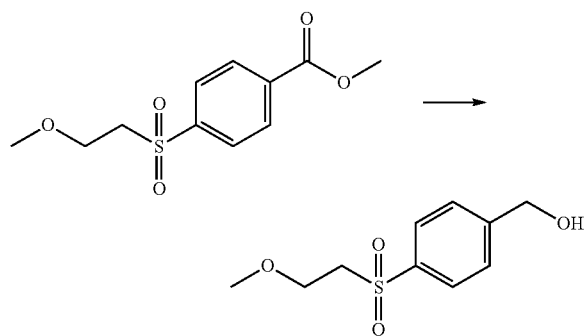

To a solution of methyl 4-((2-methoxyethyl)sulfonyl) benzoate (1.86 g, 6.84 mmol) in EtOH (20 ml) was added NaBH₄ (1.3 g, 34.24 mmol) at 0° C. followed by stirring at RT for 3 h. The reaction mixture was quenched with water and extracted with EtOAc. The organic layer was washed with water, dried with anhydrous Na₂SO₄, filtered and concentrated under reduced pressure to give 1.18 g of the title compound as a colorless oil. ¹H-NMR (400 MHz; CDCl₃): δ 8.91 (d, 2H), 8.55 (d, 2H), 5.0 (t, 1H), 4.82 (s, 2H), 3.74 (t, 2H), 3.38 (t, 2H), 3.24 (s, 3H).

The following intermediates were prepared according to the procedure described for Intermediate 9 from the starting material indicated on the table.

| No | Structure | LC-MS | Starting material |
|---|---|---|---|
| 10 | 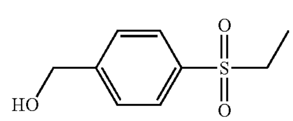 | LC-MS: m/z 201 [M + H]⁺ | 4-(Ethylsulfonyl)benzaldehyde |
| 11 | 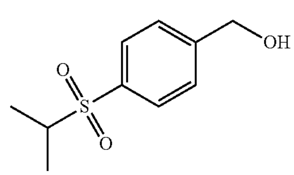 | LC-MS: m/z 215 [M + H]⁺ | 4-(Isopropylsulfonyl)benzaldehyde |
| 12 | 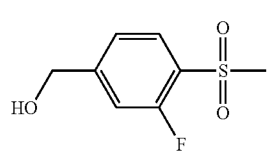 | LC-MS: m/z 205.0 (M + H)⁺ | 3-Fluoro-4-(methylsulfonyl)benzaldehyde |
| 13 | 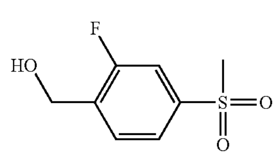 | LC-MS: m/z 205.2 (M + H)⁺ | 2-Fluoro-4-(methylsulfonyl)benzaldehyde |

-continued

| No | Structure | LC-MS | Starting material |
|---|---|---|---|
| 14 | 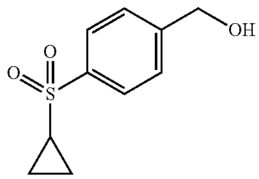 [SMILES: O=S(=O)(c1ccc(CO)cc1)C1CC1] | LC-MS: m/z 213.2 (M + H)⁺ | 4-(Cyclopropylsulfonyl)benzaldehyde |
| 15 | 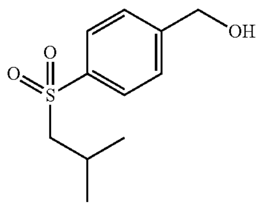 | LC-MS: m/z 229.2 (M + H)⁺ | 4-(Isobutylsulfonyl)benzaldehyde |
| 16 | 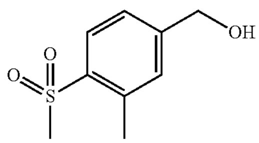 | LC-MS: m/z 201.2 (M + H)⁺ | 3-Methyl-4-(methylsulfonyl)-benzaldehyde |
| 17 | 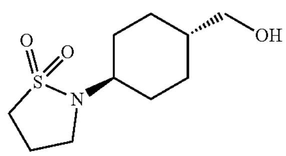 [SMILES: O=S1(=O)CCCN1[C@H]1CC[C@H](CO)CC1] | LC-MS: m/z 234.3 (M + H)⁺ | (1r,4r)-Methyl 4-(1,1-dioxidoisothiazolidin-2-yl)cyclohexanecarboxylate |
| 18 | 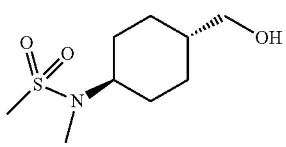 | LC-MS: m/z 222.3 (M + H)⁺ | (1r,4r)-Methyl 4-(N-methyl-methylsulfonamido)cyclohexane carboxylate |
| 19 | 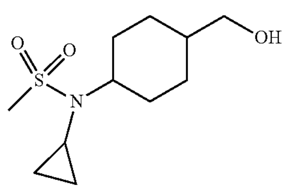 [SMILES: CS(=O)(=O)N(C1CCC(CO)CC1)C1CC1] | LC-MS: m/z 248.3 (M + H)⁺ | Ethyl 4-(N-cyclopropylmethyl-sulfonamido)cyclohexane-carboxylate |
| 20 | 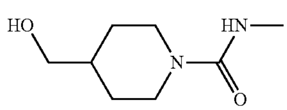 | LC-MS: m/z 173 (M + H)⁺ | Ethyl 1-(methylcarbamoyl)piperidine-4-carboxylate |
| 21 | 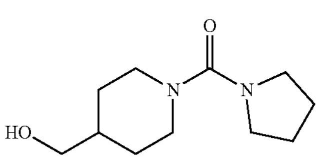 [SMILES: O=C(N1CCCC1)N1CCC(CO)CC1] | MS: m/z 213 | 4-Piperidinecarboxylic acid, 1-(pyrrolidinylcarbonyl)-ethyl ester |
| 22 | 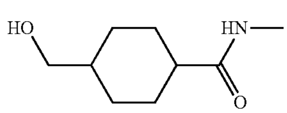 | MS: m/z 171 | Methyl-4-(methylcarbamoyl)-cyclohexane-1-carboxylate |
| 23 | 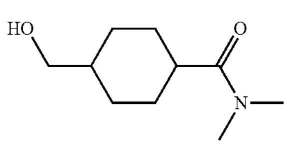 | MS: m/z 185 | Methyl-4-(dimethylcarbamoyl)-cyclohexane-1-carboxylate |

-continued

| No | Structure | LC-MS | Starting material |
|---|---|---|---|
| 24 | (structure: HO-CH2-cyclohexyl-C(=O)-N-azetidine) | MS: m/z 197 | Methyl 4-(azetidine-1-carbonyl)-cyclohexane-1-carboxylate |
| 25 | (structure: HO-CH2-cyclohexyl-C(=O)-N-pyrrolidine) | MS: m/z 212.2 | Methyl 4-(pyrrolidine-1-carbonyl)-cyclohexane-1-carboxylate |

Intermediate-26:
4-(Bromomethyl)-2-fluoro-1-(ethylsulfonyl)benzene

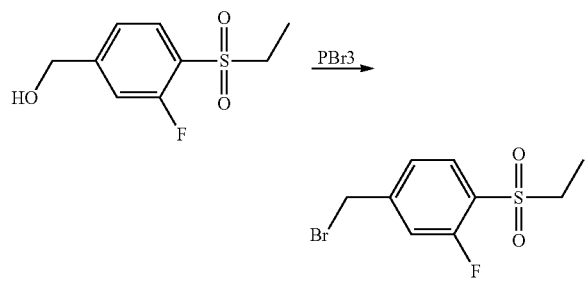

To a solution of (3-fluoro-4-(ethylsulfonyl)phenyl)methanol (3.90 g, 19.11 mmol) in dry DCM (50 ml) was added $PBr_3$ (3.63 ml, 38.23 mmol) at 0° C. followed by stirring at RT for 16 h. The reaction mixture was quenched with cold water, neutralized with aqueous $NaHCO_3$ solution and extracted with DCM. The organic layer was washed with brine, dried with anhydrous $Na_2SO_4$, filtered and concentrated under reduced pressure.

The crude product was purified by column chromatography to give 1.72 g of the title compound as a white solid. $^1$H-NMR (400 MHz; DMSO-$d_6$): δ 7.84-7.88 (t, 1H), 7.62-7.65 (d, 1H), 7.53-7.55 (d, 1H), 4.77 (s, 2H), 3.32 (s, 3H). MS: m/z 268 [M+H]$^+$.

The following intermediates were prepared according to the procedure described for Intermediate 26 from the starting material indicated on the table.

| No | Structure | LC-MS | Starting material |
|---|---|---|---|
| 27 | (structure: Br-CH2-phenyl(F)-SO2-CH3) | LC-MS: m/z 268.0 [M + H]$^+$ | 3-Fluoro-4-(methylsulfonyl)-phenyl)methanol |
| 28 | (structure: CH3-SO2-phenyl(F)-CH2-Br) | LC-MS: m/z 268.5 [M + H]$^+$ | (2-Fluoro-4-(methylsulfonyl)-phenyl)methanol |
| 29 | (structure: tetrahydrothiopyran dioxide-CH2-Br) | LC-MS: m/z 226.3 [M + H]$^+$ | 4-(hydroxymethyl)tetrahydro-2H-thiopyran 1,1-dioxide |
| 30 | (structure: MeO-CH2CH2-SO2-phenyl-CH2-Br) | LC-MS: m/z 293 [M + H]$^+$ | (4-((2-Methoxyethyl)-sulfonyl)phenyl)methanol |

Intermediate-31:
4-(Bromomethyl)-N,N-diethylbenzenesulfonamide

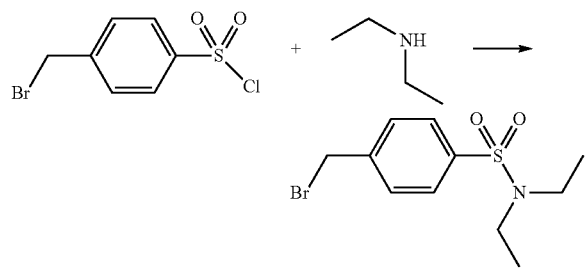

To a solution of diethylamine (0.05 g, 0.74 mmol) in DCM (5 ml) at 0° C. were added 4-(bromomethyl)benzenesulfonyl chloride (0.2 g, 0.74 mmol) and TEA (0.1 ml, 0.74 mmol) at RT followed by stirring for 1 h. The reaction mixture was diluted with water and extracted with DCM. The organic layer was washed with water, dried with Na$_2$SO$_4$, filtered and concentrated under reduced pressure. The crude product was purified by column chromatography to give 0.10 g of the title compound. H NMR (400 MHz, DMSO-d$_6$) δ ppm 1.04 (t, J=7.12 Hz, 6H) 3.16 (q, J=7.11 Hz, 4H) 4.77 (s, 2H) 7.57-7.68 (m, 2H) 7.78 (d, J=8.60 Hz, 2H).

The following intermediates were prepared according to the procedure described for Intermediate 31 from the starting material indicated on the table.

| No | Structure | LC-MS | Starting material |
|---|---|---|---|
| 32 | 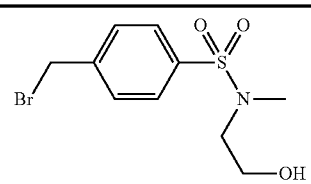 | LC-MS: m/z 320.1 (M + H)$^+$ | 2-(Methylamino)ethanol |
| 33 | 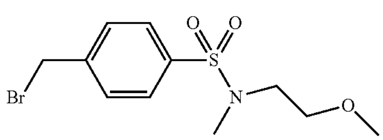 [SMILES: COCCN(C)S(=O)(=O)c1ccc(CBr)cc1] | LC-MS: m/z 322.3 (M + H)$^+$ | N-(2-Methoxyethyl)methylamine |
| 34 | 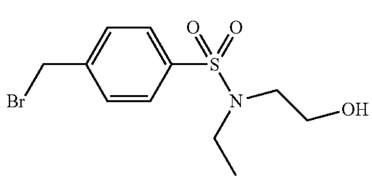 [SMILES: CCN(CCO)S(=O)(=O)c1ccc(CBr)cc1] | LC-MS: m/z 323.5 (M + H)$^+$ | 2-(Ethylamino)ethanol |

Intermediate-35:
1-(Chloromethyl)-4-(cyclopropylsulfonyl)benzene

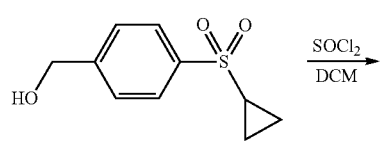

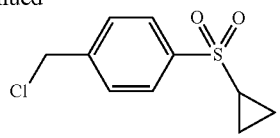

To a solution of (4-(cyclopropylsulfonyl) phenyl) methanol (0.18 g, 0.848 mmol) in DCM (5.0 ml) and DMF (0.1 ml) was added SOCl$_2$ (1.0 ml, 1.5 mmol) dropwise at 0° C. followed by refluxing for 2 h. Water was added and the reaction mixture was extracted with DCM. The organic layer was washed with water and saturated NaHCO$_3$ solution. After drying with Na$_2$SO$_4$ the solvent was evaporated and the residue was purified by column chromatography to give 0.17 g of the title compound. LC-MS: m/z 213.2 (M+H)$^+$ The following intermediates were prepared according to the procedure described for Intermediate 35 from the starting material indicated on the table.

| No | Structure | LC-MS | Starting material |
|---|---|---|---|
| 36 | 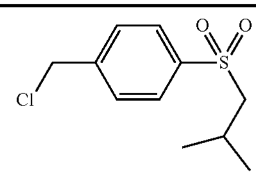 | LC-MS: m/z 247.2 (M + H)$^+$ | (4-(Isobutylsulfonyl)phenyl)methanol |
| 37 | | LC-MS: m/z 219.2 (M + H)$^+$ | (3-Methyl-4-(methylsulfonyl)phenyl)methanol |

51

Intermediate-38: (4-((1,1-Dioxidoisothiazolidin-2-yl)methyl)cyclohexyl)methyl methanesulfonate

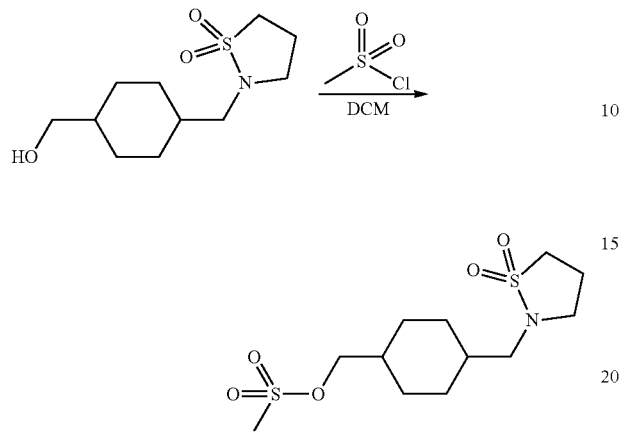

To a solution of 2-((4-(hydroxymethyl)cyclohexyl)methyl)isothiazolidine 1,1-dioxide (1.6 g, 6.47 mmol) in DCM (10 ml) at 0° C. were added Et₃N (3.0 ml, 19.0 mmol), DMAP (0.07 g, 0.6 mmol) followed by MsCl (1.4 ml, 17.5 mmol). The mixture was stirred at RT for 16 h, quenched with water and extracted with DCM. The organic layer was washed with water, dried with Na₂SO₄, filtered and concentrated under reduced pressure. The crude product was purified by column chromatography to give the title compound. LC-MS: m/z 326.2 (M+H)⁺

The following intermediates were prepared according to the procedure described for Intermediate 38 from the starting material indicated on the table.

52

Intermediate-42: ((1r,4r)-4-(N-Methylmethylsulfonamido)cyclohexyl)methyl 4-methylbenzenesulfonate

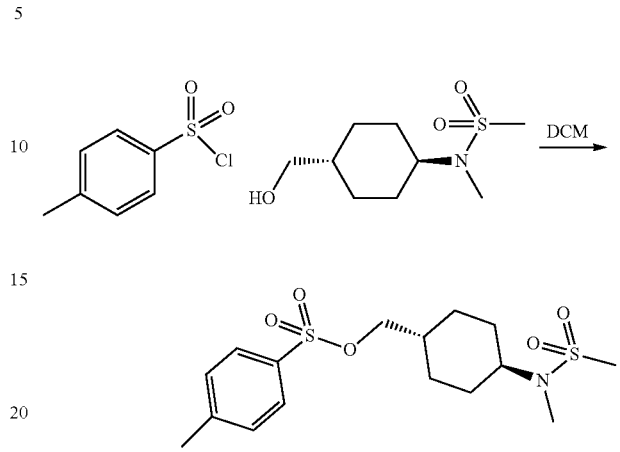

To a solution of N-((1r,4r)-4-(hydroxymethyl)cyclohexyl)-N-methylmethanesulfonamide (0.302 g, 1.365 mmol) in pyridine (3 ml) at 0° C. was added TsCl (0.31 g, 1.6 mmol). The reaction mixture was stirred at RT for 16 h then quenched with saturated aqueous NaHCO₃ solution and extracted with DCM. The organic layer was washed with water, dried with Na₂SO₄, filtered and concentrated under reduced pressure. The crude product was purified by column chromatography to give the title compound. LC-MS: m/z 375.5 (M+H)⁺

The following intermediates were prepared according to the procedure described for Intermediate 42 from the starting material indicated on the table.

| No | Structure | LC-MS | Starting material |
|---|---|---|---|
| 39 | 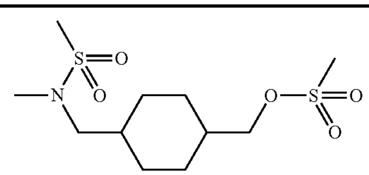 | LC-MS: m/z 300.4 (M + H)⁺ | 4-(Aminomethyl)cyclohexane methanol |
| 40 | 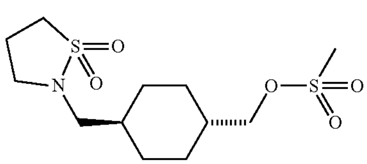 | LC-MS: m/z 292.1 (M + H)⁺ | 2-(((1r,4r)-4-(Hydroxymethyl)cyclohexyl)methyl)-isothiazolidine 1,1-dioxide |
| 41 | 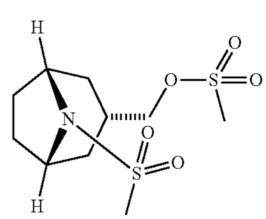 [SMILES: CS(=O)(=O)OC[C@H]1C[C@H]2CC[C@@H](C1)N2S(C)(=O)=O] | LC-MS: m/z 298.2 (M + H)⁺ | (1R,3r,5S)-8-Azabicyclo[3.2.1]octan-3-ylmethanol hydrochloride |

| No | Structure | LC-MS | Starting material |
|---|---|---|---|
| 43 | 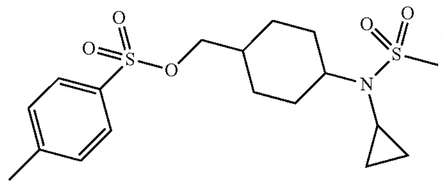 | LC-MS: m/z 402.4 (M + H)+ | N-Cyclopropyl-N-(4-(hydroxymethyl)cyclohexyl)-methanesulfonamide |
| 44 | 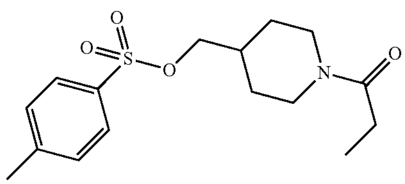 [SMILES: CCC(=O)N1CCC(COS(=O)(=O)c2ccc(C)cc2)CC1] | LC-MS: m/z 326.6 (M + H)+ | 1-(4-(Hydroxymethyl)-piperidin-1-yl)propan-1-one |
| 45 | 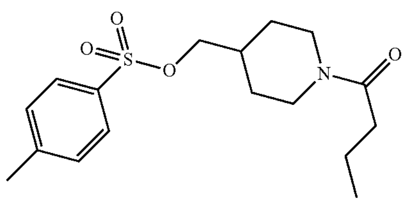 [SMILES: CCCC(=O)N1CCC(COS(=O)(=O)c2ccc(C)cc2)CC1] | LC-MS: m/z 340.2 (M + H)+ | 1-(4-(Hydroxymethyl)-piperidin-1-yl)butan-1-one |
| 46 | 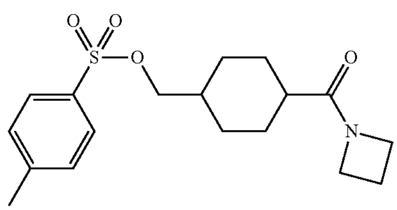 [SMILES: Cc1ccc(S(=O)(=O)OCC2CCC(C(=O)N3CCC3)CC2)cc1] | LC-MS: m/z 351 | Azetidin-1-yl(hydroxyl-methyl)cyclohexyl)methanone |
| 47 | 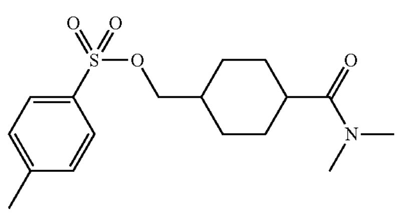 [SMILES: Cc1ccc(S(=O)(=O)OCC2CCC(C(=O)N(C)C)CC2)cc1] | LC-MS: m/z 339 | 4-(Hydroxymethyl)-N, N-dimethylcyclohexane-carboxamide |
| 48 | 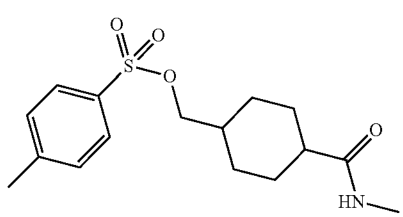 | LC-MS: m/z 325 | 4-(Hydroxymethyl)-N-methyl-cyclohexanecarboxamide |
| 49 | 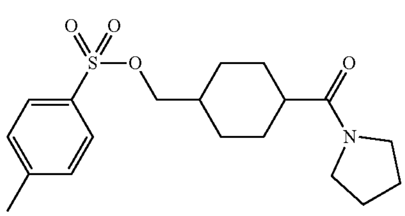 [SMILES: Cc1ccc(S(=O)(=O)OCC2CCC(C(=O)N3CCCC3)CC2)cc1] | LC-MS: m/z 367 | (4-(Hydroxymethyl)cyclo-hexyl) (pyrrolidinyl-1-yl)-methanone |

| No | Structure | LC-MS | Starting material |
|---|---|---|---|
| 50 | 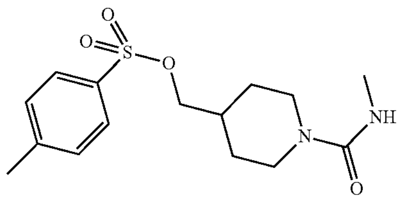 [SMILES: CNC(=O)N1CCC(COS(=O)(=O)c2ccc(C)cc2)CC1] | LC-MS: m/z 327 | 4-(Hydroxymethyl)-N-methyl-piperidine-1-carboxamide |
| 51 | 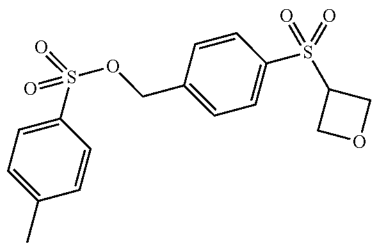 [SMILES: Cc1ccc(S(=O)(=O)OCc2ccc(S(=O)(=O)C3COC3)cc2)cc1] | LC-MS: m/z 383.1 | (4-(Oxetan-3-ylsulfonyl)-phenyl)methanol |

Intermediate-52: S-(Oxetan-3-yl)ethanethioate

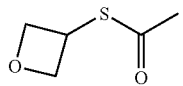

To a solution of ethanethioic S-acid (10.0 g, 54 mmol) in DMF (100 ml) was added 3-iodooxetane (6.82 g, 59 mmol) followed by stirring at RT for 16 h. The reaction was quenched with cold water and extracted with EtOAc. The organic layer was washed with brine, dried with anhydrous Na$_2$SO$_4$ and concentrated under reduced pressure to give 2.52 g of the title compound as yellow oil. $^1$H-NMR (400 MHz; DMSO-d$_6$): δ 4.94 (t, 2H), 4.56 (m, 1H), 4.42 (t, 2H), 2.33 (s, 3H).

Intermediate-53: Oxetane-3-sulfonyl chloride

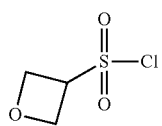

To a solution of N-chlorosuccinamide (10.0 g, 75 mmol) in MeCN (50 ml) at 0° C. were added 2 N HCl (5 ml) and S-(oxetan-3-yl)ethanethioate (2.5 g, 18 mmol) followed by stirring at RT for 16 h. The reaction was concentrated, quenched with saturated aqueous NaHCO$_3$ solution and extracted with Et$_2$O. The organic layer was dried with anhydrous Na$_2$SO$_4$ and concentrated under reduced pressure to give 2.8 g of crude title compound.

Intermediate-54: 4-(Bromomethyl)piperidine hydrobromide

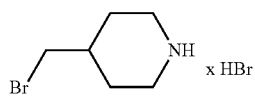

A mixture of piperidin-4-ylmethanol (0.5 g, 4.3 mmol) and aqueous HBr (10 ml) was heated at 140° C. for 3 h. The reaction mixture was concentrated under reduced pressure to give 0.5 g of the title compound as a yellow solid. $^1$H-NMR (400 MHz; DMSO-d$_6$): δ 3.70 (s, 1H), 3.50 (d, 2H), 3.25 (d, 2H), 2.84-2.93 (m, 2H), 1.86-1.97 (m, 3H), 1.36-1.46 (m, 2H).

Intermediate-55: 4-(Bromomethyl)-1-(oxetan-3-ylsulfonyl)piperidine

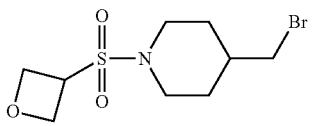 [SMILES: O=S(=O)(C1COC1)N1CCC(CBr)CC1]

To a solution of 4-(bromomethyl)piperidine hydrobromide (4.16 g, 16 mmol) in DCM (200 ml) were added Et$_3$N (3.23 ml, 44 mmol) and oxetane-3-sulfonyl chloride (2.3 g, 14 mmol) followed by stirring at RT for 16 h. The reaction mixture was quenched with water and extracted with DCM. The organic layer was dried with anhydrous Na$_2$SO$_4$ and concentrated under reduced pressure. The crude residue was purified by column chromatography over silica gel using 30% EtOAc in hexane as an eluent to give 0.780 g of the title compound as a white solid. $^1$H-NMR (400 MHz; DMSO): δ 4.76-4.80 (m, 1H), 4.67-4.74 (m, 3H), 3.6 (d, 2H), 3.46 (d, 2H), 2.75 (t, 1H), 1.72-1.81 (m, 3H), 1.08-1.23 (m, 2H).

Intermediate-56: 4-(Bromomethyl)-3-fluorobenzoic acid

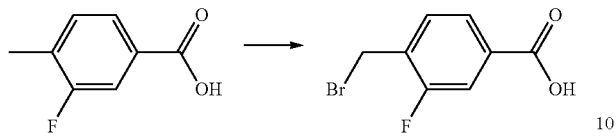

To a solution of 3-fluoro-4-methylbenzoic acid (5.0 g, 34.67 mmol) in benzene (50 ml) were added benzoyl peroxide (0.8 g, 3.46 mmol) and NBS (6.0 g, 34.6 mmol) followed by heating at 85° C. for 4 h. The reaction mixture was cooled to RT, the solid precipitated was filtered, washed with water followed by hexane and then dried to give 4.6 g of the title compound. $^1$H-NMR (400 MHz; CDCl$_3$): δ 7.8 (d, 1H), 7.76 (d, 1H), 7.51 (t, 1H), 1.79 (s, 2H). MS: m/z 231 [M–H]$^+$.

Intermediate 57: Azetidin-1-yl(4-(chloromethyl)-3-fluorophenyl)methanone

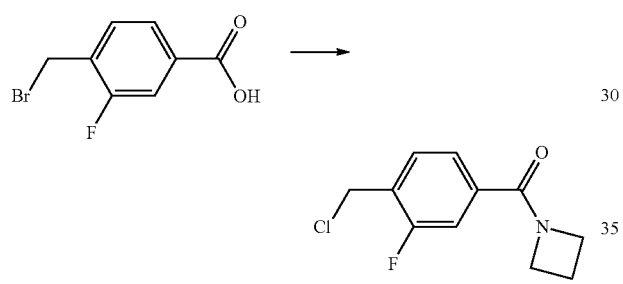

To a solution of 4-(bromomethyl)-3-fluorobenzoic acid (4.5 g, 19.4 mmol) in DCM (60 ml) at 0° C. were added azetidine hydrochloride (2.17 g, 23.3 mmol), DIPEA (17 ml, 97.4 mmol) and T$_3$P (17.5 ml, 58.4 mmol) at RT followed by stirring for 16 h.

The reaction mixture was diluted with water and extracted with DCM. The organic layer was washed with water, dried with anhydrous Na$_2$SO$_4$, filtered and concentrated under reduced pressure. The crude product was purified by column chromatography over silica gel using 30% EtOAc in hexane as an eluent to give 1.2 g of the title compound as a white solid. $^1$H-NMR (400 MHz; CDCl$_3$): δ 7.49-7.35 (m, 4H), 4.64 (s, 2H), 4.29-4.24 (m, 4H), 2.09 (m, 2H). MS: m/z 228 [M+H]$^+$.

Intermediate 58: 5-Hydroxy-2-(isoindolin-2-ylmethyl)-4H-pyran-4-one

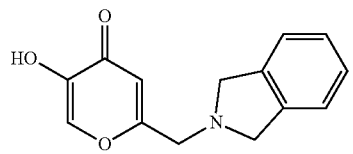 [SMILES: O=c1cc(CN2Cc3ccccc3C2)occ1O]

To a stirred solution of 2-(chloromethyl)-5-hydroxy-4H-pyran-4-one (2.0 g, 12.5 mmol) in acetonitrile (50 mL) were added DIPEA (3.22 mL, 25.0 mmol) and isoindoline (1.78 g, 25.0 mmol) at RT. When the reaction was complete, the precipitated solid was filtered and washed with EtOAc. The title compound was collected as pale brown solid (1.1 g). LC-MS: m/z 244.1 (M+H)$^+$.

Intermediate 59: 5-Hydroxy-2-((5-(trifluoromethyl)isoindolin-2-yl)methyl)-4H-pyran-4-one

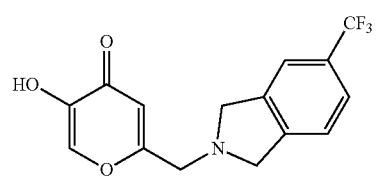 [SMILES: O=c1cc(CN2Cc3ccc(C(F)(F)F)cc3C2)occ1O]

To a stirred solution of 2-(aminomethyl)-5-hydroxy-4H-pyran-4-one (5.6 g, 17.0 mmol) in acetonitrile (40 mL) were added 1,2-bis(bromomethyl)-4-(trifluoromethyl)-benzene (2.4 g, 17.0 mmol) and DIPEA (23.78 mL, 136.2 mmol) at RT. The reaction mixture was heated to 90° C. until the reaction was complete. The reaction mixture was concentrated under reduced pressure and the obtained residue was stirred in EtOAc. The mixture was filtered and the filtrate was concentrated. The crude compound was further purified by semipreparative HPLC to afford the title compound (0.85 g). LC-MS m/z: 312.1 (M+H)$^+$.

Intermediate 60: 2-((5-Fluoroisoindolin-2-yl)methyl)-5-hydroxy-4H-pyran-4-one

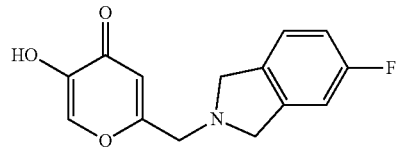 [SMILES: O=c1cc(CN2Cc3ccc(F)cc3C2)occ1O]

To a solution of 2-(amino methyl)-5-hydroxy-4H-pyran-4-one (14.2 g, 63.8 mmol) in toluene (100 mL) were added 1,2-bis-(bromomethyl)-4-fluorobenzene (19.7 g, 70.2 mmol) and Et$_3$N (35.8 mL, 255 mmol) at RT. The mixture was stirred at 100° C. until the reaction was complete. The reaction mixture was concentrated under reduced pressure and the residue was purified by column chromatography to give the title compound as a beige solid (4.60 g). LC-MS: m/z 262.2 (M+H)$^+$.

Intermediate 61: 5-(Hydroxymethyl)isoindolin-1-one

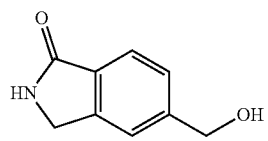 [SMILES: O=C1NCc2cc(CO)ccc21]

To a stirred solution of methyl 1-oxoisoindoline-5-carboxylate (4.0 g, 20.9 mmol) in THF (120 mL) was added DIBAL-H (1.2 M, 87.2 mL, 104.6 mmol) at -70° C. After two hours at −70° C. the mixture was allowed to warm to 0° C. and stirred for 1 h. The reaction was quenched with MeOH and the emulsion was filtered through a pad of Celite®. The filtrate was concentrated under vacuum and the crude product was purified by column chromatography to give the title compound as a pale brown solid (0.8 g). LC-MS: m/z 164.1 (M+H)+

Intermediate 62:
5-(Hydroxymethyl)-2-methylisoindolin-1-one

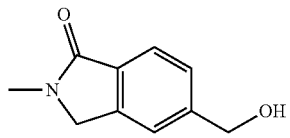

a) Methyl 2-methyl-1-oxoisoindoline-5-carboxylate

To a stirred solution of methyl 1-oxoisoindoline-5-carboxylate (5.0 g, 26.1 mmol) in DMF (100 mL) was added NaH (60% dispersion, 1.5 g, 37.5 mmol) at 0° C. After 30 min at 0° C. iodomethane (2.44 mL, 39.2 mmol) was added. The mixture was allowed to react at 0° C. When the reaction was complete the mixture was poured into ice water and extracted with EtOAc. The combined organic phase was washed with brine, dried over anhydrous Na$_2$SO$_4$ and concentrated under vacuum. Crude compound was purified by washing with pentane/diethyl ether to give the title compound as a pale brown solid (2.0 g). LC-MS: m/z 206.1 (M+H)+.

b) 5-(Hydroxymethyl)-2-methylisoindolin-1-one

To a stirred solution of methyl 2-methyl-1-oxoisoindoline-5-carboxylate (3.4 g, 16.6 mmol) in THF (150 mL) was added MeOH (0.53 mL, 13.1 mmol) and LiBH$_4$ (2.0 M solution, 16.6 mL. 33.2 mmol) at 0° C. After 3 h at 0° C. the solution was allowed to warm to RT and stirred until the reaction was complete. The reaction was quenched with MeOH:H$_2$O (1:1) and the mixture was concentrated under reduced pressure. Crude compound was purified by column chromatography to give the title compound as a pale brown solid (2.0 g). LC-MS m/z 178.1 (M+H)+.

Intermediate 63:
4-Bromo-1-(4-(bromomethyl)phenyl)-1H-pyrazole

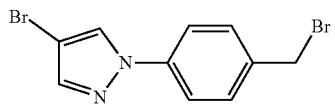

a) 1-(p-Tolyl)-1H-pyrazole

A microwave reactor was charged with copper(II) acetate monohydrate (0.02 g, 0.1 mmol), DMF (5 mL), pyrazole (0.177 g, 2.60 mmol), 4-iodotoluene (0.436 g, 2.0 mmol) and Cs$_2$CO$_3$ (1.30 g, 4 mmol). The solution was flushed with nitrogen gas before being heated under microwave irradiation at 120° C. When the reaction was complete (LC-MS) the reaction mixture was diluted with H$_2$O and EtOAc. The aqueous layer was extracted with EtOAc. Combined organic layers were washed with H$_2$O, dried over anhydrous Na$_2$SO$_4$, filtered and concentrated to give the title compound (0.26 g). LC-MS: m/z 159.1 (M+H)+.

b) 4-Bromo-1-(p-tolyl)-1H-pyrazole

A round-bottomed flask was charged with 1-(p-tolyl)-1H-pyrazole (0.26 g, 1.64 mmol), chloroform (10 mL), N-bromosuccinimide (0.336 g, 1.89 mmol) and benzoyl peroxide (0.04 g, 0.16 mmol). The solution was flushed with nitrogen and heated to reflux. When the reaction was complete (LC-MS) it was quenched with water. The aqueous layer was extracted with CH$_2$Cl$_2$. Combined organic layers were dried with anhydrous Na$_2$SO$_4$, filtered and evaporated to dryness to give the title compound (0.409 g, crude yield). LC-MS: m/z 237.1 (M+H)+.

c) 4-Bromo-1-(4-(bromomethyl)phenyl)-1H-pyrazole

A round-bottomed-flask was charged with crude bromide compound from above (0.40 g), chloroform (10 mL), N-bromosuccinimide (0.345 g, 1.94 mmol) and benzoyl peroxide (0.041 g, 0.17 mmol). The solution was flushed with nitrogen and heated to reflux. When the reaction was complete (LC-MS) it was quenched with water. The aqueous layer was extracted with CH$_2$Cl$_2$. Combined organic layers were dried with anhydrous Na$_2$SO$_4$, filtered and evaporated to dryness to provide the title compound (0.569 g, crude yield). This material was used as such in the following step. LC-MS: m/z 315.1 (M+H)+.

Intermediate 64: Ethyl 1-(4-(bromomethyl)phenyl)-1H-pyrazole-4-carboxylate

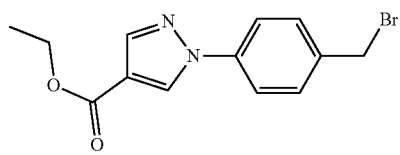 [SMILES: CCOC(=O)c1cnn(-c2ccc(CBr)cc2)c1]

a) Ethyl 1-(p-tolyl)-1H-pyrazole-4-carboxylate

Title compound was prepared from 4-iodotoluene (0.436 g, 2.0 mmol), copper (II) acetate monohydrate (0.02 g, 0.1 mmol), 4-ethoxycarbonyl pyrazole (0.392 g, 2.80 mmol) and Cs$_2$CO$_3$ (1.30 g, 4 mmol) in DMF (5 mL) as described in step (a) of Intermediate 66. The title compound was purified by column chromatography (0.11 g). LC-MS: m/z 231.3 (M+H)+.

b) Ethyl 1-(4-(bromomethyl)phenyl)-1H-pyrazole-4-carboxylate

A round-bottomed-flask was charged with ethyl 1-(p-tolyl)-1H-pyrazole-4-carboxylate (0.11 g, 0.48 mmol), acetonitrile (4 mL), N-bromosuccinimide (0.102 g, 0.57 mmol) and 2,2'-azobis(2-methylpropionitrile) (0.016 g, 0.1 mmol). The solution was refluxed until the reaction was complete (LC-MS). Reaction was quenched with saturated NaHCO₃ and extracted with EtOAc. Combined organic layers were dried with Na₂SO₄, filtered and concentrated under vacuum. Crude material was purified by column chromatography to give the title compound (0.12 g). LC-MS: m/z 309.3 (M+H)⁺.

Intermediate 65:
1-(4-(Chloromethyl)phenyl)-1H-1,2,3-triazole

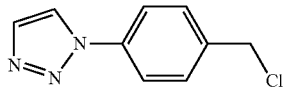

a) (4-(1H-1,2,3-Triazol-1-yl)phenyl)methanol

A vial was charged with p-iodobenzyl alcohol (0.234 g, 1 mmol), DMSO (4 mL), L-proline (0.023 g, 0.200 mmol), copper (I) iodide (0.019 g, 0.100 mmol), sodium L-ascorbate (0.040 g, 0.200 mmol), sodium azide (0.098 g, 1.500 mmol), trimethylsilyl-acetylene (0.285 mL, 2.000 mmol), H₂O (0.5 ml) and potassium carbonate (0.207 g, 1.500 mmol). Nitrogen gas was passed through the solution and the mixture was heated to 80° C. When the reaction was complete (LC-MS) 10% ammonia solution was added followed by EtOAc. The aqueous layer was extracted with EtOAc. Combined organic layers were washed with water, dried over anhydrous Na₂SO₄, filtered and evaporated to dryness. Crude material was purified by column chromatography to give the title compound (0.055 g). LC-MS: m/z 176.2 (M+H)⁺.

b) 1-(4-(Chloromethyl)phenyl)-1H-1,2,3-triazole

An oven dried round-bottomed-flask was charged with (4-(1H-1,2,3-triazol-1-yl)phenyl)methanol (0.11 g, 0.628 mmol) and CH₂Cl₂ (3 mL). A drop of DMF (~0.05 mL) followed by SOCl₂ (0.069 mL, 0.94 mmol) were added at 0° C. The solution was kept at 0° C. for 10 min before it was allowed to warm to RT. When the reaction was complete (LC-MS), solvent was evaporated under vacuum. The residue was dissolved in saturated NaHCO₃ and EtOAc. Aqueous layer was extracted with EtOAc. Combined organic layers were dried over anhydrous Na₂SO₄, filtered and evaporated under vacuum to give the title compound (0.049 g) LC-MS: m/z 194.2 (M+H)⁺.

Intermediate 66:
2-(4-(Chloromethyl)phenyl)oxazole

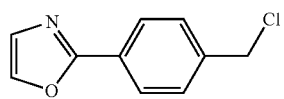 [SMILES: ClCc1ccc(-c2ncco2)cc1]

The title compound was prepared from (4-(oxazol-2-yl) phenyl)methanol (0.13 g, 0.74 mmol), SOCl₂ (0.081 mL, 1.11 mmol) and a drop of DMF (~0.05 mL) in CH₂Cl₂ (3 mL) according to the procedure described in step (b) of Intermediate 65 (0.122 g). LC-MS: m/z 194.2 (M+H)⁺.

Intermediate 67: Azetidin-1-yl(4-(hydroxymethyl) piperidin-1-yl)methanone

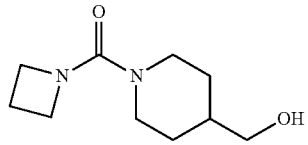 [SMILES: O=C(N1CCC1)N1CCC(CO)CC1]

A round-bottomed flask was charged with piperidin-4-ylmethanol (0.230 g, 2 mmol), acetonitrile (10 mL) and N,N-carbonyldiimidazole (0.357 g, 2.200 mmol). The mixture was allowed to react at RT for two hours. DIPEA (0.35 mL, 2.0 mmol) followed by azetidine (0.270 mL, 4.00 mmol) were added and the mixture was heated to 60° C. until the reaction was complete (LC-MS). A 1:1 mixture of saturated NaHCO₃, brine and EtOAc were added. The aqueous layer was extracted with EtOAc. Combined organic layers were dried with anhydrous Na₂SO₄, filtered and evaporated to dryness to give the title compound (0.41 g). LC-MS: m/z 199.2 (M+H)⁺.

Intermediate 68: (4-(Hydroxymethyl)piperidin-1-yl) (morpholino)methanone

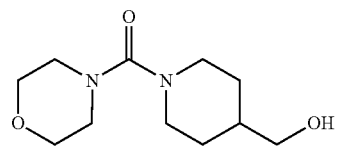 [SMILES: O=C(N1CCOCC1)N1CCC(CO)CC1]

A round-bottomed flask was charged with piperidin-4-ylmethanol (0.230 g, 2 mmol), dichloromethane (10 mL), Et₃N (0.5 mL, 3.6 mmol) and 4-morpholinecarbonyl chloride (0.257 mL, 2.20 mmol) and the mixture was allowed to react at RT until the reaction was complete (NMR). The mixture was evaporated to dryness followed by the addition of saturated NaHCO₃ and EtOAc. The aqueous layer was extracted with EtOAc. Combined organic layers were washed with brine, dried over anhydrous Na₂SO₄, filtered and concentrated under vacuum to give the title compound (0.2 g). LC-MS: m/z 229.3 (M+H)⁺.

Intermediate 69: 4-(Hydroxymethyl)-N,N-dimethylpiperidine-1-sulfonamide

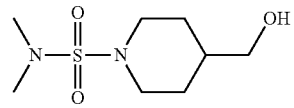

A round bottomed flask was charged with piperidin-4-ylmethanol (0.65 g, 5.6 mmol), CH₂Cl₂ (15 mL) and Et₃N (1 mL, 7.2 mmol). Dimethylsulfamoyl chloride (0.55 mL, 5.1 mmol) was added at 0° C., after which the solution was allowed to warm to RT. When the reaction was complete (TCL), the solution was concentrated under vacuum. The residue was passed through a pad of silica to give the title compound as a yellow solid (0.81 g). LC-MS: m/z 223.2 (M+H)⁺.

Intermediate 70: (1-(Cyclopropanecarbonyl)piperidin-4-yl)methyl 4-methylbenzenesulfonate

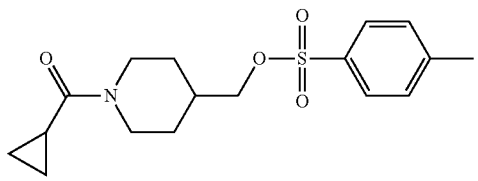 [SMILES: Cc1ccc(S(=O)(=O)OCC2CCN(C(=O)C3CC3)CC2)cc1]

An oven-dried round bottomed flask was charged with piperidin-4-ylmethanol (0.346 g, 3 mmol), $CH_2Cl_2$ (10 mL) and $Et_3N$ (1.67 ml, 12 mmol). Cyclopropanecarbonyl chloride (0.28 mL, 3.9 mmol) was added at 0° C. The solution was allowed to react at RT. When the amide formation was complete (TCL), p-toluenesulfonyl chloride (0.858 g, 4.50 mmol) was added at RT. When the reaction was complete (LC-MS) solvent was evaporated under vacuum. The residue was dissolved in saturated $NaHCO_3$ and EtOAc. The aqueous layer was extracted with EtOAc. Combined organic layers were dried with anhydrous $Na_2SO_4$, filtered and concentrated. Crude material was purified by column chromatography to give the title compound (0.548 g). LC-MS: m/z 338.4 (M+H)$^+$.

Intermediate 71: 4-(Hydroxymethyl)-N-methylcyclohexane-1-carboxamide

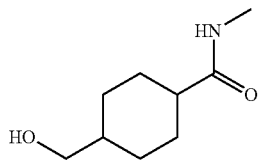

a) Methyl 4-(methylcarbamoyl)cyclohexane-1-carboxylate

To a solution of 4-(methoxycarbonyl)cyclohexane-1-carboxylic acid (1.2 g, 6.4 mmol) in $CH_2Cl_2$ (25 mL) were added DMF (1 drop) followed by $(COCl)_2$ (1.4 mL, 16.1 mmol) at 0° C. after which the mixture was stirred at RT. The reaction mixture was concentrated under reduced pressure to remove excess $(COCl)_2$. The residue was dissolved in $CH_2Cl_2$ (25 ml) and cooled to 0° C. $MeNH_2$ (17 ml) was added to the above solution followed by stirring at RT until the reaction was complete. The reaction mixture was concentrated under reduced pressure. The crude product was purified by column chromatography to give the title compound as colorless oil (0.5 g) LC-MS: m/z 200 (M+H)$^+$.

b) 4-(Hydroxymethyl)-N-methylcyclohexane-1-carboxamide

To the solution of methyl-4-(methylcarbamoyl)cyclohexane-1-carboxylate (0.4 g, 2.0 mmol) in EtOH (10 mL) was added $NaBH_4$ (0.57 g, 20.1 mmol) at 0° C. followed by stirring at RT until the reaction was complete. The reaction mixture was concentrated under reduced pressure. The crude was purified by column chromatography to give the title compound as colorless liquid (0.3 g). LC-MS: m/z 172 (M+H)$^+$.

Intermediate 72: 4-(Hydroxymethyl)-N-methylpiperidine-1-carboxamide

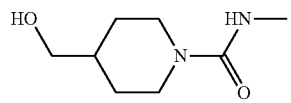

a) Ethyl 1-(methylcarbamoyl)piperidine-4-carboxylate

To a solution of ethyl piperidine-4-carboxylate (10.6 g, 68.0 mmol) in THF (25 mL) were added $Et_3N$ (13.7 mL, 136.1 mmol) and phenyl methylcarbamate (10.4 g, 68.0 mmol) followed by heating at 80° C. When the reaction was complete the mixture was concentrated under reduced pressure. The crude product was purified by column chromatography to give the title compound as a yellow solid (9.8 g). LC-MS: m/z 215 (M+H)$^+$.

b) 4-(Hydroxymethyl)-N-methylpiperidine-1-carboxamide

To a solution of ethyl 1-(methylcarbamoyl) piperidine-4-carboxylate (3.0 g, 14.0 mmol) in MeOH (100 ml) at 0° C. was added $NaBH_4$ (4.2 g, 112.0 mmol) followed by stirring at RT until the reaction was complete. The reaction mixture was quenched with cold water and concentrated under reduced pressure. The crude product was purified by column chromatography to give the title compound as a sticky mass (1.21 g). MS: m/z 173 (M+H)$^+$.

Intermediate 73: 5-(Chloromethyl)-2-methylisoindolin-1-one

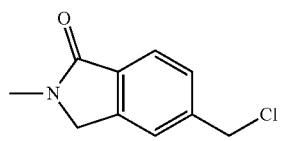

To a stirred solution of 5-(hydroxymethyl)-2-methylisoindolin-1-one (2.5 g, 14.1 mmol) in $CH_2Cl_2$ (150 mL) was added $Et_3N$ (8.86 mL, 63.5 mmol) at 0° C. MsCl (1.64 mL, 21.2 mmol) was added and the solution was stirred at 0° C. for 2 h after which it was warmed to RT. The reaction mixture was quenched with water and extracted with $CH_2Cl_2$. Combined organic phase was washed with brine, dried over anhydrous $Na_2SO_4$ and reduced under vacuum. Crude compound was purified by column chromatography to give the title compound as an off white solid (500 mg). LC-MS: m/z 196.1 (M+H)$^+$.

The following intermediates were prepared as described for Intermediate 73 from the starting material indicated on the table.

| No. | Structure | LC-MS | Starting material |
|---|---|---|---|
| 74 | 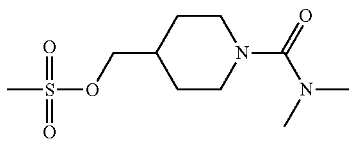 | LC-MS: m/z 265.3 (M + H)+ | 4-(Hydroxymethyl)-N,N-dimethyl-piperidine-1-carboxamide |
| 75 | 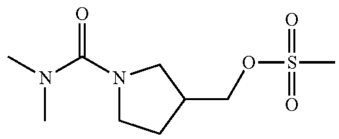 | LC-MS: m/z 251.3 (M + H)+ | 3-(Hydroxymethyl)-N,N-dimethyl-pyrrolidine-1-carboxamide |

Intermediate 76:
(1-(N,N-Dimethylsulfamoyl)piperidin-4-yl)methyl 4-methylbenzenesulfonate

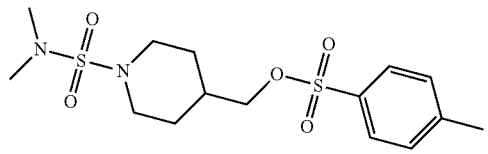

The title compound was prepared from 4-(hydroxymethyl)-N,N-dimethylpiperi-dine-1-sulfonamide (0.58 g, 2.6 mmol), p-toluenesulfonyl chloride (0.572 g, 3.0 mmol) and Et$_3$N (0.545 mL, 3.91 mmol) in CH$_2$Cl$_2$ (10 mL) according to the procedure described for Intermediate 73. Crude material was purified by column chromatography to give the title compound as an off-white solid (0.44 g). LC-MS: m/z 377.5 (M+H)+.

The following intermediates were prepared as described for Intermediate 76 from the starting material indicated on the table.

| No. | Structure | LC-MS | Starting material |
|---|---|---|---|
| 77 | 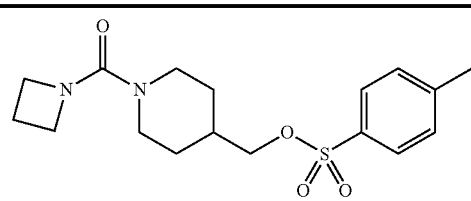 | LC-MS: m/z 353.4 (M + H)+ | Azetidin-1-yl(4-(hydroxymethyl)piperidin-1-yl)methanone |
| 78 | 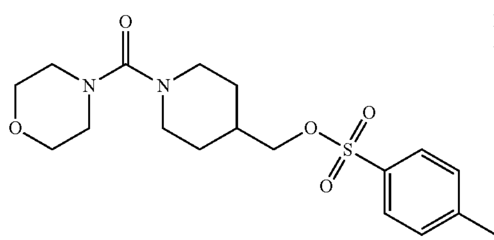 [SMILES: Cc1ccc(S(=O)(=O)OCC2CCN(C(=O)N3CCOCC3)CC2)cc1] | LC-MS: m/z 383.4 (M + H)+ | (4-(Hydroxymethyl)piperidin-1-yl)(morpholino)-methanone |

The following intermediate was prepared according to the procedure described for Intermediate 38 from the starting material indicated on the table.

| No. | Structure | LC-MS | Starting material |
|---|---|---|---|
| 79 | 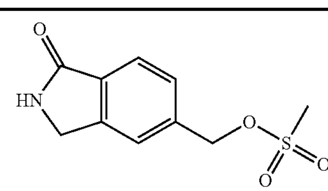 | LC-MS: m/z 242.1 (M + H)+ | 5-(Hydroxymethyl)iso-indolin-1-one |

The following intermediates were prepared according to the procedure described for Intermediate 42 from the starting material indicated on the table.

| No. | Structure | LC-MS | Starting material |
|---|---|---|---|
| 80 | 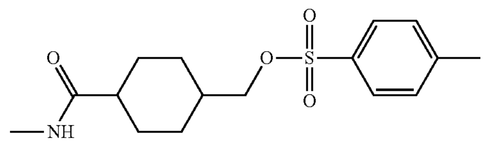 | LC-MS: m/z 326.3 (M + H)+ | 4-(Hydroxymethyl)-N-methylcyclohexane-1-carboxamide |
| 81 | 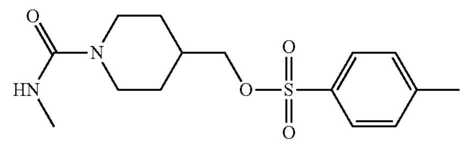 [SMILES: CNC(=O)N1CCC(COS(=O)(=O)c2ccc(C)cc2)CC1] | LC-MS: m/z 327.3 (M + H)+ | 4-(Hydroxymethyl)-N-methylpiperidine-1-carboxamide |
| 82 | 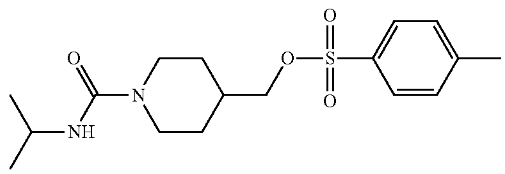 [SMILES: Cc1ccc(S(=O)(=O)OCC2CCN(C(=O)NC(C)C)CC2)cc1] | LC-MS: m/z 355.3 (M + H)+ | 4-(hydroxymethyl)-N-isopropylpiperidine-1-carboxamide |

Intermediate 83. 5-Hydroxy-2-((1-methylisoindolin-2-yl)methyl)-4H-pyran-4-one

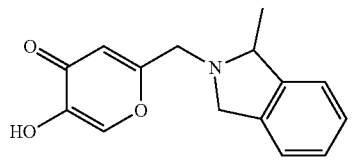 [SMILES: CC1c2ccccc2CN1Cc1cc(=O)c(O)co1]

To a stirred solution of 2,3-dihydro-1-methyl-1H-isoindole hydrochloride (480 mg, 2.83 mmol) in CH₃CN (10 mL) were added DIPEA (1.77 mL, 9.91 mmol) and 2-(chloromethyl)-5-hydroxy-4H-pyran-4-one (453 mg, 2.83 mmol) at RT. When the reaction was complete, the solid was filtered and washed with chilled CH₃CN. The title compound was collected as a pink solid (235 mg). LC-MS: m/z: 258 (M+H)⁺.

Intermediate 84: 2-((4-Fluoroisoindolin-2-yl)methyl)-5-hydroxy-4H-pyran-4-one

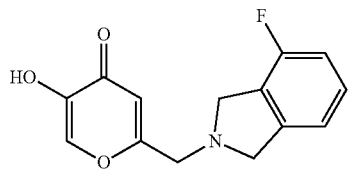 [SMILES: O=c1cc(CN2Cc3cccc(F)c3C2)occ1O]

The compound was prepared using the method described for Intermediate 83 using 4-floro-2,3-dihydro-1H-isoindole hydrochloride (2.90 g, 16.8 mmol), 2-(chloro-methyl)-5-hydroxy-4H-pyran-4-one (2.24 g, 14.0 mmol), DIPEA (5.2 ml, 29.4 mmol) and acetonitrile (50 mL). Yield 1.0 g. LC-MS: m/z 288.6 (M+H)⁺.

Intermediate 85: 2-((5,6-Difluoroisoindolin-2-yl)methyl)-5-hydroxy-4H-pyran-4-one

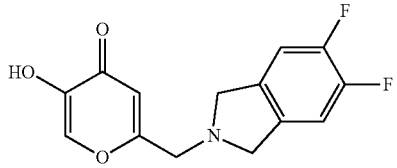 [SMILES: O=c1cc(CN2Cc3cc(F)c(F)cc3C2)occ1O]

To a stirred solution of 2-(amino methyl-5-hydroxy-4H-pyran-4-one (2.35 g, 16.7 mmol) in CH₃CN (100 mL) were added DIPEA (23.8 mL, 136 mmol) and 1,2-bis(bromomethyl)-4,5-difluoro-benzene (5.0 g, 16.7 mmol) at RT. The reaction mixture was heated at 90° C. When the reaction was complete, the reaction mixture was concentrated under reduced pressure and the residue was stirred in EtOAc (100 mL). White solid precipitated which was filtered to afford the title compound (1.10 g). LC-MS: m/z: 280 (M+H)⁺.

Intermediate 86: (4-Methylpiperidin-4-yl)methyl methanesulfonate trifluoroacetate

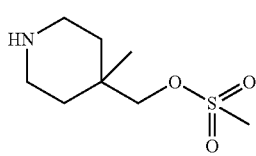

To a solution of tert-butyl 4-methyl-4-(((methylsulfonyl)oxy)methyl)piperidine-1-carboxylate (1.37 g, 4.46 mmol) in DCM (17 ml) at 0° C. trifluoroactic acid (17.2 ml, 0.22 mol) was added. The mixture was stirred for 30 min and then evaporated to dryness. The residue was triturated twice with Et₂O to afford the title compound as a white solid (1.2 g). LC-MS: m/z 208.2 (M+H)⁺.

Intermediate 87: 4-(Chloromethyl)-1,2,3,6-tetrahydropyridine trifluoroacetate

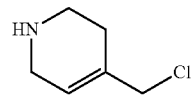

a) tert-Butyl-4-(((trifluoromethyl)sulfonyl)oxy)-3,6-dihydropyridine-1(2H)-carboxylate To a solution of tert-butyl 4-oxopiperidine-1-carboxylate (5 g, 25.1 mmol) in THF (50 ml) at −78° C. was added LiHMDS (1.0 M in THF, 27.5 ml, 27.5 mmol) followed by stirring for 30 min. A solution of 1,1,1-trifluoro-N-phenyl-N-((trifluoro-methyl)sulfonyl) methanesulfonamide (9.7 g, 27.6 mmol) in THF (15 ml) was added at -78° C. and reaction mixture was stirred for 3 h at −78° C. The reaction mixture was quenched with ice water and extracted with EtOAc. The organic layer was dried, filtered and concentrated under reduced pressure. The crude residue was purified by column chromatography to give 6.6 g of the title compound as a pale liquid. 1H-NMR (400 MHz; DMSO-d6): δ 6.01 (d, 1H), 3.98 (t, 2H), 3.55 (d, 2H), 2.38 (t, 2H), 1.40 (s, 9H).

b) 1-(tert-Butyl)4-methyl 3,6-dihydropyridine-1,4(2H)-dicarboxylate

To a mixture of tert-butyl4-(((trifluoromethyl)sulfonyl) oxy)-3,6-dihydropyridine-1(2H)-carboxylate (5.6 g, 16.8 mmol), Et₃N (4.7 ml, 33.0 mmol) in DMF (69 ml) and MeOH (52 ml) was added PPh₃ (0.2 g, 1.0 mmol) and Pd(OAc)₂ (0.1 g, 0.5 mmol) at RT under nitrogen followed by stirring under CO atmosphere for 12 h. The reaction mixture was concentrated under reduced pressure. The crude residue was purified by column chromatography to give 2.0 g of the title compound as a greenish liquid. 1H-NMR (400 MHz; DMSO-d6): δ 6.85 (d, 1H), 4.00 (t, 2H), 3.67 (s, 3H), 3.42 (d, 2H), 2.25 (t, 2H), 1.41 (s, 9H).

c) tert-Butyl-4-(hydroxymethyl)-3,6-dihydropyridine-1(2H)-carboxylate

To a solution of 1-(tert-butyl)4-methyl-3,6-dihydropyridine-1,4(2H)-dicarboxylate (1.7 g, 7.3 mmol) in DCM (20 ml) at −78° C. was added DIBAL-H (1.0 M in toluene, 10.5 ml, 10.5 mmol) followed by stirring at RT for 16 h. The reaction was cooled to 0° C. and quenched with water and extracted with DCM. The organic layer was dried, filtered and concentrated under reduced pressure to give 1.5 g of the title compound as greenish viscous liquid. LC-MS: m/z 214 (M+H)⁺.

d) tert-Butyl-4-(chloromethyl)-3,6-dihydropyridine-1(2H)-carboxylate

To the solution of tert-butyl-4-(hydroxymethyl)-3,6-dihydropyridine-1 (2H)-carboxylate (1.3 g, 6.3 mmol) in DCM (20 ml) at 0° C. were added Et₃N (1.9 ml, 18.0 mmol) and TsCl (1.8 g, 9.5 mmol). The reaction mixture was stirred at RT for 16 h. The reaction mixture was poured over crushed ice and extracted with DCM. The organic layer was washed with brine, dried, filtered and concentrated under reduced pressure. The crude residue was purified by column chromatography to give 1.1 g of the title compound. 1H-NMR (400 MHz; DMSO-d6): δ 5.85 (d, 1H), 4.19 (s, 2H), 3.79-3.81 (m, 2H), 3.42 (t, 2H), 2.05-2.15 (m, 2H), 1.40 (s, 9H).

e) 4-(Chloromethyl)-1,2,3,6-tetrahydropyridine trifluoroacetate

The title compound was prepared by the method described for Intermediate 86 using tert-butyl-4-(chloromethyl)-3,6-dihydropyridine-1(2H)-carboxylate (0.10 g, 0.43 mmol), TFA (1.7 ml, 22 mmol) and DCM (1.6 ml). Yield 0.076 g. LC-MS: m/z 132.0 (M+H)⁺.

Intermediate 88: (4-Fluoropiperidin-4-yl)methyl 4-methylbenzenesulfonate, Trifluoroacetate

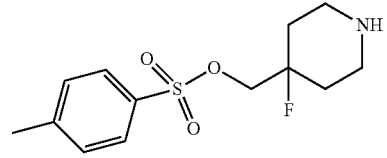 [SMILES: Cc1ccc(S(=O)(=O)OCC2(F)CCNCC2)cc1]

The title compound was prepared by the method described for Intermediate 86 using tert-butyl 4-fluoro-4-((tosyloxy)methyl)piperidine-1-carboxylate (0.30 g, 0.77 mmol), TFA (3 ml, 39 mmol) and DCM (4.5 ml). Yield 0.264 g. LC-MS: m/z 288.6 (M+H)⁺.

Intermediate 89: 4-(Chloromethyl)-5-fluoro-1,2,3,6-tetrahydropyridine trifluoroacetate

a) Ethyl-1-benzyl-5-fluoro-1,2,3,6-tetrahydropyridine-4-carboxylate

To a solution of ethyl-1-benzyl-5-hydroxy-1,2,3,6-tetrahydropyridine-4-carboxylate (25.0 g, 84.0 mmol) in DCM (500 ml) at 0° C. was added DAST (33.3 ml, 252 mmol) followed by stirring at RT for 3 h. The reaction mixture was quenched with cold saturated NaHCO₃ solution and extracted with DCM. The organic layer was dried, filtered and concentrated under reduced pressure. The crude residue was purified by column chromatography to give 9.8 g of the title compound as a yellow oil. LC-MS: m/z 264 (M+H)⁺.

b) Ethyl-5-fluoro-1,2,3,6-tetrahydropyridine-4-carboxylate

To a solution of ethyl-1-benzyl-5-fluoro-1,2,3,6-tetrahydropyridine-4-carboxylate (9.8 g, 37.0 mmol) in DCE (200 ml) at 0° C. was added 1-chloroethyl chloroformate (20.0 ml, 186 mmol). The reaction mixture was stirred at 60° C.

for 4 h. The mixture was cooled to 0° C. and MeOH (200 ml) was added followed by refluxing for 1 h. The residue was neutralized with Et₃N to pH 7 and concentrated under reduced pressure. The crude residue was purified by column chromatography to give 4.5 g of the title compound as a brown solid. LC-MS: m/z 174 (M+H)⁺.

c) 1-(tert-Butyl)-4-ethyl-5-fluoro-3,6-dihydropyridine-1,4(2H)-dicarboxylate To a solution of ethyl-5-fluoro-1,2,3,6-tetrahydropyridine-4-carboxylate (4.5 g, 26.0 mmol) in DCM (100 ml) were added Et₃N (10.8 ml, 78.0 mmol) and Boc₂O (11.3 ml, 52.0 mmol) at 0° C. and stirred at RT for 16 h. The reaction was quenched with water and extracted with DCM. The organic layer was washed with brine, filtered and concentrated under reduced pressure. The residue was purified by column chromatography to give 3.5 g of the title compound as a yellow liquid. 1H-NMR (400 MHz; CDCl3): δ 4.27 (q, 2H), 4.12 (d, 2H), 3.48 (d, 2H), 2.43 (s, 2H), 1.47 (s, 9H), 1.32 (t, 3H).

d) tert-Butyl 5-fluoro-4-(hydroxymethyl)-3,6-dihydropyridine-1(2H)-carboxylate To a solution of 1-(tert-butyl)-4-ethyl-5-fluoro-3,6-dihydropyridine-1,4(2H)-dicarboxylate (3.5 g, 12.8 mmol) in THF (60 ml) was added LAH (1.0 M in THF, 12.8 ml, 12.8 mmol) at -20 OC followed by stirring at RT for 16 h. The reaction mixture was quenched with ice and extracted with EtOAc. The organic layer was washed with brine, dried (Na₂SO₄), filtered and concentrated under reduced pressure. The crude residue was purified by column chromatography to give 1.2 g of the title compound as a colourless oil. 1H-NMR (400 MHz; DMSO-d6): δ 4.76 (t, 1H), 4.02 (d, 2H), 3.87 (s, 2H), 3.38 (d, 2H), 2.13 (d, 2H), 1.40 (s, 9H).

e) tert-Butyl 4-(chloromethyl)-5-fluoro-3,6-dihydropyridine-1 (2H)-carboxylate To a solution of tert-butyl-5-fluoro-4-(hydroxymethyl)-3,6-dihydropyridine-1(2H)-carboxylate (1.2 g, 5.1 mmol) in DCM (25 ml) at 0° C. were added Et₃N (2.1 ml, 15.0 mmol) and TsCl (1.4 g, 7.7 mmol). The reaction mixture was stirred at RT for 16 h.

The reaction was quenched with water and extracted with DCM. The organic layer was washed with brine, dried, filtered and concentrated under reduced pressure. The residue was purified by column chromatography to give 0.4 g of the title compound as a white solid. 1H-NMR (400 MHz; CDCl3): δ 4.29 (s, 2H), 3.96 (s, 2H), 3.43 (t, 2H), 2.20 (d, 2H), 1.41 (s, 9H).

f) 4-(Chloromethyl)-5-fluoro-1,2,3,6-tetrahydropyridine trifluoroacetate

The title compound was prepared by the method described for Intermediate 86 using tert-butyl 4-(chloromethyl)-5-fluoro-3,6-dihydropyridine-1(2H)-carboxylate (0.15 g, 0.60 mmol), TFA (2.3 ml, 30 mmol) and DCM (2.5 ml). Yield 0.147 g. LC-MS: m/z 150.0 (M+H)⁺.

Intermediate 90: 4-(Chloromethyl)-N-(dimethyloxido-λ⁴-sulfanylidene)-benzamide

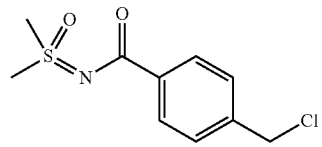

To a mixture of NaH (60% dispersion, 0.063 g, 1.6 mmol) in DCM (10 ml) under nitrogen atmosphere at RT was added S,S-dimethyl-sulfoximine, (0.15 g, 1.6 mmol) and the mixture was stirred for 1 h. The mixture was cooled to 0° C. and 4-(chloromethyl)benzoyl chloride (0.30 g, 1.6 mmol) was added and stirring continued for 1 h. Ice water was added and the product extracted with DCM. The organic phase was washed with NaOH and brine, dried and evaporated to give the title compound (0.236 g, crude yield). LC-MS: m/z 246.1 (M+H)⁺.

Intermediate 91: 4-(Chloromethyl)-N-(2-oxotetrahydrothiophen-3-yl)benzamide

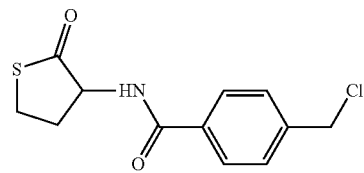 [SMILES: O=C(NC1CCSC1=O)c1ccc(CCl)cc1]

To a solution of 4-(chloromethyl)benzoyl chloride (0.60 g, 3.17 mmol) in THF (8 ml) DL-homocysteine thiolactone hydrochloride (0.49 g, 3.17 mmol) was added under nitrogen atmosphere and the mixture was cooled in ice water bath. Et₃N (1.1 ml, 7.9 mmol) was added and mixing was continued for 2 h. THF was evaporated, water added to the residue and the mixture extracted with EtOAc. The organic layer was washed with 1 M HCl, 1 M NaOH and brine, dried and evaporated to give the title compound (0.66 g, crude yield). LC-MS: m/z 270.2 (M+H)⁺.

Intermediate 92: (1-(2-(Methylsulfonyl)acetyl)piperidin-4-yl)methyl 4-methylbenzenesulfonate

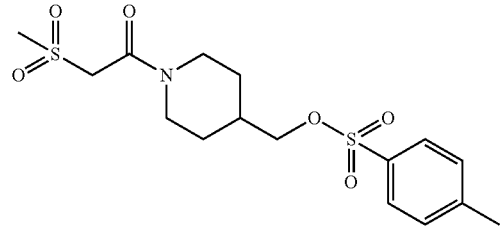 [SMILES: Cc1ccc(S(=O)(=O)OCC2CCN(C(=O)CS(C)(=O)=O)CC2)cc1]

To a solution of phosphorus pentachloride (0.232 g, 1.11 mmol) in DCM (6 ml) methanesulfonylacetic acid (0.154 g, 1.11 mmol) was added and the mixture refluxed for 30 min. Piperidin-4-ylmethyl 4-methylbenzenesulfonate (0.200 g, 0.743 mmol) in DCM (2 ml) was added at RT and then the mixture refluxed for 1 h. Water was added and the product was extracted with EtOAc. The organic phase was washed with 0.5 M NaOH, 1 M HCl and brine, dried and evaporated to give the title compound (0.122 g, crude yield). LC-MS: m/z 390.4 (M+H)⁺.

Intermediate 93: (3-Hydroxy-1-(methylsulfonyl)piperidin-4-yl)methyl methanesulfonate

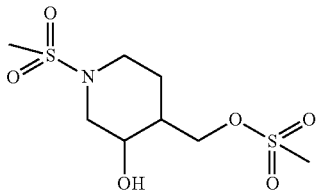

To a solution of 4-(hydroxymethyl)piperidin-3-ol (0.070 g, 0.53 mmol) in ACN (10 ml) at 0° C. were added $K_2CO_3$ (0.15 g, 1.07 mmol) and methanesulfonyl chloride (0.122 g, 1.07 mmol) in ACN (1ml) in two steps. 1 ml DMF was added to get better solubility. The reaction mixture was stirred at RT for 1 h and then evaporated to dryness to afford the title compound (0.10 g, crude yield). LC-MS: m/z 288.1 (M+1)⁺.

Intermediate 94: 1-(Chloromethyl)-4-(propan-2-ylsulfonimidoyl)benzene tosyl

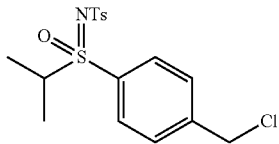

a) 4-(Isopropylthio)benzaldehyde

To a solution of propane-2-thiol (3.3 g, 44.9 mmol) in DMSO (100 ml) at 0° C. were added $K_2CO_3$ (11.0 g, 80.0 mmol) and 4-fluorobenzaldehyde (5.0 g, 40.0 mmol) followed by heating at 100° C. for 16 h. The mixture was quenched with water and extracted with EtOAc. The organic layer was washed with water, dried and concentrated under reduced pressure to give the title compound (6.4 g). LC-MS: m/z 181 (M+1)⁺.

b) (4-(Isopropylthio)phenyl)methanol

To a solution of 4-(isopropylthio)benzaldehyde (6.4 g, 35.0 mmol) in MeOH (120 ml) was added $NaBH_4$ (2.0 g, 53.0 mmol) at 0° C. followed by stirring at RT for 2 h.
The reaction was quenched with ice cold water and extracted with EtOAc. The organic layer was dried and concentrated under reduced pressure to give the title compound (5.5 g). LC-MS: m/z 183 (M+1)⁺.

c) (4-(Chloromethyl)phenyl)(isopropyl)sulfane

To a solution of (4-(isopropylthio)phenyl)metanol (5.5 g, 30.0 mmol) in dry DCM (100 ml) at 0° C. was added $SOCl_2$ (3.8 g, 33.0 mmol) followed by stirring at RT for 1 h. The reaction was quenched with aqueous $NaHCO_3$ solution and extracted with DCM. The organic layer was washed with water, dried and concentrated under reduced pressure to give the title compound (5.7 g). 1H-NMR (400 MHz; DMSO-d6): 7.36 (d, 2H), 7.30 (d, 2H), 4.56 (s, 2H), 3.38-3.41 (m, 1H), 1.30 (d, 6H).

d) N-((4-(Chloromethyl)phenyl)isopropyl)-λ4-sulfanylidene)-4-methylbenzenesulfonamide To a solution of (4-(chloromethyl)phenyl)(isopropyl)sulfane (5.7 g, 28.0 mmol) in ACN (100 ml) was added 4-methylbenzenesulfonamide (4.8 g, 28.0 mmol), iodobenzene diacetate (14.4 g, 44.0 mmol) and Fe (III) acetylacetonate (0.7 g, 1.9 mmol) at RT followed by stirring for 16 h. The reaction mixture was concentrated under reduced pressure. The crude residue was purified by column chromatography to afford the title compound (8.5 g). LC-MS: m/z 370 (M+1)⁺.

e) 1-(Chloromethyl)-4-(propan-2-ylsulfonimidoyl)benzene tosyl

To a solution of N-((4-(chloromethyl)phenyl)isopropyl)-λ4-sulfanylidene)-4-methylbenzenesulfonamide (8.0 g, 21.0 mmol) in DCM (150 ml) were added m-CPBA (70% in water, 11.1 g, 65.0 mmol), $K_2CO_3$ (11.5 g, 84.0 mmol) followed by stirring at RT for 2 days. The reaction mixture was quenched with aqueous $NaHCO_3$ solution and extracted with DCM. The organic layer was washed with water, dried and concentrated under reduced pressure. The crude residue was purified by column chromatography to afford the title compound (1.1 g). LC-MS: m/z 384 (M+1)⁺.

Intermediate 95: N-((4-(Chloromethyl)phenyl)(ethyl)(oxo)-λ4-sulfanylidene)-4-methylbenzenesulfonamide

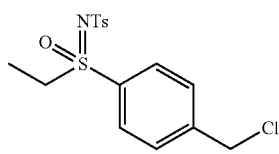

a) N-((4-(Chloromethyl)phenyl)(ethyl)-λ4-sulfanylidene)-4-methylbenzenesulfonamide The title compound was prepared by the method described in step (d) of Intermediate 94 starting from (4-chloromethyl)phenyl)-(ethyl)sulfane (11.0 g, 59.1 mmol) and 4-methylbenzenesulfonamide (10.0 g, 59.1 mmol). Yield 14.8 g. LC-MS: m/z 356 (M+1)⁺.

b) N-((4-(Chloromethyl)phenyl)(ethyl)(oxo)-λ4-sulfanylidene)-4-methylbenzenesulfonamide The title compound was prepared by the method described in step (e) of Intermediate 94 starting from N-((4-(chloromethyl)phenyl)(ethyl)-λ4-sulfanylidene)-4-methylbenzenesulfonamide (14.5 g, 40.0 mmol) and m-CPBA (70% in water, 14.0 g, 80.0 mmol). Yield: 7.1 g. LC-MS: m/z 372 (M+H)⁺.

Intermediate 96: 1-Oxido-1-(tosylimino)tetrahydro-2H-thiopyran-4-yl)methyl methanesulfonate

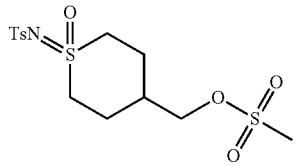

a) [1-({[(4-Methylphenyl)sulfonyl]oxy}imino)hexahydro-1λ⁴-thiopyran-4-yl]-methyl methanesulfonate The title compound was prepared by the method described in step (d) of Intermediate 94 starting from (tetrahydro-2H-thiopyran-4-yl)methyl methanesulfonate (2.1 g, 10.0 mmol), 4-methylbenzenesulfonamide (2.56 g, 15.0 mmol), iodobenzene diacetate (5.12 g, 16.0 mmol) and Fe (III) acetylacetonate (0.25 g, 0.7 mmol). Yield 0.94 g. LCMS: m/z 380.1 (M+1)$^+$.

b) (1-Oxido-1-(tosylimino)tetrahydro-2H-thiopyran-4-yl)methyl methanesulfonate

The title compound was prepared by the method described in step (e) of Intermediate 94 starting from [1-({[(4-methylphenyl)sulfonyl]oxy}imino)hexahydro-1λ⁴-thiopyran-4-yl]methyl methanesulfonate (0.86 g, 2.27 mmol), m-CPBA (77% in water, 1.0 g, 4.5 mmol) and K$_2$CO$_3$ (0.94 g, 6.8 mmol). Yield: 0.31 g. LC-MS: m/z 396.1 [M+H]$^+$.

Intermediate 97: (4-(S-methyl-N-tosylsulfonimidoyl)cyclohexyl)methyl-4-methylbenzenesulfonate

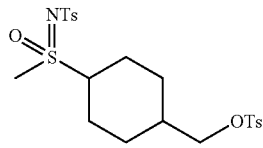

a) (4-(Methylthio)cyclohexyl)methanol

To a solution of methyl-4-(methylthio)cyclohexane-1-carboxylate (6.0 g, 31.9 mmol) in THF (100 mil) was added LiBH$_4$ (2.0 M in THF, 40 ml, 95.7 mmol) at 0° C. The reaction mixture was stirred at RT for 16 h. The reaction was quenched with aqueous NH$_4$Cl solution and extracted with EtOAc. The organic layer was dried, filtered and concentrated under reduced pressure. The crude residue was purified by column chromatography to afford the title compound. Yield 4.0 g. MS: m/z 161 (M+H)$^+$.

b) (4-(Methylthio)cyclohexyl)methyl-4-methylbenzenesulfonate

To a solution of (4-(methylthio)cyclohexyl)methanol (4.0 g, 29.3 mmol) in DCM (50 ml) was added Et$_3$N (12 ml, 87.9 mmol) and TsCl (8.4 g, 44.0 mmol) at 0° C. The reaction mixture was stirred at RT for 16 h. The reaction was quenched with ice water and extracted with DCM. The organic layer was dried, filtered and concentrated under reduced pressure. The crude residue was purified by column chromatography to afford the title compound. Yield 7.5 g. 1H-NMR (400 MHz; DMSO-d6): δ 7.78 (d, 2H), 7.48 (d, 2H), 3.83 (d, 2H), 2.89-2.90 (m, 1H), 2.44 (s, 3H), 1.99 (s, 3H), 1.60 (q, 4H), 1.58 (s, 1H), 1.41 (q, 2H), 1.33 (q, 2H).

c) (4-(S-methyl-N-tosylsulfinimidoyl)cyclohexyl)methyl-4-methylbenzenesulfonate

The title compound was prepared by the method described in step (d) of Intermediate 94 starting from (4-(methylthio)cyclohexyl)methyl-4-methylbenzenesulfonate (5.0 g, 15.9 mmol), 4-methylbenzenesulfonamide (4.0 g, 23.8 mmol), iodobenzene diacetate (8.2 g, 25.4 mmol) and Fe (III)acetylacetonate (0.36 g, 1.1 mmol). Yield 2.5 g. LC-MS: m/z 484 (M+H)$^+$.

d) (4-(S-methyl-N-tosylsulfonimidoyl)cyclohexyl)methyl-4-methylbenzenesulfonate

To a solution of (4-(S-methyl-N-tosylsulfinimidoyl)cyclohexyl)methyl-4-methylbenzenesulfonate (1.5 g, 3.1 mmol) in ethanol: ACN (1:3) (20 ml) was added H$_2$O$_2$(30% in water, 0.8 ml, 6.8 mmol) and K$_2$CO$_3$ (2.5 g, 18.8 mmol) at 0° C. The reaction mixture was stirred at RT for 16 h. The reaction mixture was filtered and the filtrate was concentrated under reduced pressure. The crude residue was purified by column chromatography to afford the title compound. LC-MS: m/z 498 (M+H)$^+$.

Intermediate 98: N-((4-(Chloromethyl)phenyl)(methyl)(oxo)-λ4-sulfanylidene)-4-methylbenzenesulfonamide

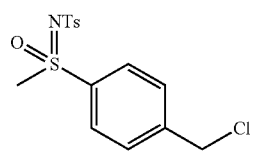

a) N-((4-(Chloromethyl)phenyl)methyl)-λ4-sulfanylidene)-4-methylbenzenesulfonamide The title compound was prepared by the method described in step (d) of Intermediate 94 starting from 4-(methylthio)benzyl chloride (2.5 g, 14.5 mmol), 4-methylbenzenesulfonamide (3.7 g, 21.7 mmol), iodobenzene diacetate (7.5 g, 23.1 mmol) and Fe (III) acetylacetonate (0.36 g, 1.0 mmol). Yield 3.3 g. LC-MS: m/z 342.1 (M+1)$^+$.

b) N-((4-(Chloromethyl)phenyl)(methyl)(oxo)-λ4-sulfanylidene)-4-methylbenzenesulfonamide The title compound was prepared by the method described in step (e) of Intermediate 94 starting from N-((4-(chloromethyl)phenyl)methyl)-λ4-sulfanylidene)-4-methylbenzenesulfonamide (3.3 g, 9.7 mmol), m-CPBA (77% in Intermediate-99:1-(Chloromethyl)-4-(S-methylsulfonimidoyl)benzene

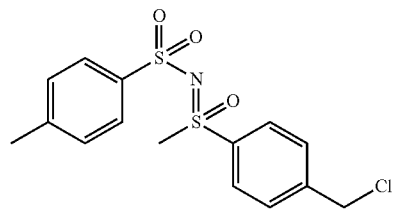

→

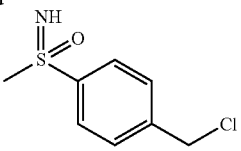

A solution of 1-(chloromethyl)-4-(methylsulfonimidoyl) benzene tosyl (0.70 g, 1.95 mmol) in sulfuric acid (3.0 ml) was stirred at RT for 1 h. The reaction mixture was poured into water, basified using 2 M NaOH solution and extracted with DCM. The organic layer was washed with water, dried with $Na_2SO_4$ and evaporated to give the titled compound. LC-MS: m/z 205.9 $(M+H)^+$ The following intermediates were prepared according to the procedure described for Intermediate 99 from the starting material indicated on the table.

water, 4.37 g, 19.5 mmol) and $K_2CO_3$ (4.0 g, 29 mmol). Yield 3.0 g (white solid). LC-MS: m/z 358.1 $(M+H)^+$.

| No | Structure | LC-MS | Starting material |
|---|---|---|---|
| 100 | 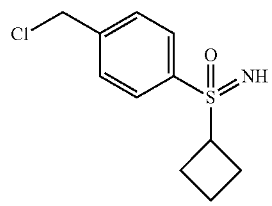 [SMILES: N=S(=O)(c1ccc(CCl)cc1)C1CCC1] | LC-MS: m/z 244.4 $(M + H)^+$ | 1-(Chloromethyl)-4-(S-cyclobutyl-N-(p-tolylsulfonyl)sulfoximine)benzene |
| 101 | 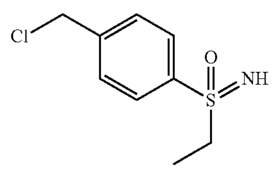 | LC-MS: m/z 218.7 $(M + H)^+$ | 1-(Chloromethyl)-4-(ethylsulfonimidoyl)benzene tosyl |
| 102 | 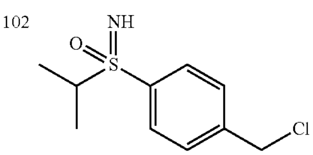 | LC-MS: m/z 233.2 $(M + H)^+$ | 1-(Chloromethyl)-4-(propan-2-ylsulfonimidoyl)benzene tosyl |
| 103 | 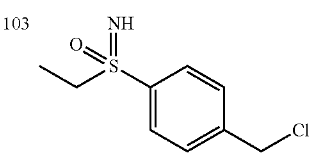 | LC-MS: m/z 219.1 $(M + H)^+$ | N-((4-(Chloromethyl)phenyl)(ethyl)-(oxo)-λ4-sulfanylidene)-4-methylbenzenesulfonamide |
| 104 | 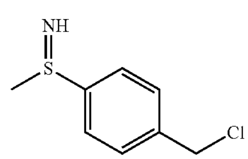 | LC-MS: m/z 189.0 $(M + H)^+$ | N-((4-(Chloromethyl)phenyl)methyl)-λ4-sulfanylidene)-4-methylbenzenesulfonamide |
| 105 | 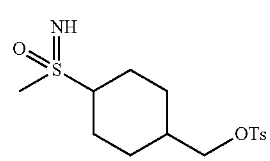 [SMILES: Cc1ccc(S(=O)(=O)OCC2CCC(S(C)(=N)=O)CC2)cc1] | LC-MS: m/z 346.7 $(M + H)^+$ | (4-(S-methyl-N-tosylsulfonimidoyl)cyclohexyl)methyl-4-methylbenzenesulfonate |
| 106 | 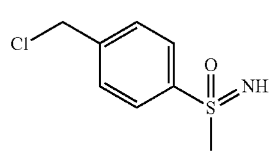 | LC-MS: m/z 205.9 $(M + H)^+$ | N-((4-(Chloromethyl)phenyl)-(methyl)(oxo)-λ4-sulfanylidene)-4-methylbenzenesulfonamide |

Intermediate 107: 1-(Chloromethyl)-4-(N,S-dimethylsulfonimidoyl)benzene

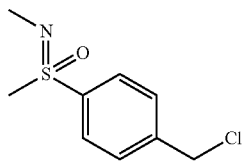

To a solution of 1-(chloromethyl)-4-(S-methylsulfonimidoyl)benzene (Intermediate 107) (0.038 g, 0.18 mmol) in DCM (4 ml) under nitrogen atmosphere was added trimethyloxonium tetrafluoroborate (0.041 g, 0.28 mmol). The mixture was stirred at RT for 5 h. The reaction was quenched with saturated NaHCO$_3$ solution and the mixture was extracted with DCM. The organic phase was dried, filtered and evaporated to dryness to afford the title compound (yield 0.025 g). LC-MS: m/z 218.2 (M+1)$^+$.

Intermediate 108: 1-(Chloromethyl)-4-(N-acetyl-S-methylsulfonimidoyl)benzene

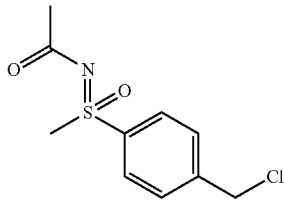

To a solution of 1-(chloromethyl)-4-(S-methylsulfonimidoyl)benzene (Intermediate 106) (0.097 g, 0.47 mmol) in DCM (5 ml) under nitrogen atmosphere was added Et$_3$N (0.072 g, 0.71 mmol) followed by cooling to 0° C. Acetyl chloride (0.037 g, 0.047 mmol) was added followed by stirring at 0° C. for 3 h. The reaction was quenched with ice water and the aqueous layer extracted with EtOAc. The organic layer was washed with 0.5 M HCl, saturated NaHCO$_3$ and brine, dried, filtered and evaporated to dryness to afford the title compound (yield 0.162 g). LC-MS: m/z 246.1 (M+1).

Intermediate 109: 1-(Chloromethyl)-4-(N-ethyl-S-methylsulfonimidoyl)benzene

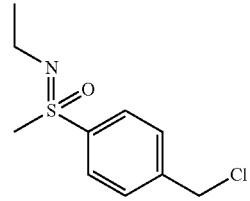

To a solution of Intermediate 108 (0.109 g, 0.44 mmol) in DCM (3 ml) under nitrogen atmosphere at 0° C. was added borane-methyl sulfide complex (0.067 g, 0.89 mmol) followed by stirring for 4 h. MeOH (1 ml) and water (2 ml) were added and the product was extracted with EtOAc. The organic phase was dried, filtered and evaporated to dryness to afford the title compound (yield 0.055 g). LC-MS: m/z 232.1 (M+1)$^+$.

Intermediate 110: (4-Methyl-1-(methylsulfonyl)piperidin-4-yl)methyl methanesulfonate

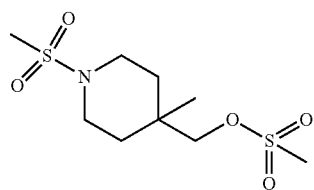

To a suspension of (4-methylpiperidin-4-yl)methyl methanesulfonate trifluoroacetate (Intermediate 86) (0.40 g, 1.24 mmol) in DCM (25 ml) were added Et$_3$N (0.52 ml, 3.73 mmol) and methanesulfonyl chloride (0.096 ml, 1.24 mmol). The reaction mixture was stirred at RT. When the reaction was complete, EtOAc was added and the mixture washed with saturated NaHCO$_3$, 0.5 M HCl and brine. The organic layer was dried and evaporated to dryness to afford the title compound (0.25 g). LC-MS: m/z 286.2 (M+1)$^+$.

The following intermediates were prepared according to the procedure described for Intermediate 110 from the starting material indicated on the table.

| No | Structure | LC-MS | Starting materials |
|---|---|---|---|
| 111 | 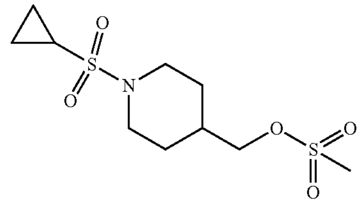 [SMILES: CS(=O)(=O)OCC1CCN(S(=O)(=O)C2CC2)CC1] | LC-MS: m/z 298.3 (M + H)+ | Cyclopropanesulfonyl chloride; Piperidin-4-ylmethyl methanesulfonate, trifluoroacetate |
| 112 | 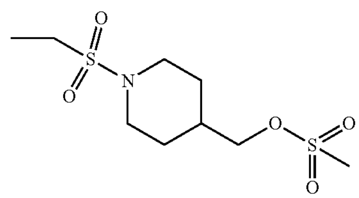 [SMILES: CCS(=O)(=O)N1CCC(COS(C)(=O)=O)CC1] | LC-MS: m/z 286.3 (M + H)+ | Ethanesulfonyl chloride; Piperidin-4-ylmethyl methanesulfonate, trifluoroacetate |

| No | Structure | LC-MS | Starting materials |
|---|---|---|---|
| 113 | 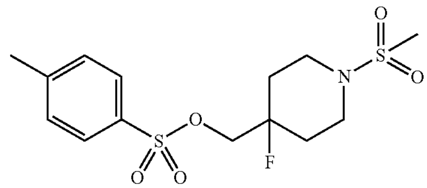 | LC-MS: m/z 366.1 (M + H)+ | Methanesulfonyl chloride, Intermediate 88 |
| 114 | 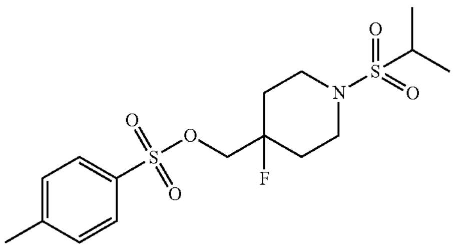 [SMILES: Cc1ccc(S(=O)(=O)OCC2(F)CCN(S(=O)(=O)C(C)C)CC2)cc1] | LC-MS: m/z 394.7 (M + 1)+ | Isopropylsulfonyl chloride, Intermediate 88 |
| 115 | 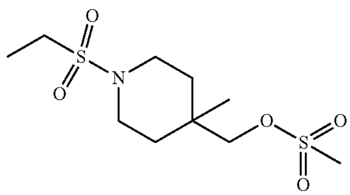 [SMILES: CCS(=O)(=O)N1CCC(C)(COS(C)(=O)=O)CC1] | LC-MS: m/z 300.3 (M + 1)+ | Ethanesulfonyl chloride, Intermediate 86 |
| 116 | 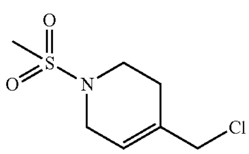 | LC-MS: m/z 210.1 (M + 1)+ | Methanesulfonyl chloride, tert-Butyl-4-(chloromethyl)-3,6-dihydropyridine-1(2H)-carboxylate |
| 117 | 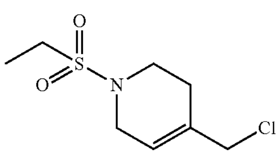 | LC-MS: m/z 224.2 (M + 1)+ | Ethanesulfonyl chloride, tert-Butyl-4-(chloromethyl)-3,6-dihydropyridine-1(2H)-carboxylate |
| 118 | 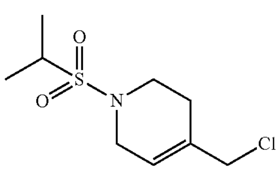 | LC-MS: m/z 238.1 (M + 1)+ | Isopropylsulfonyl chloride, tert-Butyl-4-(chloromethyl)-3,6-dihydropyridine-1(2H)-carboxylate |
| 119 | 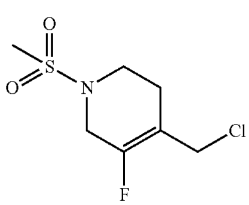 | LC-MS: m/z 228.0 (M + 1)+ | Methanesulfonyl chloride, Intermediate 89 |
| 120 | 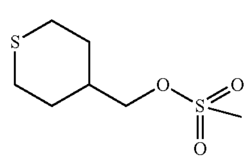 | LC-MS: m/z 211.1 (M + 1)+ | (Tetrahydro-2H-thiopyran-4-yl)methanol |

Intermediate 121: 1-(4-(Chloromethyl)phenyl)cyclobutanol

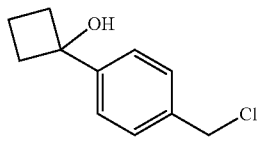 [SMILES: OC1(c2ccc(CCl)cc2)CCC1]

To a stirred solution of 4-bromobenzyl chloride (5.0 g, 24.3 mmol) in THF (50 mL) was added n-BuLi (18 ml, 29.2 mmol) and cyclobutanone (2.2 ml, 29.2 mmol) at -78° C. followed by stirring for 3 h. The reaction mixture was quenched with saturated aqueous NH$_4$Cl solution and extracted with EtOAc. The combined organic layers were washed with water, brine, dried over Na$_2$SO$_4$, filtered and concentrated under reduced pressure to obtain crude compound. Purification by column chromatography afforded the title compound (1.2 g). $^1$H NMR (Chloroform-d): δ 7.50 (d, 2H), 7.40 (d, 2H), 4.59 (s, 2H), 2.52-2.59 (m, 2H), 2.33-2.41 (m, 2H), 1.98-2.05 (m, 1H), 1.66-1.77 (m, 1H). LC-MS: m/z 179 [(M−H$_2$O)+H]$^+$

Intermediate 122: 4-(2-Chloroethyl)-N,N-dimethylbenzamide

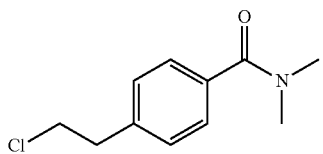

To an ice cooled mixture of p-(beta-chloroethyl)benzoic acid (0.554 g, 3 mmol), dimethylamine hydrochloride (0.306 g, 3.75 mmol) and triethylamine (2.4 ml, 17.22 mmol) in DMF (6 ml) was added dropwise 1-propanephosphonic acid cyclic anhydride (50% in EtOAc, 2.4 mL, 4.07 mmol). The mixture was stirred at RT until the reaction reached completion (analysed by LC-MS). The mixture was diluted with water and extracted with EtOAc. The combined organic phases were washed with water and brine, dried over sodium sulphate and concentrated under reduced pressure to afford the title compound (0.583 g). $^1$HNMR (400 MHz, Chloroform-d): δ 7.36-7.41 (m, 2H), 7.23-7.27 (m, 2H), 3.72 (t, 2H), 3.11 (br s, 3H), 3.09 (t, 2H), 2.99 (br s, 3H); LC-MS: m/z 212.1 (M+H)$^+$.

Intermediate 123: 3-(4-(Chloromethyl)phenyl)oxetan-3-ol

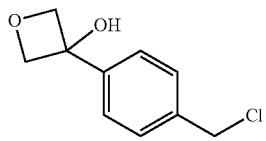 [SMILES: OC1(c2ccc(CCl)cc2)COC1]

To a stirred solution of 4-bromobenzyl chloride (7 g, 34.06 mmol) in THF (110 mL) was added n-BuLi (2.2 M, 18.60 mL, 40.87 mmol) and 3-oxetanone (2.94 g, 40.87 mmol) at −78° C. followed by stirring for 1.5 h. The reaction mixture was quenched with ice water and extracted with ethyl acetate. The combined organic layer was dried over anhydrous Na$_2$SO$_4$, filtered and concentrated under reduced pressure to afford crude compound. Purification by column chromatography afforded the title compound (1.21 g). $^1$H NMR (DMSO-d6): δ 7.68 (d, 2H), 7.45 (d, 2H), 6.36 (bs, 1H), 4.75-4.77 (m, 4H), 4.66 (d, 2H); LC-MS m/z 181 [(M−H$_2$O)+H]$^+$

Intermediate 124: cis-(4-((tert-Butoxycarbonyl)amino)cyclopent-2-en-1-yl)-methyl methanesulfonate

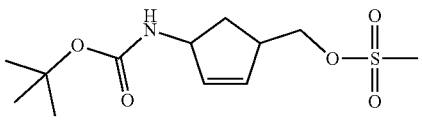 [SMILES: CC(C)(C)OC(=O)NC1C=CC(COS(C)(=O)=O)C1]

To an ice cooled solution of cis-tert-butyl (4-(hydroxymethyl)cyclopent-2-en-1-yl)carbamate (1.0 g, 4.69 mmol) and triethylamine (1.0 ml, 7.17 mmol) in DCM (20 ml) was added methanesulfonyl chloride (0.5 ml, 6.46 mmol) in DCM (2 ml). The mixture was stirred at 5-20° C. until the reaction reached completion (analysed by LC-MS). The mixture was diluted with water and saturated NH$_4$Cl solution, washed with water and brine, dried over sodium sulphate and concentrated under reduced pressure to afford the title compound (1.36 g). $^1$HNMR (400 MHz, Chloroform-d): δ 5.77-5.86 (m, 2H), 4.50-4.85 (m, 2H), 4.12-4.23 (m, 2H), 3.02 (s, 3H), 2.98-3.07 (m, 1H), 2.59 (dt, 1H), 1.45 (s, 9H), 1.35 (dt, 1H).

Intermediate 125: 2-(1-(methylsulfonyl)piperidin-4-yl)ethyl methanesulfonate

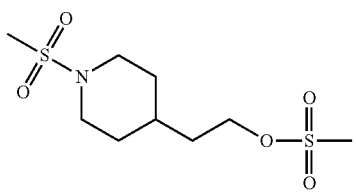

To a mixture of 4-piperidine ethanol (1.0 g, 7.74 mol) and potassium carbonate (3.53 g, 25.5 mmol) in dry ACN (20 ml) was added dropwise methanesulfonyl chloride (1.5 ml, 19.38 mmol). The mixture was stirred at RT until the reaction reached completion (analysed by LC-MS). The mixture was poured into water and stirred overnight. The precipitated product was filtered, washed with water and dried under vacuum to afford the title compound (1.06 g). $^1$H NMR (Chloroform-d): δ 4.30 (t, 2H), 3.78-3.86 (m, 2H), 3.02 (s, 3H), 2.77 (s, 3H), 2.66 (td, 2H), 1.81-1.88 (m, 2H), 1.74 (q, 2H), 1.56-1.68 (m, 1H), 1.30-1.42 (m, 2H).

Intermediate 126: 2-{[3,4-Dihydroisoquinolin-2(1H)-yl]methyl}-5-hydroxy-4H-pyran-4-one

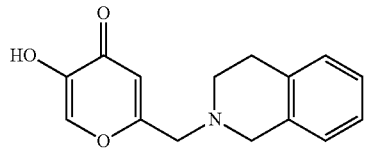 [SMILES: O=c1cc(CN2CCc3ccccc3C2)occ1O]

To a stirred solution of 2-(chloromethyl)-5-hydroxy-4H-pyran-4-one (5.0 g, 158.0 mmol) in acetonitrile (50 mL) were added DIPEA (15.0 mL, 94.92 mmol) and 1,2,3,4-tetrahydroisoquinolene (5.05 g, 37.96 mmol) at RT followed by stirring for 16 h. The precipitated solid was filtered, washed with EtOAc and dried under reduced pressure to afford the title compound (2.6 g). $^1$H NMR (DMSO-d6): δ 9.06 (s, 1H), 8.05 (s, 1H), 7.0-7.11 (m, 4H), 6.40 (s, 1H), 3.62 (s, 1H), 3.58 (s, 2H), 2.81-2.84 (m, 1H), 2.74-2.76 (m, 2H). LC-MS m/z 258.2 (M+H)$^+$ Intermediate 127: 5-Hydroxy-2-((5-(trifluoromethoxy)isoindolin-2-yl)methyl)-4H-pyran-4-one

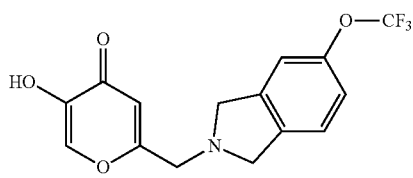 [SMILES: O=c1cc(CN2Cc3ccc(OC(F)(F)F)cc3C2)occ1O]

a) tert-Butyl-5-(((methylthio)carbonothioyl)oxy)isoindoline-2-carboxylate

To a solution of tert-butyl-5-hydroxyisoindoline-2-carboxylate (3.0 g, 12.7 mmol) in DMF (60 ml) was added NaH (60% in mineral oil, 0.8 g, 19.1 mmol) at 0° C. followed by stirring for 30 min. To this reaction mixture was added CS$_2$ (1.0 ml, 16.5 mmol) followed by stirring for 1 h. MeI (1.1 ml, 16.5 mmol) was added to the mixture followed by stirring at RT for 16 h. The reaction was quenched with ice water and extracted with EtOAc. The organic layer was washed with water, dried, filtered and concentrated under reduced pressure to afford the title compound (4.4 g). $^1$H-NMR (400 MHz; CDCl$_3$): δ 7.39 (d, 1H), 7.16 (s, 1H), 7.08 (d, 1H), 4.5 (d, 4H), 2.68 (s, 3H), 1.45 (s, 9H); LC-MS: m/z 324 (M−H)$^+$.

b) 5-(Trifluoromethoxy)isoindoline

To a solution of tert-butyl-5-(((methylthio)carbonothioyl)oxy)isoindoline-2-carboxylate (4.4 g, 13.5 mmol) in hydrogen-fluoride pyridine complex (31.0 ml, 108.0 mmol) was added 1,3-dibromo-5,5-dimethylhydantoin (11.6 g, 40.6 mmol) at 0° C. followed by stirring at RT for 16 h. The reaction was quenched with ice water and extracted with EtOAc. The organic layer was washed with water, dried, filtered and concentrated under reduced pressure to obtain crude product. Purification by column chromatography afforded the title compound (1.3 g). $^1$H-NMR (400 MHz; DMSO-d$_6$): δ 9.36 (s, 1H), 7.55 (d, 1H), 7.47 (s, 1H), 7.38 (d, 1H), 4.53 (d, 4H); LC-MS: m/z 204 (M+H)$^+$.

c) 5-Hydroxy-2-((5-(trifluoromethoxy)isoindolin-2-yl)methyl)-4H-pyran-4-one

To a solution of 2-(chloromethyl)-5-hydroxy-4H-pyran-4-one (0.788 g, 4.9 mmol) in dioxane (20 ml) were added 5-(trifluoromethoxy)isoindoline (1.0 g, 4.9 mmol) and DIPEA (4.5 ml, 24.5 mmol) at RT followed by stirring at 80° C. for 16 h. The reaction was concentrated under reduced pressure to obtain crude product. Purification by column chromatography afforded the title compound (0.4 g). $^1$H-NMR (400 MHz; DMSO-d$_6$): δ 9.11 (s, 1H), 8.05 (s, 1H), 7.35 (d, 1H), 7.20 (s, 1H), 7.18 (d, 1H), 6.41 (s, 1H), 3.96 (d, 4H), 3.7 (s, 2H); MS: m/z 328 (M+H)$^+$.

Intermediate 128: 2-Chloro-4-(hydroxymethyl)benzonitrile

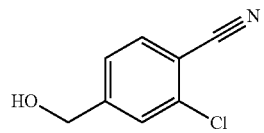 [SMILES: N#Cc1ccc(CO)cc1Cl]

To a solution of 2-chloro-4-formylbenzonitrile (0.25 g, 1.510 mmol) in THF (15 mil) was added sodium borohydride (0.228 g, 6.04 mmol) in 5 batches in 15 min. The reaction mixture was heated at reflux for 15 min. The mixture was cooled in an ice-bath, and saturated NH$_4$Cl solution (5 mil) was added to the solution followed by addition of EtOAc (10 mil). The resulting mixture was filtered through a 5 mm layer of Celite®. The Celite® was washed with EtOAc (10 ml), and the combined organic layers were washed with NH$_4$Cl solution, dried with Na$_2$SO$_4$, filtered, and evaporated to afford the title compound (0.12 g). $^1$H NMR (400 MHz, Chloroform-d) δ ppm 7.66 (d, 1H), 7.54-7.56 (m, 1H), 7.36 (d, 1H), 4.78 (s, 2H).

Intermediate 129: 3-Chloro-4-cyanobenzyl methanesulfonate

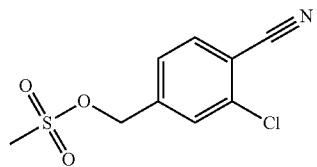

To a solution of 2-chloro-4-(hydroxymethyl)benzonitrile (0.119 g, 0.710 mmol) and triethylamine (0.109 ml, 0.781 mmol) in DCM (2 mil) at 0-5° C. was added dropwise methanesulfonyl chloride (0.060 ml, 0.781 mmol) in DCM (2 mil). The reaction mixture was stirred at RT for 1 h. Water (15 ml) was added, and the aqueous layer was extracted with DCM. The organic layers were combined, washed with saturated NaHCO$_3$ solution, water and brine, dried with Na$_2$SO$_4$, filtered, and evaporated to afford the title compound (0.12 g). $^1$H NMR (400 MHz, Chloroform-d) δ ppm 7.72 (d, 1H), 7.51-7.64 (m, 1H), 7.33-7.49 (m, 1H), 3.08 (s, 3H).

Intermediate 130:
1-(4-(Bromomethyl)phenyl)-2-methylpropan-2-ol

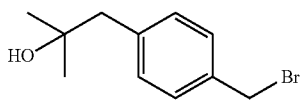

To a solution of methyl 2-(4-(bromomethyl)phenyl)acetate (1 g, 4.11 mmol) in THF (10 ml) at −78° C. was added dropwise 3 M methylmagnesium bromide solution (3.93 ml, 11.79 mmol). The reaction mixture was stirred at −78° C. for 2 h, at 0° C. for 4 h and at RT for 16 h. Saturated NH$_4$Cl solution and water were added, and the aqueous layer was extracted with Et$_2$O. The organic layers were combined, washed with water and brine, dried with Na$_2$SO$_4$, filtered, and evaporated to afford the title compound (0.81 g). $^1$H NMR (400 MHz, DMSO-d$_6$) δ ppm 7.29-7.35 (m, 2H), 7.15-7.23 (m, 2H), 4.67-4.75 (m, 2H), 2.63-2.65 (m, 2H), 1.05 (s, 6H).

Intermediate 131:
4-(Bromomethyl)-3-fluorobenzamide

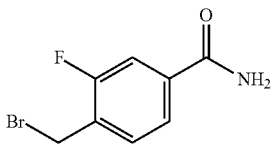 [SMILES: NC(=O)c1ccc(CBr)c(F)c1]

To a suspension of 4-(bromomethyl)-3-fluorobenzonitrile (1 g, 4.67 mmol) and water (0.185 ml, 10.28 mmol) was added sulfuric acid (4.58 ml, 93 mmol) followed by stirring at 100° C. for 1 h, cooling to 50° C., and pouring on ice. The mixture was stirred, and the precipitated material was filtered, washed with water, and dried in a vacuum-oven at 40° C. for 16 h to afford the title compound (0.94 g). LC-MS: m/z 232.0 (M+H)$^+$.

Intermediate 132: 2-((6-Fluoro-3,4-dihydroisoquinolin-2(1H)-yl)methyl)-5-hydroxy-4H-pyran-4-one

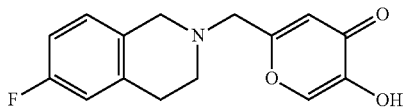 [SMILES: O=c1cc(CN2CCc3cc(F)ccc3C2)occ1O]

To a solution of 6-fluoro-1,2,3,4-tetrahydroisoquinoline (0.301 g, 1.993 mmol) and 2-(chloromethyl)-5-hydroxy-4H-pyran-4-one (0.32 g, 1.993 mmol) in 1,2-dichloroethane (5 ml) at 0° C. was added dropwise TEA (0.972 ml, 6.98 mmol). The solution was stirred at 60° C. for 3 h, and washed with saturated NaHCO$_3$ solution. The aqueous layer was extracted with DCM, the organic layers were combined, washed with water and brine, dried with Na$_2$SO$_4$, filtered, and evaporated. The crude product was purified by column chromatography to afford the title compound (70 mg). LC-MS: m/z 276.2 (M+H)$^+$.

Intermediate 133:
4-(Chloromethyl)-N,N-diethylbenzamide

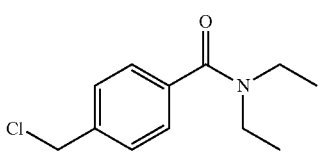

To a suspension of sodium hydride (0.099 g, 2.476 mmol) and 4-(chloromethyl)-benzamide (0.14 g, 0.825 mmol) in DMF (3 ml) was added dropwise iodoethane (0.664 ml, 8.25 mmol) in DMF (2 ml) at 0° C. The reaction mixture was stirred at 20° C. for 3 h and quenched with water to form a precipitate. The precipitate was filtered, washed with water and dried to afford the title compound (0.14 g) $^1$H NMR (400 MHz, Chloroform-d) δ ppm 7.28-7.44 (m, 4H), 4.42-4.64 (m, 2H), 3.38-3.62 (m, 2H), 3.15-3.38 (m, 2H), 1.05-1.30 (m, 6H).

Intermediate 134:
4-(Bromomethyl)-3-fluoro-N,N-dimethylbenzamide

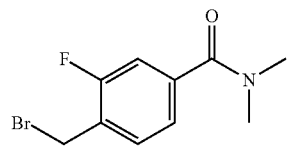

To a solution of 4-(bromomethyl)-3-fluorobenzamide (0.2 g, 0.862 mmol) and NaH (0.103 g, 2.59 mmol) in DMF (1 ml) at 0° C. was added iodomethane (0.537 ml, 8.62 mmol) in DMF (2 ml). The reaction mixture was stirred at 0° C. for 1 h and poured on ice. The aqueous layer was extracted with EtOAc. The organic layers were combined, washed with water and brine, dried with Na$_2$SO$_4$, filtered, and evaporated. The crude product was purified by column chromatography to afford the title compound (0.10 g). $^1$H NMR (400 MHz, Chloroform-d) δ ppm 7.39 (t, 1H), 7.08-7.17 (m, 2H), 4.38-4.51 (m, 2H), 3.10 (br s, 3H), 2.99 (br s, 3H).

Intermediate 135:
(4-(Chloromethyl)phenyl)(piperidin-1-yl)methanone

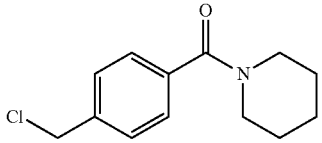 [SMILES: O=C(c1ccc(CCl)cc1)N1CCCCC1]

To a suspension of 4-(chloromethyl)benzoyl chloride (0.88 g, 4.66 mmol) and piperidine hydrochloride (0.566 g, 4.66 mmol) in DCM (10 ml) at 0° C. was added dropwise triethylamine (1.363 ml, 9.78 mmol). The reaction mixture was stirred at 0° C. for 1 h and at 20° C. for 1 h, and washed with 1M NaOH, 1M HCl, brine and water. The organic layer was dried with Na$_2$SO$_4$, filtered, and evaporated to afford the title compound (0.98 g). $^1$H NMR (400 MHz, DMSO-d$_6$) δ ppm 7.48-7.52 (m, 2H), 7.35-7.41 (m, 2H), 4.80 (s, 2H), 3.25 (br s, 2H), 1.37-1.65 (m, 8H).

Intermediate 136: Azetidin-1-yl(4-(chloromethyl)phenyl)methanone

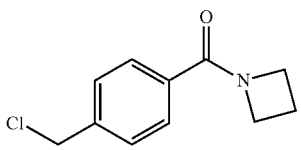 [SMILES: O=C(c1ccc(CCl)cc1)N1CCC1]

To a suspension of 4-(chloromethyl)benzoyl chloride (2.1 g, 9.22 mmol) and azetidine hydrochloride (0.863 g, 9.22 mmol) in DCM (20 ml) at 0° C. was added dropwise triethylamine (2.70 ml, 19.36 mmol). The reaction mixture was stirred at 0° C. for 1 h, and washed with 1M NaOH, 1M HCl, brine and water. The organic layer was dried with $Na_2SO_4$, filtered, and evaporated to afford the title compound (1.52 g). LC-MS: m/z 210.1 $(M+H)^+$.

Intermediate 137: 2-((5-Bromoisoindolin-2-yl)methyl)-5-hydroxy-4H-pyran-4-one

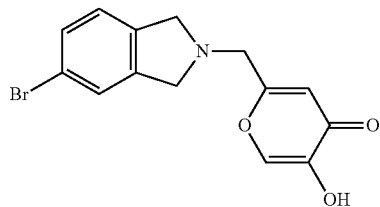 [SMILES: O=c1cc(CN2Cc3ccc(Br)cc3C2)occ1O]

To a solution of 5-bromoisoindoline (1.21 g, 6.11 mmol) and 2-(chloromethyl)-5-hydroxy-4H-pyran-4-one (0.981 g, 6.11 mmol) in DMF (10 ml) at 0° C. was added DIPEA (2.66 ml, 15.27 mmol) dropwise. The reaction mixture was stirred at 50° C. for 2.5 h and poured on ice. The aqueous layer was extracted with EtOAc. The organic layers were combined, washed with water and brine, dried with $Na_2SO_4$, filtered, and evaporated. The crude product was purified by column chromatography to afford the title compound (0.22 g). LC-MS: m/z 322.2 $(M+H)^+$.

Intermediate 138: N-(tert-Butyl)-4-(chloromethyl)benzamide

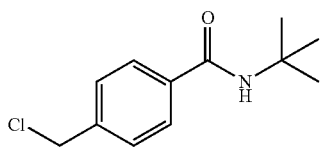

To a suspension of 4-(bromomethyl)phenylacetic acid (0.82 g, 3.72 mmol) and oxalyl chloride (1.351 ml, 18.60 mmol) was added one drop of DMF. The reaction mixture was stirred at 20° C. for 16 h. The excess of oxalyl chloride was evaporated. DCM (15 ml) and 2-methylpropan-2-amine hydrochloride (0.408 g, 3.72 mmol) were added followed by addition of DIPEA (1.620 ml, 9.30 mmol) at 0° C. The reaction mixture was stirred at 0° C. for 1 h. Water was added, and the layers were separated. The aqueous layer was extracted with DCM. The organic layers were combined and washed with 1M NaOH, 1M HCl and brine, dried with $Na_2SO_4$, filtered, and evaporated to afford the title compound (0.85 g). $^1$H NMR (400 MHz, DMSO-$d_6$) δ ppm 7.76-7.78 (m, 2H), 7.47-7.50 (m, 2H), 4.80 (s, 2H), 1.37 (s, 9H).

Intermediate 139: 2-(4-(Chloromethyl)phenyl)-N,N-dimethylacetamide

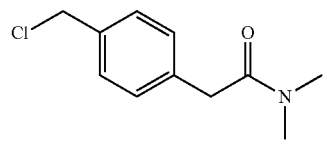

To a suspension of 4-(bromomethyl)phenylacetic acid (2 g, 8.73 mmol) and oxalyl chloride (3 ml, 34.9 mmol) was added one drop of DMF. The reaction mixture was stirred at 20° C. for 16 h. The excess of oxalyl chloride was evaporated. DCM (20 ml) and dimethylamine hydrochloride (0.783 g, 9.60 mmol) were added followed by addition of triethylamine (2.74 ml, 19.64 mmol) in DCM (5 ml) at 0° C. The reaction mixture was stirred at 0° C. for 3.5 h. Water (20 ml) was added, and the layers were separated. The aqueous layer was extracted with DCM. The organic layers were combined and washed with 1M NaOH, 1M HCl and brine, dried with $Na_2SO_4$, filtered, and evaporated to afford the title compound (0.64 g). LC-MS: m/z 212.2 $(M+H)^+$.

Intermediate 140: Ethyl 2-(4-(chloromethyl)-N-methylbenzamido)acetate

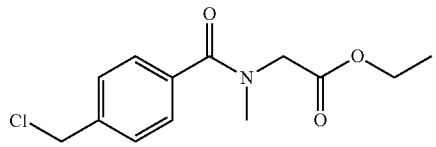 [SMILES: CCOC(=O)CN(C)C(=O)c1ccc(CCl)cc1]

To a suspension of alpha-bromo-p-toluic acid (1 g, 4.65 mmol) and oxalyl chloride (1.35 ml, 18.60 mmol) was added one drop of DMF. The reaction mixture was stirred at 20° C. for 16 h. The excess of oxalyl chloride was evaporated. DCM (40 ml) and sarcosine ethyl ester hydrochloride (0.714 g, 4.65 mmol) were added. The mixture was cooled to 0° C., and DIPEA (2.03 ml, 11.63 mmol) was added dropwise at 0° C. The reaction mixture was stirred for 1 h. The organic layer was washed with water and brine, dried with $Na_2SO_4$, filtered, and evaporated to afford the title compound (0.14 g). LC-MS: m/z 270.2 $(M+H)^+$.

Intermediate 141: 4-(Chloromethyl)-N-isopropylbenzamide

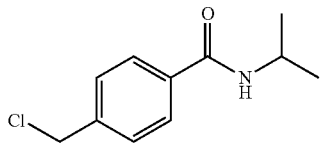

To a suspension of propan-2-amine hydrochloride (0.531 g, 5.55 mmol) and 4-(chloromethyl)benzoyl chloride (1 g, 5.29 mmol) in DCM (20 ml) was added dropwise TEA (1.659 ml, 11.90 mmol) under 5° C. The reaction mixture was stirred at 0° C. for 30 min. Water was added to the mixture, the layers were separated, and the aqueous layer was extracted with DCM. The organic layers were combined, washed with 1M NaOH, 1M HCl and brine, dried with $Na_2SO_4$, filtered, and evaporated to afford the title compound (1.05 g). $^1$H NMR (400 MHz, DMSO-$d_6$) δ ppm 8.23 (br d, J=7.5 Hz, 1H), 7.81-7.87 (m, 2H), 7.48-7.53 (m, 2H), 4.80 (s, 2H), 4.09 (dt, J=7.7, 6.6 Hz, 1H), 1.16 (d, J=6.6 Hz, 6H).

Intermediate 142: 4-(Chloromethyl)-N-(prop-2-yn-1-yl)benzamide

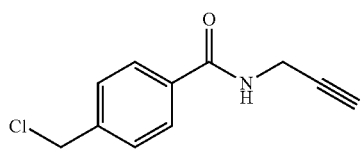

To a suspension of prop-2-yn-1-amine hydrochloride (0.508 g, 5.55 mmol) and 4-(chloromethyl)benzoyl chloride (1 g, 5.29 mmol) in DCM (20 ml) was added dropwise TEA (1.659 ml, 11.90 mmol) under 5° C. The reaction mixture was stirred at 0° C. for 45 min. Water was added to the mixture, the layers were separated, and the aqueous layer was extracted with DCM. The organic layers were combined, washed with 1M NaOH, 1M HCl and brine, dried with $Na_2SO_4$, filtered, and evaporated to afford the title compound (0.82 g). LC-MS: m/z 208.1 (M+H)$^+$.

Intermediate 143: N-butyl-4-(chloromethyl)benzamide

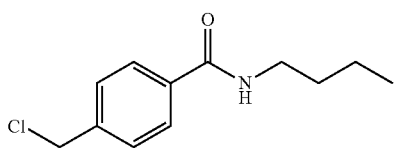

To a suspension of butan-1-amine hydrochloride (0.609 g, 5.55 mmol) and 4-(chloromethyl)benzoyl chloride (1 g, 5.29 mmol) in DCM (20 ml) was added dropwise TEA (1.659 ml, 11.90 mmol) under 5° C. followed by stirring at 0° C. for 45 min. Water was added to the mixture, the layers were separated, and the aqueous layer was extracted with EtOAc. The organic layers were combined, washed with 1 M NaOH, 1 M HCl and brine, dried with $Na_2SO_4$, filtered, and evaporated. The crude product was triturated with heptane:MTBE to afford the title compound (1.01 g). LC-MS: m/z 226.2 (M+H)$^+$.

Intermediate 144: 4-(Chloromethyl)-N-hexylbenzamide

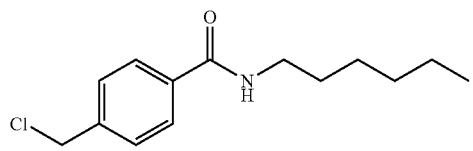 [SMILES: CCCCCCNC(=O)c1ccc(CCl)cc1]

To a suspension of 4-(chloromethyl)benzoyl chloride (1 g, 5.29 mmol) and hexan-1-amine hydrochloride (0.765 g, 5.55 mmol) in DCM (20 ml) was added dropwise TEA (1.659 ml, 11.90 mmol) under 5° C. The reaction mixture was stirred at 0° C. for 45 min. Water was added to the mixture, the layers were separated, and the aqueous layer was extracted with DCM. The organic layers were combined, washed with 1M NaOH, 1M HCl and brine, dried with $Na_2SO_4$, filtered, and evaporated to afford the title compound (1.24 g). LC-MS: m/z 254.2 (M+H)$^+$.

Intermediate 145: 4-(Chloromethyl)-N-(1-hydroxy-2-methylpropan-2-yl)-benzamide

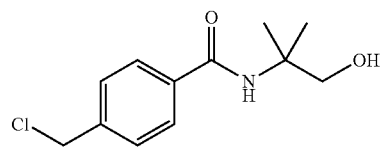 [SMILES: CC(C)(CO)NC(=O)c1ccc(CCl)cc1]

To a suspension of 4-(chloromethyl)benzoyl chloride (0.92 g, 4.87 mmol) and 2-amino-2-methylpropan-1-ol hydrochloride (0.64 g, 5.11 mmol) in DCM (20 ml) was added dropwise TEA (1.526 ml, 10.95 mmol) under 5° C. The reaction mixture was stirred at 0° C. for 30 min. Water was added to the mixture, the layers were separated, and the aqueous layer was extracted with DCM. The organic layers were combined, washed with 1 M NaOH, 1 M HCl and brine, dried with $Na_2SO_4$, filtered, and evaporated to afford the title compound (0.80 g). LC-MS: m/z 242.2 (M+H)$^+$.

Intermediate 146: 2-(4-(Chloromethyl)benzamido)-2-methylpropyl acetate

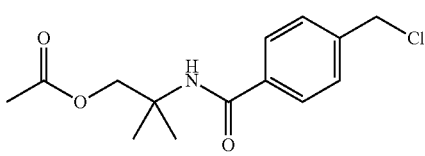 [SMILES: CC(=O)OCC(C)(C)NC(=O)c1ccc(CCl)cc1]

To a solution of 4-(chloromethyl)-N-(1-hydroxy-2-methylpropan-2-yl)benzamide (0.367 g, 1.518 mmol) in pyridine (5 ml) at 0° C. was added acetic anhydride (0.215 ml, 2.277 mmol) dropwise. The reaction mixture was stirred at 0° C. for 15 min and then at 20° C. for 2 h. The volatiles were removed in vacuo, and the residue was dissolved in DCM. The solution was washed with 1 M HCl, 5% NaHCO$_3$ and brine, dried with Na$_2$SO$_4$, filtered, and evaporated to afford the title compound (0.26 g). $^1$H NMR (400 MHz, DMSO-d$_6$) δ ppm 7.84 (s, 1H), 7.76-7.81 (m, 2H), 7.47-7.53 (m, 2H), 4.80 (s, 2H), 4.25 (s, 2H), 3.86 (s, 1H), 2.02 (s, 3H), 1.36 (s, 6H).

Intermediate 147:
4-(Chloromethyl)-N-(4-hydroxybutyl)benzamide

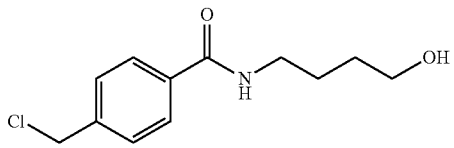 [SMILES: O=C(NCCCCO)c1ccc(CCl)cc1]

To a suspension of 4-(chloromethyl)benzoyl chloride (1 g, 5.29 mmol) and 4-aminobutan-1-ol hydrochloride (0.664 g, 5.29 mmol) in DCM (20 ml) was added dropwise TEA (1.659 ml, 11.90 mmol) at 0° C. The reaction mixture was stirred at 0° C. for 30 min. Water was added to the mixture, the layers were separated, and the aqueous layer was extracted with DCM. The organic layers were combined, washed with 1 M NaOH, 1 M HCl and brine, dried with Na$_2$SO$_4$, filtered, and evaporated. Diethyl ether was added to the residue. The mixture was stirred, filtrated, and dried to afford the title compound (0.44 g). LC-MS: m/z 242.2 (M+H)$^+$.

Intermediates 148 and 149: (E)-3-(4-(chloromethyl) phenyl)-N,N-dimethylacrylamide and (E)-3-(4-(bromomethyl)phenyl)-N,N-dimethylacrylamide

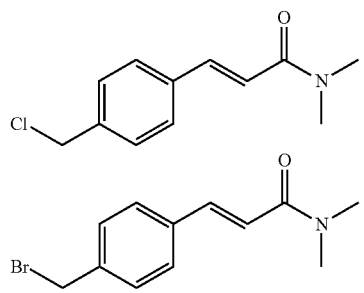

To a suspension of (E)-3-(4-(bromomethyl)phenyl)acrylic acid (0.76 g, 3.15 mmol) and oxalyl chloride (1.083 ml, 12.6 mmol) was added one drop of DMF. The mixture was stirred at 20° C. for 16 h. The excess of oxalyl chloride was evaporated. DCM (20 ml) and dimethylamine hydrochloride (0.27 g, 3.31 mmol) were added followed by addition of triethylamine (0.989 ml, 7.09 mmol) at 0° C. The mixture was stirred at 0° C. for 1 h. Water (20 ml) was added, and the layers were separated. The aqueous layer was extracted with DCM. The organic layers were combined and washed with 1 M NaOH, 1 M HCl and brine, dried with Na$_2$SO$_4$, filtered, and evaporated to afford the title compound as mixture of (E)-3-(4-(chloromethyl)phenyl)-N,N-dimethylacrylamide and (E)-3-(4-(bromomethyl)phenyl)-N,N-dimethylacrylamide (0.33 g). LC-MS: m/z 224.2 (M+H)$^+$. LC-MS: m/z 270.1 (M+H)$^+$.

Intermediate 150: 2-(4-(Chloromethyl)phenyl)-N-(2-hydroxyethyl)-N-methylacetamide

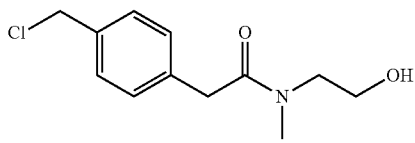 [SMILES: CN(CCO)C(=O)Cc1ccc(CCl)cc1]

To a suspension of 4-(bromomethyl)phenylacetic acid (2 g, 8.73 mmol) and oxalyl chloride (3 ml, 34.9 mmol) was added one drop of DMF. The reaction mixture was stirred at 20° C. for 16 h. The excess of oxalyl chloride was evaporated. DCM (15 ml) and N-methyl ethanolamine HCl (0.974 g, 8.73 mmol), were added followed by addition of TEA (2.738 ml, 19.64 mmol) at 0° C. The reaction mixture was stirred at 0° C. for 1 h. Water was added, and the layers were separated. The aqueous layer was extracted with DCM. The organic layers were combined and washed with 1 M NaOH, 1 M HCl and brine, dried with Na$_2$SO$_4$, filtered, and evaporated to afford the title compound (0.23 g). LC-MS: m/z 242.2 (M+H)$^+$.

Intermediate 151:
4-(Chloromethyl)-N-(3-hydroxypropyl)benzamide

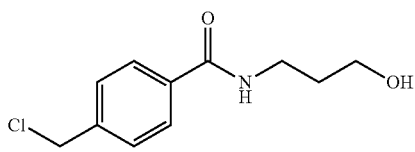 [SMILES: O=C(NCCCO)c1ccc(CCl)cc1]

To a solution of 4-(chloromethyl)benzoyl chloride (2.97 g, 15.71 mmol) in DCM (10 ml) was added 3-amino-1-propanol (1.180 g, 15.71 mmol) in DCM (20 ml) followed by dropwise addition of TEA (2.409 ml, 17.28 mmol) at 0° C. The mixture was stirred at 0° C. for 45 min. Water was added to the mixture, the layers were separated, and the aqueous layer was extracted with DCM. The organic layers were combined, washed with 1 M NaOH, 1 M HCl and brine, dried with Na$_2$SO$_4$, filtered, and evaporated. The crude product was purified by column chromatography followed by trituration with diethyl ether to afford the title compound (1.79 g). LC-MS: m/z 228.2 (M+H)$^+$.

Intermediate 152:
3-(4-(Chloromethyl)benzamido)propyl acetate

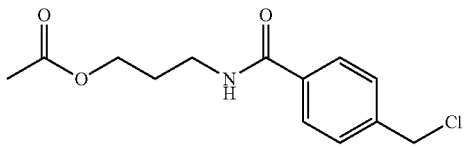 [SMILES: CC(=O)OCCCNC(=O)c1ccc(CCl)cc1]

To a solution of 4-(chloromethyl)-N-(3-hydroxypropyl) benzamide (1.79 g, 7.86 mmol) in pyridine (15 ml) was added acetic anhydride (1.115 ml, 11.79 mmol) at 0° C. The reaction mixture was stirred at 0° C. for 15 min and at 20° C. for 30 min. The solvent was evaporated, and water was added to the residue. The aqueous layer was extracted with EtOAc. The organic layers were combined, washed with 1 M HCl, water, 5% NaHCO$_3$ and brine, dried with Na$_2$SO$_4$, filtered, and evaporated to afford the title compound (1.29 g). LC-MS: m/z 270.2 (M+H)$^+$.

Intermediate 155: (E)-3-(4-(chloromethyl)phenyl)-N-methylacrylamide

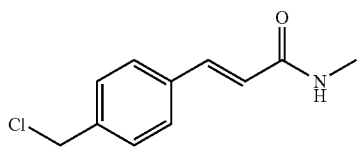

To a suspension of (E)-3-(4-(bromomethyl)phenyl)acrylic acid (1.0 g, 4.15 mmol) and oxalyl chloride (1.424 ml, 16.59 mmol) was added one drop of DMF followed by stirring at 20° C. for 16 h. The excess of oxalyl chloride was evaporated, and DCM (20 ml) and methylamine hydrochloride (0.28 g, 4.15 mmol) were added followed by addition of triethylamine (1.301 ml, 9.33 mmol) at 0° C. The reaction mixture was stirred at 0° C. for 1 h. Water (20 ml) was added, and the layers were separated. The aqueous layer was extracted with DCM. The organic layers were combined and washed with 1 M NaOH, 1 M HCl and brine, dried with Na$_2$SO$_4$, filtered, evaporated, and triturated with diethyl ether to afford the title compound (0.42 g). $^1$H NMR (400 MHz, DMSO-d$_6$) δ ppm 8.01-8.11 (m, 1H), 7.51-7.58 (m, 2H), 7.44-7.50 (m, 2H), 7.37-7.44 (m, 1H), 6.52-6.69 (m, 1H), 4.71-4.79 (m, 2H), 2.68-2.75 (m, 3H).

Intermediate 156: (4-(Chloromethyl)phenyl)(3-hydroxypiperidin-1-yl)methanone

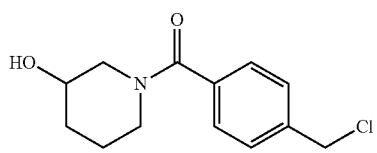 [SMILES: O=C(c1ccc(CCl)cc1)N1CCCC(O)C1]

To a suspension of 4-(chloromethyl)benzoyl chloride (1 g, 5.29 mmol) and piperidin-3-ol hydrochloride (0.728 g, 5.29 mmol) in DCM (20 ml) was added dropwise TEA (0.811 ml, 5.82 mmol) at 0° C. The reaction mixture was stirred at 0° C. for 30 min. Water was added to the mixture, the layers were separated, and the aqueous layer was extracted with DCM. The organic layers were combined, washed with 1 M NaOH, 1 M HCl and brine, dried with Na$_2$SO$_4$, filtered, and evaporated. Heptane was added to the residue followed by stirring, filtration, and drying to afford the title compound (0.62 g). LC-MS: m/z 254.2 (M+H)$^+$.

Intermediate 157: 4-(Chloromethyl)-N-(3-hydroxy-2,2-dimethylpropyl)-benzamide

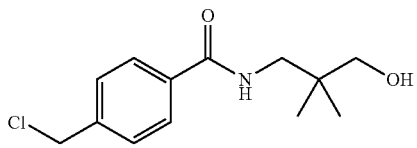 [SMILES: CC(C)(CO)CNC(=O)c1ccc(CCl)cc1]

To a suspension of 4-(chloromethyl)benzoyl chloride (2.058 g, 10.89 mmol) and 3-amino-2,2-dimethylpropan-1-ol hydrochloride (1.520 g, 10.89 mmol) in DCM (25 ml) was added dropwise TEA (1.669 ml, 11.98 mmol) at 0° C. The reaction mixture was stirred at 0° C. for 30 min. Water was added to the mixture, the layers were separated, and the aqueous layer was extracted with DCM. The organic layers were combined, washed with 1 M NaOH, 1 M HCl and brine, dried with Na$_2$SO$_4$, filtered, and evaporated. The residue was purified by column chromatography to afford the title compound (0.67 g). LC-MS: m/z 256.2 (M+H)$^+$.

Intermediate 158: (4-(Chloromethyl)phenyl)(4-hydroxypiperidin-1-yl)methanone

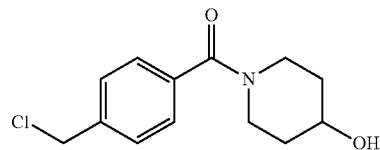 [SMILES: O=C(c1ccc(CCl)cc1)N1CCC(O)CC1]

To a suspension of 4-(chloromethyl)benzoyl chloride (3.3 g, 17.46 mmol) and piperidin-4-ol hydrochloride (2.376 g, 17.27 mmol) in DCM (35 ml) was added dropwise TEA (5.41 ml, 38.9 mmol) at 0° C. The reaction mixture was stirred at 0° C. for 30 min. Water was added to the mixture, the layers were separated, and the aqueous layer was extracted with DCM. The organic layers were combined, washed with 1 M NaOH, 1 M HCl and brine, dried with Na$_2$SO$_4$, filtered, and evaporated to afford the title compound (3.62 g). LC-MS: m/z 254.3 (M+H)$^+$.

Intermediate 159: 2-Chloro-1-(4-(phenylsulfonyl)piperazin-1-yl)ethanone

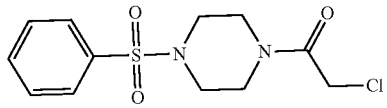 [SMILES: O=C(CCl)N1CCN(S(=O)(=O)c2ccccc2)CC1]

To a solution of 1-(phenylsulfonyl)piperazine (1 g, 4.42 mmol) and TEA (1.355 ml, 9.72 mmol) in DCM (15 ml) was added chloroacetyl chloride (0.422 ml, 5.30 mmol) in DCM (5 ml) at 0° C. The reaction mixture was stirred at 20° C. for 50 min, washed with water and brine. The organic layer was dried with Na$_2$SO$_4$, filtered, and evaporated to afford the title compound (1.12 g). LC-MS: m/z 303.3 (M+H)$^+$.

Intermediate 160: 2-Chloro-1-(4-tosylpiperazin-1-yl)ethanone

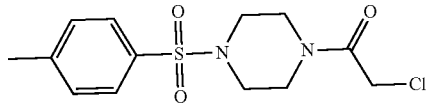

To a solution of 1-tosylpiperazine (1 g, 4.16 mmol) and TEA (0.696 ml, 4.99 mmol) in DCM (15 ml) was added chloroacetyl chloride (0.397 ml, 4.99 mmol) in DCM (5 ml) at 0° C. The mixture was stirred at 20° C. for 50 min, washed with water and brine. The organic layer was dried with $Na_2SO_4$, filtered, and evaporated to afford the title compound (1.30 g). $^1$H NMR (400 MHz, DMSO-$d_6$) δ ppm 7.59-7.66 (m, 2H), 7.44-7.49 (m, 2H), 4.34 (s, 2H), 3.47-3.59 (m, 4H), 2.80-3.00 (m, 4H), 2.41 (s, 3H).

Intermediate 161: (4-(Chloromethyl)phenyl)(3,3-difluoroazetidin-1-yl)-methanone

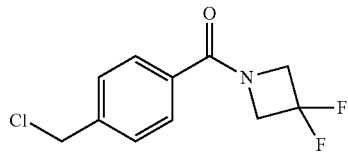 [SMILES: O=C(c1ccc(CCl)cc1)N1CC(F)(F)C1]

To a suspension of 4-(chloromethyl)benzoyl chloride (1.0 g, 5.29 mmol) and 3,3-difluoroazetidine hydrochloride (0.685 g, 5.29 mmol) in tert-butylmethyl ether (15 ml) at 0° C. was added dropwise triethylamine (1.659 ml, 11.90 mmol). The reaction mixture was stirred at 0° C. for 1 h. Water was added to the reaction mixture, and the organic phase was extracted with EtOAc. The organic layers were combined, washed with 1 M NaOH, 1 M HCl, brine and water. The organic layer was dried with $Na_2SO_4$, filtered, and the majority of the solvents were evaporated. Diethyl ether and heptane were added, and the precipitation was filtered, washed with heptane and dried to afford the title compound (0.9 g). $^1$H NMR (400 MHz, DMSO-$d_6$) δ ppm 7.67-7.73 (m, 2H), 7.51-7.57 (m, 2H), 4.82 (s, 2H), 4.61-4.81 (m, 2H), 4.38-4.58 (m, 2H).

Intermediate 162: 2-Chloro-1-(4-(3-(methoxymethyl)pyridin-2-yl)piperazin-1-yl)ethanone

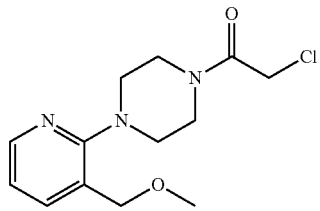 [SMILES: COCc1cccnc1N1CCN(C(=O)CCl)CC1]

To a solution of 1-(3-(methoxymethyl)pyridin-2-yl)piperazine hydrochloride (0.75 g, 3.08 mmol) and TEA (0.944 ml, 6.77 mmol) in DCM (15 ml) was added chloroacetyl chloride (0.294 ml, 3.69 mmol) in DCM (5 ml) at 0° C. The reaction mixture was stirred at 20° C. for 50 min, washed with water and brine. The organic layer was dried with $Na_2SO_4$, filtered, and evaporated to afford the title compound (0.59 g). $^1$H NMR (400 MHz, DMSO-$d_6$) δ ppm 8.21 (dd, J=4.8, 1.9 Hz, 1H), 7.72 (dd, J=7.4, 1.9 Hz, 1H), 7.05 (dd, J=7.5, 4.8 Hz, 1H), 4.43 (s, 2H), 4.42 (s, 2H), 4.27 (s, 2H), 3.57-3.64 (m, 4H), 3.11-3.18 (m, 2H), 3.03-3.11 (m, 2H)

Intermediate 163: 5-Hydroxy-2-((5-(methylthio)isoindolin-2-yl)methyl)-4H-pyran-4-one

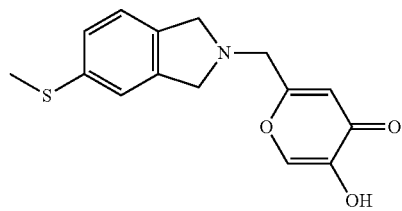 [SMILES: CSc1ccc2c(c1)CN(Cc1cc(=O)c(O)co1)C2]

To a solution of 5-(methylthio)isoindoline HCl (0.1 g, 0.496 mmol) and 2-(chloromethyl)-5-hydroxy-4H-pyran-4-one (0.080 g, 0.496 mmol) in DMSO (1 ml) at 60° C. was added DIPEA (0.181 ml, 1.041 mmol) dropwise. The reaction mixture was stirred at 60° C. for 35 min, and poured on ice. The aqueous layer was extracted with DCM. The organic layers were combined, dried with $Na_2SO_4$, filtered, and evaporated. The crude product was triturated with diethyl ether to afford the title compound (0.12 g). $^1$H NMR (400 MHz, Chloroform-d) δ ppm 7.85 (s, 1H), 7.11-7.18 (m, 3H), 6.56 (s, 1H), 4.17-4.24 (m, 1H), 3.98-4.04 (m, 4H), 3.79 (s, 2H), 2.47 (s, 3H).

Intermediate 164: 5-Hydroxy-2-((5-methylisoindolin-2-yl)methyl)-4H-pyran-4-one

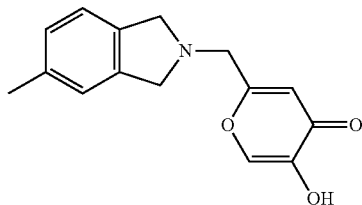 [SMILES: Cc1ccc2c(c1)CN(Cc1cc(=O)c(O)co1)C2]

A solution of 5-methylisoindoline (0.207 g, 1.557 mmol), 2-(chloromethyl)-5-hydroxy-4H-pyran-4-one (0.25 g, 1.557 mmol) and DIPEA (0.298 ml, 1.713 mmol) in DMSO (2 ml) was stirred at 75° C. for 1 h, and poured on water. The precipitation was filtered, washed with water, and dried to afford the title compound (0.28 g). $^1$H NMR (400 MHz, DMSO-$d_6$) δ ppm 8.98-9.12 (m, 1H), 8.06 (s, 1H), 7.10-7.13 (m, 1H), 7.05 (s, 1H), 6.97-7.02 (m, 1H), 6.41 (s, 1H), 3.90 (s, 4H), 3.77 (s, 2H), 2.28 (s, 3H).

Intermediate 165: 3-(Piperidin-4-yl)propan-1-ol, HCl

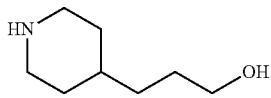

A suspension of 4-pyridinepropanol (3.29 g, 24 mmol), platinum (IV) oxide (0.545 g, 2.400 mmol), 37% HCl (6.00 ml, 24 mmol) and ethanol (35 ml) was shaked in a Parr apparatus under 8 kPa hydrogen pressure for 3.5 h. The reaction mixture was filtered, and the filtrate was evaporated to dryness to afford the title compound (5.80 g). $^1$H NMR (400 MHz, DMSO-$d_6$) δ ppm 9.09-9.32 (m, 1H), 8.85-9.09 (m, 1H), 3.35-3.40 (m, 2H), 3.15-3.23 (m, 2H), 2.73-2.84 (m, 2H), 1.71-1.80 (m, 2H), 1.27-1.51 (m, 5H), 1.19-1.25 (m, 2H).

Intermediate 166: 3-(1-(Methylsulfonyl)piperidin-4-yl)propyl methanesulfonate

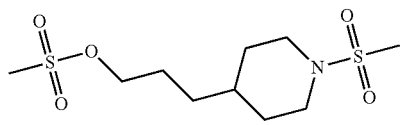

To a suspension of 3-(piperidin-4-yl)propan-1-ol-hydrochloride (1g, 5.57 mmol) and $K_2CO_3$ (3.31 g, 23.93 mmol) in ACN (10 ml) was added dropwise methanesylfonyl chloride (12.92 ml, 16.70 mmol) at 0° C. The reaction mixture was stirred at 30° C. for 1.5 h. The reaction mixture was filtered, and the filtrate was evaporated to dryness. The residue was stirred in brine, filtered, washed with brine and water, and dried to afford the title compound (0.68 g). $^1$H NMR (400 MHz, Chloroform-d) δ ppm 4.19-4.26 (m, 2H), 3.76-3.83 (m, 2H), 3.02 (s, 3H), 2.77 (s, 3H), 2.59-2.69 (m, 2H), 1.74-1.85 (m, 4H), 1.26-1.45 (m, 5H).

Intermediate 167: (1-Imino-1-oxidotetrahydro-2H-thiopyran-4-yl)methyl 4-methylbenzenesulfonate

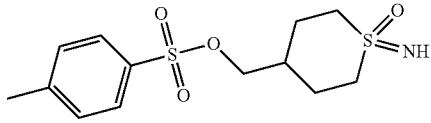 [SMILES: Cc1ccc(S(=O)(=O)OCC2CCS(=N)(=O)CC2)cc1]

A mixture of (1-oxido-1-(tosylimino)tetrahydro-2H-thiopyran-4-yl)methyl 4-methylbenzenesulfonate (0.4 g, 0.848 mmol) and sulfuric acid (1.260 ml, 25.4 mmol) was stirred at 20° C. for 2 h. Ice was added to the reaction mixture followed by the adjustment of pH to 10 with NaOH. The aqueous layer was extracted with DCM, and the organic layer was washed with brine, dried with $Na_2SO_4$, filtered, and evaporated to afford the title compound (0.23 g). $^1$H NMR (400 MHz, DMSO-$d_6$) δ ppm 7.77-7.81 (m, 2H), 7.47-7.51 (m, 2H), 3.90-3.97 (m, 2H), 3.66 (s, 1H), 2.87-3.05 (m, 4H), 2.43 (s, 3H), 1.80-1.99 (m, 3H), 1.49-1.64 (m, 2H).

Intermediate 168: (1-(Acetylimino)-1-oxidotetrahydro-2H-thiopyran-4-yl)-methyl 4-methylbenzenesulfonate

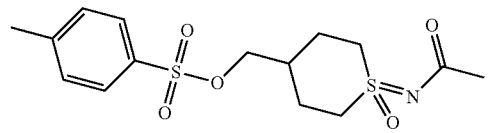 [SMILES: CC(=O)N=S1(=O)CCC(COS(=O)(=O)c2ccc(C)cc2)CC1]

To a solution of (1-imino-1-oxidotetrahydro-2H-thiopyran-4-yl)methyl 4-methylbenzenesulfonate (0.28 g, 0.882 mmol) and TEA (0.307 ml, 2.205 mmol) in DCM (10 ml) was added acetyl chloride (0.069 ml, 0.970 mmol) at 0° C. The reaction mixture was stirred at 0° C. for 3 h, washed with 1 M HCl, 1 M NaOH and brine. The organic layer was dried with $Na_2SO_4$, filtered, and evaporated to afford the title compound (0.31 g). LC-MS: m/z 360.2 (M+H)$^+$.

Intermediate 169: 2-((5-Hydroxy-4-oxo-4H-pyran-2-yl)methyl)-5-(trifluoro-methyl)isoindoline-1,3-dione

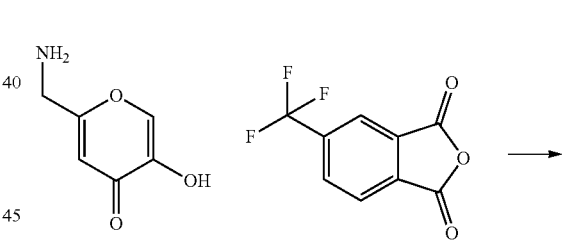

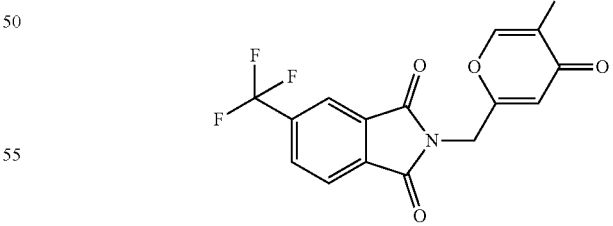

A solution of 2-(Aminomethyl)-5-hydroxy-4H-pyran-4-one (1.1 g, 7.91 mmol) and 5-(trifluoromethyl)isobenzofuran-1,3-dione (1.7 g, 7.91 mmol) in acetic acid (12 ml) was stirred by heating for 1 h. The reaction mixture was poured into water. The obtained precipitate was filtered and dried to afford 2.45 g of the title compound. LC-MS: m/z 340.1 (M+H)$^+$.

Intermediate 170: Mixture of 3-Hydroxy-2-((5-hydroxy-4-oxo-4H-pyran-2-yl)methyl)-5-(trifluoromethyl)isoindolin-1-one and 3-Hydroxy-2-((5-hydroxy-4-oxo-4H-pyran-2-yl)methyl)-6-(trifluoromethyl)isoindolin-1-one

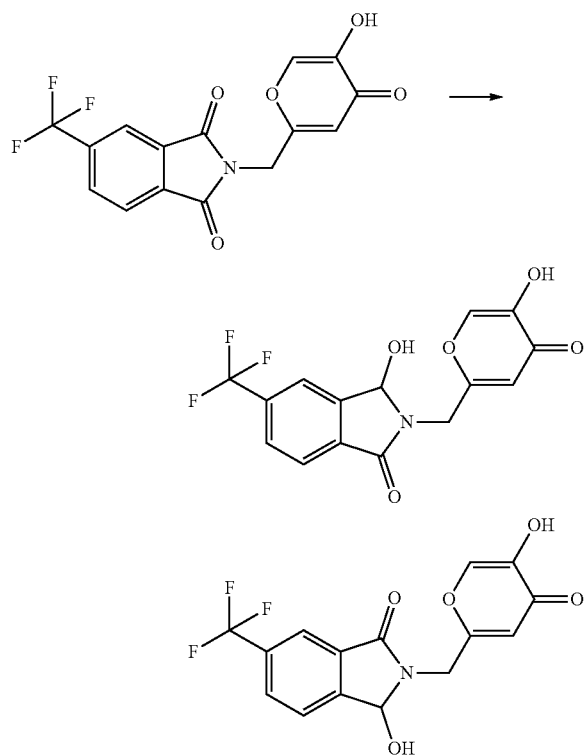

2-((5-Hydroxy-4-oxo-4H-pyran-2-yl)methyl)-5-(trifluoromethyl)isoindoline-1,3-dione 2.82 g, 8.31 mmol in methanol (50 ml) was treated with NaBH$_4$ (0.94 g, 24.94 mmol) at 0° C. for 1 h. After evaporation of solvent, water (20 ml) was added. The product was extracted EtOAc. The organic layer was washed with water, dried with Na$_2$SO$_4$, filtered and concentrated under reduced pressure. The crude product was purified by column chromatography to afford 1.2 g of the title mixture. LC-MS: m/z 342.1 (M+H)$^+$.

Intermediate 171: Mixture of 2-((5-Hydroxy-4-oxo-4H-pyran-2-yl)methyl)-5-(trifluoromethyl)isoindolin-1-one and 2-((5-Hydroxy-4-oxo-4H-pyran-2-yl)methyl)-6-(trifluoromethyl)isoindolin-1-one

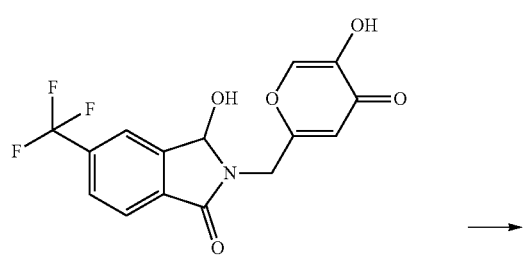

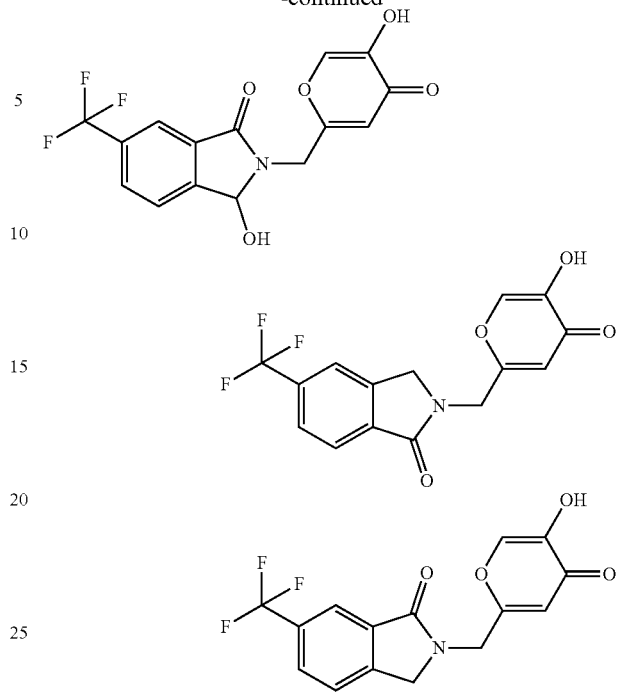

To a mixture of 3-hydroxy-2-((5-hydroxy-4-oxo-4H-pyran-2-yl)methyl)-5-(tri-fluoromethyl)isoindolin-1-one and 3-hydroxy-2-((5-hydroxy-4-oxo-4H-pyran-2-yl)methyl)-6-(trifluoromethyl)isoindolin-1-one (230 mg, 0.67 mmol) and triethylsilane (0.60 ml, 3.81 mmol) was added TFAA (5 ml) at 0° C. The mixture was stirred at RT for 2 h, then poured into water (10 ml) and basified with 2 M NaOH. The product was extracted with DCM. The organic layer was washed with water, dried with Na$_2$SO$_4$, filtered and concentrated under reduced pressure. The crude product was purified by column chromatography to afford 0.20 g of the title mixture. LC-MS: m/z 326.1 (M+H)$^+$.

Example 1

2-(Isoindolin-2-ylmethyl)-5-((4-(methylsulfonyl)benzyl)oxy)-4H-pyran-4-one (Compound 1)

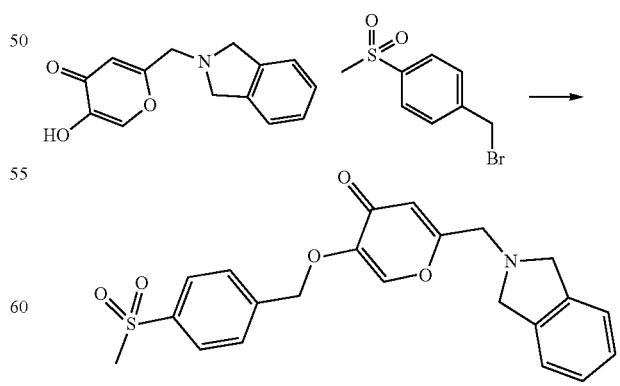

To a solution of 5-hydroxy-2-(isoindolin-2-ylmethyl)-4H-pyran-4-one (0.20 g, 0.82 mmol) in DMF (5 ml) were added 4-methylsulfonylbenzyl bromide (0.20 g, 0.82 mmol) and K$_2$CO$_3$ (0.23 g, 1.6 mmol). The reaction mixture was heated at 60° C. for 1 h. The mixture was cooled to RT, water (10 ml) was added and the product was extracted with EtOAc. The combined extracts were washed with water, dried with Na$_2$SO$_4$ filtered and evaporated. The crude product was purified by column chromatography to afford 0.21 g of the title compound. $^1$H NMR (Chloroform-d) δ: 7.95-7.98 (m, 2H), 7.62-7.65 (m, 3H), 7.21 (d, 4H), 6.52 (s, 1H), 5.18 (s, 2H), 4.04 (s, 4H), 3.77 (s, 2H), 3.06 (s, 3H). LC-MS: m/z 413.4 (M+H)$^+$.

The following compounds were prepared according to the procedure described for Compound 1 of Example 1 starting from 5-hydroxy-2-(isoindolin-2-ylmethyl)-4H-pyran-4-one or 5-hydroxy-2-((3,4-dihydroisoquinolin-2(1H)-yl)methyl)-4H-pyran-4-one or a derivative thereof and another appropriate starting material. The characterization data, starting material and possible deviations in reaction conditions (solvent, base, reaction temperature, reaction time, purification method), if any, are indicated on the table.

Purification Methods Used:
A=Crystallization
B=Column chromatography
C=Precipitation in aqueous media
D=Semipreparative HPLC
E=Trituration
F=Salt formation
G=As such

| No | Structure and starting material | Deviating reaction conditions/ $^1$H NMR (400 MHz)/LC-MS |
|---|---|---|
| 2 | 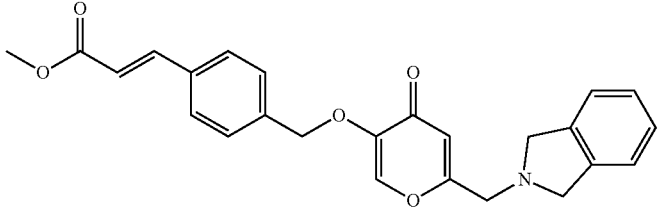 [SMILES: COC(=O)/C=C/c1ccc(COc2coc(CN3Cc4ccccc4C3)cc2=O)cc1]<br>Starting material: Methyl-p-bromo-methylcinnamate | $^1$H NMR (Chloroform-d) δ: 7.68 (d, 1H), 7.57 (s, 1H), 7.51-7.55 (m, 2H), 7.43 (d, 2H), 7.17-7.22 (m, 4H), 6.50 (s, 1H), 6.45 (d, 1H), 5.11 (s, 2H), 4.03 (s, 4H), 3.81 (s, 3H), 3.75 (s, 2H). LC-MS: m/z 419.6 (M + H)$^+$. |
| 3 | 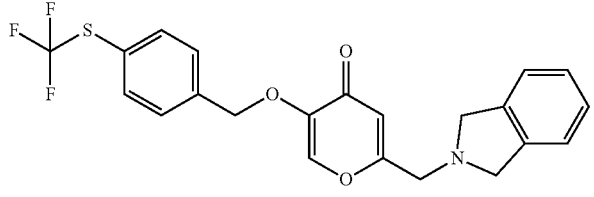 [SMILES: O=c1cc(CN2Cc3ccccc3C2)occ1OCc1ccc(SC(F)(F)F)cc1]<br>Starting material: 4-(Trifluoromethyl-thio)benzyl bromide | $^1$H NMR (Chloroform-d) δ: 7.66 (d, 2H), 7.59-7.62 (m, 1H), 7.59-7.62 (m, 1H), 7.48 (d, 2H), 7.18-7.26 (m, 4H), 6.51 (s, 1H), 5.12 (s, 2H), 4.04 (s, 4H). LC-MS: m/z 434.3 (M + H)$^+$. |
| 4 | 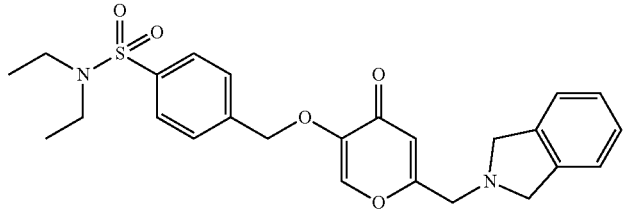 [SMILES: CCN(CC)S(=O)(=O)c1ccc(COc2coc(CN3Cc4ccccc4C3)cc2=O)cc1]<br>Starting material: 4-(Bromomethyl)-N,N-diethylbenzenesulfonamide | Conditions: THF, 80° C.<br>$^1$H NMR (Chloroform-d) δ: 7.79-7.83 (m, 2H), 7.62-7.64 (m, 1H), 7.53-7.57 (m, 2H), 7.19-7.22 (m, 4H), 6.52 (s, 1H), 5.13 (s, 2H), 4.04 (s, 4H), 3.77 (s, 2H), 3.20-3.27 (m, 4H), 1.11-1.16 (m, 6H). LCMS: m/z 469.4 (M + H)$^+$. |
| 5 | 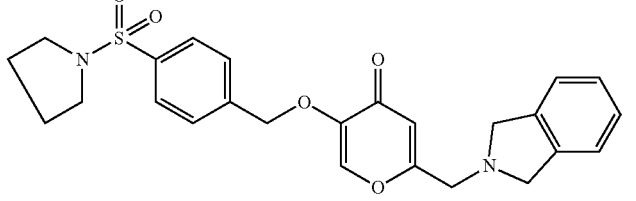<br>Starting material: 1-((4-(Bromo-methyl)phenyl)sulfonyl)pyrrolidine | Conditions: 80° C.<br>$^1$H NMR (Chloroform-d) δ: 7.84 (d, 2H), 7.64 (s, 1H), 7.59 (d, 2H), 7.19-7.25 (m, 4H), 6.53 (s, 1H), 5.14 (s, 2H), 4.05 (s, 4H), 3.78 (s, 2H), 3.21-3.29 (m, 4H), 1.72-1.82 (m, 4H). LC-MS: m/z 467.4 (M + H)$^+$. |

-continued

| No | Structure and starting material | Deviating reaction conditions/ $^1$H NMR (400 MHz)/LC-MS |
|---|---|---|
| 6 | 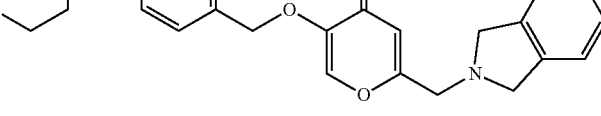
Starting material: 4-((4-(Bromo-methyl)phenyl)sulfonyl)morpholine | Conditions: 80° C.
$^1$H NMR (Chloroform-d) δ: 7.77 (br d, 2H), 7.60-7.67 (m, 3H), 7.18-7.25 (m, 4H), 6.53 (s, 1H), 5.17 (s, 2H), 4.05 (s, 4H), 3.76 (br d, 6H), 3.01 (br s, 4H). LC-MS: m/z 483.4 (M + H)$^+$. |
| 7 | 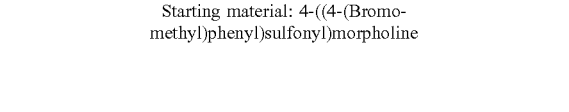
Starting material: 1-((4-(Bromo-methyl)phenyl)sulfonyl)piperidine | Conditions: 80° C.
$^1$H NMR (Chloroform-d) δ: 7.77 (d, 2H), 7.71 (s, 1H), 7.56 (d, 2H), 7.29-7.38 (m, 4H), 6.67 (s, 1H), 5.10 (s, 2H), 4.47-4.68 (m, 4H), 4.18 (br s, 2H), 2.95-3.03 (m, 4H), 1.65 (m, 4H), 1.44 (br d, 2H). LC-MS: m/z 481.4 (M + H)$^+$. |
| 8 | 
Starting material: 4-(Bromomethyl)-N-methylbenzenesulfonamide | Conditions: 80° C.
$^1$H NMR (Chloroform-d) δ: 7.85-7.88 (m, 2H), 7.63-7.65 (m, 1H), 7.56-7.60 (m, 2H), 7.18-7.22 (m, 4H), 6.53 (s, 1H), 5.14 (s, 2H), 4.71 (m, 1H), 4.04 (s, 4H), 3.77 (s, 2H), 2.66 (d, 3H). LCMS: m/z 427.3 (M + H)$^+$. |
| 9 | 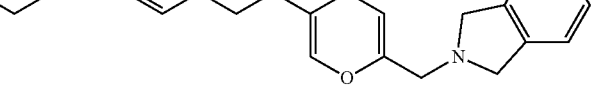
Starting material: 1-((4-(Bromo-methyl)phenyl)sulfonyl)azetidine | Conditions: 80° C.
$^1$H NMR (Chloroform-d) δ: 7.84-7.88 (m, 2H), 7.62-7.67 (m, 3H), 7.20-7.22 (m, 4H), 6.54 (s, 1H), 5.16 (s, 2H), 4.05 (s, 4H), 3.74-3.85 (m, 6H), 2.09 (m, 2H). LCMS: m/z 453.4 (M + H)$^+$. |
| 10 | 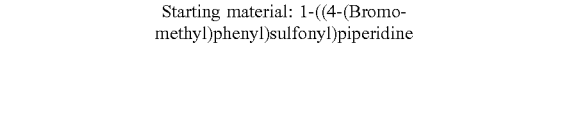
Starting material: 4-(Bromomethyl)-N,N-dimethylbenzenesulfonamide | Conditions: 80° C.
$^1$H NMR (DMSO-d$_6$) δ: 8.27 (s, 1H), 7.77-7.81 (m, 2H), 7.69 (d, 2H), 7.18-7.26 (m, 4H), 6.44 (s, 1H), 5.08 (s, 2H), 3.96 (s, 4H), 3.81 (s, 2H), 2.61 (s, 6H). LCMS: m/z 441.3 (M + H)$^+$. |

| No | Structure and starting material | Deviating reaction conditions/ ¹H NMR (400 MHz)/LC-MS |
|---|---|---|
| 11 | 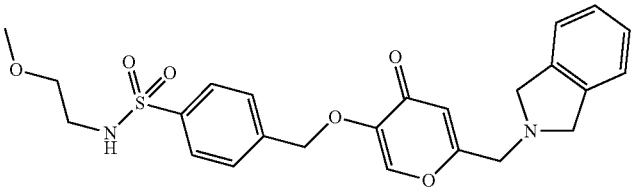 [SMILES: COCCNS(=O)(=O)c1ccc(COc2coc(CN3Cc4ccccc4C3)cc2=O)cc1]<br>Starting material: 4-(Bromomethyl)-N-(2-methoxyethyl) benzenesulfonamide | Conditions: 80° C.<br>¹H NMR (Chloroform-d) δ: 7.85-7.88 (m, 2H), 7.64 (s, 1H), 7.57 (d, 2H), 7.19-7.22 (m, 4H), 6.53 (s, 1H), 5.08-5.15 (m, 3H), 4.04 (s, 4H), 3.77 (s, 2H), 3.40 (m, 2H), 3.26 (s, 3H), 3.07-3.15 (m, 2H). LCMS: m/z 471.3 (M + H)⁺. |
| 12 | 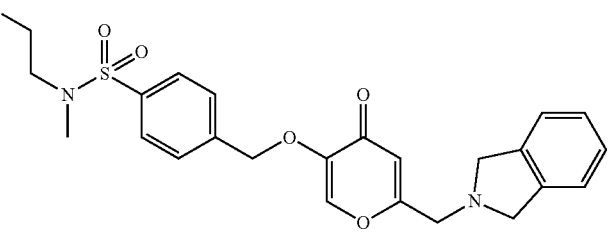<br>Starting material: 4-(Bromomethyl)-N-(2-hydroxyethyl)-N-methylbenzene-sulfonamide | Conditions: 80° C.<br>¹H NMR (Chloroform-d) δ: 7.80-7.83 (m, 2H), 7.64 (s, 1H), 7.58-7.62 (m, 2H), 7.20-7.22 (m, 4H), 6.53 (s, 1H), 5.14 (s, 2H), 4.04 (s, 4H), 3.74-3.79 (m, 5H), 3.15-3.20 (m, 3H), 2.85 (s, 3H). LCMS: m/z 371.3 (M + H)⁺. |
| 13 | 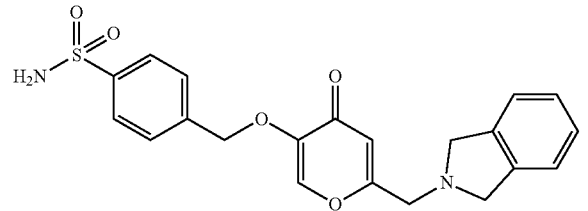 [SMILES: NS(=O)(=O)c1ccc(COc2coc(CN3Cc4ccccc4C3)cc2=O)cc1]<br>Starting material: 4-(Bromomethyl)-benzenesulfonamide | Conditions: 80° C.<br>¹H NMR (Chloroform-d) δ: 7.93-7.96 (m, 2H), 7.61 (s, 1H), 7.58 (d, 2H), 7.21 (d, 4H), 6.52 (s, 1H), 5.17 (s, 2H), 4.76 (s, 2H), 4.04 (s, 4H), 3.77 (s, 2H). LCMS: m/z 413.3 (M + H)⁺. |
| 14 | 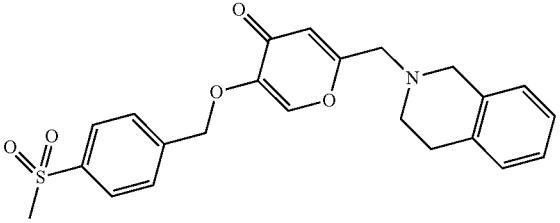 [SMILES: CS(=O)(=O)c1ccc(COc2coc(CN3CCc4ccccc4C3)cc2=O)cc1]<br>Starting material: 4-Methylsulfonyl-benzyl bromide | ¹H NMR (Chloroform-d) δ: 7.96 (d, 2H), 7.61-7.66 (m, 3H), 6.97-7.17 (m, 4H), 6.53 (s, 1H), 5.18 (s, 2H), 3.71 (s, 2H), 3.55 (s, 2H), 3.05 (s, 3H), 2.80-2.97 (m, 4H). LCMS: m/z 426.4 (M + H)⁺. |
| 15 | 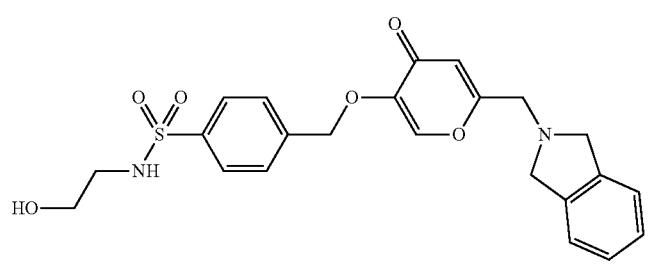 [SMILES: O=c1cc(CN2Cc3ccccc3C2)occ1OCc1ccc(S(=O)(=O)NCCO)cc1]<br>Starting material: 4-(Bromomethyl)-N-(2-hydroxyethyl)benzenesulfonamide | ¹H NMR (Chloroform-d) δ: 7.85-7.94 (m, 2H), 7.75 (br d, 1H), 7.60 (br d, 2H), 7.23 (br s, 4H), 6.55 (br d, 1H), 5.12 (br d, 2H), 4.06 (br d, 4H), 3.81 (br d, 2H), 3.60 (br d, 2H), 3.38 (br d, 1H), 2.97-3.12 (m, 2H). LCMS: m/z 457.4 (M + H)⁺. |

-continued

| No | Structure and starting material | Deviating reaction conditions/ $^1$H NMR (400 MHz)/LC-MS |
|---|---|---|
| 16 | 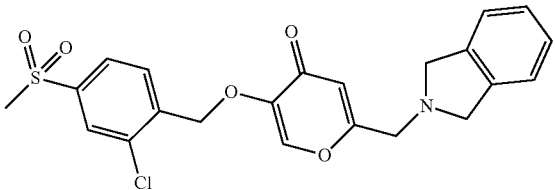 [SMILES: CS(=O)(=O)c1ccc(COc2coc(CN3Cc4ccccc4C3)cc2=O)c(Cl)c1]<br>Starting material: 1-(Bromomethyl)-2-chloro-4-(methylsulfonyl)benzene | $^1$H NMR (Chloroform-d) δ: 7.96-8.00 (m, 1H), 7.88 (d, 2H), 7.71 (s, 1H), 7.19-7.23 (m, 4H), 6.54 (s, 1H), 5.24 (s, 2H), 4.05 (s, 4H), 3.79 (s, 2H), 3.07 (s, 3H). LCMS: m/z 446.4 (M + H)$^+$. |
| 17 | 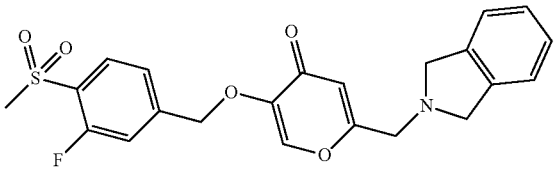 [SMILES: CS(=O)(=O)c1ccc(COc2coc(CN3Cc4ccccc4C3)cc2=O)cc1F]<br>Starting material: 4-(Bromomethyl)-2-fluoro-1-(methylsulfonyl)benzene | $^1$H NMR (Chloroform-d) δ: 7.97 (m, 1H), 7.67 (s, 1H), 7.33-7.41 (m, 2H), 7.20-7.22 (m, 4H), 6.53 (s, 1H), 5.18 (s, 2H), 4.05 (s, 4H), 3.78 (s, 2H), 3.22 (s, 3H). LC-MS: m/z 430.4 (M + H)$^+$. |
| 18 | 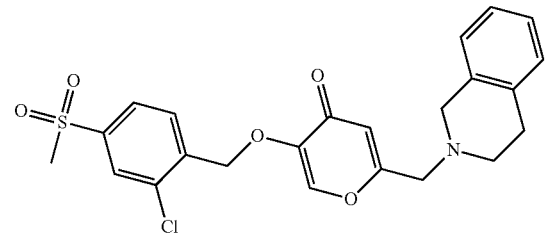 [SMILES: CS(=O)(=O)c1ccc(COc2coc(CN3CCc4ccccc4C3)cc2=O)c(Cl)c1]<br>Starting material: 1-(Bromomethyl)-2-chloro-4-(methylsulfonyl)benzene | $^1$H NMR (Chloroform-d) δ: 7.97 (m, 1H), 7.87 (d, 2H), 7.70 (s, 1H), 6.96-7.18 (m, 4H), 6.55 (s, 1H), 5.24 (s, 2H), 3.72 (s, 2H), 3.57 (s, 2H), 3.07 (s, 3H), 2.81-3.06 (m, 4H). LCMS: m/z 460.4 (M + H)$^+$. |
| 19 | 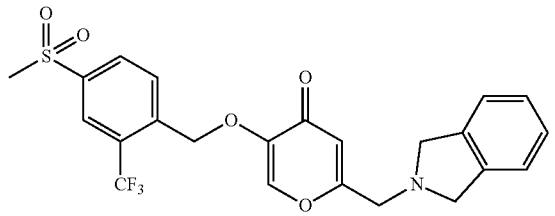 [SMILES: CS(=O)(=O)c1ccc(COc2coc(CN3Cc4ccccc4C3)cc2=O)c(C(F)(F)F)c1]<br>Starting material: 4-(Methylsulfonyl)-2-(trifluoromethyl)benzyl bromide | $^1$H NMR (Chloroform-d) δ: 8.25 (s, 1H), 8.10-8.20 (m, 2H), 7.69 (s, 1H), 7.19-7.22 (m, 4H), 6.55 (s, 1H), 5.33 (s, 2H), 4.05 (s, 4H), 3.79 (s, 2H), 3.10 (s, 3H). LCMS: m/z 380.4 (M + H)$^+$. |
| 20 | 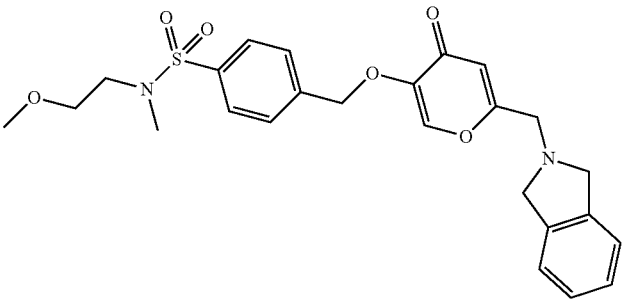 [SMILES: COCCN(C)S(=O)(=O)c1ccc(COc2coc(CN3Cc4ccccc4C3)cc2=O)cc1]<br>Starting material: 4-(Bromomethyl)-N-(2-methoxyethyl)-N-methylbenzene-sulfonamide | Conditions: 50° C.<br>$^1$H NMR (Chloroform-d) δ: 7.80 (d, 2H), 7.63 (s, 1H), 7.58 (d, 2H), 7.18-7.24 (m, 4H), 6.53 (s, 1H), 5.14 (s, 2H), 4.04 (s, 4H), 3.77 (s, 2H), 3.55 (m, 2H), 3.32 (s, 3H), 3.23 (m, 2H), 2.85 (s, 3H). LCMS: m/z 485.6 (M + H)$^+$. |

| No | Structure and starting material | Deviating reaction conditions/ $^1$H NMR (400 MHz)/LC-MS |
|---|---|---|
| 21 | 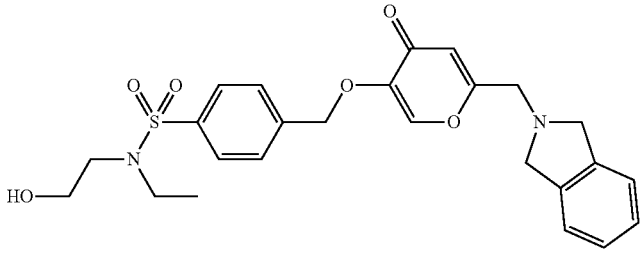 [SMILES: CCN(CCO)S(=O)(=O)c1ccc(COc2coc(CN3Cc4ccccc4C3)cc2=O)cc1]<br>Starting material: 4-(Bromomethyl)-N-ethyl-N-(2-hydroxyethyl)benzene-sulfonamide | Conditions: 50° C.<br>$^1$H NMR (Chloroform-d) δ: 7.82 (d, 2H), 7.66 (s, 1H), 7.57 (d, 2H), 7.17-7.23 (m, 4H), 6.52 (s, 1H), 5.11 (s, 2H), 4.03 (s, 4H), 3.77 (s, 2H), 3.73 (m, 2H), 3.23-3.31 (m, 4H), 1.13 (m, 3H). LC-MS: m/z 485.6 (M + H)$^+$. |
| 22 | 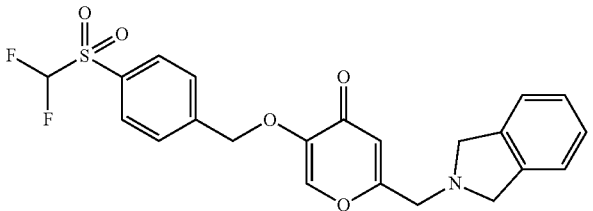 [SMILES: O=c1cc(CN2Cc3ccccc3C2)occ1OCc1ccc(S(=O)(=O)C(F)F)cc1]<br>Starting material: 1-(Bromomethyl)-4-[(difluoromethyl)sulfonyl]benzene | Conditions: 50° C.<br>$^1$H NMR (Chloroform-d) δ: 8.00 (d, 2H), 7.72 (d, 2H), 7.68 (s, 1H), 7.18-7.24 (m, 4H), 6.54 (s, 1H), 6.05-6.36 (m, 1H), 5.23 (s, 2H), 4.05 (s, 4H), 3.78 (s, 2H). LCMS: m/z 448.5 (M + H)$^+$. |
| 23 | 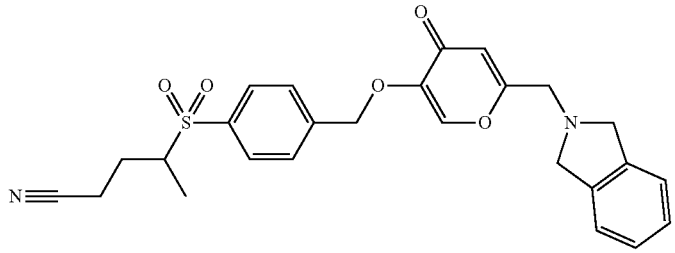 [SMILES: CC(CCC#N)S(=O)(=O)c1ccc(COc2coc(CN3Cc4ccccc4C3)cc2=O)cc1]<br>Starting material: 4-(Bromomethyl)-N-(2-cyanoethyl)-N-methylbenzene-sulfonamide | Conditions: 50° C.<br>$^1$H NMR (Chloroform-d) δ: 7.80 (d, 2H), 7.68 (s, 1H), 7.62 (d, 2H), 7.17-7.24 (m, 4H), 6.52 (s, 1H), 5.13 (s, 2H), 4.04 (s, 4H), 3.77 (s, 2H), 3.33 (m, 2H), 2.88 (s, 3H), 2.67 (m, 2H). LCMS: m/z 480.5 (M + H)$^+$. |
| 24 | 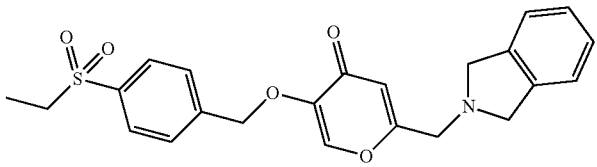 [SMILES: CCS(=O)(=O)c1ccc(COc2coc(CN3Cc4ccccc4C3)cc2=O)cc1]<br>Starting material: 1-(Bromomethyl)-4-(ethylsulfonyl)benzene | Conditions: 50° C.<br>$^1$H NMR (Chloroform-d) δ: 7.90-7.94 (m, 2H), 7.60-7.67 (m, 3H), 7.18-7.24 (m, 4H), 6.53 (s, 1H), 5.18 (s, 2H), 4.04 (s, 4H), 3.77 (s, 2H), 3.12 (m, 2H), 1.28 (m, 3H). LCMS: m/z 426.5 (M + H)$^+$. |
| 25 | 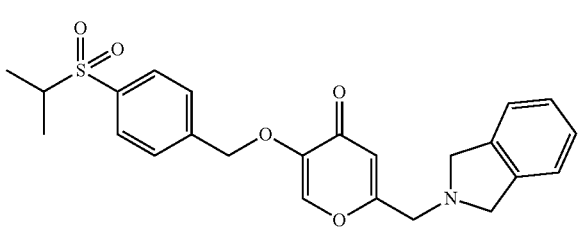 [SMILES: CC(C)S(=O)(=O)c1ccc(COc2coc(CN3Cc4ccccc4C3)cc2=O)cc1]<br>Starting material: 1-(Bromomethyl)-4-(propane-2-sulfonyl)benzene | Conditions: 50° C.<br>$^1$H NMR (Chloroform-d) δ: 7.87-7.92 (m, 2H), 7.60-7.65 (m, 3H), 7.18-7.22 (m, 4H), 6.53 (s, 1H), 5.17 (s, 2H), 4.04 (s, 4H), 3.77 (s, 2H), 3.14-3.24 (m, 1H), 1.30 (d, 6H).<br>LC-MS: m/z 440.5 (M + H)$^+$. |

| No | Structure and starting material | Deviating reaction conditions/ $^1$H NMR (400 MHz)/LC-MS |
|---|---|---|
| 26 | Starting material: 4-Methylsulfonyl-benzyl bromide | Conditions: 50° C.<br>$^1$H NMR (Chloroform-d) δ: 7.96 (d, 2H), 7.61-7.66 (m, 3H), 7.00 (m, 2H), 6.50 (s, 1H), 5.18 (s, 2H), 3.99 (s, 4H), 3.75 (s, 2H), 3.06 (s, 3H). LC-MS: m/z 448.4 (M + H)$^+$. |
| 27 | Starting material: 4-Methylsulfonylbenzyl bromide | Conditions: 50° C.<br>$^1$H NMR (Chloroform-d) δ: 7.94-7.99 (m, 2H), 7.62-7.66 (m, 3H), 7.17-7.26 (m, 1H), 6.87-7.01 (m, 2H), 6.52 (s, 1H), 5.18 (s, 2H), 4.09 (d, 4H), 3.78 (s, 2H), 3.06 (s, 3H). LCMS: m/z 430.4 (M + H)$^+$. |
| 28 | Starting material: 1-(Bromomethyl)-4-((2-methoxyethyl)sulfonyl)benzene | Conditions: 50° C.<br>$^1$H NMR (Chloroform-d) δ: 7.91-7.95 (m, 2H), 7.60-7.65 (m, 3H), 7.19-7.23 (m, 4H), 6.53 (s, 1H), 5.18 (s, 2H), 4.04 (s, 4H), 3.71-3.79 (m, 4H), 3.39 (m, 2H), 3.24 (s, 3H). LC-MS: m/z 456.5 (M + H)$^+$. |
| 29 | Starting material: 1-(Bromomethyl)-4-((2-methoxyethyl)sulfonyl)benzene | Conditions: 50° C.<br>$^1$H NMR (Chloroform-d) δ: 7.93 (d, 2H), 7.60-7.65 (m, 3H), 7.10-7.17 (m, 1H), 6.87-6.94 (m, 2H), 6.52 (s, 1H), 5.18 (s, 2H), 4.01 (br d, 4H), 3.72-3.78 (m, 4H), 3.39 (m, 2H), 3.24 (s, 3H). LC-MS: m/z 474.5 (M + H)$^+$. |
| 30 | Starting material: 3-(Bromomethyl)-1-((5-chlorothiophen-3-yl)sulfonyl)-azetidine | Conditions: 50° C.<br>$^1$H NMR (Chloroform-d) δ: 7.63 (s, 1H), 7.43 (d, 1H), 7.20-7.22 (m, 4H), 7.02 (d, 1H), 6.48 (s, 1H), 4.05 (s, 4H), 3.98-4.01 (m, 2H), 3.97 (s, 2H), 3.81 (m, 2H), 3.78 (s, 2H), 2.81-2.97 (m, 1H). LCMS: m/z 493.4 (M + H)$^+$. |

| No | Structure and starting material | Deviating reaction conditions/ $^1$H NMR (400 MHz)/LC-MS |
|---|---|---|
| 31 | 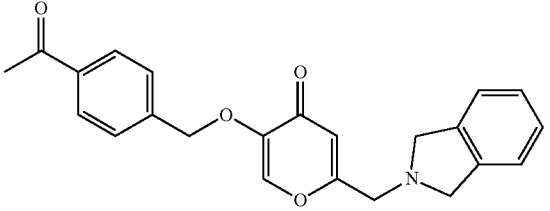 [SMILES: CC(=O)c1ccc(COc2coc(CN3Cc4ccccc4C3)cc2=O)cc1]<br>Starting material: 1-[4-(Bromomethyl)-phenyl]ethanone | Conditions: DMSO, 80° C.<br>$^1$H NMR (Chloroform-d) δ: 7.94-7.99 (m, 2H), 7.58 (s, 1H), 7.51 (d, 2H), 7.14-7.23 (m, 4H), 6.51 (s, 1H), 5.15 (s, 2H), 4.03 (s, 4H), 3.75 (s, 2H), 2.61 (d, 3H). LCMS: m/z 376.46 (M + H)$^+$. |
| 32 | 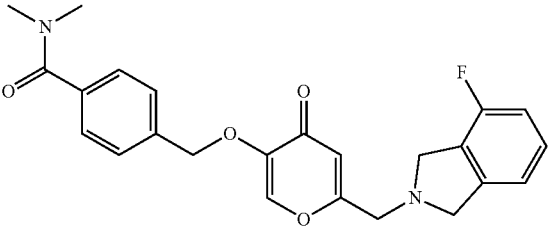 [SMILES: CN(C)C(=O)c1ccc(COc2coc(CN3Cc4cccc(F)c4C3)cc2=O)cc1]<br>Starting material: 4-(Bromomethyl)-N,N-dimethyl-benzamide | Conditions: 50° C.<br>1H NMR (Chloroform-d) δ: 7.57 (s, 1H), 7.46-7.41 (m, 4H), 7.22-7.17 (m, 1H), 6.68 (d, J = 7.4 Hz, 1H), 6.92-6.88 m, 1H), 6.50 (s, 1H), 5.11 (s, 2H), 4.11-4.05 (m, 4H), 3.76 (d, J = 0.52 Hz, 2H), 3.11 (s, 3H), 2.97 (s, 3H); LC-MS: m/z 423.1 (M + 1)+. |
| 33 | 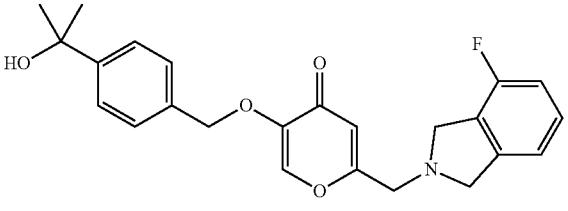 [SMILES: CC(C)(O)c1ccc(COc2coc(CN3Cc4cccc(F)c4C3)cc2=O)cc1]<br>Starting materials: 4-(Bromomethyl)-α,α-dimethylbenzenemethanol | Conditions: 50° C.<br>1H NMR (Chloroform-d) δ: 7.57 (s, 1H), 7.51-7.48 (m, 2H), 7.39-7.36 (m, 2H), 7.27-7.17 (m, 1H), 6.98 (d, J = 7.4 Hz, 1H), 6.92-6.87 (m, 1H), 6.49 (s, 1H), 5.07 (s, 2H), 4.11-4.05 (m, 4H), 3.76 (s, 2H), 1.70 (s, 1H), 1.54 (s, 6H); LC-MS: m/z 410.1 (M + 1)+. |
| 34 | 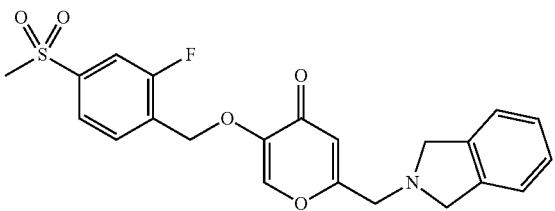 [SMILES: CS(=O)(=O)c1ccc(COc2coc(CN3Cc4ccccc4C3)cc2=O)c(F)c1]<br>Starting material: 1-(Bromomethyl)-2-fluoro-4-(methylsulfonyl)benzene | Conditions: B and E (EtOH)<br>1H NMR (Chloroform-d) δ: 7.79 (m, 2 H), 7.70 (s, 1 H), 7.67 (m, 1 H), 7.21 (m, 4 H), 6.53 (s, 1 H), 5.23 (s, 2 H), 4.05 (s, 4 H), 3.78 (s, 2 H), 3.07 (s, 3 H); LC-MS: m/z 430.2 (M + 1)+. |
| 35 | 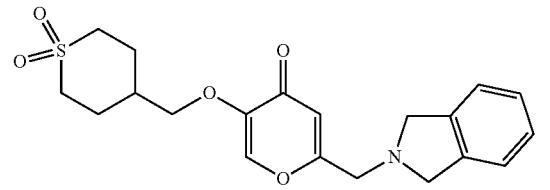 [SMILES: O=c1cc(CN2Cc3ccccc3C2)occ1OCC1CCS(=O)(=O)CC1]<br>Starting material: 4-(Bromomethyl)-tetrahydro-2H-thiopyran 1,1-dioxide | 1H NMR (Chloroform-d) δ: 7.63 (s, 1 H), 7.21 (m, 4 H), 6.50 (s, 1 H), 4.05 (s, 4 H), 3.80 (d, 2 H), 3.78 (s, 2 H), 3.11 (m, 2 H), 3.02 (m, 2 H), 2.31 (m, 2 H), 2.12 (m, 1 H), 1.97 (m, 2 H); LC-MS: m/z 390.3 (M + 1)+. |

| No | Structure and starting material | Deviating reaction conditions/ $^1$H NMR (400 MHz)/LC-MS |
|---|---|---|
| 36 | 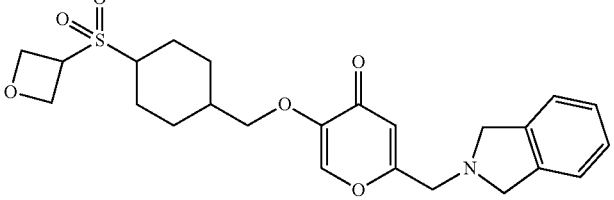<br>Starting material: 4-(Bromomethyl)-1-(oxetan-3-ylsulfonyl)piperidine | 1H NMR (Chloroform-d) δ: 7.60 (s, 1 H), 7.21 (m, 4 H), 6.49 (s, 1 H), 4.94 (m, 2 H), 4.87 (m, 2 H), 4.42 (tt, 1 H), 4.04 (s, 4 H), 3.88 (br d, 2 H), 3.77 (s, 2 H), 3.74 (d, 2 H), 2.82 (td, 2 H), 2.00 (m, 3 H), 1.38 (br dd, 2 H); LC-MS: m/z 461.3 (M + 1)+. |
| 37 | 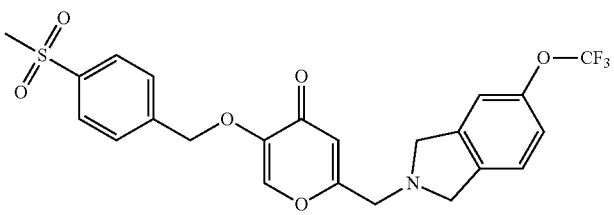 [SMILES: CS(=O)(=O)c1ccc(COc2coc(CN3Cc4ccc(OC(F)(F)F)cc4C3)cc2=O)cc1]<br>Starting material: 4-Methylsulfonyl-benzyl bromide | Conditions: DMSO, C and A (EtOH). 1H NMR (Chloroform-d) δ: 7.96 (d, 2H), 7.64 (d, 2H), 7.63 (s, 1H), 7.21 (d, 1H), 7.10-7.06 (m, 2H), 6.52 (s, 1H), 5.18 (s, 2H), 4.05 (s, 2H), 4.03 (s, 2H), 3.77 (s, 2H), 3.06 (s, 3H); LC-MS: m/z 496.4 (M + 1)+. |
| 38 | 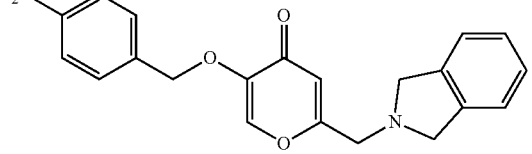<br>Starting material: 1-(Bromomethyl)-4-nitrobenzene | Conditions: 60° C., C.<br>$^1$H NMR (Chloroform-d) δ: 8.21-8.27 (m, 2H), 7.65 (s, 1H), 7.61 (m, 2H), 7.17-7.24 (m, 4H), 6.53 (s, 1H), 5.21 (s, 2H), 4.04 (s, 4H), 3.77 (s, 2H). LC-MS: m/z 379.5 (M + H)+. |
| 39 | 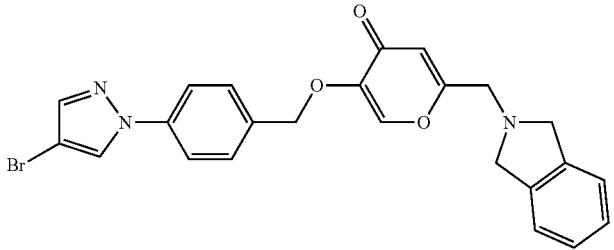 [SMILES: O=c1cc(CN2Cc3ccccc3C2)occ1OCc1ccc(-n2cc(Br)cn2)cc1]<br>Starting material: 4-Bromo-1-(4-(bromomethyl)phenyl)-1H-pyrazole | $^1$H NMR (Chloroform-d) δ: 7.94 (d, 1H), 7.62-7.68 (m, 3H), 7.59 (s, 1H), 7.48-7.54 (m, 2H), 7.15-7.25 (m, 4H), 6.51 (s, 1H), 5.12 (s, 2H), 4.03 (s, 4H), 3.75 (s, 2H). LC-MS: m/z 478.9 (M + H)+. |
| 40 | 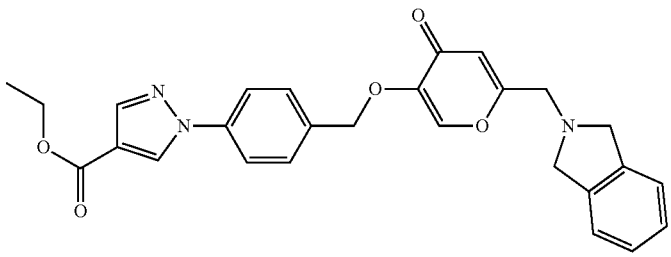 [SMILES: CCOC(=O)c1cnn(-c2ccc(COc3coc(CN4Cc5ccccc5C4)cc3=O)cc2)c1]<br>Starting material: Ethyl 1-(4-(bromo-methyl)phenyl)-1H-pyrazole-4-carboxylate | $^1$H NMR (Chloroform-d) δ: 8.41 (s, 1H), 8.10 (s, 1H), 7.68-7.77 (m, 2H), 7.60 (s, 1H), 7.49-7.57 (m, 2H), 7.15-7.24 (m, 4H), 6.51 (s, 1H), 5.14 (s, 2H), 4.34 (q, 2H), 4.03 (s, 4H), 3.76 (s, 2H), 1.38 (t, 3H). LC-MS: m/z 472.6 (M + H)+. |

-continued

| No | Structure and starting material | Deviating reaction conditions/ $^1$H NMR (400 MHz)/LC-MS |
|---|---|---|
| 41 | 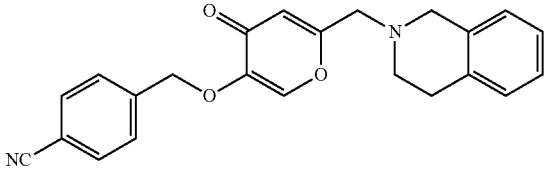 [SMILES: N#Cc1ccc(COc2coc(CN3CCc4ccccc4C3)cc2=O)cc1]  Starting material: 4-(Bromomethyl) benzonitrile | Conditions: MeOH:water, NaOH, reflux, B and E. 1H NMR (Chloroform-d) δ: 7.65-7.70 (m, 2 H), 7.63 (s, 1 H), 7.52-7.56 (m, 2 H), 7.09-7.18 (m, 3 H), 6.96-7.02 (m, 1 H), 6.53 (s, 1 H), 5.14 (s, 2 H), 3.71 (s, 2 H), 3.54-3.56 (m, 2 H), 2.89-2.96 (m, 2 H), 2.80-2.86 (m, 2 H), 1.57 (s, 3 H); LC-MS: m/z 373.4 (M + H)$^+$. |
| 42 | 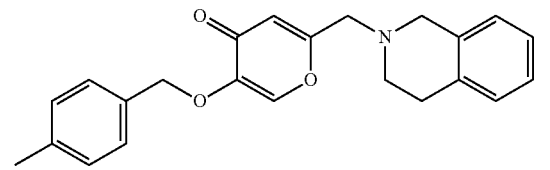 [SMILES: Cc1ccc(COc2coc(CN3CCc4ccccc4C3)cc2=O)cc1]  Starting material: 1-(Bromomethyl)-4-methylbenzene | Conditions: THF, reflux, B and A. 1H NMR (DMSO-d6) δ: 8.19 (s, 1 H), 7.30 (m, J = 7.7 Hz, 2 H), 7.20 (m, J = 7.6 Hz, 2 H), 7.07-7.14 (m, 3 H), 6.98-7.07 (m, 1 H), 6.40 (s, 1 H), 4.89 (s, 2 H), 3.60 (br d, 4 H), 2.66-2.87 (m, 4 H), 2.31 (s, 3 H); LC-MS: m/z 362.4 (M + H)+. |
| 43 | 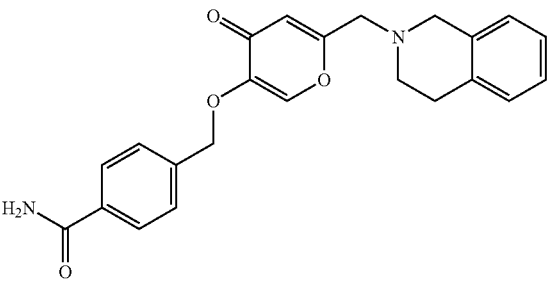 [SMILES: NC(=O)c1ccc(COc2coc(CN3CCc4ccccc4C3)cc2=O)cc1]  Starting material: 4-(Bromomethyl) benzamide | Conditions: THF, reflux, A. 1H NMR (Chloroform-d) δ: 7.82 (m, 2 H), 7.58 (s, 1 H), 7.49 (m, 2 H), 7.08-7.17 (m, 3 H), 6.94-7.04 (m, 1 H), 6.52 (s, 1 H), 5.98-6.32 (m, 1 H), 5.54-5.86 (m, 1 H), 5.13 (s, 2 H), 3.70 (s, 2 H), 3.53 (s, 2 H), 2.88-2.96 (m, 2 H), 2.77-2.87 (m, 2 H); LC-MS: m/z 391.3 (M + H)+. |
| 44 | 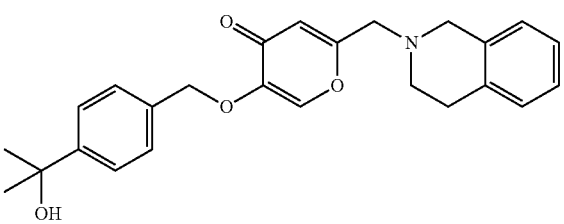 [SMILES: CC(C)(O)c1ccc(COc2coc(CN3CCc4ccccc4C3)cc2=O)cc1]  Starting material: 4-(Bromomethyl)-α,α-dimethylbenzenemethanol | Conditions: THF, reflux, B and E. 1H NMR (Chloroform-d) δ: 7.56 (s, 1 H), 7.47-7.51 (m, 2 H), 7.35-7.40 (m, 2 H), 7.04-7.17 (m, 4 H), 6.99 (d, J = 6.6 Hz, 1 H), 6.50 (s, 1 H), 5.06 (s, 2 H), 3.69 (s, 2 H), 3.52 (s, 2 H), 2.87-2.97 (m, 2 H), 2.77-2.86 (m, 2 H); LC-MS: m/z 406.4 (M + H)+. |
| 45 | 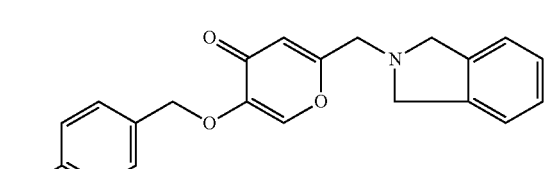  Starting material: 4-(Bromomethyl) benzonitrile | Conditions: THF, reflux. 1H NMR (Chloroform-d) δ ppm 7.64-7.69 (m, 2 H), 7.63 (s, 1 H), 7.52-7.56 (m, 2 H), 7.11-7.23 (m, 4 H), 6.52 (s, 1 H), 5.14 (s, 2 H), 4.04 (s, 4 H), 3.77 (s, 2 H); LC-MS: m/z 359.2 (M + H)+. |

-continued

| No | Structure and starting material | Deviating reaction conditions/ $^1$H NMR (400 MHz)/LC-MS |
|---|---|---|
| 46 | 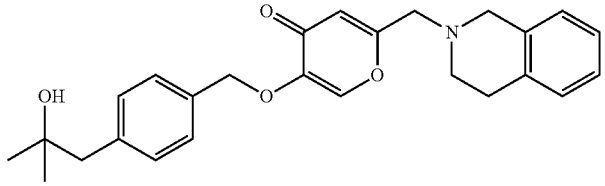 [SMILES: CC(C)(O)Cc1ccc(COc2coc(CN3CCc4ccccc4C3)cc2=O)cc1]<br>Starting material: 1-(4-(Bromomethyl)-phenyl)-2-methylpropan-2-ol | Conditions: THF, reflux. 1H NMR (Chloroform-d) δ: 7.58 (s, 1 H), 7.31-7.38 (m, 2 H), 7.20-7.25 (m, 1 H), 7.07-7.17 (m, 3 H), 6.99 (d, J = 6.6 Hz, 1 H), 6.50 (s, 1 H), 5.04 (s, 2 H), 3.69 (s, 2 H), 3.53 (s, 2 H), 2.87-2.96 (m, 2 H), 2.78-2.86 (m, 2 H), 2.76 (s, 2 H), 1.39 (s, 1 H), 1.19-1.23 (m, 6 H); LC-MS: m/z 420.4 (M + H)+. |
| 47 | 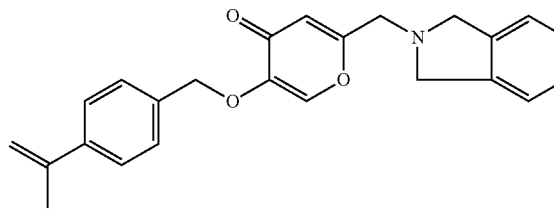<br>Starting material: 2-(4-(Bromomethyl)-phenyl)propan-2-ol | Conditions: THF, reflux, D.<br>1H NMR (Chloroform-d) δ: 7.55 (s, 1 H), 7.41-7.49 (m, 1 H), 7.33-7.40 (m, 1 H), 7.16-7.24 (m, 4 H), 6.49 (s, 1 H), 5.37 (s, 1 H), 5.05-5.12 (m, 3 H), 4.02 (s, 4 H), 3.74 (s, 2 H), 2.14 (s, 3 H), 1.51-1.68 (m, 2 H); LC-MS: m/z 374.8 (M + H)+. |
| 48 | 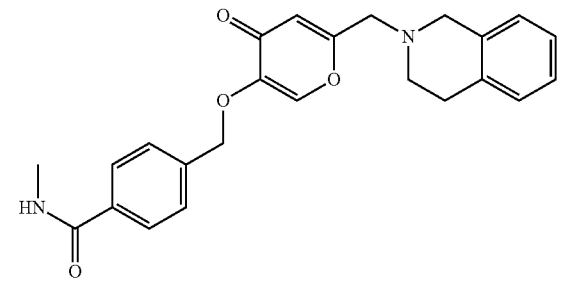 [SMILES: CNC(=O)c1ccc(COc2coc(CN3CCc4ccccc4C3)cc2=O)cc1]<br>Starting material: 4-(Bromomethyl)-N-methylbenzamide | Conditions: THF/DMF, reflux, C.<br>1H NMR (Chloroform-d) δ: 7.69-7.82 (m, 2 H), 7.57 (s, 1 H), 7.41-7.52 (m, 2 H), 7.07-7.18 (m, 3 H), 6.93-7.02 (m, 1 H), 6.51 (s, 1 H), 6.09-6.24 (m, 1 H), 5.12 (s, 2 H), 3.70 (s, 2 H), 3.53 (s, 2 H), 3.01 (d, J = 4.9 Hz, 3 H), 2.88-2.96 (m, 2 H), 2.79-2.86 (m, 2 H); LC-MS: m/z 405.4 (M + H)+. |
| 49 | 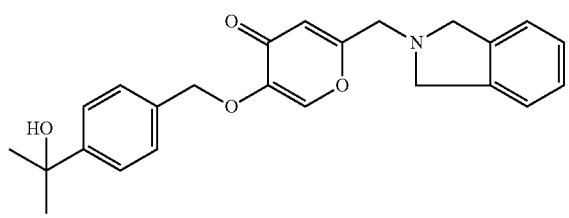 [SMILES: CC(C)(O)c1ccc(COc2coc(CN3Cc4ccccc4C3)cc2=O)cc1]<br>Starting material: 4-(Bromomethyl)-α,α-dimethylbenzenemethanol | Conditions: 70° C. 1H NMR (Chloroform-d) δ: 7.56 (s, 1 H), 7.49 (m, J = 8.4 Hz, 2 H), 7.37 (m, J = 8.5 Hz, 2 H), 7.17-7.23 (m, 4 H), 6.49 (s, 1 H), 5.06 (s, 2 H), 4.02 (s, 4 H), 3.74 (s, 2 H), 1.57 (s, 6 H); LC-MS: m/z 392.5 (M + H)+. |
| 50 | 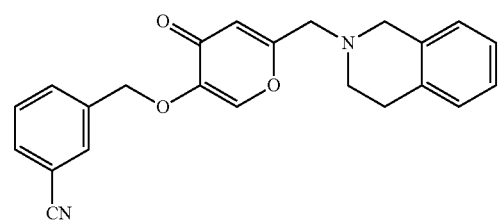 [SMILES: N#Cc1cccc(COc2coc(CN3CCc4ccccc4C3)cc2=O)c1]<br>Starting material: 3-(Bromomethyl)benzonitrile | Conditions: THF, reflux, C.<br>1H NMR (Chloroform-d) δ: 7.71-7.75 (m, 1 H), 7.66-7.70 (m, 1 H), 7.59-7.66 (m, 2 H), 7.46-7.53 (m, 1 H), 7.09-7.25 (m, 3 H), 6.96-7.05 (m, 1 H), 6.53 (s, 1 H), 5.11 (s, 2 H), 3.71 (s, 2 H), 3.55 (s, 2 H), 2.90-2.96 (m, 2 H), 2.79-2.87 (m, 2 H); LC-MS: m/z 373.5 (M + H)+. |

| No | Structure and starting material | Deviating reaction conditions/ $^1$H NMR (400 MHz)/LC-MS |
|---|---|---|
| 51 | Starting material: 4-(Bromomethyl)-3-fluorobenzamide | Conditions: THF, reflux, C, E and B. 1H NMR (Chloroform-d) δ: 7.70-7.75 (m, 1 H), 7.70 (s, 1 H), 7.47-7.52 (m, 1 H), 7.35-7.40 (m, 1 H), 7.09-7.18 (m, 3 H), 6.96-7.03 (m, 1 H), 6.53 (s, 1 H), 5.20 (s, 2 H), 3.71 (s, 2 H), 3.56 (s, 2 H), 2.90-2.96 (m, 2 H), 2.80-2.87 (m, 2 H); LC-MS: m/z 391.3 (M + H)+. |
| 52 | Starting material: 4-(Bromomethyl)-α,α-dimethylbenzenemethanol | Conditions: THF, reflux, C. 1H NMR (Chloroform-d) δ: 7.56 (s, 1 H), 7.26-7.52 (m, 5 H), 6.86-6.93 (m, 1 H), 6.68-6.72 (m, 1 H), 6.63 (s, 1 H), 6.49 (s, 1 H), 5.04-5.14 (m, 2 H), 3.72-3.83 (m, 3 H), 3.57-3.68 (m, 2 H), 3.51 (s, 2 H), 2.86-2.92 (m, 2 H), 2.73-2.84 (m, 2 H), 1.53-1.59 (m, 6 H); LC-MS: m/z 436.4 (M + H)+. |
| 53 | Starting material: 4-(Bromomethyl) benzonitrile | Conditions: THF, reflux, C, E, B and D. 1H NMR (DMSO-d6) δ: 8.25 (s, 1 H), 7.89 (s, 1 H), 7.87 (s, 1 H), 7.60-7.64 (m, 2 H), 6.92-6.97 (m, 1 H), 6.66-6.71 (m, 2 H), 6.42 (s, 1 H), 5.07 (s, 2 H), 3.70 (s, 3 H), 3.57 (s, 2 H), 3.55 (s, 2 H), 2.65-2.86 (m, 4 H); LC-MS: m/z 403.3 (M + H)+. |
| 54 | Starting material: 4-(Bromomethyl)-α,α-dimethylbenzenemethanol | Conditions: 70° C. 1H NMR (Chloroform-d) δ: 7.55-7.61 (m, 1 H), 7.53 (s, H), 7.40-7.48 (m, 1 H), 7.23-7.36 (m, 2 H), 7.08-7.17 (m, 3 H), 6.95-7.02 (m, 1 H), 6.50 (s, 1 H), 5.07 (s, 2 H), 3.69 (s, 2 H), 3.52 (s, 2 H), 2.87-2.97 (m, 2 H), 2.76-2.87 (m, 2 H), 1.96 (s, 1 H), 1.55-1.59 (m, 6 H); LC-MS: m/z 406.4 (M + H)+. |
| 55 | Starting material: 4-(Bromomethyl)-3-fluorobenzamide | Conditions: 70° C., C, B and E. 1H NMR (Chloroform-d) δ: 7.65 (s, 1 H), 7.52-7.65 (m, 3 H), 7.09-7.17 (m, 3 H), 6.97-7.02 (m, 1 H), 6.53 (s, 1 H), 5.83-6.28 (m, 1 H), 5.32-5.77 (m, 1 H), 5.18 (s, 2 H), 3.71 (s, 2 H), 3.55 (s, 2 H), 2.90-2.97 (m, 2 H), 2.80-2.87 (m, 2 H); m/z 409.3 (M + H)+. |

| No | Structure and starting material | Deviating reaction conditions/ $^1$H NMR (400 MHz)/LC-MS |
|---|---|---|
| 56 | Starting material: 4-(Bromomethyl)-3-fluorobenzamide | Conditions: 70° C., C. 1H NMR (Chloroform-d) δ: 7.65 (s, 1 H), 7.61-7.64 (m, 1 H), 7.54-7.61 (m, 2 H), 7.18-7.26 (m, 4 H), 6.52 (s, 1 H), 6.04 (br s, 1 H), 5.60 (br s, 1 H), 5.20 (s, 2 H), 4.04 (s, 4 H), 3.77 (s, 2 H); LC-MS: m/z 395.6 (M + H)+. |
| 57 | Starting material: 4-(Bromomethyl)benzamide | 1H NMR (DMSO-d6) δ: 8.23 (s, 1 H), 7.96-8.03 (m, 1 H), 7.85-7.94 (m, 2 H), 7.44-7.54 (m, 2 H), 7.34-7.40 (m, 1 H), 7.17-7.27 (m, 4 H), 6.43 (s, 1 H), 5.02 (s, 2 H), 3.95 (s, 4 H), 3.79 (s, 2 H); LC-MS: m/z 377.6 (M + H)+. |
| 58 | Starting material: 1-Bromo-4-(chloromethyl)benzene | Conditions: 70° C., B and E. 1H NMR (Chloroform-d) δ: 7.56 (s, 1 H), 7.47-7.52 (m, 2 H), 7.27-7.30 (m, 2 H), 7.16-7.24 (m, 4 H), 6.48-6.51 (m, 1 H), 5.04 (s, 2 H), 4.03 (s, 4 H), 3.74-3.76 (m, 2 H); LC-MS: m/z 412.4 (M + H)+. |
| 59 | Starting material: 4-(Bromomethyl)-α,α-dimethylbenzenemethanol | Conditions: 70° C., E. 1H NMR (Chloroform-d) δ: 7.54 (s, 1 H), 7.46-7.52 (m, 2 H), 7.35-7.40 (m, 2 H), 7.03-7.18 (m, 4 H), 6.54 (s, 1 H), 5.06 (s, 2 H), 3.83-3.89 (m, 1 H), 3.57 (s, 2 H), 3.09-3.18 (m, 1 H), 2.84-2.96 (m, 1 H), 2.70-2.83 (m, 2 H), 1.71 (s, 1 H), 1.58 (s, 6 H), 1.35-1.40 (m, 3 H); LC-MS: m/z 420.5 (M + H)+. |
| 60 | Starting material: 4-(Bromomethyl)benzoic acid, methyl ester | Conditions: 70° C., D. 1H NMR (DMSO-d6) δ: 8.24 (s, 1 H), 7.98-8.02 (m, 2 H), 7.55-7.59 (m, 2 H), 7.16-7.26 (m, 4 H), 6.43 (s, 1 H), 5.06 (s, 2 H), 3.95 (s, 3 H), 3.89 (s, 1 H), 3.86 (s, 3 H), 3.77-3.83 (m, 2 H); LC-MS: m/z 392.3 (M + H)+. |

| No | Structure and starting material | Deviating reaction conditions/ ¹H NMR (400 MHz)/LC-MS |
|---|---|---|
| 61 | Starting material: 4-(Bromomethyl)-3-fluoro-N,N-dimethylbenzamide | Conditions: 70° C., D. 1H NMR (Chloroform-d) δ: 7.65 (s, 1 H), 7.54-7.59 (m, 1 H), 7.21-7.23 (m, 4 H), 7.19-7.21 (m, 1 H), 7.14-7.17 (m, 1 H), 6.53 (s, 1 H), 5.15 (s, 2 H), 4.10 (s, 4 H), 3.82 (s, 2 H), 3.11 (br s, 3 H), 2.98 (br s, 3 H); LC-MS: m/z 423.4 (M + H)+. |
| 62 | Starting material: 4-(Bromomethyl)-N-methylbenzamide | Conditions: 85° C., C. 1H NMR (DMSO-d6) δ: 8.37-8.51 (m, 1 H), 8.23 (s, 1 H), 7.82-7.88 (m, 2 H), 7.46-7.52 (m, 2 H), 7.16-7.27 (m, 4 H), 6.42 (s, 1 H), 5.01 (s, 2 H), 3.95 (s, 4 H), 3.79 (s, 2 H), 2.73-2.89 (m, 3 H); LC-MS: m/z 391.4 (M + H)+. |
| 63 | Starting material: 1-(Bromomethyl)-4-(methylsulfonyl)benzene | Conditions: 85° C., C. 1H NMR (DMSO-d6) δ: 8.32 (s, 1 H), 8.00-8.10 (m, 2 H), 7.71-7.81 (m, 2 H), 7.27-7.35 (m, 1 H), 7.12-7.20 (m, 1 H), 7.03-7.11 (m, 1 H), 6.49 (s, 1 H), 5.15 (s, 2 H), 3.99 (br d, J = 13.3 Hz, 4 H), 3.85 (s, 2 H), 3.26-3.31 (m, 3 H); LC-MS: m/z 430.3 (M + H)+. |
| 64 | Starting material: 1-(Bromomethyl)-4-(methylsulfonyl)benzene | Conditions: 80° C., A. 1H NMR (DMSO-d6) δ: 8.26 (s, 1 H), 7.92-8.00 (m, 2 H), 7.65-7.73 (m, 2 H), 7.33 (s, 1 H), 7.26 (s, 2 H), 6.43 (s, 1 H), 5.09 (s, 2 H), 3.94 (br d, J = 6.9 Hz, 4 H), 3.79 (s, 2 H), 3.22 (s, 3 H); LC-MS: m/z 446.3 (M + H)+. |

| No | Structure and starting material | Deviating reaction conditions/ $^1$H NMR (400 MHz)/LC-MS |
|---|---|---|
| 65 | 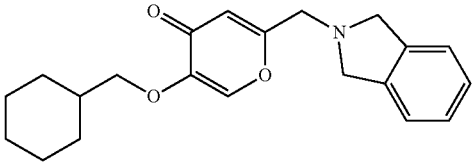 [SMILES: O=c1cc(CN2Cc3ccccc3C2)occ1OCC1CCCCC1]<br>Starting material: (Bromomethyl)cyclohexane | Conditions: 65° C., C. 1H NMR (DMSO-d6) δ: 8.12 (s, 1 H), 7.18-7.26 (m, 4 H), 6.37 (s, 1 H), 3.95 (s, 4 H), 3.78 (s, 2 H), 3.57-3.67 (m, 2 H), 1.61-1.81 (m, 6 H), 1.12-1.29 (m, 3 H), 0.94-1.07 (m, 2 H); LC-MS: m/z 340.7 |
| 66 | 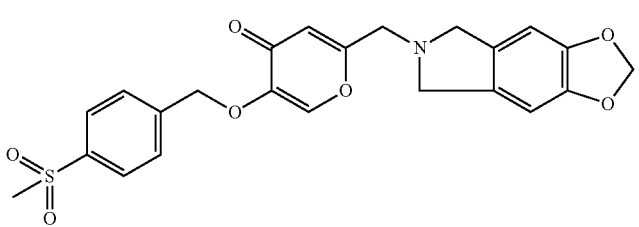 [SMILES: CS(=O)(=O)c1ccc(COc2coc(CN3Cc4cc5c(cc4C3)OCO5)cc2=O)cc1]<br>Starting material: 1-(Bromomethyl)-4-(methylsulfonyl)benzene | Conditions: 80° C., D.<br>1H NMR (DMSO-d6) δ: 8.26 (s, 1 H), 7.94-7.98 (m, 2 H), 7.67-7.71 (m, 2 H), 6.82 (s, 2 H), 6.42 (s, 1 H), 5.97 (s, 2 H), 5.09 (s, 2 H), 3.85 (s, 4 H), 3.76 (s, 2 H), 3.22-3.24 (m, 3 H); LC-MS: m/z 456.3 (M + H)+. |
| 67 | 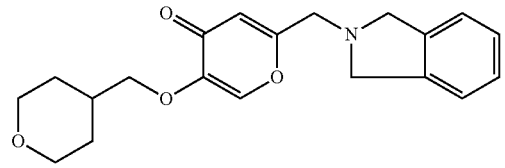 [SMILES: O=c1cc(CN2Cc3ccccc3C2)occ1OCC1CCOCC1]<br>Starting material: 2H-4-(Bromomethyl)tetrahydropyran | Conditions: 140° C., D.<br>1H NMR (DMSO-d6) δ: 8.14-8.15 (m, 1 H), 7.18-7.26 (m, 4 H), 6.38 (s, 1 H), 3.95 (s, 4 H), 3.83-3.89 (m, 2 H), 3.78 (s, 2 H), 3.66-3.70 (m, 2 H), 3.28-3.36 (m, 3 H), 1.60-1.68 (m, 2 H), 1.22-1.33 (m, 2 H); LC-MS: m/z 342.7 |
| 68 | 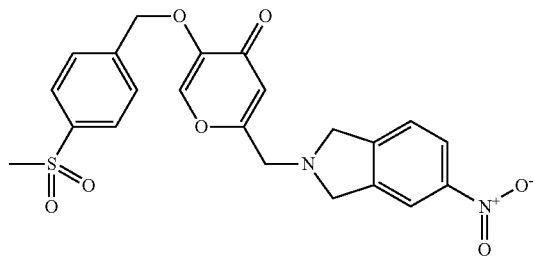 [SMILES: CS(=O)(=O)c1ccc(COc2coc(CN3Cc4ccc([N+](=O)[O-])cc4C3)cc2=O)cc1]<br>Starting material: 1-(Bromomethyl)-4-(methylsulfonyl)benzene | Conditions: E and A.<br>1H NMR (DMSO-d6) δ: 8.27 (s, 1 H), 8.15 (s, 1 H), 8.10-8.14 (m, 1 H), 7.93-7.99 (m, 2 H), 7.68-7.75 (m, 2 H), 7.51-7.55 (m, 1 H), 6.46 (s, 1 H), 5.10 (s, 2 H), 4.07 (s, 4 H), 3.84 (s, 2 H), 3.23 (s, 3 H); LC-MS: m/z 457.5 |
| 69 | 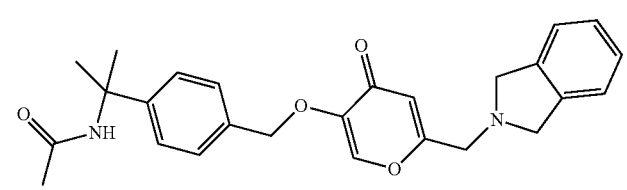 [SMILES: CC(=O)NC(C)(C)c1ccc(COc2coc(CN3Cc4ccccc4C3)cc2=O)cc1]<br>Starting material: N-(2-(4-(Bromomethyl)phenyl)propan-2-yl)acetamide | Conditions: 80° C., D.<br>1H NMR (DMSO-d6) δ: 8.22 (s, 1 H), 8.15 (s, 1 H), 8.05 (s, 1 H), 7.31-7.33 (m, 4 H), 7.19-7.26 (m, 4 H), 6.40 (s, 1 H), 4.89 (s, 2 H), 3.95 (s, 4 H), 3.78-3.80 (m, 2 H), 1.82 (s, 2 H), 1.53 (s, 6 H); LC-MS: m/z 433.5 (M + H)+. |

| No | Structure and starting material | Deviating reaction conditions/ $^1$H NMR (400 MHz)/LC-MS |
|---|---|---|
| 69a | 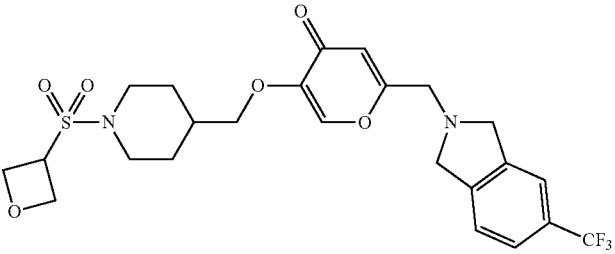 [SMILES: O=c1cc(CN2Cc3ccc(C(F)(F)F)cc3C2)occ1OCC1CCN(S(=O)(=O)C2COC2)CC1]<br>Starting material: 4-(Bromomethyl)-1-(oxetan-3-ylsulfonyl)piperidine | Conditions: DMSO, 80° C., B.<br>$^1$H NMR (Chloroform-d) δ: 7.60 (s, 1H), 7.50 (d, 1H), 7.46 (s, 1H), 7.31 (d, 1H), 6.49 (s, 1H), 4.84-4.96 (m, 4H), 4.42 (m, 1H), 4.09 (s, 4H), 3.88 (br d, 2H), 3.79 (s, 2H), 3.74 (d, 2H), 2.82 (m, 2H), 2.00-2.09 (m, 1H), 1.97 (br d, 2H), 1.32-1.44 (m, 2H)<br>LC-MS: m/z 529.2 (M + H)$^+$. |

Example 2

N-((4-(((6-(Isoindolin-2-ylmethyl)-4-oxo-4H-pyran-3-yl)oxy)methyl)phenyl)-sulfonyl)-N-methylacetamide (Compound 70)

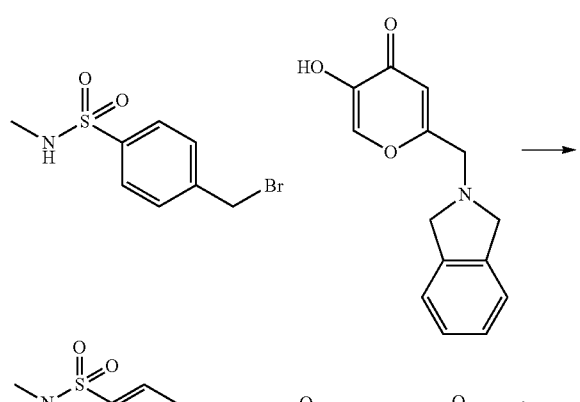

To a solution of 5-hydroxy-2-(isoindolin-2-ylmethyl)-4H-pyran-4-one (0.36 g, 1.5 mmol) in DMF (5 ml) were added 4-methylsulfonylbenzyl bromide (0.40 g, 1.5 mmol) and K$_2$CO$_3$ (0.41 g, 2.9 mmol). The reaction mixture was heated at 60° C. for 1 h. The mixture was cooled to RT, water (10 ml) was added and the product was extracted with EtOAc. The combined extracts were washed with water, dried with Na$_2$SO$_4$, filtered and evaporated to afford 0.14 g of 4-(((6-(isoindolin-2-ylmethyl)-4-oxo-4H-pyran-3-yl)oxy)methyl)-N-methylbenzenesulfonamide.

To a solution of 4-((((6-(isoindolin-2-ylmethyl)-4-oxo-4H-pyran-3-yl)oxy)-methyl)-N-methylbenzenesulfonamide (0.02 g, 0.05 mmol) in DCM (20 ml) were added acetic anhydride (0.24 g, 2.4 mmol) and zinc chloride (6.1 mg, 0.05 mmol). The reaction mixture was heated at 60° C. for 0.5 h. Water (5 ml) was added the product was extracted with DCM. The combined extracts were washed with water, dried with Na$_2$SO$_4$, filtered and evaporated to afford the crude product that was purified by column chromatography to afford 0.002 g of N-((4-(((6-(isoindolin-2-ylmethyl)-4-oxo-4H-pyran-3-yl)oxy)methyl)phenyl)sulfonyl)-N-methylacetamide. $^1$H NMR (Chloroform-d) δ: 7.88-7.92 (m, 2H), 7.66 (s, 1H), 7.63 (d, 2H), 7.20-7.23 (m, 4H), 6.54 (s, 1H), 5.17 (s, 2H), 4.05 (s, 4H), 3.78 (s, 2H), 3.30 (s, 3H), 2.39 (s, 3H). LC-MS: m/z 469.5 (M+H)$^+$.

Example 3

5-((4-(Cyclobutanesulfonimidoyl)benzyl)oxy)-2-(isoindolin-2-ylmethyl)-4H-pyran-4-one (Compound 71)

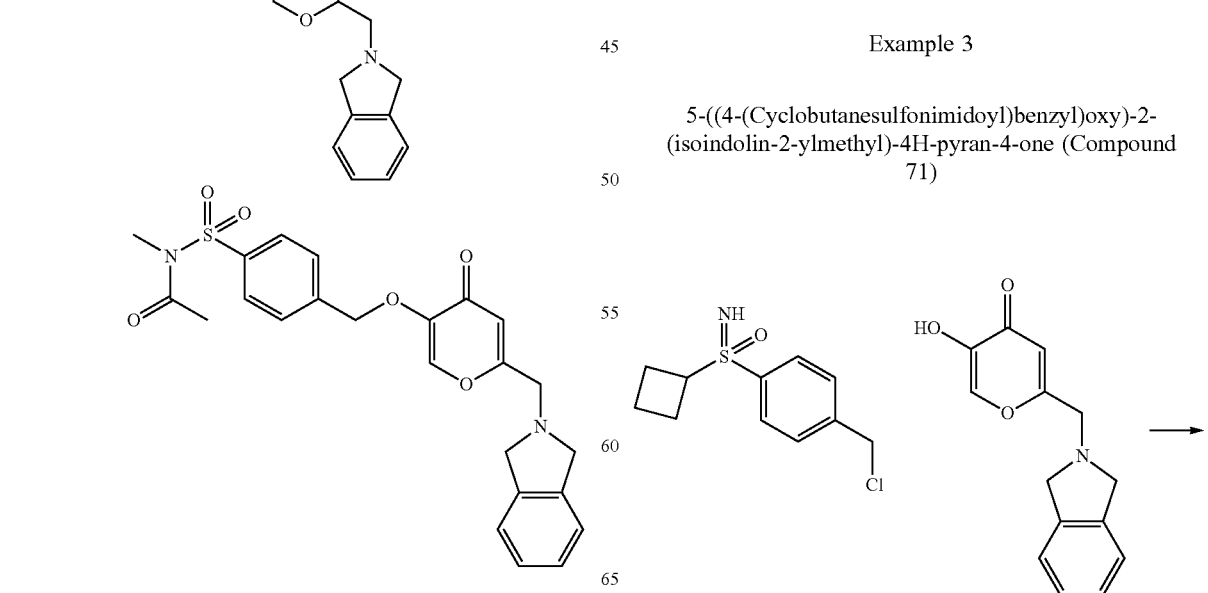

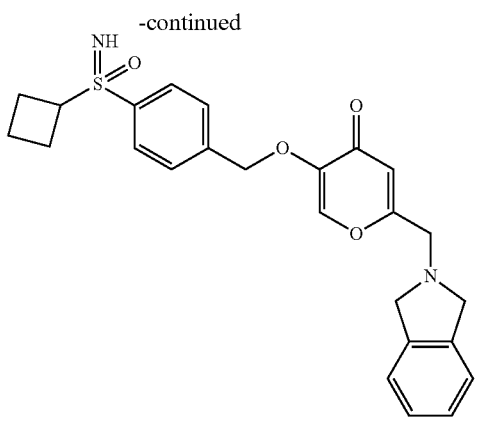

To a solution of 5-hydroxy-2-(isoindolin-2-ylmethyl)-4H-pyran-4-one (0.11 g, 0.46 mmol) in DMSO (4 ml) were added 1-(chloromethyl)-4-(cyclobutanesulfon-imidoyl)benzene (0.14 g, 0.55 mmol) and K₂CO₃ (0.14 g, 1.0 mmol). The reaction mixture was heated at 80° C. for 2 h. The mixture was cooled to RT, water (10 ml) was added and the product was extracted with EtOAc. The combined extracts were washed with water, dried with Na₂SO₄, filtered and evaporated. The crude product was purified by column chromatography to afford (0.02 g) of 5-((4-(cyclobutane-sulfonimidoyl)-benzyl)oxy)-2-(isoindolin-2-ylmethyl)-4H-pyran-4-one. $^1$H NMR (Chloroform-d) δ: 7.94 (d, 2H), 7.64 (s, 1H), 7.59 (d, 2H), 7.18-7.24 (m, 4H), 6.54 (s, 1H), 5.14 (s, 2H), 4.07 (s, 4H), 3.87-3.95 (m, 1H), 3.80 (s, 2H), 2.58-2.68 (m, 1H), 2.39-2.51 (m, 1H), 2.21-2.33 (m, 1H), 1.89-2.07 (m, 3H)

The following compounds were prepared according to the procedure described for Compound 71 of Example 3 starting from 5-hydroxy-2-(isoindolin-2-ylmethyl)-4H-pyran-4-one or 5-hydroxy-2-((3,4-dihydroisoquinolin-2(1H)-yl)methyl)-4H-pyran-4-one or a derivative thereof and another appropriate starting material. The characterization data, starting material and possible deviations in reaction conditions (solvent, reaction temperature, reaction time, purification method), if any, are indicated on the table.

Purification Methods Used:
A=Crystallization
B=Column chromatography
C=Precipitation in aqueous media
D=Semipreparative HPLC
E=Trituration
F=Salt formation
G=As such Alternative methods of preparation: NaOH/KOH in MeOH/EtOH, NaH in DMF, K₂CO₃ in THF/1,4-dioxane.

| No | Structure and starting material | Deviating reaction conditions/ $^1$H NMR (400 MHz)/LC-MS |
|---|---|---|
| 72 | Starting material: 1-(Chloromethyl)-4-(cyclopropylsulfonyl)benzene | Conditions: DMF, 50° C. $^1$H NMR (Chloroform-d) δ: 7.89-7.94 (m, 2H), 7.60-7.65 (m, 3H), 7.19-7.23 (m, 4H), 6.53 (s, 1H), 5.17 (s, 2H), 4.04 (s, 4H), 3.77 (s, 2H), 2.46 (m, 1H), 1.32-1.41 (m, 2H), 1.00-1.09 (m, 2H). LCMS: m/z 438.5 (M + H)⁺. |
| 73 | Starting material: 1-(Chloromethyl)-4-(isobutylsulfonyl)benzene | Conditions: DMF, 50° C. $^1$H NMR (Chloroform-d) δ: 7.90-7.95 (m, 2H), 7.61-7.64 (m, 3H), 7.19-7.23 (m, 3H), 7.19-7.23 (m, 1H), 6.53 (s, 1H), 5.18 (s, 2H), 4.04 (s, 4H), 3.77 (s, 2H), 2.99 (d, 2H), 2.23 (dm, 1H), 1.06 (d, 6H). LC-MS: m/z 434.5 (M + H)⁺. |
| 74 | Starting material: (4-(Chloromethyl)-phenyl)(methyl)-λ4-sulfanimine | Conditions: DMSO, 80° C., B. $^1$H NMR (Chloroform-d) δ: 7.57-7.69 (m, 6H), 7.49 (d, 1H), 7.46 (s, 1H), 7.31 (d, 1H), 6.51 (s, 1H), 5.14 (s, 2H), 4.08 (s, 4H), 3.78 (s, 2H), 2.73 (s, 3H) |

| No | Structure and starting material | Deviating reaction conditions/ $^1$H NMR (400 MHz)/LC-MS |
|---|---|---|
| 75 | 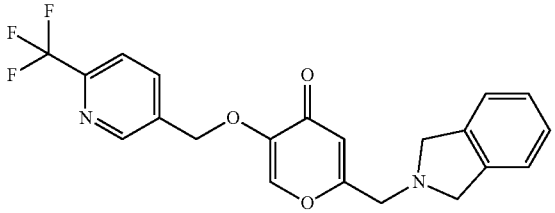 [SMILES: O=c1cc(CN2Cc3ccccc3C2)occ1OCc1ccc(C(F)(F)F)nc1]

Starting material: 5-(Chloromethyl)-2-(trifluoromethyl)pyridine | Conditions: 50° C., C.<br>$^1$H NMR (Chloroform-d) δ: 8.75-8.74 (m, 1H), 8.04-8.01 (m, 1H), 7.71 (d, J = 7.9 Hz, 1H), 7.10 (s, 1H), 7.24-7.19 (m, 4H), 6.54 (s, 1H), 5.22 (s, 2H), 4.05 (s, 4H), 3.79 (s, 2H); LC-MS: m/z 404.4 (M + 2)$^+$. |
| 76 | 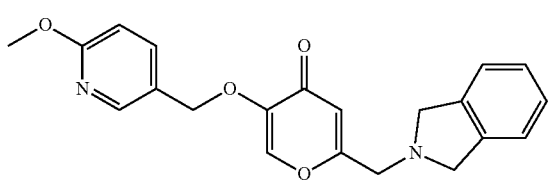 [SMILES: COc1ccc(COc2coc(CN3Cc4ccccc4C3)cc2=O)cn1]

Starting material: 5-(Chloromethyl)-2-methoxypyridine | Conditions: 50° C.<br>$^1$H NMR (Chloroform-d) δ: 8.14 (d, 1H), 7.81-7.56 (m, 2H), 7.60 (s, 1H), 7.23-7.19 (m, 4H), 6.80-6.75 (m, 1H), 6.50 (s, 1H), 5.02 (s, 2H), 4.03 (s, 4H), 3.94 (s, 3H), 3.75 (s, 2H); LC-MS: m/z 365.3 (M + 1)$^+$. |
| 77 | 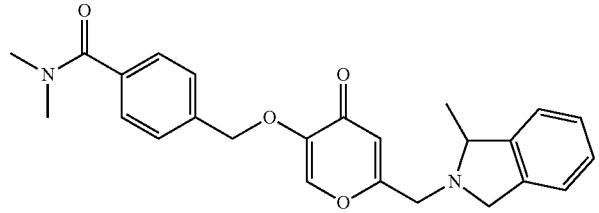 [SMILES: CC1c2ccccc2CN1Cc1cc(=O)c(OCc2ccc(C(=O)N(C)C)cc2)co1]

Starting material: 4-(Chloromethyl)-N,N-dimethylbenzamide | Conditions: 50° C., E (Et$_2$O).<br>$^1$H NMR (Methanol-d$_4$) δ: 8.11 (s, 1 H), 7.57 (d, 2 H), 7.46 (d, 2 H), 7.23 (m, 4 H), 6.60 (s, 1 H), 5.10 (s, 2 H), 4.22 (d, 1 H), 4.06 (m, 2 H), 3.79 (dd, 1 H), 3.69 (d, 1 H), 3.11 (s, 3 H), 3.00 (s, 3 H), 1.44 (d, 3 H); LC-MS: m/z 419.4 (M + 1)$^+$. |
| 78 | 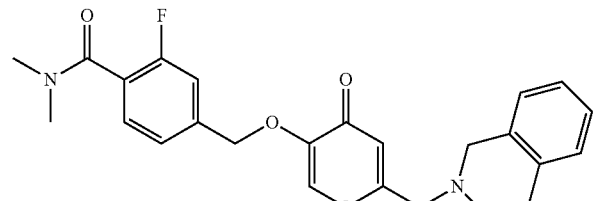

Starting material: 4-(Chloromethyl)-2-fluoro-N-methylbenzamide | Conditions: 60° C., C and E (Et$_2$O).<br>$^1$H NMR (Chloroform-d) δ: 7.60 (s, 1H), 7.37-7.42 (m, 1H), 7.16-7.25 (m, 2H), 7.08-7.16 (m, 3H), 6.97-7.02 (m, 1H), 6.47-6.57 (m, 1H), 5.09 (s, 2H), 3.71 (s, 2H), 3.55 (s, 2H), 3.13 (s, 3H), 2.90-2.97 (m, 5H), 2.81-2.86 (m, 2H); LC-MS: m/z 437.3 (M + 1)$^+$. |
| 79 | 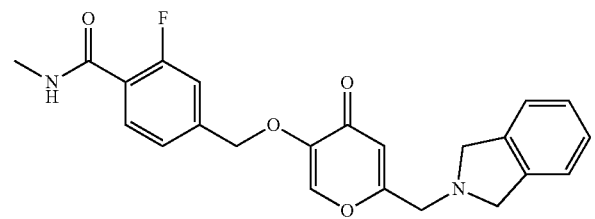 [SMILES: CNC(=O)c1ccc(COc2coc(CN3Cc4ccccc4C3)cc2=O)cc1F]

Starting material: 4-(Chloromethyl)-2-fluoro-N-methylbenzamide | Conditions: 60° C., C and E (Et$_2$O)<br>$^1$H NMR (Chloroform-d) δ: 8.11 (m, 1 H), 7.61 (m, 1 H), 7.26 (m, 2 H), 7.21 (m, 4 H), 6.72 (br d, 1 H), 6.52 (s, 1 H), 5.12 (s, 2 H), 4.04 (s, 4 H), 3.76 (s, 2 H), 3.04 (dd, 3 H); LC-MS: m/z 409.3 (M + 1)$^+$. |

| No | Structure and starting material | Deviating reaction conditions/ $^1$H NMR (400 MHz)/LC-MS |
|---|---|---|
| 80 | 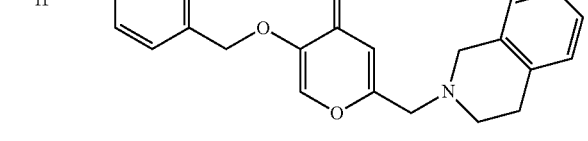<br>Starting material: 4-(Chloromethyl)-2-fluoro-N-methylbenzamide | Conditions: 60° C., C.<br>$^1$H NMR (Chloroform-d) δ: 8.11 (m, 1 H), 7.61 (s, 1 H), 7.26 (m, 2 H), 7.13 (m, 3 H), 6.99 (dd, 1 H), 6.72 (br d, 1 H), 6.53 (s, 1 H), 5.12 (s, 2 H), 3.71 (s, 2 H), 3.54 (s, 2 H), 3.04 (dd, 3 H), 2.93 (m, 2 H), 2.83 (m, 2 H); LC-MS: m/z 423.3 (M + 1)$^+$. |
| 81 | 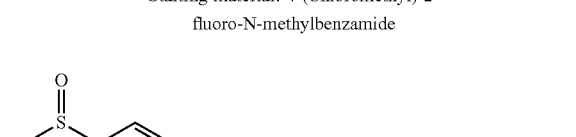<br>Starting material: 1-(Chloromethyl)-4-(methylsulfinyl)benzene | Conditions: 60° C.<br>$^1$H NMR (Chloroform-d δ: 7.66 (m, 2 H), 7.60 (m, 3 H), 7.21 (m, 4 H), 6.52 (s, 1 H), 5.14 (s, 2 H), 4.04 (s, 4 H), 3.77 (s, 2 H), 2.73 (s, 3 H); LC-MS: m/z 396.3 (M + 1)$^+$. |
| 82 | 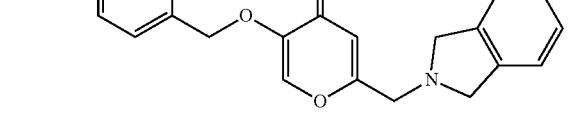<br>Starting material: p-(Methylthio)benzyl chloride | Conditions: 60° C.<br>$^1$H NMR (Chloroform-d) δ: 7.55 (s, 1 H), 7.26 (m, 4 H), 7.20 (m, 4 H), 6.49 (s, 1 H), 5.04 (s, 2 H), 4.03 (s, 4 H), 3.74 (s, 2 H), 2.48 (s, 3 H); LC-MS: m/z 380.3 (M + 1)$^+$. |
| 82a | 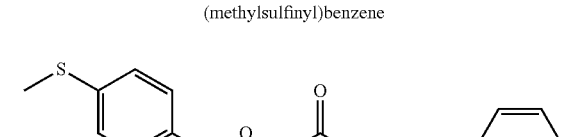<br>Starting material: 4-Bromo-N,N-dimethylbenzamide | Conditions: 50° C.<br>$^1$H NMR (Chloroform-d) δ: 7.56 (s, 1 H), 7.43 (m, 4 H), 7.00 (t, 2 H), 6.48 (s, 1 H), 5.11 (s, 2 H), 3.98 (s, 4 H), 3.74 (s, 2H), 3.11 (s, 3 H), 2.97 (s, 3 H); LC-MS: m/z 441.4 (M + 1)$^+$. |
| 83 | 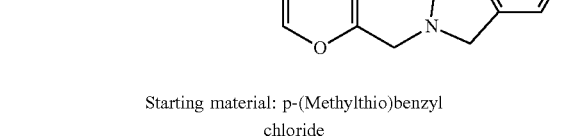<br>Starting material: 4-(Chloromethyl)-N-(dimethyloxido-λ$^4$-sulfanylidene) benzamide | Conditions: 60° C.<br>$^1$H NMR (Chloroform-d) δ: 8.12 (d, 2 H), 7.54 (s, 1 H), 7.44 (d, 2 H), 7.22 (m, 4 H), 6.51 (s, 1 H), 5.14 (s, 2 H), 4.10 (br s, 4 H), 3.79 (s, 2 H), 3.39 (s, 6 H); LC-MS: m/z 453.2 (M + 1)$^+$. |

| No | Structure and starting material | Deviating reaction conditions/ $^1$H NMR (400 MHz)/LC-MS |
|---|---|---|
| 84 | 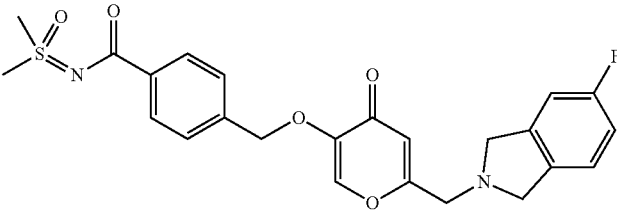<br>Starting material: 4-(Chloromethyl)-N-(dimethyloxido-λ$^4$-sulfanylidene)benzamide | Conditions: 60° C., B and E (EtOH).<br>$^1$H NMR (Chloroform-d) δ: 8.12 (m, 2 H), 7.53 (s, 1 H), 7.44 (m, 2 H), 7.13 (dd, 1 H), 6.90 (m, 2 H), 6.49 (s, 1 H), 5.15 (s, 2 H), 4.00 (s, 2 H), 3.97 (s, 2 H), 3.73 (m, 2 H), 3.39 (s, 6 H); LC-MS: m/z 471.3 (M + 1)$^+$. |
| 85 | 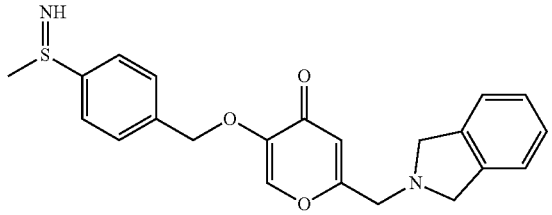 [SMILES: CS(=N)c1ccc(COc2coc(CN3Cc4ccccc4C3)cc2=O)cc1]<br>Starting material: 4-Methyl-N-[(S)-methyl(4-chloromethylphenyl)-λ$^4$-sulfanylidene]benzenesulfonamide | Conditions: 60° C., C.<br>$^1$H NMR (Chloroform-d) δ: 7.66 (m, 2 H), 7.60 (m, 3 H), 7.21 (m, 4 H), 6.52 (s, 1 H), 5.14 (s, 2 H), 4.04 (s, 4 H), 3.77 (s, 2 H), 2.73 (s, 3 H), 1.66 (s, 1H); LC-MS: m/z 396.4 (M + 2)$^+$. |
| 86 | 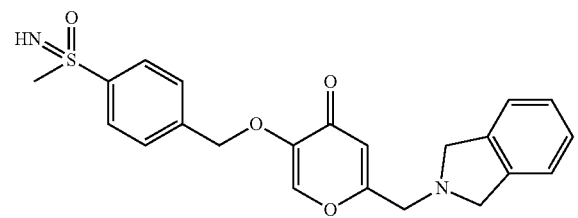 [SMILES: CS(=N)(=O)c1ccc(COc2coc(CN3Cc4ccccc4C3)cc2=O)cc1]<br>Starting material: 1-(Chloromethyl)-4-(S-methylsulfonimidoyl)benzene | Conditions: 60° C., C.<br>$^1$H NMR (Chloroform-d) δ: 8.02 (m, 2 H), 7.62 (m, 3 H), 7.21 (m, 4 H), 6.52 (s, 1 H), 5.17 (s, 2 H), 4.04 (s, 4 H), 3.77 (s, 2 H), 3.11 (s, 3 H), 2.69 (br s, 1 H); LC-MS: m/z 411.3 (M + 1)$^+$. |
| 87 | 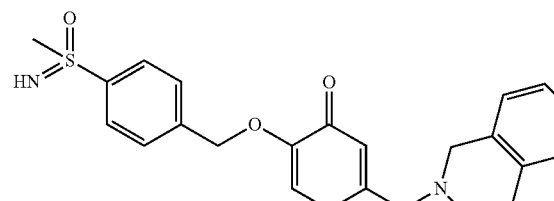<br>Starting material: 1-(Chloromethyl)-4-(S-methylsulfonimidoyl)benzene | Conditions: 60° C., C.<br>$^1$H NMR (Chloroform-d) δ: 8.02 (m, 2 H), 7.62 (m, 3 H), 7.13 (m, 3 H), 6.99 (dd, 1 H), 6.53 (s, 1 H), 5.17 (s, 2 H), 3.71 (s, 2 H), 3.55 (s, 2 H), 3.11 (s, 3 H), 2.93 (m, 2 H), 2.84 (m, 2 H), 2.69 (br s, 1 H); LC-MS: m/z 425.4 (M + 1)$^+$. |
| 88 | 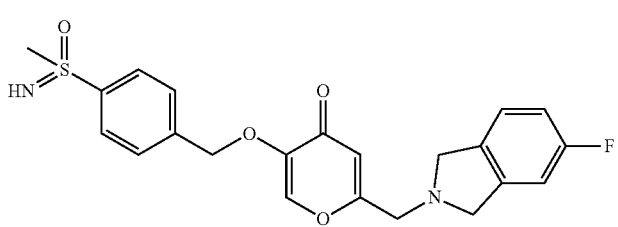 [SMILES: CS(=N)(=O)c1ccc(COc2coc(CN3Cc4ccc(F)cc4C3)cc2=O)cc1]<br>Starting material: 1-(Chloromethyl)-4-(S-methylsulfonimidoyl)benzene | Conditions: 60° C., C and A (IPA).<br>$^1$H NMR (Chloroform-d) δ: 8.02 (d, 2 H), 7.62 (m, 3 H), 7.13 (dd, 1 H), 6.91 (m, 2 H), 6.51 (s, 1 H), 5.17 (s, 2 H), 4.02 (br s, 2 H), 3.99 (br s, 2 H), 3.76 (s, 2 H), 3.11 (s, 3 H), 2.70 (br s, 1 H); LC-MS: m/z 429.2 (M + 1)$^+$. |

-continued

| No | Structure and starting material | Deviating reaction conditions/ ¹H NMR (400 MHz)/LC-MS |
|---|---|---|
| 89 | 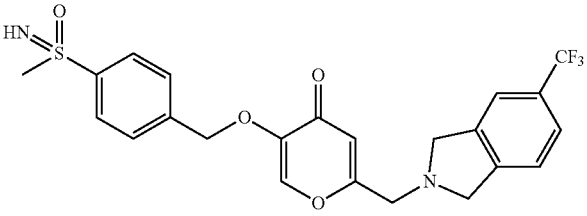 [SMILES: CS(=N)(=O)c1ccc(COc2coc(CN3Cc4ccc(C(F)(F)F)cc4C3)cc2=O)cc1]<br>Starting material: 1-(Chloromethyl)-4-(S-methylsulfonimidoyl)benzene | Conditions: 60° C.<br>¹H NMR (Chloroform-d) δ: 8.04-8.01 (m, 2H), 7.64 (s, 1H), 7.63-7.60 (m, 2H), 7.48-7.51 (m, 1H), 7.46 (s, 1H) 7.33-7.30 (m, 1H), 6.52 (s, 1H), 5.12 (s, 2H), 4.09 (s, 4H), 3.79 (s, 2H), 3.11 (s, 3H), 2.69 (s, 1H); LC-MS: m/z 479.3 (M + 1)⁺. |
| 90 | 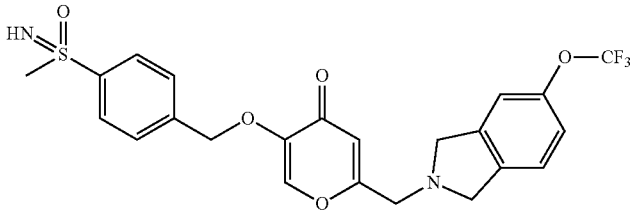 [SMILES: CS(=N)(=O)c1ccc(COc2coc(CN3Cc4ccc(OC(F)(F)F)cc4C3)cc2=O)cc1]<br>Starting material: 1-(Chloromethyl)-4-(S-methylsulfonimidoyl)benzene | Conditions: C.<br>¹H NMR (Chloroform-d) δ: 8.03 (d, 2H), 7.58-7.65 (m, 3H), 7.21 (d, 1H), 7.05-7.11 (m, 2H), 6.51 (s, 1H), 5.17 (s, 2H), 4.04 (br d, 4H), 3.77 (s, 2H), 3.11 (d, 3H), 2.70 (s, 1H); LC-MS: m/z 495.3 (M + 1)⁺. |
| 91 | 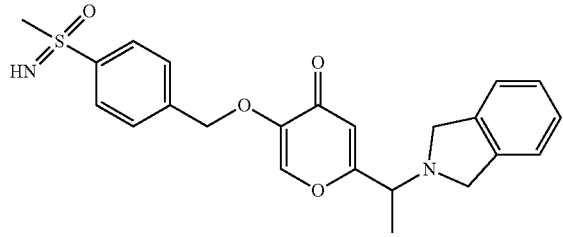 [SMILES: CC(c1cc(=O)c(OCc2ccc(S(C)(=N)=O)cc2)co1)N1Cc2ccccc2C1]<br>Starting material: 1-(Chloromethyl)-4-(S-methylsulfonimidoyl)benzene | ¹H NMR (Chloroform-d) δ: 8.03 (m, 2 H), 7.66 (d, 1 H), 7.62 (d, 2 H), 7.20 (m, 4 H), 6.49 (s, 1 H), 5.17 (s, 2 H), 3.98 (m, 4 H), 3.64 (q, 1 H), 3.11 (s, 3 H), 2.7 (br, 1H), 1.51 (d, 3 H); LC-MS: m/z 425.3 (M + 1)⁺. |
| 92 | 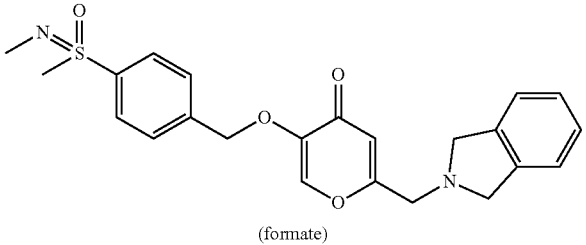 [SMILES: CN=S(C)(=O)c1ccc(COc2coc(CN3Cc4ccccc4C3)cc2=O)cc1]<br>(formate)<br>Starting material: N,S-dimethyl-S-(4-chloromethylphenyl)sulfoximine | Conditions: 60° C., D.<br>¹H NMR (Chloroform-d) δ: 8.08 (s, 1 H), 7.93 (m, 2 H), 7.68 (s, 1 H), 7.65 (m, 2 H), 7.22 (m, 4 H), 6.56 (s, 1 H), 5.16 (s, 2 H), 4.09 (s, 4 H), 3.82 (s, 2 H), 3.16 (s, 3 H), 2.63 (s, 3 H); LC-MS: m/z 425.4 (M + 1)⁺. |
| 93 | 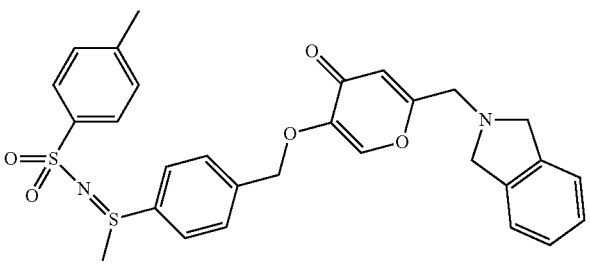 [SMILES: Cc1ccc(S(=O)(=O)N=S(C)c2ccc(COc3coc(CN4Cc5ccccc5C4)cc3=O)cc2)cc1]<br>Starting material: N-((4-(Chloromethyl)phenyl)methyl)-λ4-sulfanylidene)-4-methylbenzenesulfonamide | Conditions: 60° C., C and E (EtOH).<br>¹H NMR (Chloroform-d) δ: 7.73 (m, 4 H), 7.63 (s, 1 H), 7.57 (m, 2 H), 7.20 (m, 6 H), 6.52 (s, 1 H), 5.11 (s, 2 H), 4.04 (s, 4 H), 3.78 (s, 2 H), 2.83 (m, 3 H), 2.36 (s, 3 H); LC-MS: m/z 549.5 (M + 1)⁺. |

| No | Structure and starting material | Deviating reaction conditions/ $^1$H NMR (400 MHz)/LC-MS |
|---|---|---|
| 94 | 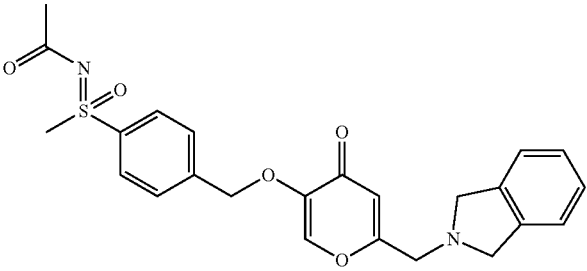 [SMILES: CC(=O)N=S(C)(=O)c1ccc(COc2coc(CN3Cc4ccccc4C3)cc2=O)cc1]<br>Starting material: 1-(Chloromethyl)-4-(N-acetyl-S-methylsulfonimidoyl)-benzene | Conditions: 60° C.<br>$^1$H NMR (Chloroform-d) δ: 7.99 (m, 2 H), 7.65 (m, 3 H), 7.21 (m, 4 H), 6.53 (s, 1 H), 5.18 (s, 2 H), 4.05 (s, 4 H), 3.78 (s, 2 H), 3.33 (s, 3 H), 2.16 (s, 3 H); LC-MS: m/z 453.5 (M + 1)$^+$. |
| 95 | 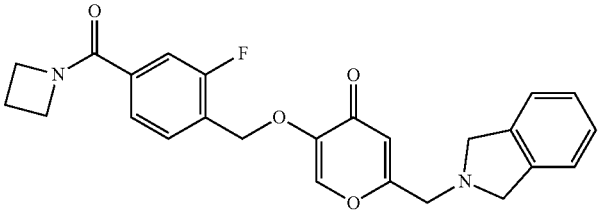 [SMILES: O=C(c1ccc(COc2coc(CN3Cc4ccccc4C3)cc2=O)c(F)c1)N1CCC1]<br>Starting material: Azetidin-1-yl(4-(chloromethyl)-3-fluorophenyl)-methanone | Conditions: 60° C., C.<br>$^1$H NMR (Chloroform-d) δ: 7.64 (s, 1 H), 7.57 (m, 1 H), 7.39 (m, 2 H), 7.21 (m, 4 H), 6.51 (s, 1 H), 5.16 (s, 2 H), 4.26 (m, 4 H), 4.04 (s, 4 H), 3.77 (s, 2 H), 2.36 (m, 2 H); LC-MS: m/z 435.5 (M + 1)$^+$. |
| 96 | 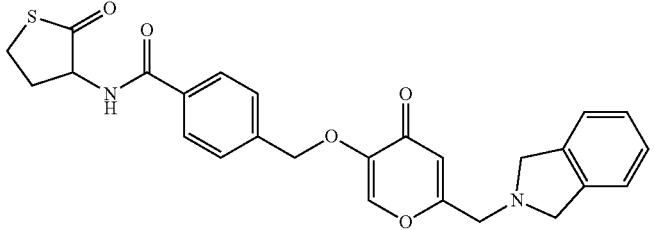 [SMILES: O=C(NC1CCSC1=O)c1ccc(COc2coc(CN3Cc4ccccc4C3)cc2=O)cc1]<br>Starting material: 4-(Chloromethyl)-N-(2-oxotetrahydrothiophen-3-yl)-benzamide | Conditions: 60° C.<br>$^1$H NMR (Chloroform-d) δ: 7.81 (d, 2 H), 7.56 (s, 1 H), 7.49 (d, 2 H), 7.21 (s, 4 H), 6.61 (br d, 1 H), 6.51 (s, 1 H), 5.15 (s, 2 H), 4.67 (dt, 1 H), 4.03 (s, 4 H), 3.75 (s, 2 H), 3.43 (m, 1 H), 3.32 (m, 1 H), 3.11 (m, 1 H), 2.03 (qd, 1 H); LC-MS: m/z 477.4 (M + 1)$^+$. |
| 97 | 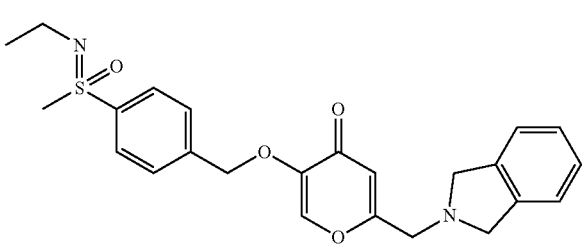 [SMILES: CCN=S(C)(=O)c1ccc(COc2coc(CN3Cc4ccccc4C3)cc2=O)cc1]<br>Starting material: 1-(Chloromethyl)-4-(N-ethyl-S-methylsulfonimidoyl)-benzene | Conditions: 60° C.<br>$^1$H NMR (Chloroform-d) δ: 7.92 (m, 2 H), 7.65 (s, 1 H), 7.62 (m, 2 H), 7.21 (m, 4 H), 6.53 (s, 1 H), 5.16 (s, 2 H), 4.04 (s, 4 H), 3.77 (s, 2 H), 3.08 (m, 3 H), 3.02 (m, 1 H), 2.85 (dq, 1 H), 1.18 (t, 3 H); LC-MS: m/z 439.1 (M + 1)$^+$. |

| No | Structure and starting material | Deviating reaction conditions/ ¹H NMR (400 MHz)/LC-MS |
|---|---|---|
| 98 | 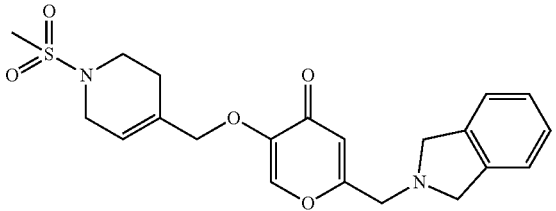 [SMILES: CS(=O)(=O)N1CC=C(COc2coc(CN3Cc4ccccc4C3)cc2=O)CC1]<br>Starting material: 4-(Chloromethyl)-1-(methylsulfonyl)-1,2,3,6-tetrahydropyridine | Conditions: 60° C., C.<br>¹H NMR (Chloroform-d) δ: 7.65 (s, 1 H), 7.21 (m, 4 H), 6.50 (s, 1 H), 5.83 (m, 1 H), 4.45 (s, 2 H), 4.05 (s, 4 H), 3.82 (m, 2 H), 3.78 (s, 2 H), 3.42 (t, 2 H), 2.82 (s, 3 H), 2.36 (br d, 2 H); LC-MS: m/z 417.8 (M + 1)⁺. |
| 99 | 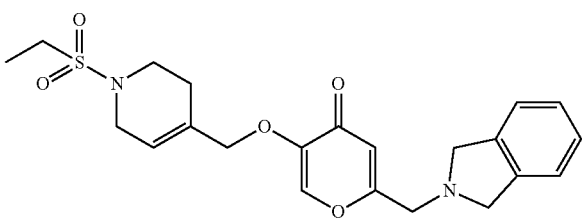 [SMILES: CCS(=O)(=O)N1CC=C(COc2coc(CN3Cc4ccccc4C3)cc2=O)CC1]<br>Starting material: 4-(Chloromethyl)-1-(ethylsulfonyl)-1,2,3,6-tetrahydropyridine | Conditions: 60° C., C.<br>¹H NMR (Chloroform-d) δ: 7.65 (s, 1H), 7.24-7.18 (m, 4H), 6.49 (s, 1H), 5.83-5.80 (m, 1H), 4.43 (s, 2H), 4.05 (s, 4H), 3.88-3.85 (m, 2H), 3.77 (s, 2H), 3.47 (t, 2H, J = 5.7 Hz), 2.98 (q, 2H, J = 7.3 Hz), 2.35-2.30 (m, 2H), 1.36 (t, 3H, J = 7.4 Hz); LC-MS: m/z 431.9 (M + 1)⁺. |
| 100 | 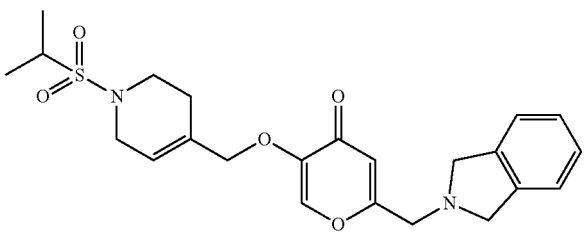 [SMILES: CC(C)S(=O)(=O)N1CC=C(COc2coc(CN3Cc4ccccc4C3)cc2=O)CC1]<br>Starting material: 4-(Chloromethyl)-1-(isopropylsulfonyl)-1,2,3,6-tetrahydropyridine | Conditions: 60° C.<br>¹H NMR (Chloroform-d) δ: 7.64 (s, 1H), 7.23.7.18 (m, 4H), 6.49 (s, 1H), 5.83-5.80 (m, 1H), 4.43 (s, 2H), 4.04 (s, 4H), 3.92-3.89 (m, 2H), 3.78 (s, 2H), 3.50 (t, 2H, J = 5.7 Hz), 3.23-3.16 (m, 1H), 2.39-2.29 (m, 2H), 1.34 (d, 6H, J = 6.8 Hz); LC-MS: m/z 446.0 (M + 1)⁺. |
| 101 | 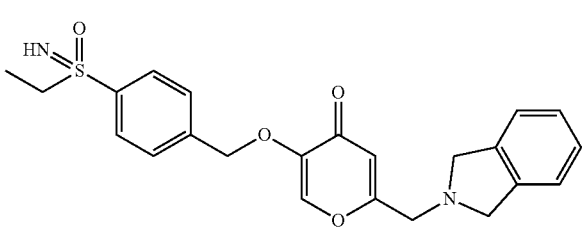 [SMILES: CCS(=N)(=O)c1ccc(COc2coc(CN3Cc4ccccc4C3)cc2=O)cc1]<br>Starting material: 1-(Chloromethyl)-4-(ethylsulfonimidoyl)benzene | Conditions: 60° C.<br>¹H NMR (Chloroform-d) δ: 7.99-7.96 (m, 2H), 7.63 (s, 1H), 7.62-7.59 (m, 2H), 7.23-7.19 (m, 4H), 6.52 (s, 1H), 5.17 (s, 2H), 4.04 (s, 4H), 3.77 (s, 2H), 3.20-3.14 (m, 2H), 2.4 (br, 1H) 1.28-1.24 (m, 3H); LC-MS: m/z 425.3 (M + 1)⁺. |
| 102 | 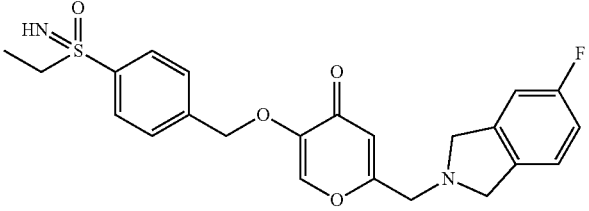 [SMILES: CCS(=N)(=O)c1ccc(COc2coc(CN3Cc4ccc(F)cc4C3)cc2=O)cc1]<br>Starting material: 1-(Chloromethyl)-4-(ethylsulfonimidoyl)benzene | Conditions: 60° C.<br>¹H NMR (Chloroform-d) δ: 7.99-7.96 (m, 2H), 7.63 (s, 1H), 7.62-7.59 (m, 2H), 7.15-7.11 (m, 1H), 6.94-6.88 (m, 2H), 6.51 (s, 1H), 5.17 (s, 2H), 4.03-3.98 (m, 4H), 3.76 (s, 2H), 3.30-3.14 (m, 2H), 2.7 (br, 1H), 1.28-1.24 (m, 3H); LC-MS: m/z 443.3 (M + 1)⁺. |

| No | Structure and starting material | Deviating reaction conditions/ $^1$H NMR (400 MHz)/LC-MS |
|---|---|---|
| 103 | 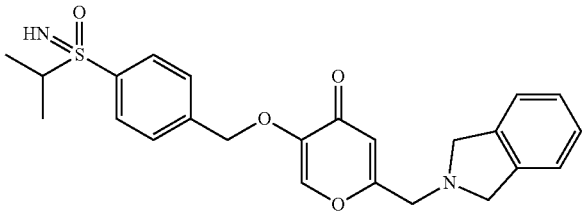 [SMILES: CC(C)S(=N)(=O)c1ccc(COc2coc(CN3Cc4ccccc4C3)cc2=O)cc1]<br>Starting material: 1-(Chloromethyl)-4-(propan-2-ylsulfonimidoyl)benzene | Conditions: 50° C.<br>$^1$H NMR (Chloroform-d) δ: 7.97-7.93 (m, 2H), 7.63 (s, 1H), 7.61-7.58 (m, 2H), 7.23-7.18 (m, 4H), 6.62 (s, 1H), 5.17 (s, 2H), 4.06-4.03 (m, 4H), 3.77 (d, 2H, J = 0.52 Hz), 3.29-3.18 (m, 1H), 1.33-1.25 (m, 7H); LC-MS: m/z 439.2 (M + 1)$^+$. |
| 104 | 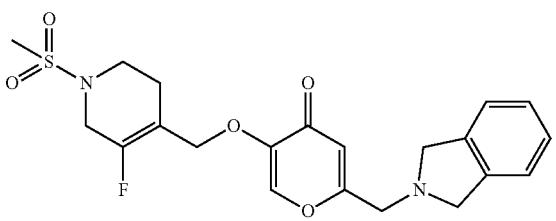 [SMILES: CS(=O)(=O)N1CCC(COc2coc(CN3Cc4ccccc4C3)cc2=O)=C(F)C1]<br>Starting material: 4-(Chloromethyl)-5-fluoro-1-(methylsulfonyl)-1,2,3,6-tetrahydropyridine | Conditions: 60° C., C.<br>$^1$H NMR (Chloroform-d) δ: 7.66 (s, 1H), 7.24-7.18 (m, 4H), 6.50 (s, 1H), 4.62 (s, 2H), 4.05 (s, 4H), 3.88 (s, 2H), 3.78 (s, 2H), 3.40 (m, 2H), 2.86 (s, 3H), 2.40-2.53 (m, 2H); LC-MS: m/z 435.8 (M + 1)$^+$. |
| 105 | 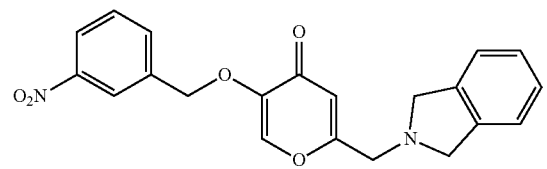 [SMILES: O=c1cc(CN2Cc3ccccc3C2)occ1OCc1cccc([N+](=O)[O-])c1]<br>Starting material: 1-(Chloromethyl)-3-nitrobenzene | Conditions: DMF, 60° C., C.<br>$^1$H NMR (Chloroform-d) δ: 8.24-8.32 (m, 1H), 8.20 (br d, 1H), 7.72-7.87 (m, 1H), 7.68 (s, 1H), 7.57 (m, 1H), 7.21 (s, 4H), 6.53 (s, 1H), 5.19 (s, 2H), 4.04 (s, 4H), 3.77 (s, 2H). LC-MS: m/z 379.3 (M + H)$^+$. |
| 106 | 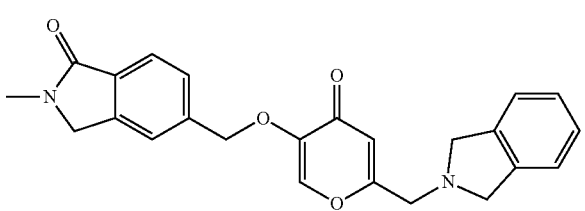 [SMILES: CN1Cc2cc(COc3coc(CN4Cc5ccccc5C4)cc3=O)ccc2C1=O]<br>Starting material: 5-(Chloromethyl)-2-methylisoindolin-1-one | Conditions: DMF, RT, C.<br>$^1$H NMR (Chloroform-d) δ: 7.83 (d, 1H), 7.61 (s, 1H), 7.57 (m, 1H), 7.45 (m, 1H), 7.16-7.24 (m, 4H), 6.52 (s, 1H), 5.16 (s, 2H), 4.38 (s, 2H), 4.04 (s, 4H), 3.76 (s, 2H), 3.20 (s, 3H). LC-MS: m/z 403.4 (M + H)$^+$. |
| 107 | 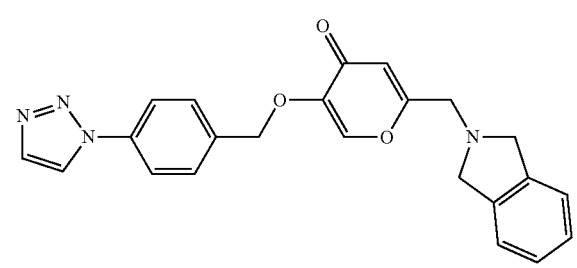 [SMILES: O=c1cc(CN2Cc3ccccc3C2)occ1OCc1ccc(-n2ccnn2)cc1]<br>Starting material: 1-(4-(Chloromethyl)-phenyl)-1H-1,2,3-triazole | Conditions: DMF, 60° C.<br>$^1$H NMR (Chloroform-d) δ: 8.00 (d, 1H), 7.86 (d, 1H), 7.74-7.79 (m, 2H), 7.63 (s, 1H), 7.60 (d, 2H), 7.17-7.24 (m, 4H), 6.52 (s, 1H), 5.17 (s, 2H), 4.04 (s, 4H), 3.77 (s, 2H). LC-MS: m/z 401.5 (M + H)$^+$. |

| No | Structure and starting material | Deviating reaction conditions/ $^1$H NMR (400 MHz)/LC-MS |
|---|---|---|
| 108 | 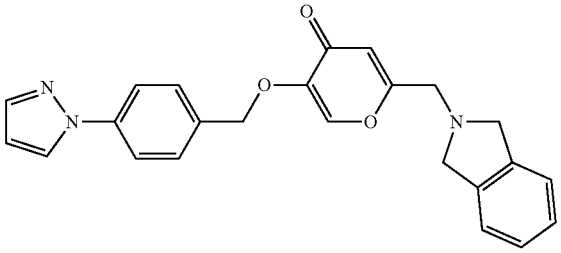 [SMILES: O=c1cc(CN2Cc3ccccc3C2)occ1OCc1ccc(-n2cccn2)cc1]<br>Starting material: 1-(4-(Chloromethyl)-phenyl)-1H-pyrazole | Conditions: DMF, 60° C.<br>$^1$H NMR (Chloroform-d) δ: 7.93 (d, 1H), 7.67-7.75 (m, 3H), 7.58 (s, 1H), 7.50 (d, 2H), 7.16-7.23 (m, 4H), 6.51 (s, 1H), 6.45-6.49 (m, 1H), 5.13 (s, 2H), 4.03 (s, 4H), 3.75 (s, 2H). LC-MS: m/z 400.5 (M + H)$^+$. |
| 109 | 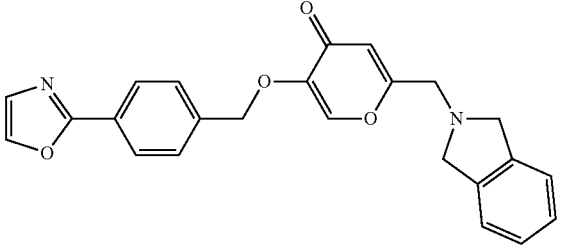 [SMILES: O=c1cc(CN2Cc3ccccc3C2)occ1OCc1ccc(-c2ncco2)cc1]<br>Starting material: 2-(4-(Chloromethyl)-phenyl)oxazole | Conditions: DMF, 60° C.<br>$^1$H NMR (Chloroform-d) δ: 8.06 (d, 2H), 7.72 (s, 1H), 7.59 (s, 1H), 7.51 (d, 2H), 7.24 (s, 1H), 7.20 (d, 4H), 6.51 (s, 1H), 5.09-5.17 (m, 2H), 4.03 (s, 4H), 3.75 (s, 2H). LC-MS: m/z 401.5 (M + H)$^+$. |
| 110 | 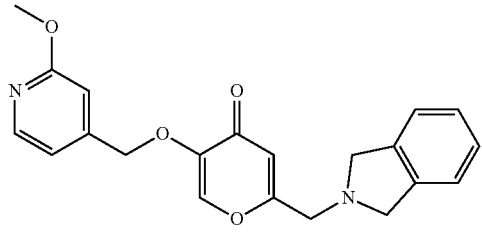 [SMILES: COc1cc(COc2coc(CN3Cc4ccccc4C3)cc2=O)ccn1]<br>Starting material: 4-(Chloromethyl)-2-methoxypyridine | Conditions: C.<br>$^1$H NMR (Chloroform-d) δ: 8.16 (dd, 1H), 7.58 (s, 1H), 7.18-7.24 (m, 4H), 6.89-6.92 (m, 1H), 6.76-6.78 (m, 1H), 6.51 (m, 1H), 5.07 (s, 2H), 4.04 (s, 4H), 3.94 (s, 3H), 3.76 (d, 2H).<br>LC-MS: m/z 365.3 (M + H)$^+$ |
| 111 | 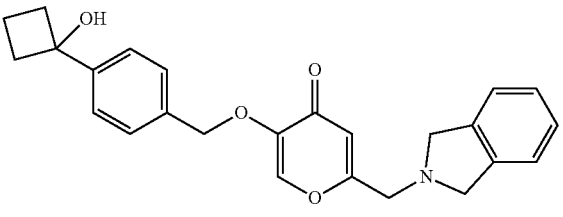 [SMILES: O=c1cc(CN2Cc3ccccc3C2)occ1OCc1ccc(C2(O)CCC2)cc1]<br>Starting material: 1-(4-(Chloromethyl)-phenyl)cyclobutanol | $^1$H NMR (Chloroform-d) δ: 7.56 (s, 1H), 7.48-7.52 (m, 2H), 7.38-7.42 (m, 2H), 7.16-7.23 (m, 4H), 6.48 (m, 1H), 5.07 (s, 2H), 4.01 (s, 4H), 3.73 (d, 2H), 2.49-2.58 (m, 2H), 2.31-2.41 (m, 2H), 1.96-2.06 (m, 1H), 1.62-1.74 (m, 1H). LC-MS: m/z 404.4 (M + H)$^+$ |
| 112 | 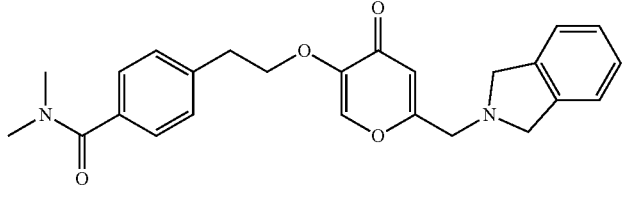 [SMILES: CN(C)C(=O)c1ccc(CCOc2coc(CN3Cc4ccccc4C3)cc2=O)cc1]<br>Starting material: 4-(2-Chloroethyl)-N,N-dimethylbenzamide | $^1$H NMR (Chloroform-d) δ: 7.56 (s, 1H), 7.35-7.39 (m, 2H), 7.29-7.33 (m, 2H), 7.17-7.24 (m, 4H), 6.49 (m, 1H), 4.11 (t, 2H), 4.04 (s, 4H), 3.76 (d, 2H), 3.15 (t, 2H), 3.10 (br s, 3H), 2.98 (s, 3H). LC-MS: m/z 419.4 (M + H)$^+$ |

| No | Structure and starting material | Deviating reaction conditions/ $^1$H NMR (400 MHz)/LC-MS |
|---|---|---|
| 113 | Starting material: N-(4-(Chloromethyl)benzyl)methanesulfonamide | Conditions: 60° C., B. 1H NMR (DMSO-d6) δ: 8.21 (s, 1H), 7.58 (t, 1H), 7.35-7.44 (m, 4H), 7.17-7.28 (m, 4H), 6.42 (s, 1H), 4.95 (s, 2H), 4.17 (d, 2H), 3.96 (s, 4H), 3.80 (s, 2H), 2.86 (s, 3H). LC-MS: m/z 441.8 (M + H)+ |
| 114 | Starting material: 3-(4-(Chloromethyl)phenyl)oxetan-3-ol | $^1$H NMR (Chloroform-d) δ: 7.59-7.64 (m, 2H), 7.58 (s, 1H), 7.45-7.49 (m, 2H), 7.18-7.23 (m, 4H), 6.50 (s, 1H), 5.10 (s, 2H), 4.88-4.94 (m, 4H), 4.03 (s, 4H), 3.75 (s, 2H), 2.52 (s, 1H). LC-MS: m/z 406.5 (M + H)$^+$ |
| 115 | Starting material: 3-(4-(Chloromethyl)phenyl)oxetan-3-ol | $^1$H NMR (Chloroform-d) δ: 7.60-7.63 (m, 2H), 7.58 (s, 1H), 7.45-7.49 (m, 2H), 7.10-7.15 (m, 1H), 6.87-6.94 (m, 2H), 6.49 (m, 1H), 5.10 (s, 2H), 4.88-4.94 (m, 4H), 4.01 (m, 2H), 3.98 (m, 2H), 3.74 (d, 2H), 2.52 (s, 1H). LC-MS: m/z 424.5 (M + H)$^+$ |
| 116 | Starting material: 3-(4-(Chloromethyl)phenyl)oxetan-3-ol | Conditions: 60° C., C. $^1$H NMR (Chloroform-d) δ: 7.60-7.64 (m, 2H), 7.58 (s, 1H), 7.44-7.52 (m, 4H), 7.31 (d, 1H), 6.50 (s, 1H), 5.10 (s, 2H), 4.87-4.95 (m, 4H), 4.07 (s, 4H), 3.77 (s, 2H). LC-MS: m/z 474.8 (M + H)$^+$ |
| 117 | Starting material: 3-(4-(Chloromethyl)phenyl)oxetan-3-ol | Conditions: 60° C., C. $^1$H NMR (Chloroform-d) δ: 7.59-7.64 (m, 2H), 7.57 (s, 1H), 7.45-7.49 (m, 2H), 7.08-7.16 (m, 3H), 6.97-7.01 (m, 1H), 6.51 (s, 1H), 5.10 (s, 2H), 4.88-4.94 (m, 4H), 3.70 (s, 2H), 3.53 (s, 2H), 2.92 (t, 2H), 2.82 (t, 2H), 2.49 (s, 1H). LC-MS: m/z 420.8 (M + H)$^+$ |

| No | Structure and starting material | Deviating reaction conditions/ ¹H NMR (400 MHz)/LC-MS |
|---|---|---|
| 118 | 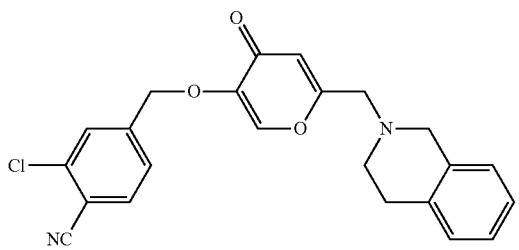 [SMILES: N#Cc1ccc(COc2coc(CN3CCc4ccccc4C3)cc2=O)cc1Cl]<br>Starting material: 3-Chloro-4-cyano-benzyl methanesulfonate | Conditions: THF, reflux, C.<br>1H NMR (DMSO-d6) δ: 8.27 (s, 1 H), 8.02 (m, J = 7.9 Hz, 1 H), 7.80 (s, 1 H), 7.59 (m, J = 7.9 Hz, 1 H), 7.11 (br s, 3 H), 6.98-7.08 (m, 1 H), 6.45 (s, 1 H), 5.08 (s, 2 H), 3.63 (s, 2 H), 3.60 (br s, 2 H), 2.72-2.92 (m, 4 H); LC-MS: m/z 407.7 (M + H)+. |
| 119 | 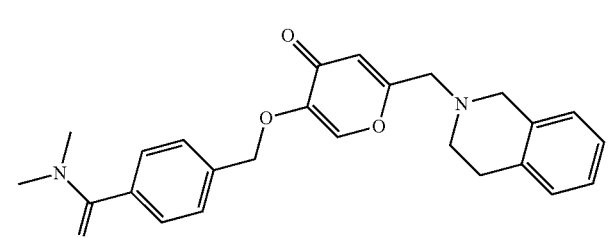<br>Starting material: 4-(Chloromethyl)-N,N-dimethylbenzamide | Conditions: THF, reflux. 1H NMR (Chloroform-d) δ: 7.57 (s, 1 H), 7.39-7.47 (m, 1 H), 7.39-7.47 (m, 3 H), 7.09-7.18 (m, 3 H), 6.96-7.01 (m, 1 H), 6.51 (s, 1 H), 5.10 (s, 2 H), 3.70 (s, 2 H), 3.53 (s, 2 H), 3.11 (br s, 3 H), 2.95-3.03 (m, 3 H), 2.90-2.95 (m, 2 H), 2.79-2.86 (m, 2 H); LC-MS: m/z 419.4 (M + H)+. |
| 120 | 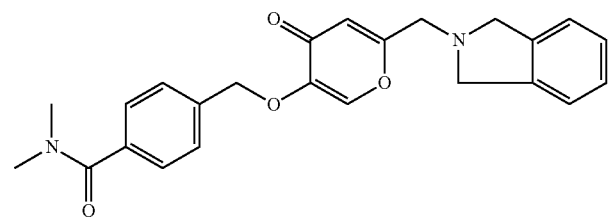<br>Starting material: 4-(Chloromethyl)-N,N-dimethylbenzamide | Conditions: THF/DMF, reflux, C.<br>1H NMR (DMSO-d6) δ: 8.24 (s, 1 H), 7.46-7.51 (m, 2 H), 7.44 (s, 2 H), 7.18-7.26 (m, 4 H), 6.43 (s, 1 H), 4.99 (s, 2 H), 3.96 (s, 4 H), 3.80 (s, 2 H), 2.98 (br s, 3 H), 2.91 (br s, 3 H). LC-MS: m/z 405.3 (M + H)+. |
| 121 | 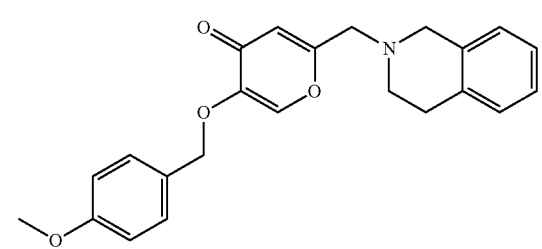 [SMILES: COc1ccc(COc2coc(CN3CCc4ccccc4C3)cc2=O)cc1]<br>Starting material: 1-(Chloromethyl)-4-methoxybenzene | Conditions: DMF, 70° C.<br>1H NMR (Chloroform-d) δ ppm 7.54 (s, 1 H), 7.30-7.36 (m, 2 H), 7.13 (s, 3 H), 6.95-7.01 (m, 1 H), 6.89 (m, J = 8.7 Hz, 2 H), 6.49 (s, 1 H), 5.02 (s, 2 H), 3.80 (s, 3 H), 3.69 (s, 2 H), 3.52 (s, 2 H), 2.87-2.96 (m, 2 H), 2.81 (s, 2 H); LC-MS: m/z 378.8 (M + H)+. |
| 122 | 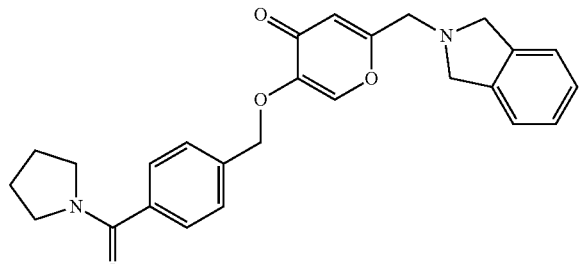<br>Starting material: [4-(Chloromethyl)phenyl]-1-pyrrolidinylethanone | Conditions: DMF, 70° C., C and E.<br>1H NMR (400 MHz, DMSO-d6) δ: 8.23 (s, 1 H), 7.41-7.59 (m, 4 H), 7.13-7.31 (m, 4 H), 6.42 (s, 1 H), 4.99 (s, 2 H), 3.95 (s, 4 H), 3.79 (s, 2 H), 3.36-3.53 (m, 4 H), 1.72-1.94 (m, 4 H); LC-MS: m/z 431.4 (M + H)+. |

-continued

| No | Structure and starting material | Deviating reaction conditions/ ¹H NMR (400 MHz)/LC-MS |
|---|---|---|
| 123 | 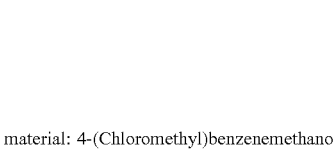<br>Starting material: 4-(Chloromethyl)benzenemethanol | Conditions: B and E.<br>1H NMR (DMSO-d6) δ: 8.19 (s, 1 H), 7.32-7.42 (m, 4 H), 7.18-7.26 (m, 4 H), 6.41 (s, 1 H), 5.16-5.28 (m, 1 H), 4.86-4.96 (m, 2 H), 4.47-4.55 (m, 2 H), 3.95 (s, 4 H), 3.78 (s, 2 H); LC-MS: m/z 364.2 (M + H)+. |
| 124 | 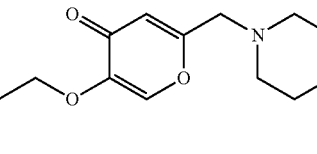<br>Starting material: 4-(Chloromethyl)-N,N-dimethylbenzamide | Conditions: DMF, 70° C., D.<br>1H NMR (DMSO-d6) δ: 8.24 (s, 1 H), 7.41-7.49 (m, 4 H), 7.03-7.13 (m, 1 H), 6.91-6.97 (m, 2 H), 6.42 (s, 1 H), 4.98 (s, 2 H), 3.59 (s, 4 H), 2.98 (br s, 3 H), 2.90 (br s, 3 H), 2.80-2.87 (m, 2 H), 2.71-2.78 (m, 2 H); LC-MS: m/z 437.5 (M + H)+. |
| 125 | 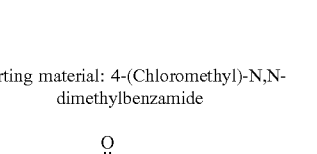<br>Starting material: [4-(Chloromethyl)phenyl]-1-pyrrolidinylmethanone | Conditions: DMF, 70° C., G.<br>1H NMR (Chloroform-d) δ ppm 7.51-7.54 (m, 3 H), 7.41-7.46 (m, 2 H), 7.03-7.26 (m, 4 H), 6.55 (s, 1 H), 5.10 (s, 2 H), 3.61-3.67 (m, 2 H), 3.58 (s, 2 H), 3.37-3.45 (m, 2 H), 2.76 (s, 2 H), 1.93-2.00 (m, 2 H), 1.84-1.92 (m, 2 H), 1.56 (s, 3 H), 1.38 (d, J = 6.7 Hz, 3 H); LC-MS: m/z 459.7 (M + H)+. |
| 126 | 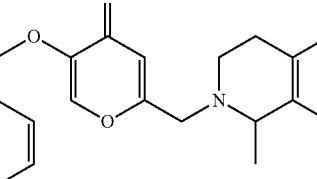<br>Starting material: 4-(Chloromethyl)-N,N-diethylbenzamide | Conditions: DMF, 70° C.<br>1H NMR (Chloroform-d) δ: 7.58 (s, 1 H), 7.42-7.46 (m, 2 H), 7.36-7.39 (m, 2 H), 7.17-7.23 (m, 4 H), 6.51 (s, 1 H), 5.09 (s, 2 H), 4.04 (s, 4 H), 3.76 (s, 2 H), 3.54 (br s, 2 H), 3.25 (br s, 2 H), 1.20-1.30 (m, 3 H), 1.06-1.15 (m, 3 H); LC-MS: m/z 433.4 (M + H)+. |
| 127 | 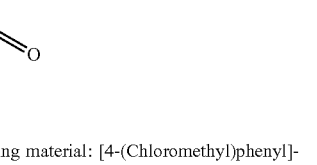<br>Starting material: 4-(Chloromethyl)-N,N-dimethylbenzamide | Conditions: DMF, C.<br>1H NMR (DMSO-d6) δ: 8.24 (s, 1 H), 7.41-7.50 (m, 4 H), 7.21-7.29 (m, 1 H), 6.95-7.15 (m, 2 H), 6.42 (s, 1 H), 4.99 (s, 2 H), 3.87-4.00 (m, 4 H), 3.79 (s, 2 H), 2.98 (br s, 3 H), 2.91 (br s, 3 H); LC-MS: m/z 423.4 (M + H)+. |

| No | Structure and starting material | Deviating reaction conditions/ $^1$H NMR (400 MHz)/LC-MS |
|---|---|---|
| 128 | Starting material: (4-(Chloromethyl)-phenyl)(piperidin-1-yl)methanone | Conditions: DMF, E and B.<br>1H NMR (DMSO-d6) δ: 8.24 (s, 1 H), 7.45-7.51 (m, 2 H), 7.37-7.41 (m, 2 H), 7.18-7.26 (m, 4 H), 6.43 (s, 1 H), 4.98 (s, 2 H), 3.96 (s, 4 H), 3.80 (s, 2 H), 3.46-3.67 (m, 2 H), 3.19-3.31 (m, 2 H), 1.38-1.65 (m, 6 H); LC-MS: m/z 445.4 (M + H)+. |
| 129 | Starting material: Azetidin-1-yl(4-(chloromethyl)phenyl)methanone | Conditions: DMF, 70° C., C.<br>1H NMR (DMSO-d6) δ: 8.24 (s, 1 H), 7.61-7.68 (m, 2 H), 7.43-7.55 (m, 2 H), 7.17-7.27 (m, 4 H), 6.43 (s, 1 H), 5.00 (s, 2 H), 4.23-4.35 (m, 2 H), 3.99-4.10 (m, 2 H), 3.95 (s, 4 H), 3.79 (s, 2 H), 2.20-2.30 (m, 2 H); LC-MS: m/z 417.4 (M + H)+. |
| 130 | Starting material: [4-(Chloromethyl)phenyl]-1-pyrrolidinylmethanone | Conditions: DMF, 85° C., E.<br>1H NMR (DMSO-d6) δ: 8.23 (s, 1 H), 7.43-7.57 (m, 5 H), 7.35-7.42 (m, 1 H), 7.18-7.25 (m, 1 H), 6.42 (s, 1 H), 4.99 (s, 2 H), 3.90-3.98 (m, 4 H), 3.42-3.51 (m, 2 H), 3.36-3.41 (m, 2 H), 3.35 (s, 2 H), 1.76-1.92 (m, 4 H); LC-MS: m/z 510.4 (M + H)+. |
| 131 | Starting material: N-(tert-Butyl)-4-(chloromethyl)benzamide | Conditions: DMF, 85° C., B and E.<br>1H NMR (DMSO-d6) δ: 8.21 (s, 1 H), 7.79-7.84 (m, 2 H), 7.76 (s, 1 H), 7.43-7.58 (m, 2 H), 7.18-7.26 (m, 4 H), 6.42 (s, 1 H), 5.01 (s, 2 H), 3.95 (s, 4 H), 3.79 (s, 2 H), 1.38 (s, 9 H); LC-MS: m/z 433.4 (M + H)+. |
| 132 | Starting material: 4-(Chloromethyl)-N,N-dimethylbenzamide | Conditions: DMF, 85° C., E.<br>1H NMR (DMSO-d6) δ: 8.24 (s, 1 H), 7.39-7.51 (m, 4 H), 7.17-7.26 (m, 4 H), 6.44 (s, 1 H), 4.99 (s, 2 H), 4.08-4.16 (m, 1 H), 3.94-4.04 (m, 2 H), 3.70-3.77 (m, 1 H), 3.58-3.68 (m, 1 H), 2.98 (br s, 3 H), 2.90 (br s, 3 H), 1.32-1.38 (m, 3 H); LC-MS: m/z 463.3 (M + H)+. |

-continued

| No | Structure and starting material | Deviating reaction conditions/ $^1$H NMR (400 MHz)/LC-MS |
|---|---|---|
| 133 | <br>Starting material: 4-(Chloromethyl)-N,N-dimethylbenzamide | Conditions: DMF, 85° C., E.<br>1H NMR (DMSO-d6) δ: 8.24 (s, 1 H), 7.40-7.50 (m, 4 H), 7.17-7.26 (m, 4 H), 6.44 (s, 1 H), 4.99 (s, 2 H), 4.09-4.16 (m, 1 H), 3.93-4.05 (m, 2 H), 3.69-3.78 (m, 1 H), 3.56-3.64 (m, 1 H), 2.98 (br s, 3 H), 2.90 (br s, 3 H), 1.32-1.37 (m, 3 H); LC-MS: m/z 419.4 (M + H)+. |
| 134 | 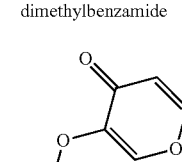<br>Starting material: 4-(Chloromethyl)-N,N-bis(1-methylethyl)benzamide | Conditions: DMF, 85° C., D.<br>1H NMR (DMSO-d6) δ: 8.25 (s, 1 H), 8.13 (s, 1 H), 7.43-7.49 (m, 2 H), 7.28-7.32 (m, 2 H), 7.18-7.26 (m, 4 H), 6.42 (s, 1 H), 4.96 (s, 1 H), 3.96 (s, 4 H), 3.80 (s, 2 H), 3.61 (br s, 1 H), 0.92-1.62 (m, 1 H); LC-MS: m/z 461.2 (M + H)+. |
| 135 | 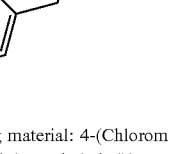<br>Starting material: N-(tert-Butyl)-4-(chloromethyl)benzamide | Conditions: DMF, 85° C., E.<br>1H NMR (DMSO-d6) δ: 8.21 (s, 1 H), 7.78-7.89 (m, 2 H), 7.73-7.77 (m, 1 H), 7.44-7.49 (m, 2 H), 7.06-7.17 (m, 3 H), 7.01-7.05 (m, 1 H), 6.42 (s, 1 H), 5.01 (s, 2 H), 3.53-3.68 (m, 4 H), 2.76 (s, 4 H), 1.38 (s, 9 H); LC-MS: m/z 447.4 (M + H)+. |
| 136 | 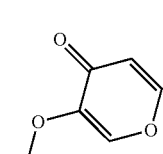<br>Starting material: 2-(4-(Chloromethyl)-phenyl)-N,N-dimethylacetamide | Conditions: DMF, 85° C., E.<br>1H NMR (DMSO-d6): δ: 8.21 (s, 1 H), 7.30-7.41 (m, 2 H), 7.18-7.26 (m, 6 H), 6.41 (s, 1 H), 4.91 (s, 2 H), 3.95 (s, 4 H), 3.79 (s, 2 H), 3.69 (s, 2 H), 2.97-3.01 (m, 3 H), 2.83 (s, 3 H); LC-MS: m/z 419.4 (M + H)+. |
| 137 | 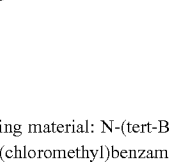<br>Starting material: 4-(Chloromethyl)-N,N-dimethylbenzamide | Conditions: DMF, 85° C., E.<br>1H NMR (DMSO-d6): δ: 8.24 (s, 1 H), 7.45-7.49 (m, 2 H), 7.41-7.45 (m, 2 H), 7.34 (s, 1 H), 7.22-7.28 (m, 2 H), 6.42 (s, 1 H), 4.99 (s, 2 H), 3.91-3.97 (m, 4 H), 3.79 (s, 2 H), 2.98 (br s, 3 H), 2.90 (br s, 3 H); LC-MS: m/z 439.3 (M + H)+. |

| No | Structure and starting material | Deviating reaction conditions/ $^1$H NMR (400 MHz)/LC-MS |
|---|---|---|
| 138 | Starting material: 4-(Chloromethyl)-N,N-dimethylbenzamide | Conditions: DMF, 85° C., C. 1H NMR (DMSO-d6): δ: 8.24 (s, 1 H), 7.41-7.50 (m, 4 H), 7.10-7.16 (m, 1 H), 6.81-6.86 (m, 1 H), 6.73-6.78 (m, 1 H), 6.41 (s, 1 H), 4.99 (s, 2 H), 3.84-3.95 (m, 4 H), 3.78 (s, 2 H), 3.72 (s, 3 H), 2.98 (br s, 3 H), 2.91 (br s, 3 H); LC-MS: m/z 435.4 (M + H)+. |
| 139 | Starting material: 4-(Chloromethyl)-N,N-dimethylbenzamide | Conditions: DMF, 85° C., C. 1H NMR (DMSO-d6): δ: 8.24 (s, 1 H), 7.64 (s, 1 H), 7.55-7.60 (m, 1 H), 7.41-7.50 (m, 5 H), 6.44 (s, 1 H), 4.99 (s, 2 H), 4.03 (s, 4 H), 3.82 (s, 2 H), 2.98 (br s, 3 H), 2.91 (br s, 3 H); LC-MS: m/z 473.5 (M + H)+. |
| 140 | Starting material: 4-(Chloromethyl)-N-(1-methylethyl)benzamide | Conditions: DMF, 85° C., C. 1H NMR (DMSO-d6): δ: 8.18-8.27 (m, 2 H), 7.81-7.92 (m, 2 H), 7.43-7.54 (m, 2 H), 7.13-7.30 (m, 4 H), 6.43 (s, 1 H), 5.02 (s, 2 H), 4.03-4.15 (m, 1 H), 3.95 (s, 4 H), 3.79 (s, 2 H), 1.17 (d, J = 6.6 Hz, 6 H); LC-MS: m/z 419.3 (M + H)+. |
| 141 | Starting material: 4-(Chloromethyl)-N-(prop-2-yn-1-yl)benzamide | Conditions: DMF, 85° C., E. 1H NMR (DMSO-d6): δ: 8.96 (t, J = 5.8 Hz, 1 H), 8.23 (s, 1 H), 7.85-7.94 (m, 2 H), 7.43-7.60 (m, 2 H), 7.15-7.29 (m, 4 H), 6.43 (s, 1 H), 5.02 (s, 2 H), 4.00-4.12 (m, 2 H), 3.95 (s, 4 H), 3.79 (s, 2 H), 3.13 (t, J = 2.5 Hz, 1 H); LC-MS: m/z 415.4 (M + H)+. |
| 142 | Starting material: 4-(Chloromethyl)-N-hexylbenzamide | Conditions: DMF. 1H NMR (Chloroform-d) δ: 7.73-7.78 (m, 2 H), 7.56 (s, 1 H), 7.43-7.51 (m, 2 H), 7.18-7.24 (m, 4 H), 6.50 (s, 1 H), 6.07-6.18 (m, 1 H), 5.13 (s, 2 H), 4.03 (s, 4 H), 3.75 (s, 2 H), 3.41-3.48 (m, 2 H), 1.57-1.65 (m, 3 H), 1.29-1.38 (m, 5 H), 0.86-0.93 (m, 3 H); LC-MS: m/z 461.5 (M + H)+. |

-continued

| No | Structure and starting material | Deviating reaction conditions/ $^1$H NMR (400 MHz)/LC-MS |
|---|---|---|
| 143 | Starting material: 2-(4-(Chloromethyl)-benzamido)-2-methylpropyl acetate | Conditions: DMF, G.<br>1H NMR (DMSO-d6): δ: 8.21 (s, 1 H), 7.80-7.84 (m, 3 H), 7.49 (s, 2 H), 7.18-7.28 (m, 4 H), 6.42 (s, 1 H), 5.02 (s, 2 H), 4.25 (s, 2 H), 3.95 (s, 4 H), 3.79 (s, 2 H), 2.02 (s, 3 H), 1.36 (s, 6 H); LC-MS: m/z 491.5 (M + H)+. |
| 144 | Starting material: 1-(Chloromethyl)-4-ethenylbenzene | Conditions: DMF, C.<br>1H NMR (DMSO-d6): δ: 8.21 (s, 1 H), 7.45-7.55 (m, 2 H), 7.36-7.43 (m, 2 H), 7.14-7.29 (m, 4 H), 6.69-6.80 (m, 1 H), 6.42 (s, 1 H), 5.82-5.89 (m, 1 H), 5.25-5.31 (m, 1 H), 4.94 (s, 2 H), 3.95 (s, 4 H), 3.79 (s, 2 H); LC-MS: m/z 360.4 (M + H)+. |
| 145 | Starting material: 4-(Chloromethyl)-N-(4-hydroxybutyl)benzamide | Conditions: DMF, E.<br>1H NMR (DMSO-d6): δ: 8.38-8.57 (m, 1 H), 8.23 (s, 1 H), 7.81-7.92 (m, 2 H), 7.40-7.59 (m, 2 H), 7.16-7.28 (m, (s, 4 H), 6.43 (s, 1 H), 5.02 (s, 2 H), 4.41 (t, J = 5.1 Hz, 1 H), 3.95 (s, 4 H), 3.79 2 H), 3.35-3.47 (m, 2 H), 3.21-3.31 (m, 2 H), 1.50-1.60 (m, 2 H), 1.41-1.50 (m, 2 H); LC-MS: m/z 449.5 (M + H)+. |
| 146 | Starting material: (E)-3-(4-(chloromethyl)phenyl)-N,N-dimethylacrylamide and (E)-3-(4-(bromomethyl)phenyl)-N,N-dimethylacrylamide | Conditions: DMF, 85° C., C.<br>1H NMR (DMSO-d6): δ: 8.22 (s, 1 H), 7.71-7.76 (m, 2 H), 7.43-7.50 (m, 3 H), 7.17-7.27 (m, 5 H), 6.42 (s, 1 H), 4.98 (s, 2 H), 3.95 (s, 4 H), 3.79 (s, 2 H), 3.16 (s, 3 H), 2.93 (s, 3 H); LC-MS: m/z 431.6 (M + H)+. |

| No | Structure and starting material | Deviating reaction conditions/ $^1$H NMR (400 MHz)/LC-MS |
|---|---|---|
| 147 | 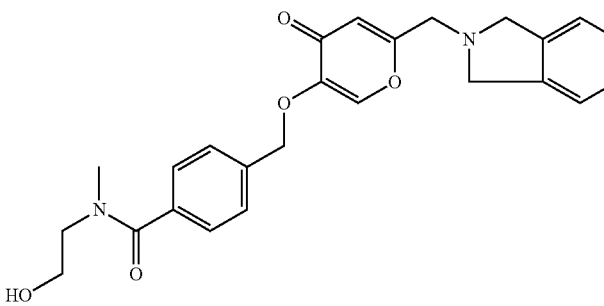<br>Starting material: 2-(4-(Chloromethyl)-phenyl)-N-(2-hydroxyethyl)-N-methyl-acetamide | Conditions: DMF, 85° C., D.<br>1H NMR (DMSO-d6): δ: 8.19-8.25 (m, 1 H), 7.33-7.37 (m, 2 H), 7.18-7.26 (m, 6 H), 6.41 (s, 1 H), 4.91 (s, 2 H), 3.95 (s, 4 H), 3.74 (s, 1 H), 3.69 (s, 1 H), 3.51-3.55 (m, 2 H), 3.45-3.49 (m, 2 H), 3.38-3.42 (m, 3 H), 3.32-3.37 (m, 3 H); LC-MS: m/z 449.5 (M + H)+. |
| 148 | 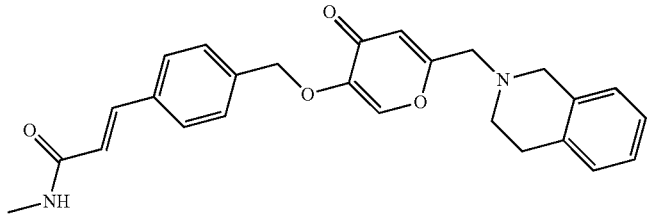 [SMILES: CNC(=O)/C=C/c1ccc(COc2coc(CN3CCc4ccccc4C3)cc2=O)cc1]<br>Starting material: (E)-3-(4-(chloro-methyl)phenyl)-N-methylacrylamide | Conditions: DMF, E.<br>1H NMR (Chloroform-d) δ: 8.08 (s, 1 H), 7.57-7.63 (m, 2 H), 7.49 (m, J = 8.2 Hz, 2 H), 7.36-7.43 (m, 2 H), 7.09-7.18 (m, 3 H), 6.96-7.02 (m, 1 H), 6.53 (s, 1 H), 6.40 (d, J = 15.6 Hz, 1 H), 5.80-5.90 (m, 1 H), 5.07 (s, 2 H), 3.72 (s, 2 H), 3.56 (s, 2 H), 2.90-2.97 (m, 5 H), 2.80-2.89 (m, 2 H); LC-MS: m/z 431.6 (M + H)+. |
| 149 | 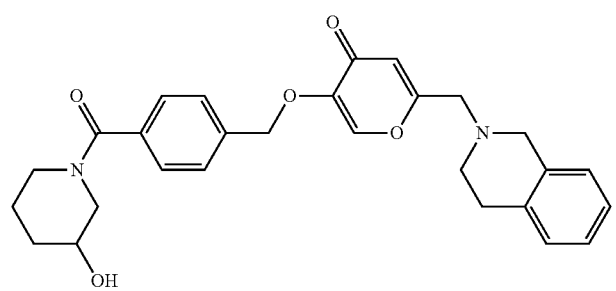 [SMILES: O=C(c1ccc(COc2coc(CN3CCc4ccccc4C3)cc2=O)cc1)N1CCCC(O)C1]<br>Starting material: (4-(Chloromethyl)-phenyl)(3-hydroxypiperidin-1-yl)-methanone | Conditions: DMF, D.<br>1H NMR (Chloroform-d) δ: 7.58 (s, 1 H), 7.40-7.47 (m, 4 H), 7.09-7.17 (m, 3 H), 6.97-7.02 (m, 1 H), 6.52 (s, 1 H), 5.09 (s, 2 H), 3.78-4.02 (m, 1 H), 3.70 (s, 2 H), 3.54 (s, 2 H), 2.89-2.96 (m, 2 H), 2.80-2.86 (m, 2 H), 1.80-1.97 (m, 2 H), 1.66 (s, 5 H); LC-MS: m/z 475.6 (M + H)+. |
| 150 | 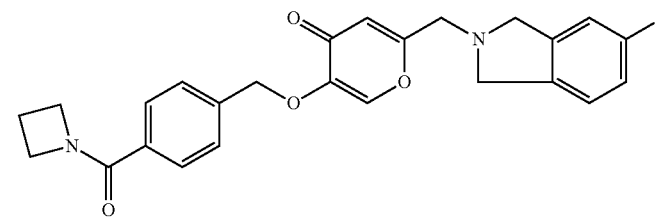<br>Starting material: Azetidin-1-yl(4-(chloromethyl)phenyl)methanone | Conditions: DMF, G.<br>1H NMR (Chloroform-d) δ: 7.64 (s, 1 H), 7.62-7.63 (m, 1 H), 7.57 (s, 1 H), 7.42-7.47 (m, 2 H), 6.82-7.00 (m, 2 H), 6.50 (s, 1 H), 5.11 (s, 2 H), 4.20-4.33 (m, 5 H), 4.00 (br d, J = 12.4 Hz, 4 H), 3.75 (s, 2 H), 2.31-2.39 (m, 2 H); LC-MS: m/z 435.6 (M + H)+. |

-continued

| No | Structure and starting material | Deviating reaction conditions/ $^1$H NMR (400 MHz)/LC-MS |
|---|---|---|
| 151 | 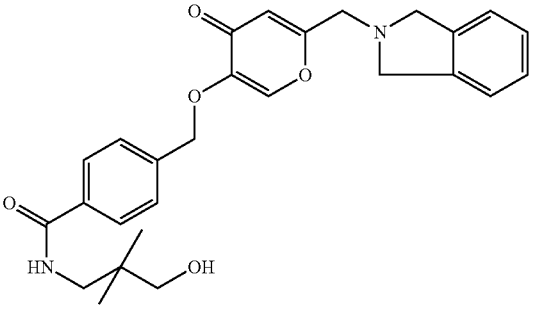 [SMILES: CC(C)(CO)CNC(=O)c1ccc(COc2coc(CN3Cc4ccccc4C3)cc2=O)cc1]<br>Starting material: 4-(Chloromethyl)-N-(3-hydroxy-2,2-dimethylpropyl)-benzamide | Conditions: DMF, D.<br>1H NMR (DMSO-d6): δ: 8.35-8.45 (m, 1 H), 8.23 (s, 1 H), 8.15 (s, 1 H), 7.84-7.88 (m, 2 H), 7.49-7.53 (m, 2 H), 7.18-7.26 (m, 4 H), 6.43 (s, 1 H), 5.03 (s, 2 H), 3.95 (s, 4 H), 3.78-3.81 (m, 2 H), 3.15-3.17 (m, 2 H), 3.13 (s, 2 H), 0.82-0.97 (m, 6 H); LC-MS: m/z 463.6 (M + H)+. |
| 152 | 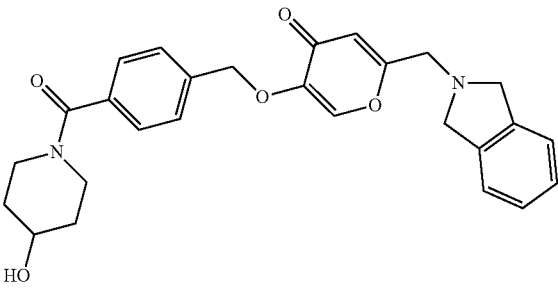 [SMILES: O=C(c1ccc(COc2coc(CN3Cc4ccccc4C3)cc2=O)cc1)N1CCC(O)CC1]<br>Starting material: (4-(Chloromethyl)-phenyl)(4-hydroxypiperidin-1-yl)-methanone | Conditions: DMF, B and E.<br>1H NMR (DMSO-d6): δ: 8.25 (s, 1 H), 7.46-7.51 (m, 2 H), 7.36-7.44 (m, 2 H), 7.18-7.27 (m, 4 H), 6.43 (s, 1 H), 4.98 (s, 2 H), 4.78 (d, J = 4.0 Hz, 1 H), 3.96 (s, 4 H), 3.80 (s, 2 H), 3.71-3.79 (m, 1 H), 3.33-3.57 (m, 1 H), 3.06-3.31 (m, 2 H), 1.78 (br s, 1 H), 1.70 (br s, 1 H), 1.35 (br s, 2 H); LC-MS: m/z 461.6 (M + H)+. |
| 153 | 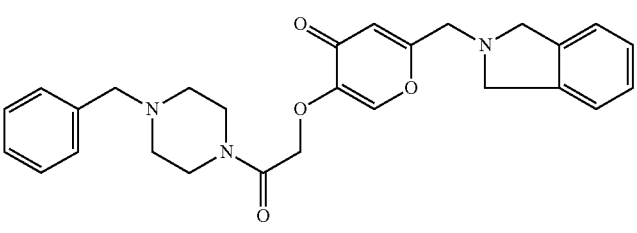 [SMILES: O=C(COc1coc(CN2Cc3ccccc3C2)cc1=O)N1CCN(Cc2ccccc2)CC1]<br>Starting material: 2-Chloro-1-[4-(phenylmethyl)-1-piperazinyl]ethanone | Conditions: DMF, A.<br>1H NMR (Chloroform-d) δ: 7.98 (s, 1 H), 7.26-7.35 (m, 5 H), 7.17-7.25 (m, 4 H), 6.50 (s, 1 H), 4.78 (s, 2 H), 4.05 (s, 4 H), 3.77 (s, 2 H), 3.52-3.64 (m, 4 H), 3.51 (s, 2 H), 2.38-2.48 (m, 4 H); LC-MS: m/z 460.4 (M + H)+. |
| 154 | 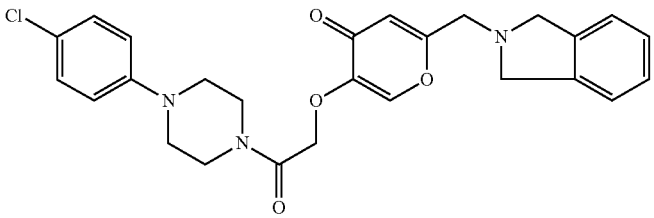 [SMILES: O=C(COc1coc(CN2Cc3ccccc3C2)cc1=O)N1CCN(c2ccc(Cl)cc2)CC1]<br>Starting material: 2-Chloro-1-[4-(4-chlorophenyl)-1-piperazinyl]ethanone | Conditions: DMF, C.<br>1H NMR (DMSO-d6): δ: 8.15 (s, 1 H), 7.20-7.26 (m, 6 H), 6.96-6.99 (m, 2 H), 6.41 (s, 1 H), 4.77 (s, 2 H), 3.96 (s, 4 H), 3.80 (s, 2 H), 3.59 (br s, 4 H), 3.12-3.21 (m, 4 H); LC-MS: m/z 480.3 (M + H)+. |

| No | Structure and starting material | Deviating reaction conditions/ $^1$H NMR (400 MHz)/LC-MS |
|---|---|---|
| 155 | Starting material: 2-Chloro-1-[4-(phenylmethyl)-1-piperidinyl]ethanone | Conditions: DMF, A.<br>1H NMR (DMSO-d6): δ: 8.10 (s, 1 H), 7.15-7.31 (m, 9 H), 6.40 (s, 1 H), 4.62-4.79 (m, 2 H), 4.21-4.35 (m, 1 H), 3.95 (s, 4 H), 3.79 (s, 2 H), 3.70-3.77 (m, 1 H), 2.93 (br s, 1 H), 2.51-2.57 (m, 2 H), 1.68-1.82 (m, 1 H), 1.48-1.67 (m, 2 H), 0.95-1.22 (m, 2 H); LC-MS: m/z 459.7 (M + H)+. |
| 156 | Starting material: 2-Chloro-1-(4-(phenylsulfonyl)piperazin-1-yl)-ethanone | Conditions: DMF, A.<br>1H NMR (Chloroform-d) δ: 7.88 (s, 1 H), 7.71-7.78 (m, 2 H), 7.59-7.65 (m, 1 H), 7.52-7.59 (m, 2 H), 7.18-7.24 (m, 4 H), 6.46 (s, 1 H), 4.71 (s, 2 H), 4.03 (s, 4 H), 3.76 (s, 2 H), 3.70 (s, 2 H), 3.67-3.70 (m, 2 H), 2.98-3.11 (m, 4 H); LC-MS: m/z 510.5 (M + H)+. |
| 157 | Starting material: 2-Chloro-1-(4-tosyl-piperazin-1-yl)ethanone | Conditions: DMF, A.<br>1H NMR (DMSO-d6) δ: 8.07 (s, 1 H), 7.59-7.65 (m, 2 H), 7.43-7.49 (m, 2 H), 7.17-7.27 (m, 4 H), 6.38 (s, 1 H), 4.66 (s, 2 H), 3.94 (s, 4 H), 3.77 (s, 2 H), 3.53 (br s, 2 H), 3.47 (br s, 2 H), 2.93 (br s, 2 H), 2.87 (br s, 2 H), 2.41 (s, 3 H); LC-MS: m/z 524.6 (M + H)+. |
| 158 | Starting material: (4-(Chloromethyl)-phenyl)(3,3-difluoroazetidin-1-yl)-methanone | Conditions: DMF, 85° C., E.<br>1H NMR (DMSO-d6) δ: 8.25 (s, 1 H), 7.69-7.76 (m, 2 H), 7.46-7.60 (m, 2 H), 7.14-7.29 (m, 4 H), 6.43 (s, 1 H), 5.02 (s, 2 H), 4.82 (s, 2 H), 4.38-4.58 (m, 2 H), 3.96 (s, 4 H), 3.80 (s, 2 H); LC-MS: m/z 453.4 (M + H)+. |

| No | Structure and starting material | Deviating reaction conditions/ $^1$H NMR (400 MHz)/LC-MS |
|---|---|---|
| 159 | 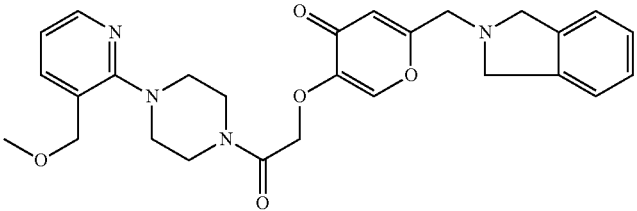 [SMILES: COCc1cccnc1N1CCN(C(=O)COc2coc(CN3Cc4ccccc4C3)cc2=O)CC1]<br>Starting material: 2-Chloro-1-(4-(3-(methoxymethyl)pyridin-2-yl)-piperazin-1-yl)ethanone | Conditions: DMF, 80° C., D.<br>1H NMR (Chloroform-d) δ: 8.24-8.27 (m, 1 H), 8.06 (s, 1 H), 8.02 (s, 1 H), 7.71-7.74 (m, 1 H), 7.19-7.25 (m, 4 H), 6.99-7.03 (m, 1 H), 6.54 (s, 1 H), 4.84 (s, 2 H), 4.43 (s, 2 H), 4.10 (s, 4 H), 3.83 (s, 2 H), 3.66-3.78 (m, 4 H), 3.43 (s, 3 H), 3.14-3.25 (m, 4 H); LC-MS: m/z 491.6 (M + H)+. |
| 160 | 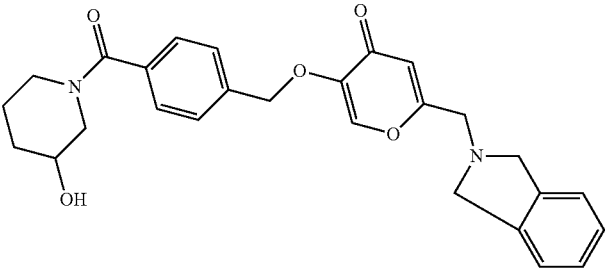 [SMILES: O=C(c1ccc(COc2coc(CN3Cc4ccccc4C3)cc2=O)cc1)N1CCCC(O)C1]<br>Starting material: (4-(Chloromethyl)-phenyl)(3-hydroxypiperidin-1-yl)-methanone | Conditions: DMF, 85° C., D.<br>1H NMR (Chloroform-d) δ ppm 7.59 (s, 1 H), 7.38-7.49 (m, 4 H), 7.16-7.25 (m, 4 H), 6.52 (s, 1 H), 5.09 (s, 2 H), 4.05 (s, 4 H), 3.77 (s, 2 H), 3.13-3.64 (m, 3 H), 2.45-2.83 (m, 3 H), 1.76-2.02 (m, 2 H), 1.34-1.74 (m, 2 H); LC-MS: m/z 461.5 (M + H)+. |
| 161 | 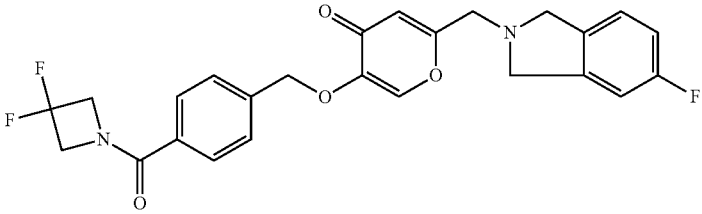 [SMILES: O=C(c1ccc(COc2coc(CN3Cc4ccc(F)cc4C3)cc2=O)cc1)N1CC(F)(F)C1]<br>Starting material: (4-(Chloromethyl)-phenyl)(3,3-difluoroazetidin-1-yl)-methanone | Conditions: DMF, 85° C., C.<br>1H NMR (Chloroform-d) δ: 7.62-7.68 (m, 2 H), 7.60 (s, 1 H), 7.47-7.54 (m, 2 H), 7.10-7.17 (m, 1 H), 6.88-6.94 (m, 2 H), 6.50 (s, 1 H), 5.12 (s, 2 H), 4.48-4.59 (m, 4 H), 3.96-4.04 (m, 4 H), 3.75 (s, 2 H); LC-MS: m/z 471.5 (M + H) |
| 162 | 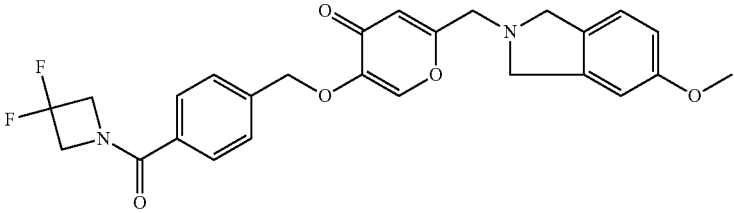 [SMILES: COc1ccc2c(c1)CN(Cc1cc(=O)c(OCc3ccc(C(=O)N4CC(F)(F)C4)cc3)co1)C2]<br>Starting material: (4-(Chloromethyl)-phenyl)(3,3-difluoroazetidin-1-yl)-methanone | Conditions: DMF, 85° C., C.<br>1H NMR (DMSO-d6): δ: 8.24 (s, 1 H), 7.68-7.78 (m, 2 H), 7.49-7.57 (m, 2 H), 7.07-7.19 (m, 1 H), 6.80-6.87 (m, 1 H), 6.73-6.78 (m, 1 H), 6.42 (s, 1 H), 5.02 (s, 2 H), 4.66-4.91 (m, 2 H), 4.38-4.60 (m, 2 H), 3.83-3.97 (m, 4 H), 3.78 (s, 2 H), 3.72 (s, 3 H); LC-MS: m/z 483.5 (M + H)+. |
| 163 | 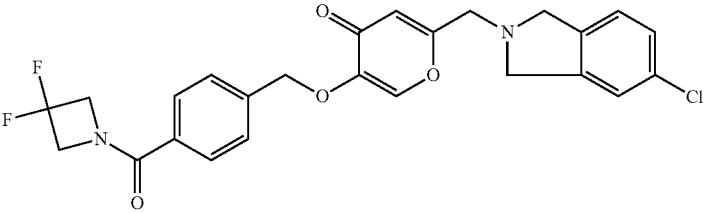 [SMILES: O=C(c1ccc(COc2coc(CN3Cc4ccc(Cl)cc4C3)cc2=O)cc1)N1CC(F)(F)C1]<br>Starting material: (4-(Chloromethyl)-phenyl)(3,3-difluoroazetidin-1-yl)-methanone | Conditions: DMF, 85° C., C.<br>1H NMR (DMSO-d6): δ: 8.24 (s, 1 H), 7.69-7.79 (m, 2 H), 7.50-7.56 (m, 2 H), 7.34 (s, 1 H), 7.27 (s, 2 H), 6.43 (s, 1 H), 5.03 (s, 2 H), 4.69-4.91 (m, 2 H), 4.51 (br s, 2 H), 3.90-3.99 (m, 4 H), 3.77-3.85 (m, 2 H); LC-MS: m/z 487.4 (M + H)+. |

-continued

| No | Structure and starting material | Deviating reaction conditions/ ¹H NMR (400 MHz)/LC-MS |
|----|-------------------------------|--------------------------------------------------------|
| 164 | <br>Starting material: 4-(Chloromethyl)-1,1'-biphenyl | Conditions: DMF, 85° C., E and A.<br>1H NMR (DMSO-d6): δ: 8.25 (s, 1 H), 7.64-7.75 (m, 4 H), 7.43-7.54 (m, 4 H), 7.33-7.41 (m, 1 H), 7.18-7.27 (m, 4 H), 6.43 (s, 1 H), 5.00 (s, 2 H), 3.96 (s, 4 H), 3.80 (s, 2 H); LC-MS: m/z 410.7 |
| 165 | 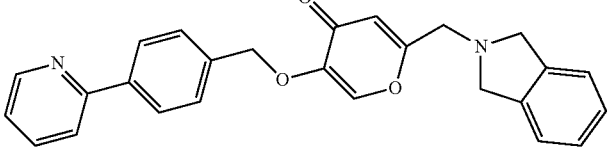<br>Starting material: 2-[4-(Chloromethyl)phenyl]pyridine | Conditions: DMF, 85° C., E.<br>1H NMR (DMSO-d6): δ: 8.64-8.76 (m, 1 H), 8.20-8.37 (m, 1 H), 8.06-8.19 (m, 2 H), 7.95-8.06 (m, 2 H), 7.87-7.95 (m, 1 H), 7.50-7.70 (m, 2 H), 7.34-7.41 (m, 1 H), 7.17-7.26 (m, 3 H), 6.44 (br s, 1 H), 5.03 (br s, 2 H), 3.96 (br s, 4 H), 3.80 (br s, 2 H); LC-MS: m/z 411.3 |
| 166 | 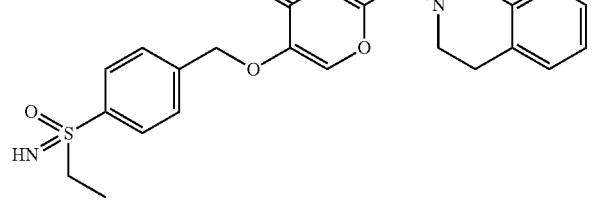<br>Starting material: 1-(Chloromethyl)-4-(ethylsulfonimidoyl)benzene | Conditions: DMF, 80° C., C.<br>1H NMR (Chloroform-d) δ: 7.95-7.99 (m, 2 H), 7.63 (s, 1 H), 7.58-7.62 (m, 2 H), 7.09-7.17 (m, 3 H), 6.98-7.02 (m, 1 H), 6.53 (s, 1 H), 5.16 (s, 2 H), 3.71 (s, 2 H), 3.55 (s, 2 H), 3.12-3.22 (m, 2 H), 2.91-2.96 (m, 2 H), 2.80-2.87 (m, 2 H), 2.68 (s, 1 H), 1.23-1.29 (m, 3 H); LC-MS: m/z 439.3 |
| 167 | 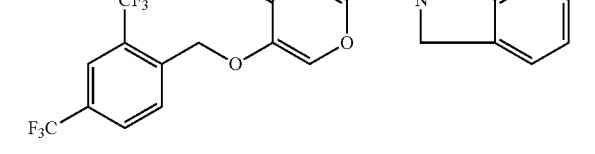<br>Starting material: 1-(Chloromethyl)-2,4-bis(trifluoromethyl)benzene | Conditions: CsCO₃, 1,4-dioxane, reflux. 1H NMR (Methanol-d4) δ: 8.17-8.18 (m, 1 H), 8.11-8.14 (m, 1 H), 7.99-8.04 (m, 2 H), 7.20-7.25 (m, 4 H), 6.61 (s, 1 H), 5.30 (s, 2 H), 4.04 (s, 4 H), 3.88 (s, 2 H); LC-MS: m/z 470.7 |
| 168 | 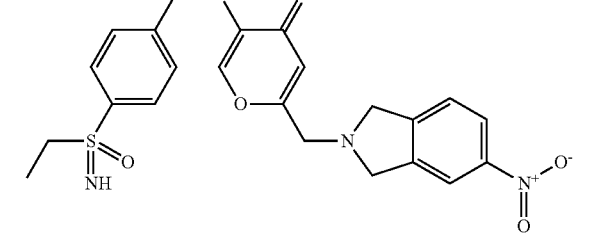<br>Starting material: 1-(Chloromethyl)-4-(ethylsulfonimidoyl)benzene | Conditions: E.<br>1H NMR (DMSO-d6): δ: 8.26 (s, 1 H), 8.15 (s, 2 H), 8.10-8.14 (m, 1 H), 7.86-7.99 (m, 2 H), 7.62-7.66 (m, 2 H), 7.50-7.56 (m, 1 H), 6.45 (s, 1 H), 5.07 (s, 2 H), 4.06 (s, 4 H), 3.84 (s, 2 H), 3.10-3.16 (m, 2 H), 1.06 (t, J = 7.4 Hz, 3 H); LC-MS: m/z 470.4 |

| No | Structure and starting material | Deviating reaction conditions/ $^1$H NMR (400 MHz)/LC-MS |
|---|---|---|
| 169 | 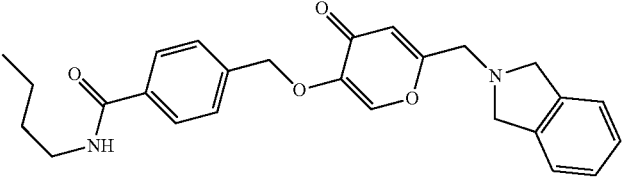 [SMILES: CCCCNC(=O)c1ccc(COc2coc(CN3Cc4ccccc4C3)cc2=O)cc1]<br>Starting material: N-Butyl-4-(chloromethyl)benzamide | Conditions: DMF, 85° C., E.<br>1H NMR (DMSO-d6): δ: 8.39-8.49 (m, 1 H), 8.23 (s, 1 H), 7.81-7.90 (m, 2 H), 7.46-7.52 (m, 2 H), 7.14-7.29 (m, 4 H), 6.43 (s, 1 H), 5.02 (s, 2 H), 3.95 (s, 4 H), 3.79 (s, 2 H), 3.21-3.30 (m, 2 H), 1.46-1.55 (m, 2 H), 1.28-1.38 (m, 2 H), 0.90 (t, J = 7.3 Hz, 3 H); LC-MS: m/z 433.4 (M + H)+. |
| 170 | 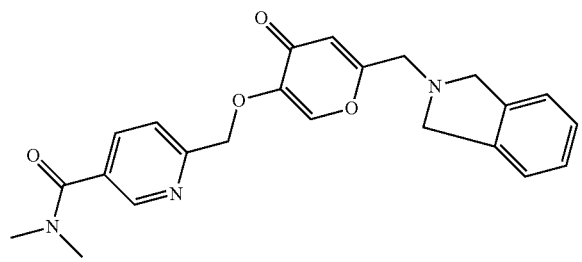 [SMILES: CN(C)C(=O)c1ccc(COc2coc(CN3Cc4ccccc4C3)cc2=O)nc1]<br>Starting material: 6-(Chloromethyl)-N,N-dimethylnicotinamide | Conditions: DMF, B and E.<br>1H NMR (DMSO-d6): δ: 8.60-8.63 (m, 1 H), 8.30 (s, 1 H), 7.91-7.95 (m, 1 H), 7.60-7.64 (m, 1 H), 7.18-7.27 (m, 4 H), 6.44 (s, 1 H), 5.08 (s, 2 H), 3.96 (s, 4 H), 3.81 (s, 2 H), 3.01 (s, 3 H), 2.94 (s, 3 H); LC-MS: m/z 406.4 (M + H)+. |
| 171 | 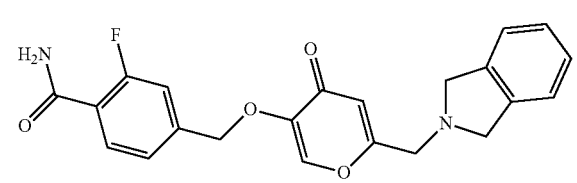 [SMILES: NC(=O)c1ccc(COc2coc(CN3Cc4ccccc4C3)cc2=O)cc1F]<br>Starting material: 4-(Chloromethyl)-2-fluorobenzamide | Condition: DMF, C.<br>1H NMR (DMSO-d6): δ: 8.25 (s, 1 H), 7.62-7.75 (m, 3 H), 7.29-7.38 (m, 2 H), 7.17-7.29 (m, 3 H), 7.04-7.17 (m, 1 H), 6.44 (s, 1 H), 4.96-5.05 (m, 2 H), 3.85-3.97 (m, 4 H), 3.80 (s, 2 H); LC-MS: m/z 395.4 (M + H)+. |
| 172 | 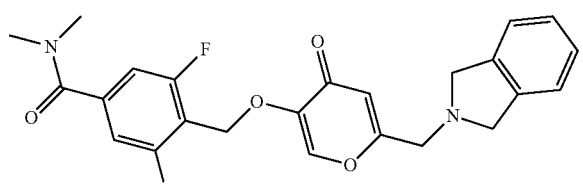<br>Starting material: 4-(Chloromethyl)-3,5-difluoro-N,N-dimethylbenzamide | Condition: DMF, C.<br>1H NMR (DMSO-d6): δ: 8.26 (s, 1 H), 7.17-7.30 (m, 6 H), 6.44 (s, 1 H), 5.05 (s, 2 H), 3.96 (s, 4 H), 3.80 (s, 2 H), 2.98 (s, 3 H), 2.90 (s, 3 H); LC-MS: m/z 441.4 (M + H)+. |

Example 4

N-((4-(((6-(Isoindolin-2-ylmethyl)-4-oxo-4H-pyran-3-yl)oxy)methyl)cyclohexyl)-methyl)methanesulfonamide (Compound 173)

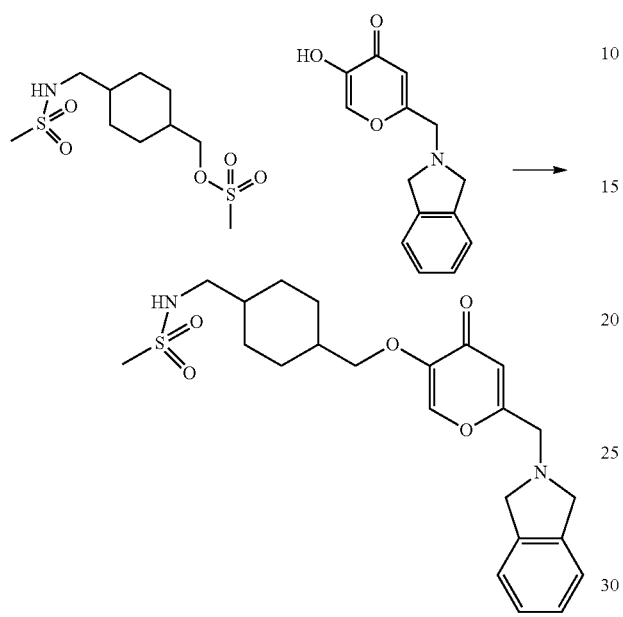

To a solution of 5-hydroxy-2-(isoindolin-2-ylmethyl)-4H-pyran-4-one (0.10 g, 0.41 mmol) in DMF (2 ml) were added (4-(methylsulfonamidomethyl)cyclohexyl)methyl methanesulfonate (0.14 g, 0.45 mmol) and K$_2$CO$_3$ (0.12 g, 0.8 mmol). The reaction mixture was heated at 80° C. for 2 h. The mixture was cooled to RT, water (10 ml) was added and the product was extracted with EtOAc. The combined extracts were washed with water, dried with Na$_2$SO$_4$, filtered and evaporated. The crude product was purified by column chromatography to afford the title compound (0.06 g). $^1$H NMR (400 MHz, Chloroform-d) δ ppm 0.92-1.11 (m, 4H) 1.40-1.63 (m, 2H) 1.78-2.00 (m, 4H) 2.91-2.99 (m, 5H) 3.65 (d, J=6.46 Hz, 2H) 3.77 (s, 2H) 4.03 (s, 4H) 5.04 (br t, J=6.31 Hz, 1H) 6.49 (s, 1H) 7.20 (s, 4H) 7.59 (s, 1H).

The following compounds were prepared according to the procedure described for Compound 173 of Example 4 starting from 5-hydroxy-2-(isoindolin-2-ylmethyl)-4H-pyran-4-one or 5-hydroxy-2-((3,4-dihydroisoquinolin-2 (1H)-yl)methyl)-4H-pyran-4-one or a derivative thereof and another appropriate starting material. The characterization data, starting material and possible deviations in reaction conditions (solvent, reaction temperature, reaction time, purification method), if any, are indicated on the table.

Purification Methods Used:
A=Crystallization
B=Column chromatography
C=Precipitation in aqueous media
D=Semipreparative HPLC
E=Trituration
F=Salt formation
G=As such

| No | Structure and starting material | Deviating reaction conditions/ $^1$H NMR (400 MHz)/LC-MS |
|---|---|---|
| 174 | Starting material: 4-(Dimethyl-carbamoyl)-3,5-difluorobenzyl methane-sulfonate | Conditions: 50° C. $^1$H NMR (Chloroform-d) δ: 7.64 (s, 1H), 7.21 (s, 4H), 7.03 (d, 2H), 6.53 (s, 1H), 5.09 (s, 2H), 4.05 (s, 4H), 3.78 (s, 1H), 3.77-3.79 (m, 1H), 2.94 (s, 3H). LCMS: m/z 44.5 (M + H)$^+$. |
| 176 | Starting material: (4-((1,1-Dioxidoiso-thiazolidin-2-yl)methyl)cyclohexyl)-methyl methanesulfonate | Conditions: 90° C. $^1$H NMR (Chloroform-d) δ: 7.59 (s, 1H), 7.20 (s, 4H), 6.47 (s, 1H), 4.03 (s, 4H), 3.77 (s, 2H), 3.67 (d, 2H), 3.10-3.27 (m, 2H), 2.83-2.86 (m, 2H), 2.27-2.39 (m, 2H), 0.88-2.01 (m, 10H). LCMS: m/z 473.6 (M + H)$^+$. |

| No | Structure and starting material | Deviating reaction conditions/ $^1$H NMR (400 MHz)/LC-MS |
|---|---|---|
| 177 | 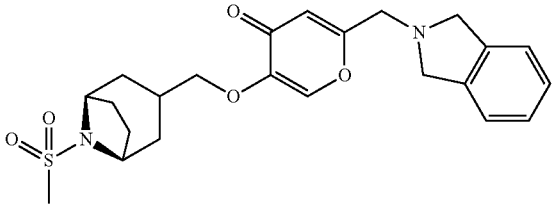<br>Starting material: ((1R,3r,5S)-8-(Methylsulfonyl)-8-azabicyclo[3.2.1]-octan-3-yl)methyl methanesulfonate | Conditions: DMSO, 100° C.<br>$^1$H NMR (Chloroform-d) δ: 7.66 (s, 1H), 7.17-7.25 (m, 4H), 6.52 (s, 1H), 4.25 (br s, 2H), 4.09 (s, 4H), 3.90 (d, 2H), 3.82 (s, 2H), 2.91 (s, 3H), 2.05-2.37 (m, 5H), 1.66-1.82 (m, 4H) LC-MS: m/z 445.6(M + H)$^+$. |
| 178 | 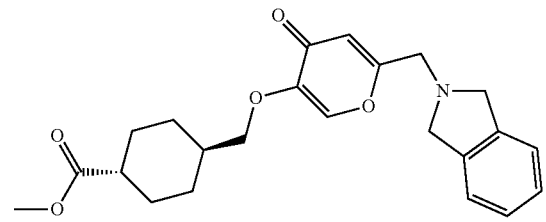<br>Starting material: (1r,4r)-Methyl 4-(((methylsulfonyl)oxy)methyl)cyclo-hexanecarboxylate | Conditions: DMSO, 100° C.<br>1H NMR (Chloroform-d) δ: 7.61 (s, 1H), 7.23 (br d, 4H), 6.54 (s, 1H), 4.15 (s, 4H), 3.87 (s, 2H), 3.64-3.71 (m, 4H), 2.20-2.35 (m, 1H), 2.01 (br m, 5H), 1.79-1.92 (m, 1H), 1.38-1.56 (m, 2H), 0.98-1.17 (m, 2H). LCMS: m/z 398.1 (M + H)+. |
| 179 | 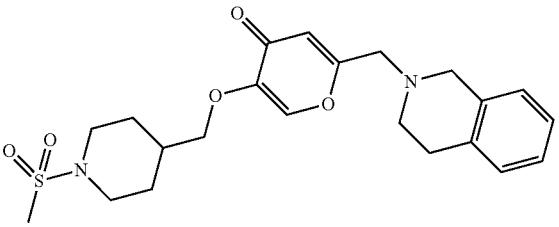<br>Starting material: 4-(Methanesulphonyl-oxymethyl)-1-methanesulphonyl-piperidine | Conditions: DMSO.<br>1H NMR (Chloroform-d) δ: 7.60 (s, 1H), 7.09-7.17 (m, 3H), 6.98-7.01 (m, 1H), 6.50 (s, 1H), 3.85 (br d, 2H), 3.74 (d, 2H), 3.71 (s, 2H), 3.56 (s, 2H), 2.91-2.96 (m, 2H), 2.81-2.86 (m, 2H), 2.79 (s, 3H), 2.69 (m, 2H), 2.00 (br d, 3H), 1.43 (br m, 2H). LCMS: m/z 433.4 (M + H)+. |
| 180 | 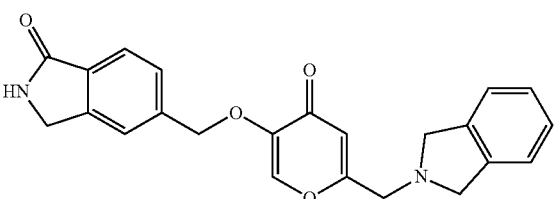<br>Starting material: (1-Oxoisoindolin-5-yl)methyl methanesulfonate | Conditions: RT, E (in 2-propanol) and B. $^1$H NMR (Chloroform-d) δ: 7.88 (d, 1H), 7.59-7.64 (m, 2H), 7.49 (d, 1H), 7.16-7.24 (m, 4H), 6.52 (s, 1H), 6.15 (br s, 1H), 5.18 (s, 2H), 4.46 (s, 2H), 4.04 (s, 4H), 3.76 (s, 2H). LC-MS: m/z 389.4 (M + H)$^+$. |
| 181 | 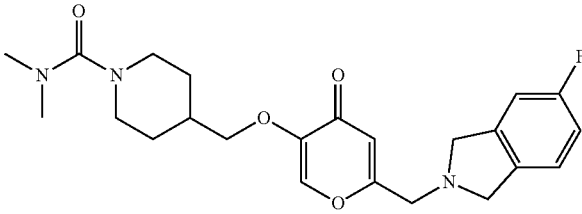<br>Starting material: (1-(Dimethyl-carbamoyl)piperidin-4-yl)methyl methanesulfonate | Conditions: 60° C.<br>$^1$H NMR (Chloroform-d) δ: 7.59 (s, 1H), 7.13 (m, 1H), 6.85-6.95 (m, 2H), 6.48 (s, 1H), 4.02 (s, 2H), 3.99 (s, 2H), 3.76 (s, 2H), 3.66-3.74 (m, 4H), 2.82 (s, 6H), 2.78 (br d, 2H), 2.01-2.13 (m, 1H), 1.83-1.90 (m, 2H), 1.23-1.36 (m, 2H). LC-MS: m/z 430.5 (M + H)$^+$. |

| No | Structure and starting material | Deviating reaction conditions/ ¹H NMR (400 MHz)/LC-MS |
|---|---|---|
| 182 | 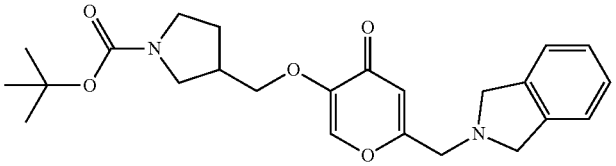<br>Starting material: tert-butyl 3-(((methyl-sulfonyl)oxy)methyl)pyrrolidine-1-carboxylate | Conditions: 60° C.<br>¹H NMR (Chloroform-d) δ: 7.60-7.67 (m, 1H), 7.21 (d, 4H), 6.49 (s, 1H), 4.04 (s, 4H), 3.80-3.92 (m, 2H), 3.77 (s, 2H), 3.58 (br m, 1H), 3.27-3.52 (m, 2H), 3.18 (br m, 1H), 2.65-2.77 (m, 1H), 2.00-2.14 (m, 1H), 1.65-1.88 (m, 1H), 1.44-1.51 (m, 9H). LC-MS: m/z 421.5 (M + H)⁺. |
| 183 | 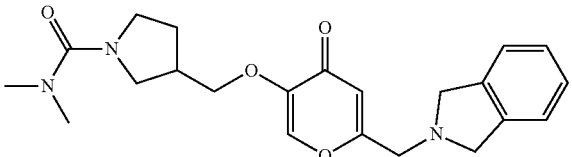<br>Starting material: (1-(Dimethyl-carbamoyl)pyrrolidin-3-yl)methyl methanesulfonate | Conditions: 60° C.<br>¹H NMR (Chloroform-d) δ: 7.61-7.65 (m, 1H), 7.15-7.25 (m, 4H), 6.49 (s, 1H), 4.04 (s, 4H), 3.81-3.94 (m, 2H), 3.77 (s, 2H), 3.56 (m, 1H), 3.36-3.50 (m, 2H), 3.29 (m, 1H), 2.84 (s, 6H), 2.62-2.74 (m, 1H), 2.01-2.12 (m, 1H), 1.74 (m, 1H). LC-MS: m/z 398.5 (M + H)⁺. |
| 184 | 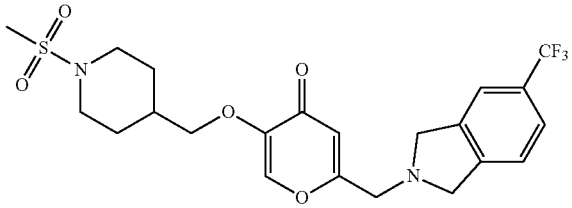<br>Starting material: (1-(Methylsulfonyl)-piperidin-4-yl)methyl methanesulfonate | ¹H NMR (Chloroform-d) δ: 7.60 (s, 1H), 7.50 (d, 1H), 7.46 (s, 1H), 7.31 (d, 1H), 6.49 (s, 1H), 4.09 (s, 4H), 3.82-3.90 (m, 2H), 3.79 (s, 2H), 3.74 (d, 2H), 2.79 (s, 3H), 2.69 (m, 2H), 1.96-2.08 (m, 3H), 1.36-1.49 (m, 2H). LC-MS: m/z 487.5 (M + H)⁺. |
| 185 | 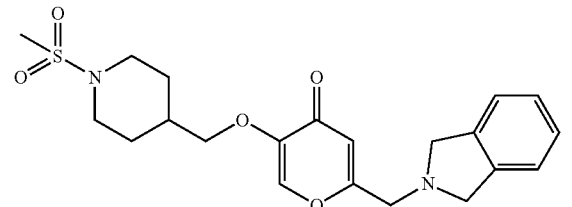<br>Starting material: (1-(Methylsulfonyl)-piperidin-4-yl)methyl methanesulfonate | Conditions: 50-80° C., C.<br>¹H NMR (Chloroform-d) δ: 7.60 (s, 1 H), 7.21 (m, 4 H), 6.49 (s, 1 H), 4.04 (s, 4 H), 3.85 (m, 2 H), 3.78 (s, 2 H), 3.75 (d, 2 H), 2.79 (s, 3 H), 2.69 (td, 2 H), 2.00 (m, 3 H), 1.43 (m, 2 H); LC-MS: m/z 419.3 (M + 1)⁺. |
| 186 | 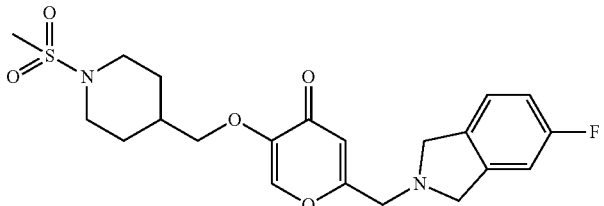<br>Starting material: (1-(Methylsulfonyl)-piperidin-4-yl)methyl methanesulfonate | Conditions: 60-80° C.<br>¹H NMR (Chloroform-d) δ: 7.60 (s, 1 H), 7.13 (m, 1 H), 6.91 (m, 2 H), 6.48 (s, 1 H), 4.02 (br s, 2 H), 3.99 (br s, 2 H), 3.86 (br d, 2 H), 3.75 (m, 4 H), 2.79 (s, 3 H), 2.69 (br t, 2 H), 2.00 (br d, 3 H), 1.43 (m, 2 H); LC-MS: m/z 437.3 (M + 1)⁺. |

| No | Structure and starting material | Deviating reaction conditions/ <br> $^1$H NMR (400 MHz)/LC-MS |
|---|---|---|
| 187 | 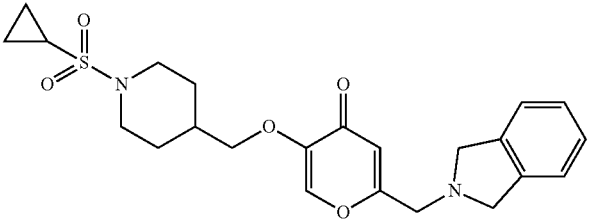 <br> Starting material: (1-(Cyclopropyl-sulfonyl)piperidin-4-yl)methyl methanesulfonate | Conditions: C and E (Et$_2$O—EtOH). $^1$H NMR (Chloroform-d) δ: 7.60 (s, 1 H), 7.21 (m, 4 H), 6.49 (s, 1 H), 4.04 (s, 4 H), 3.86 (br d, 2 H), 3.77 (s, 2 H), 3.74 (d, 2 H), 2.84 (td, 2 H), 2.27 (tt, 1 H), 2.01 (m, 3 H), 1.42 (qd, 2 H), 1.18 (m, 2 H), 0.99 (m, 2 H); LC-MS: m/z 445.5 (M + 1)$^+$. |
| 188 | 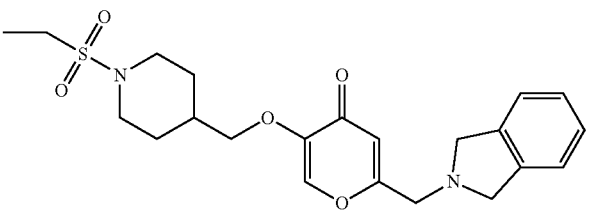 <br> Starting material: (1-(Ethylsulfonyl)-piperidin-4-yl)methyl methanesulfonate | $^1$H NMR (Chloroform-d) δ: 7.60 (s, 1 H), 7.21 (m, 4 H), 6.49 (s, 1 H), 4.04 (s, 4 H), 3.86 (br d, 2 H), 3.77 (s, 2 H), 3.74 (d, 2 H), 2.96 (q, 2 H), 2.81 (td, 2 H), 2.00 (m, 3 H), 1.37 (m, 5 H); LC-MS: m/z 433.3 (M + 1)$^+$. |
| 189 | 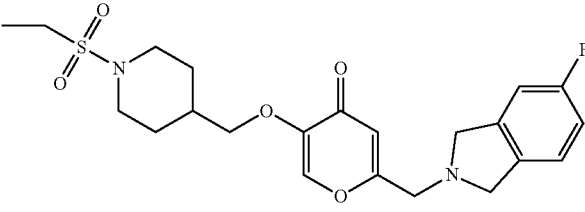 <br> Starting material: (1-(Ethylsulfonyl)-piperidin-4-yl)methyl methanesulfonate | $^1$H NMR (Chloroform-d) δ: 7.60 (s, 1 H), 7.13 (m, 1 H), 6.91 (m, 2 H), 6.48 (s, 1 H), 4.03 (s, 2 H), 4.00 (s, 2 H), 3.86 (br d, 2 H), 3.77 (s, 2 H), 3.73 (d, 2 H), 2.96 (q, 2 H), 2.81 (td, 2 H), 2.00 (m, 3 H), 1.37 (m, 5 H); LC-MS: m/z 451.3 (M + 1)$^+$. |
| 190 | 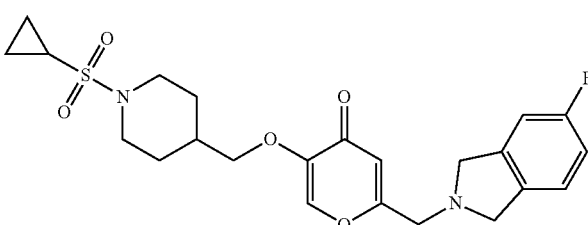 <br> Starting material: (1-(Cyclopropyl-sulfonyl)piperidin-4-yl)methyl methanesulfonate | Conditions: C. $^1$H NMR (Chloroform-d) δ: 7.60 (s, 1 H), 7.13 (dd, 1 H), 6.91 (m, 2 H), 6.48 (s, 1 H), 4.02 (s, 2 H), 3.99 (s, 2 H), 3.86 (br d, 2 H), 3.76 (s, 2 H), 3.74 (d, 2 H), 2.83 (td, 2 H), 2.27 (tt, 1 H), 2.00 (m, 3 H), 1.42 (m, 2 H), 1.17 (m, 2 H), 0.98 (m, 2 H); LC-MS: m/z 463.4 (M + 1)$^+$. |
| 191 | 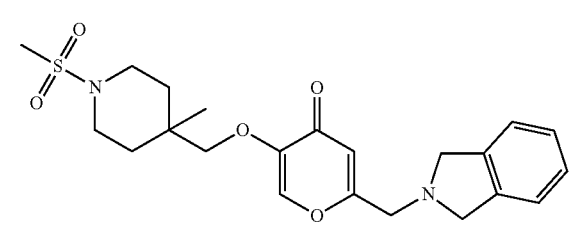 <br> Starting material: (4-Methyl-1-(methyl-sulfonyl)piperidin-4-yl)methyl methanesulfonate | Conditions: DMSO, 80° C., microwave. $^1$H NMR (Chloroform-d) δ: 7.63 (s, 1 H), 7.21 (m, 4 H), 6.48 (s, 1 H), 4.04 (s, 4 H), 3.77 (s, 2 H), 3.69 (s, 2 H), 3.47 (m, 2 H), 3.15 (ddd, 2 H), 2.83 (s, 3 H), 1.78 (ddd, 2 H), 1.62 (ddd, 2 H), 1.12 (s, 3 H); LC-MS: m/z 433.4 (M + 1)$^+$. |

| No | Structure and starting material | Deviating reaction conditions/ $^1$H NMR (400 MHz)/LC-MS |
|---|---|---|
| 192 | 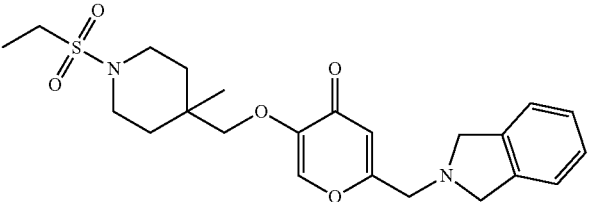<br>Starting material: (1-(Ethylsulfonyl)-4-methylpiperidin-4-yl)methyl methanesulfonate | Conditions: DMSO, 80° C. microwave. $^1$H NMR (Chloroform-d) δ: 7.63 (s, 1 H), 7.21 (m, 4 H), 6.48 (s, 1 H), 4.04 (s, 4 H), 3.77 (s, 2 H), 3.68 (s, 2 H), 3.50 (m, 2 H), 3.20 (m, 2 H), 2.98 (m, 2 H), 1.74 (ddd, 2 H), 1.59 (m, 2 H), 1.38 (m, 3 H), 1.12 (s, 3 H); LC-MS: m/z 447.4 (M + 1)$^+$. |
| 193 | 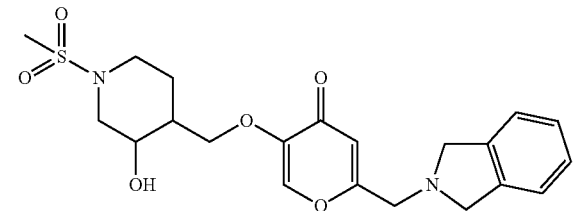<br>Starting material: (3-Hydroxy-1-(methylsulfonyl)piperidin-4-yl)methyl methanesulfonate | $^1$H NMR (Chloroform-d) δ: 7.81 (d, 1 H), 7.21 (m, 4 H), 6.55 (d, 1 H), 4.22 (m, 1 H), 4.05 (d, 4 H), 3.70-3.93 (m, 5 H), 2.50-2.98 (s, 5 H), 1.4-2.1 (m, 4 H), 0.87 (m, 1 H); LC-MS: m/z 435.3 (M + 1)$^+$. |
| 194 | 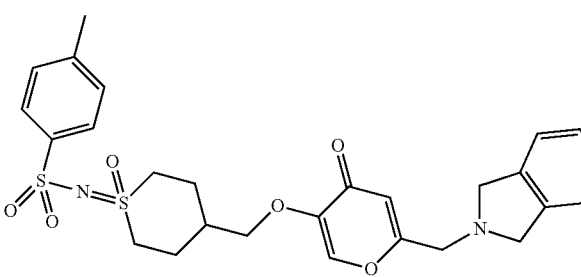<br>(Formate)<br>Starting material: (1-Oxido-1-(tosylimino)tetrahydro-2H-thiopyran-4-yl)-methyl methanesulfonate | Conditions: 70° C. $^1$H NMR (Chloroform-d) δ: 8.09 (s, 1 H), 7.86 (dd, 2 H), 7.67 (d, 1 H), 7.28 (br d, 2 H), 7.23 (m, 4 H), 6.55 (d, 1 H), 4.13 (br d, 4 H), 3.91 (br d, 1 H), 3.87 (br d, 2 H), 3.80 (dd, 2 H), 3.72 (br d, 1 H), 3.36 (m, 1 H), 3.14 (m, 1 H), 2.40 (m, 5 H), 2.32 (m, 1 H), 2.09 (m, 1 H), 1.98 (m, 1 H); LC-MS: m/z 543.7 (M + 1)$^+$. |
| 195 | 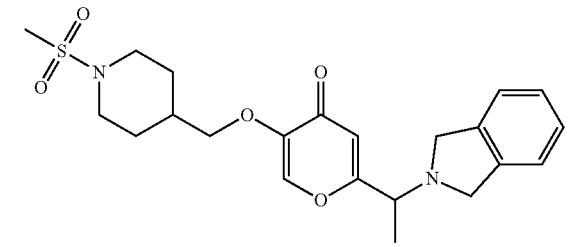<br>Starting material: 4-(Methanesulphonyl-oxymethyl)-1-methanesulphonyl-piperidine | Conditions: DMSO, 60° C.<br>$^1$H NMR (Chloroform-d) δ: 7.62 (s, 1H), 7.26-7.17 (m, 4H), 6.47 (s, 1H), 4.06-3.95 (m, 4H), 3.90-3.83 (m, 2H), 3.74 (d, 2H), 3.65 (m, 1H), 2.79 (s, 3H), 2.73-2.66 (m, 2H), 2.04-1.98 (m, 3H), 1.52 (d, 3H), 1.45-1.40 (m, 2H); LC-MS: m/z 433.6 (M + 1)$^+$. |
| 196 | 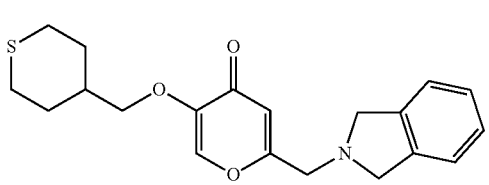<br>Starting material: (Tetrahydro-2H-thiopyran-4-yl)methyl methanesulfonate | Conditions: DMSO, C.<br>$^1$H NMR (Chloroform-d) δ: 7.59 (m, 1 H), 7.21 (s, 4 H), 6.49 (s, 1 H), 4.04 (s, 4 H), 3.77 (s, 2 H), 3.67 (br d, 2 H), 2.67 (m, 4 H), 2.20 (br d, 2 H), 1.94 (m, 1 H), 1.46 (m, 2 H); LC-MS: m/z 358.8 (M + 1)$^+$. |

| No | Structure and starting material | Deviating reaction conditions/ $^1$H NMR (400 MHz)/LC-MS |
|---|---|---|
| 197 | 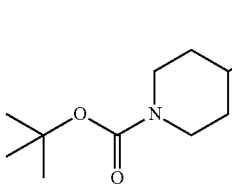<br>Starting material: tert-Butyl 4-(2-((methylsulfonyl)oxy)ethyl)piperidine-1-carboxylate | Conditions: DMSO, 60° C., G.<br>1H NMR (DMSO-d6) δ: 8.14 (s, 1H), 7.17-7.26 (m, 4H), 6.38 (s, 1H), 3.95 (s, 4H), 3.88-3.96 (m, 2H), 3.86 (t, 2H), 3.78 (s, 2H), 2.56-2.82 (m, 2H), 1.53-1.72 (m, 5H), 1.39 (s, 9H), 0.95-1.09 )m, 1H). LC-MS: m/z 455.8 (M + H)+ |
| 198 | 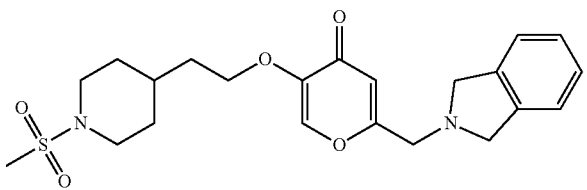<br>Starting material: 2-(1-(Methylsulfonyl)-piperidin-4-yl)ethyl methanesulfonate | Conditions: DMSO, 60° C., C.<br>1H NMR (Chloroform-d) δ: 7.61 (1H, s), 7.17-7.24 (m, 4H), 6.49 (s, 1H), 4.04 (s, 4H), 3.94 (s, 2H), 3.76-3.84 (m, 2H), 3.78 (d, 2H), 2.76 (s, 3H), 2.66 (td, 2H), 1.83-1.90 (m, 2H), 1.68-1.82 (m, 3H), 1.29-1.42 (m, 2H). LC-MS: m/z 433.8 (M + H)+ |
| 199 | 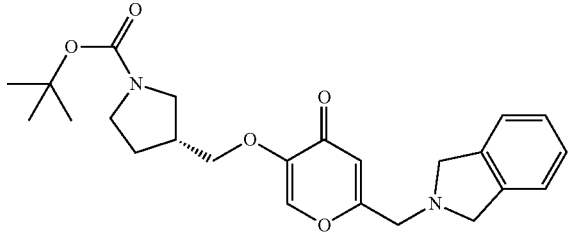<br>Starting material: (R)-tert-Butyl 3-(((methylsulfonyl)oxy)methyl)-pyrrolidine-1-carboxylate | Conditions: DMSO, 60° C.<br>1H NMR (Chloroform-d) δ: 7.63 (s, 1H), 7.17-7.24 (m, 4H), 6.49 (s, 1H), 4.04 (s, 4H), 3.80-3.92 (m, 2H), 3.77 (s, 2H), 3.58 (dd, 1H), 3.27-3.53 (m, 2H), 3.18 (dd, 1H), 2.63-2.80 (m, 1H), 2.01-2.17 (m, 1H), 1.68-1.92 (m, 1H), 1.46 (s, 9H). LC-MS: m/z 427.7 (M + H)+ |
| 200 | 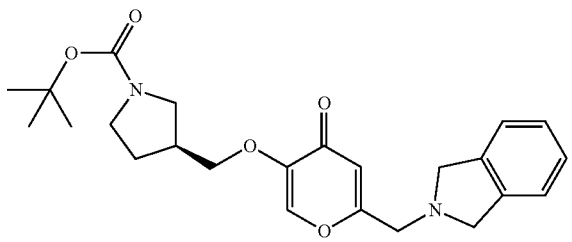<br>Starting material: (S)-tert-Butyl 3-(((methylsulfonyl)oxy)methyl)-pyrrolidine-1-carboxylate | Conditions: DMSO.<br>1H NMR (Chloroform-d) δ: 7.63 (s, 1H), 7.17-7.24 (m, 4H), 6.49 (s, 1H), 4.04 (s, 4H), 3.80-3.92 (m, 2H), 3.77 (s, 2H), 3.58 (dd, 1H), 3.27-3.53 (m, 2H), 3.18 (dd, 1H), 2.63-2.80 (m, 1H), 2.01-2.17 (m, 1H), 1.68-1.92 (m, 1H), 1.46 (s, 9H). LC-MS: m/z 427.7 (M + H)+ |
| 201 | 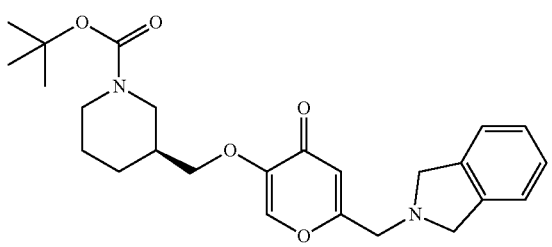<br>Starting material: (S)-tert-Butyl 3-(((methylsulfonyl)oxy)methyl)piperidine-1-carboxylate | Conditions: DMSO.<br>1H NMR (Chloroform-d) δ: 7.63 (s, 1H), 7.17-7.24 (m, 4H), 6.48 (m, 1H), 4.04 (s, 4H), 3.90-4.02 (br, 1H), 3.75-3.85 (m, 3H), 3.77 (d, 2H), 2.67-3.02 (m, 2H), 1.98-2.11 (m, 1H), 1.82-1.96 (m, 1H), 1.59-1.77 (m, 2H), 1.45 (s, 9H), 1.31-1.42 (m, 1H). LC-MS: m/z 441.9 (M + H)+ |

| No | Structure and starting material | Deviating reaction conditions/ $^1$H NMR (400 MHz)/LC-MS |
|---|---|---|
| 202 | Starting material: (R)-tert-Butyl 3-(((methylsulfonyl)oxy)methyl)piperidine-1-carboxylate | Conditions: DMSO, C.<br>1H NMR (Chloroform-d) δ: 7.63 (s, 1H), 7.17-7.24 (m, 4H), 6.48 (m, 1H), 4.04 (s, 4H), 3.90-4.02 (br, 1H), 3.75-3.85 (m, 3H), 3.77 (d, 2H), 2.67-3.02 (m, 2H), 1.98-2.10 (m, 1H), 1.82-1.96 (m, 1H), 1.6-1.76 (m, 2H), 1.45 (s, 9H), 1.31-1.42 (m, 1H).<br>LC-MS: m/z 441.7 (M + H)+ |
| 203 | Starting material: tert-Butyl 4-((methyl-sulfonyl)oxy)piperidine-1-carboxylate | Conditions: DMSO.<br>1H NMR (Chloroform-d) δ: 7.71 (s, 1H), 7.18-7.24 (m, 4H), 6.49 (m, 1H), 4.48-4.56 (m, 1H), 4.05 (s, 4H), 3.77-3.85 (m, 2H), 3.78 (d, 2H), 3.15 (ddd, 2H), 1.87-1.96 (m, 2H), 1.61-1.72 (m, 2H), 1.46 (s, 9H).<br>LC-MS: m/z 427.8 (M + H)+ |
| 204 | Starting material: cis-(4-((tert-Butoxy-carbonyl)amino)cyclopent-2-en-1-yl)-methyl methanesulfonate | Conditions: 60° C.<br>1H NMR (Chloroform-d): δ 7.54 (s, 1H), 7.17-7.24 (m, 4H), 6.48 (m, 1H), 6.02 (br d, 1H), 5.80-5.87 (m, 1H), 5.72-5.80 (m, 1H), 4.76-4.91 (m, 1H), 4.03 (s, 4H), 3.73-3.85 (m, 2H), 3.76 (s, 2H), 2.99-3.08 (br, 1H), 2.5-2.62 (m, 1H), 1.50-1.58 (m, 1H), 1.48 (s, 9H). LC-MS: m/z 439.5 (M + H)+ |
| 205 | Starting material: (1-(Methylsulfonyl)-piperidin-4-yl)methyl methanesulfonate | Conditions: DMSO, G.<br>$^1$H NMR (Chloroform-d): δ 7.60 (s, 1H), 7.19-7.23 (m, 1H), 7.05-7.10 (m, 2H), 6.48 (s, 1H), 4.05 (br s, 2H), 4.03 (br s, 2H), 3.92-3.89 (m, 2H), 3.77 (s, 2H), 3.74 (d, 2H), 2.79 (s, 3H), 2.69 (td, 2H), 1.96-2.08 (m, 3H), 1.36-1.50 (m, 2H); LC-MS: m/z 504.0 (M + H)$^+$ |
| 206 | Starting material: 2-(1-Acetylpiperidin-4-yl)ethyl methanesulfonate | Conditions: D. 1H NMR (DMSO-d6) δ: 8.16-8.28 (m, 1 H), 8.14 (s, 1 H), 8.14 (s, 1 H), 7.18-7.26 (m, 4 H), 6.38 (s, 1 H), 3.95 (s, 4 H), 3.84-3.90 (m, 2 H), 3.78 (s, 2 H), 2.98 (s, 2 H), 1.97 (s, 3 H), 1.56-1.78 (m, 5 H), 0.82-1.22 (m, 2 H); LC-MS: m/z 397.5 (M + H)+. |

| No | Structure and starting material | Deviating reaction conditions/ ¹H NMR (400 MHz)/LC-MS |
|---|---|---|
| 207 | 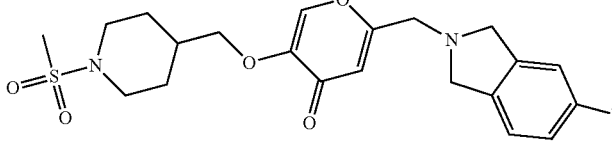<br>Starting material:<br>1-(Methanesulfonyl)piperidin-4-yl)-<br>methyl methanesulfonate | Conditions: 85° C., D.<br>1H NMR (DMSO-d6) δ: 8.16 (s, 1 H), 8.15 (s, 2 H), 8.10-8.14 (m, 1 H), 7.50-7.56 (m, 1 H), 6.41 (s, 1 H), 4.06 (s, 4 H), 3.82 (s, 2 H), 3.70-3.74 (m, 2 H), 3.54-3.63 (m, 4 H), 2.85 (s, 3 H), 2.66-2.78 (m, 3 H), 1.83-1.88 (m, 2 H); LC-MS: m/z 464.4 (M + H)+. |
| 208 | 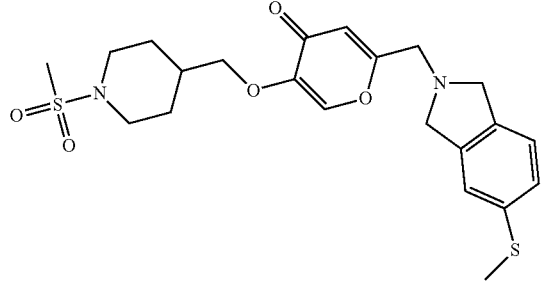<br>Starting material: 1-(Methanesulfonyl)-<br>piperidin-4-yl)propyl methanesulfonate | Condition: 85° C.<br>1H NMR (DMSO-d6) δ: 8.15 (s, 1 H), 7.17 (s, 2 H), 7.07-7.13 (m, 1 H), 6.38 (s, 1 H), 3.88-3.95 (m, 4 H), 3.77 (s, 2 H), 3.69-3.75 (m, 2 H), 3.60-3.62 (m, 1 H), 3.56-3.62 (m, 1 H), 2.85 (s, 2 H), 2.64-2.77 (m, 3 H), 2.44-2.46 (m, 3 H), 1.81-1.90 (m, 3 H), 1.26-1.33 (m, 2 H); LC-MS: m/z 465.6 |
| 209 | 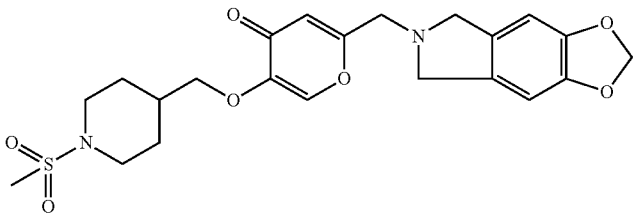<br>Starting material: 1-(Methanesulfonyl)-<br>piperidin-4-yl)methyl methanesulfonate | Conditions: D. 1H NMR (DMSO-d6) δ: 8.15 (s, 1 H), 6.81 (s, 2 H), 6.37 (s, 1 H), 5.97 (s, 2 H), 3.84 (s, 4 H), 3.75 (s, 2 H), 3.70-3.74 (m, 2 H), 3.55-3.61 (m, 3 H), 2.85 (s, 2 H), 2.68-2.76 (m, 2 H), 1.78-1.91 (m, 3 H), 1.18-1.36 (m, 2 H); LC-MS: m/z 463.3 (M + H)+. |
| 210 | 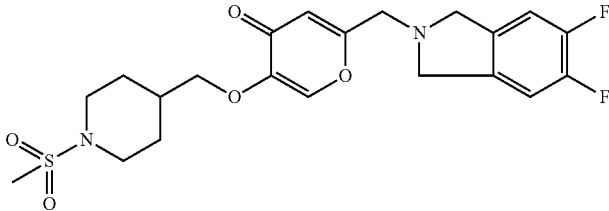<br>Starting material: 1-(Methanesulfonyl)-<br>piperidin-4-yl)methyl methanesulfonate | Condition: E. 1H NMR (Chloroform-d) δ: 7.60 (s, 1 H), 6.96-7.04 (m, 2 H), 6.47 (s, 1 H), 3.99 (s, 4 H), 3.80-3.91 (m, 2 H), 3.71-3.79 (m, 4 H), 2.79 (s, 3 H), 2.64-2.75 (m, 2 H), 1.95-2.07 (m, 3 H), 1.35-1.50 (m, 2 H); LC-MS: m/z 455.4 (M + H)+. |
| 211 | 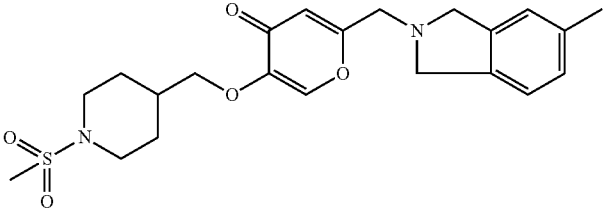<br>Starting material: 1-(Methanesulfonyl)-<br>piperidin-4-yl)methyl methanesulfonate | Conditions: E. 1H NMR (DMSO-d6) δ: 8.15 (s, 1 H), 7.10 (s, 1 H), 7.05 (s, 1 H), 6.99-7.03 (m, 1 H), 6.38 (s, 1 H), 3.90 (s, 4 H), 3.77 (s, 2 H), 3.70-3.74 (m, 2 H), 3.55-3.60 (m, 2 H), 2.85 (s, 3 H), 2.69-2.76 (m, 2 H), 2.28 (s, 3 H), 1.80-1.88 (m, 3 H), 1.24-1.35 (m, 2 H); LC-MS: m/z 433.7 |

| No | Structure and starting material | Deviating reaction conditions/ $^1$H NMR (400 MHz)/LC-MS |
|---|---|---|
| 212 | 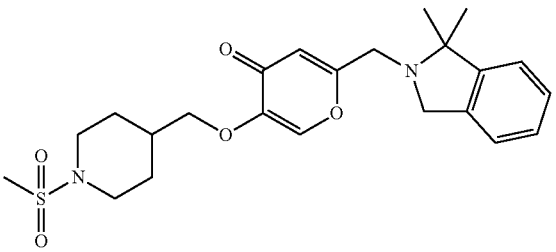<br>Starting material: 1-(Methanesulfonyl)-piperidin-4-yl)methyl methanesulfonate | Condition: DMSO, 100° C., E.<br>1H NMR (DMSO-d6) δ: 8.16 (s, 1 H), 7.17-7.24 (m, 4 H), 6.39 (s, 1 H), 3.86 (s, 2 H), 3.68-3.76 (m, 4 H), 3.54-3.64 (m, 2 H), 2.85 (s, 3 H), 2.68-2.76 (m, 2 H), 1.81-1.88 (m, 3 H), 1.27-1.36 (m, 2 H), 1.26 (s, 6 H); LC-MS: m/z 447.3 |
| 213 | 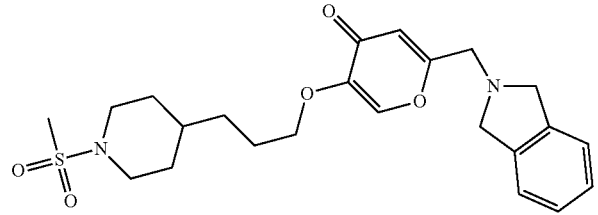<br>Starting material: 3-(1-(Methylsulfonyl)-piperidin-4-yl)propyl methanesulfonate | Condition: DMSO, E.<br>1H NMR (DMSO-d6) δ: 8.13 (s, 1 H), 7.18-7.27 (m, 4 H), 6.39 (s, 1 H), 3.95 (s, 4 H), 3.75-3.85 (m, 4 H), 3.51-3.57 (m, 2 H), 2.84 (s, 3 H), 2.62-2.69 (m, 2 H), 1.65-1.82 (m, 5 H), 1.33-1.37 (m, 2 H), 1.11-1.20 (m, 2 H); LC-MS: m/z 447.8 |
| 214 | 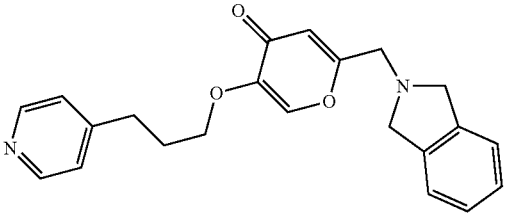<br>Starting material: 4-Methanesulfonate-4-pyridinepropanol | Condition: DMSO, D.<br>1H NMR (DMSO-d6) δ: 8.45-8.48 (m, 2 H), 8.15-8.17 (m, 2 H), 7.19-7.29 (m, 7 H), 6.40 (s, 1 H), 3.94-3.97 (m, 5 H), 3.78-3.81 (m, 3 H), 2.71-2.76 (m, 2 H), 1.97-2.08 (m, 2 H); LC-MS: m/z 363.3 |
| 214a | 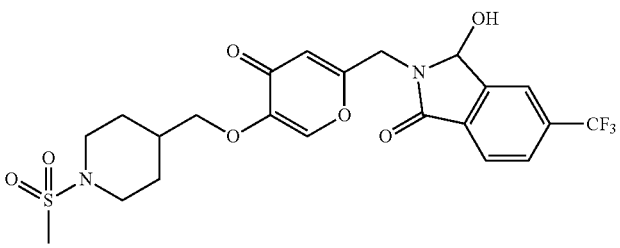<br>Starting material: 4-(Methanesulphonyl-oxymethyl)-1-methanesulphonyl-piperidine | Conditions: DMSO, 100° C., B.<br>$^1$H NMR (DMSO-d$_6$) δ: 8.12 (s, 1H), 7.90-8.01 (m, 3H), 6.99 (d, 1H), 6.35 (s, 1H), 5.97 (d, 1H), 4.39-4.72 (m, 2H), 3.70 (d, 2H), 3.52-3.57 (m, 4H), 2.85 (s, 3H), 1.64-1.90 (m, 5H); LC-MS: m/z 517.2(M + H)$^+$. |

-continued

| No | Structure and starting material | Deviating reaction conditions/ $^1$H NMR (400 MHz)/LC-MS |
|---|---|---|
| 214b | ![structure] Starting material: 4-(Methanesulphonyl-oxymethyl)-1-methanesulphonyl-piperidine | Conditions: DMF, 90° C., D. $^1$H NMR (DMSO-$d_6$) δ: 8.13 (s, 1H), 7.85-8.06 (m, 3H), 6.36 (s, 1H), 4.66-4.71 (m, 2H), 4.60-4.64 (m, 2H), 3.68 (d, 2H), 3.56 (br d, 2H), 2.84 (s, 3H), 2.67-2.73 (m, 2H), 1.81 (br d, 3H), 1.21-1.31 (m, 2H) LC-MS: m/z 501.2(M + H)$^+$. |
| 214c | ![structure] Starting material: 4-(Methanesulphonyl-oxymethyl)-1-methanesulphonyl-piperidine | Conditions: DMF, 90° C., D. $^1$H NMR (DMSO-$d_6$) δ: 8.13 (s, 1H), 7.85-8.06 (m, 3H), 6.36 (s, 1H), 4.66-4.71 (m, 2H), 4.60-4.64 (m, 2H), 3.68 (d, 2H), 3.56 (br d, 2H), 2.84 (s, 3H), 2.67-2.73 (m, 2H), 1.81 (br d, 3H), 1.21-1.31 (m, 2H); LC-MS: m/z 501.2(M + H)$^+$. |

Example 5

2-(Isoindolin-2-ylmethyl)-5-((1-(pyrrolidine-1-carbonyl)piperidin-4-yl)methoxy)-4H-pyran-4-one (Compound 215)

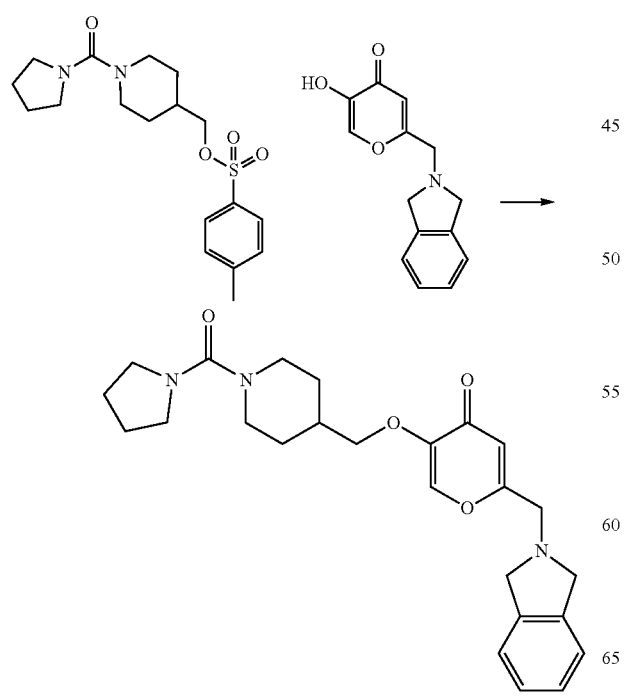

To a solution of 5-hydroxy-2-(isoindolin-2-ylmethyl)-4H-pyran-4-one (0.20 g, 0.82 mmol) in DMF (4 ml) were added (1-(pyrrolidine-1-carbonyl)piperidin-4-yl)methyl 4-methylbenzenesulfonate (0.30 g, 0.82 mmol) and $K_2CO_3$ (0.25 g, 1.8 mmol). The reaction mixture was heated at 80° C. for 2 h. The mixture was cooled to RT. Water (10 ml) was added and the product was extracted with EtOAc. The combined extracts were washed with water, dried with $Na_2SO_4$, filtered and evaporated. The crude product was purified by column chromatography to afford the title compound (0.084 g). $^1$H NMR (Chloroform-d) δ: 7.60 (s, 1H), 7.17-7.22 (m, 4H), 6.48 (s, 1H), 4.04 (s, 4H), 3.75-3.84 (m, 4H), 3.72 (d, 2H), 3.32-3.38 (m, 4H), 2.76 (m, 2H), 2.00-2.11 (m, 1H), 1.77-1.90 (m, 6H), 1.22-1.36 (m, 2H). LCMS: m/z 438.5 (M+H)$^+$.

The following compounds were prepared according to the procedure described for Compound 215 of Example 5 starting from 5-hydroxy-2-(isoindolin-2-ylmethyl)-4H-pyran-4-one and another appropriate starting material. The characterization data, starting material and possible deviations in reaction conditions (solvent, reaction temperature, reaction time, purification method), if any, are indicated on the table.

Purification Methods Used:
A=Crystallization
B=Column chromatography
C=Precipitation in aqueous media
D=Semipreparative HPLC
E=Trituration
F=Salt formation
G=As such

| No | Structure and starting material | Deviating reaction conditions/ ¹H NMR (400 MHz)/LC-MS |
|---|---|---|
| 216 | 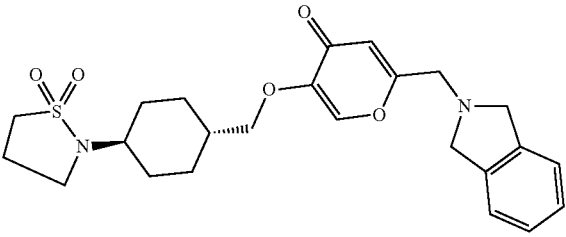 [SMILES: O=c1cc(CN2Cc3ccccc3C2)occ1OC[C@H]1CC[C@H](N2CCCS2(=O)=O)CC1]<br>Starting material: ((1r,4r)-4-(1,1-Di-oxidoisothiazolidin-2-yl)cyclohexyl)-methyl 4-methylbenzenesulfonate | Conditions: 90° C.<br>¹H NMR (Chloroform-d) δ: 7.59 (s, 1H), 7.17-7.22 (m, 4H), 6.48 (s, 1H), 4.03 (s, 4H), 3.76 (s, 2H), 3.65 (d, 2H), 3.36-3.47 (m, 1H), 3.24-3.33 (m, 2H), 3.07-3.15 (m, 2H), 2.28-2.40 (m, 2H), 1.90-2.08 (m, 4H), 1.76-1.91 (m, 1H), 1.41-1.58 (m, 2H), 1.00-1.25 (m, 2H). LC-MS: m/z 460.5 (M + H)⁺. |
| 217 | 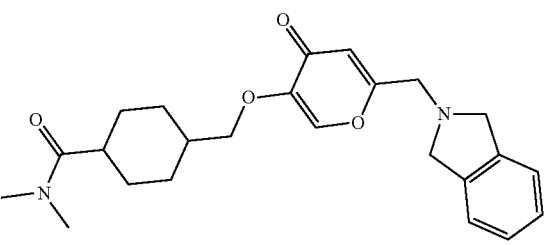 [SMILES: CN(C)C(=O)C1CCC(COc2coc(CN3Cc4ccccc4C3)cc2=O)CC1]<br>Starting material: (4-(Dimethyl-carbamoyl)cyclohexyl)methyl 4-methyl-benzenesulfonate | Conditions: 90° C.<br>¹H NMR (Chloroform-d) δ: 7.46-7.64 (m, 1H), 7.16-7.23 (m, 4H), 6.48 (s, 1H), 4.03 (s, 4H), 3.76 (s, 2H), 3.69 (d, 2H), 3.02-3.08 (m, 3H), 2.90-2.96 (m, 3H), 2.33-2.55 (m, 1H), 1.78-2.06 (m, 5H), 1.51-1.67 (m, 2H), 1.00-1.26 (m, 2H). LCMS: m/z 411.6 (M + H)⁺. |
| 218 | 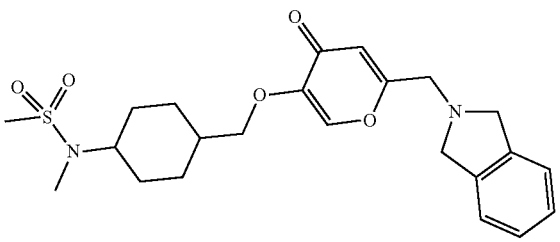 [SMILES: CN(C1CCC(COc2coc(CN3Cc4ccccc4C3)cc2=O)CC1)S(C)(=O)=O]<br>Starting material: ((1r,4r)-4-(N-methylmethylsulfonamido)cyclohexyl)-methyl 4-methylbenzenesulfonate | Conditions: 90° C.<br>¹H NMR (Chloroform-d) δ: 7.57-7.70 (m, 1H), 7.19-7.22 (m, 4H), 6.48 (d, 1H), 4.04 (d, 4H), 3.77 (s, 2H), 3.66 (d, 2H), 2.82-2.85 (m, 3H), 2.77-2.80 (m, 3H), 1.93-2.13 (m, 3H), 1.76-1.90 (m, 2H), 1.65-1.75 (m, 1H), 1.47-1.61 (m, 2H), 1.08-1.29 (m, 2H). LCMS: m/z 447.5 (M + H)⁺. |
| 219 | 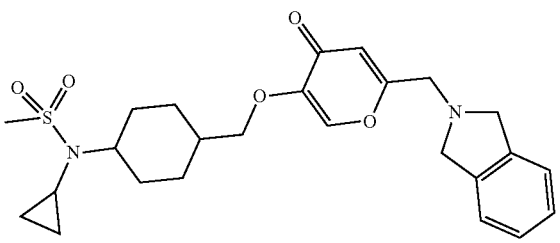 [SMILES: CS(=O)(=O)N(C1CCC(COc2coc(CN3Cc4ccccc4C3)cc2=O)CC1)C1CC1]<br>Starting material: (4-(N-cyclopropyl-methylsulfonamido)cyclohexyl)methyl 4-methylbenzenesulfonate | Conditions: 90° C.<br>¹H NMR (Chloroform-d) δ: 7.65 (s, 1H), 7.19-7.22 (m, 4H), 6.47 (s, 1H), 4.04 (s, 4H), 3.94 (d, 2H), 3.77 (s, 2H), 2.93 (s, 3H), 2.36 (m, 1H), 1.78-2.08 (m, 10H), 0.91-1.01 (m, 2H), 0.76-0.84 (m, 2H). LCMS: m/z 473.53 (M + H)⁺. |

| No | Structure and starting material | Deviating reaction conditions/ $^1$H NMR (400 MHz)/LC-MS |
|---|---|---|
| 220 | 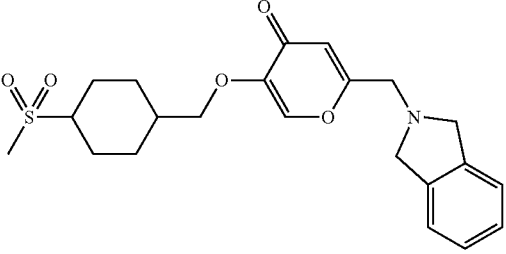 [SMILES: CS(=O)(=O)C1CCC(COc2coc(CN3Cc4ccccc4C3)cc2=O)CC1]<br>Starting material: (4-(Methylsulfonyl)-cyclohexyl)methyl 4-methylbenzene-sulfonate | Conditions: DMSO.<br>1H NMR (Chloroform-d) δ: 7.61 (s, 1H), 7.19-7.24 (m, 4H), 6.49 (s, 1H), 4.03-4.07 (m, 4H), 3.84 (d, 2H), 3.76-3.79 (m, 2H), 2.90-3.01 (m, 1H), 2.88 (s, 3H), 2.82-2.84 (m, 1H), 2.48-2.54 (m, 1H), 2.20-2.35 (m, 2H), 1.92-2.03 (m, 3H), 1.63-1.76 (m, 2H). LC-MS: m/z 418.2 (M + H)+. |
| 221 | 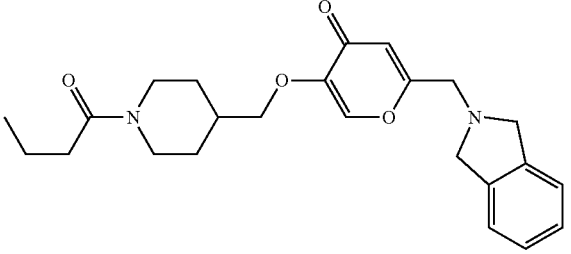 [SMILES: CCCC(=O)N1CCC(COc2coc(CN3Cc4ccccc4C3)cc2=O)CC1]<br>Starting material: (1-butyrylpiperidin-4-yl)methyl 4-methylbenzenesulfonate | Conditions: DMSO.<br>$^1$H NMR (Chloroform-d) δ: 7.61 (s, 1H), 7.22 (d, 4H), 6.52 (s, 1H), 4.68 (br d, 1H), 4.53 (s, 1H), 4.08 (s, 4H), 3.81 (s, 2H), 3.65-3.78 (m, 2H), 3.00-3.10 (m, 1H), 2.54-2.65 (m, 1H), 2.30-2.35 (m, 2H), 2.06-2.14 (m, 1H), 2.01 (br d, 1H), 1.84 (br d, 1H), 1.61-1.70 (m, 2H), 1.16-1.30 (m, 2H), 0.97 (m, 3H). LC-MS: m/z 411.3 (M + H)+. |
| 222 | 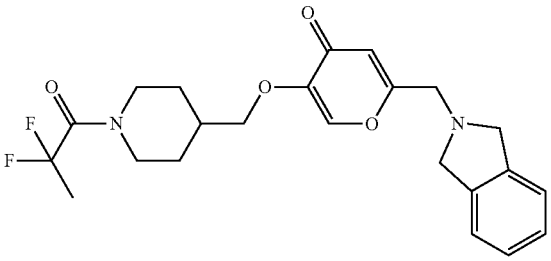 [SMILES: CC(F)(F)C(=O)N1CCC(COc2coc(CN3Cc4ccccc4C3)cc2=O)CC1]<br>Starting material: (1-(2,2-Difluoro-propanoyl)piperidin-4-yl)methyl 4-methylbenzenesulfonate | Conditions: DMSO.<br>$^1$H NMR (Chloroform-d) δ: 7.60 (s, 1H), 7.18-7.23 (m, 4H), 6.49 (s, 1H), 4.54-4.61 (m, 1H), 4.35 (br d, 1H), 4.04 (s, 4H), 3.77 (s, 2H), 3.73 (m, 2H), 3.03-3.15 (m, 1H), 2.72 (br m, 1H), 2.11-2.23 (m, 1H), 1.97 (br m, 2H), 1.83 (m, 3H), 1.22-1.40 (m, 2H). LC-MS: m/z 433.3 (M + H)$^+$. |
| 223 | 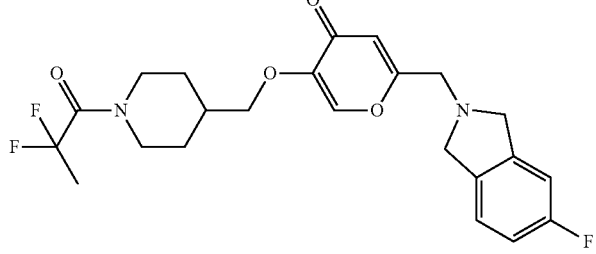<br>Starting material: (1-(2,2-Difluoro-propanoyl)piperidin-4-yl)methyl 4-methylbenzenesulfonate | Conditions: DMSO.<br>$^1$H NMR (Chloroform-d) δ: 7.59 (s, 1H), 7.13 (m, 1H), 6.87-6.94 (m, 2H), 6.48 (s, 1H), 4.57 (br d, 1H), 4.35 (br d, 1H), 4.01 (br d, 4H), 3.76 (s, 2H), 3.73 (m, 2H), 2.99-3.14 (m, 1H), 2.72 (br m, 1H), 2.13-2.25 (m, 1H), 1.96 (br m, 2H), 1.83 (m, 3H), 1.30 (dqd, 2H). LC-MS: m/z 451.6 (M + H)$^+$. |

-continued

| No | Structure and starting material | Deviating reaction conditions/ $^1$H NMR (400 MHz)/LC-MS |
|---|---|---|
| 224 | 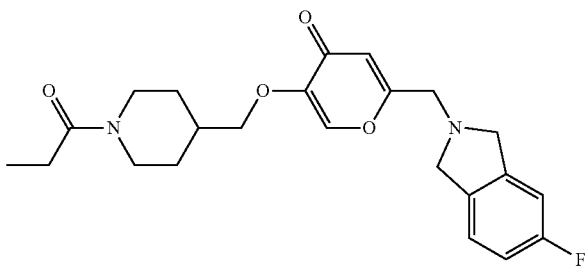 [SMILES: CCC(=O)N1CCC(COc2coc(CN3Cc4ccc(F)cc4C3)cc2=O)CC1]<br>Starting material: (1-Propionyl-piperidin-4-yl)methyl 4-methylbenzene-sulfonate | Conditions: DMSO.<br>$^1$H NMR (Chloroform-d) δ: 7.63 (s, 1H), 7.15 (m, 1H), 6.87-6.96 (m, 2H), 6.53 (s, 1H), 4.67 (br d, 1H), 4.06 (d, 4H), 3.90 (br d, 1H), 3.83 (s, 2H), 3.64-3.78 (m, 2H), 3.06 (m, 1H), 2.60 (m, 1H), 2.38 (m, 2H), 2.07-2.19 (m, 1H), 1.97-2.05 (m, 1H), 1.84 (br d, 1H), 1.19-1.33 (m, 2H), 1.15 (m, 3H). LCMS: m/z 415.2 (M + H)$^+$. |
| 225 | 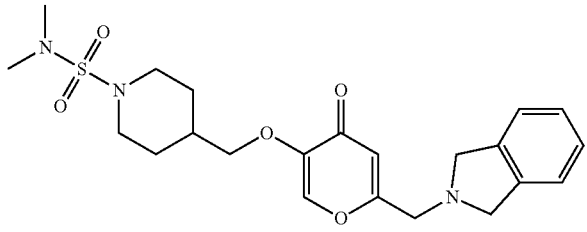 [SMILES: CN(C)S(=O)(=O)N1CCC(COc2coc(CN3Cc4ccccc4C3)cc2=O)CC1]<br>Starting material: (1-(N,N-dimethyl-sulfamoyl)piperidin-4-yl)methyl 4-methylbenzenesulfonate | Conditions: 60° C.<br>$^1$H NMR (Chloroform-d) δ: 7.60 (s, 1H), 7.17-7.24 (m, 4H), 6.49 (s, 1H), 4.04 (s, 4H), 3.77 (s, 2H), 3.70-3.76 (m, 4H), 2.81 (s, 6H), 2.77-2.89 (m, 2H), 1.97-2.07 (m, 1H), 1.93 (m, 2H), 1.38 (m, 2H). LCMS: m/z 448.6 (M + H)$^+$. |
| 226 | 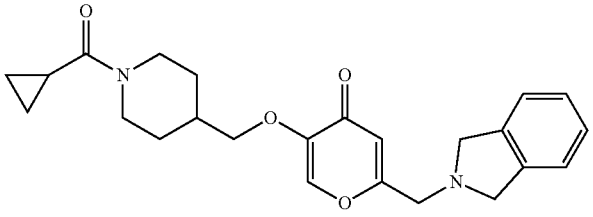 [SMILES: O=C(C1CC1)N1CCC(COc2coc(CN3Cc4ccccc4C3)cc2=O)CC1]<br>Starting material: (1-(Cyclopropane-carbonyl)piperidin-4-yl)methyl 4-methylbenzenesulfonate | Conditions: 60° C.<br>$^1$H NMR (Chloroform-d) δ: 7.60 (s, 1H), 7.16-7.24 (m, 4H), 6.49 (s, 1H), 4.65 (m, 1H), 4.18-4.32 (m, 1H), 4.04 (s, 4H), 3.77 (s, 2H), 3.73 (br m, 2H), 3.12 (m, 1H), 2.63 (m, 1H), 2.08-2.22 (m, 1H), 2.01-2.08 (m, 1H), 1.84 (m, 1H), 1.75 (m, 1H), 1.16-1.37 (m, 2H), 0.92-1.01 (m, 2H), 0.74 (m, 2H). LC-MS: m/z 409.5 (M + H)$^+$. |
| 227 | 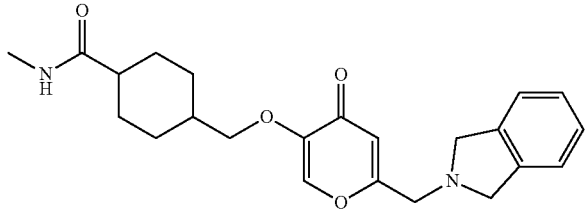<br>Starting material: (4-(Methyl-carbamoyl)cyclohexyl)methyl 4-methyl-benzenesulfonate | $^1$H NMR (Chloroform-d) δ: 7.59 (s, 1H), 7.18-7.23 (m, 4H), 6.49 (s, 1H), 4.39 (br s, 1H), 4.04 (s, 4H), 3.97 (m, 2H), 3.77 (s, 2H), 3.71 (m, 2H), 2.81 (d, 5H), 1.98-2.13 (m, 1H), 1.89 (m, 2H), 1.17-1.32 (m, 2H). LC-MS: m/z 397.5 (M + H)$^+$. |

| No | Structure and starting material | Deviating reaction conditions/ ¹H NMR (400 MHz)/LC-MS |
|---|---|---|
| 228 | Starting material: (1-(Methyl-carbamoyl)piperidin-4-yl)methyl 4-methylbenzenesulfonate | ¹H NMR (Chloroform-d) δ: 7.59 (s, 1H), 7.15-7.23 (m, 4H), 6.49 (s, 1H), 4.39 (br s, 1H), 4.04 (s, 4H), 3.97 (m, 2H), 3.77 (s, 2H), 3.71 (d, 2H), 2.75-2.86 (m, 5H), 1.99-2.11 (m, 1H), 1.89 (m, 2H), 1.25 (m, 2H). LC-MS: m/z 398.5 (M + H)⁺. |
| 229 | Starting material: (1-(Isopropyl-carbamoyl)piperidin-4-yl)methyl 4-methylbenzenesulfonate | Condition: E (in Et₂O). ¹H NMR (Chloroform-d) δ: 7.59 (s, 1H), 7.17-7.24 (m, 4H), 6.49 (s, 1H), 4.20 (br d, 1H), 4.04 (s, 4H), 3.91-3.99 (m, 3H), 3.77 (s, 2H), 3.72 (d, 2H), 2.72-2.85 (m, 2H), 1.98-2.11 (m, 1H), 1.88 (m, 2H), 1.20-1.33 (m, 2H), 1.15 (d, 6H). LC-MS: m/z 426.6 (M + H)⁺. |
| 230 | Starting material: (1-(N,N-Dimethyl-sulfamoyl)piperidin-4-yl)methyl 4-methylbenzenesulfonate | Conditions: C. ¹H NMR (Chloroform-d) δ: 7.59 (s, 1H), 7.11-7.16 (m, 1H), 6.87-6.95 (m, 2H), 6.48 (s, 1H), 4.02 (s, 2H), 3.99 (s, 2H), 3.70-3.78 (m, 6H) 2.81 (s, 6H), 2.78-2.88 (m, 2H), 1.97-2.06 (m, 1H), 1.93 (m, 2H), 1.38 (m, 2H). LC-MS: m/z 466.5 (M + H)⁺. |
| 231 | Starting material: (1-(Azetidine-1-carbonyl)piperidin-4-yl)methyl 4-methylbenzenesulfonate | ¹H NMR (Chloroform-d) δ: 7.55-7.62 (s, 1H), 7.15-7.25 (m, 4H), 6.48 (s, 1H), 4.04 (s, 4H), 3.94-4.01 (m, 4H), 3.89 (m, 2H), 3.77 (s, 2H), 3.70 (d, 2H), 2.69-2.83 (m, 2H), 2.15-2.27 (m, 2H), 1.99-2.12 (m, 1H), 1.85 (m, 2H), 1.23 (m, 2H). LC-MS: m/z 424.5 (M + H)⁺. |
| 232 | Starting material: (1-(Morpholine-4-carbonyl)piperidin-4-yl)methyl 4-methylbenzenesulfonate | Conditions: C and E. ¹H NMR (Chloroform-d) δ: 7.59 (s, 1H), 7.16-7.24 (m, 4H), 6.49 (s, 1H), 4.04 (s, 4H), 3.77 (s, 2H), 3.71-3.78 (m, 4H), 3.64-3.70 (m, 4H), 3.22-3.28 (m, 4H), 2.81 (m, 2H), 1.99-2.12 (m, 1H), 1.87 (m, 2H), 1.24-1.35 (m, 2H). LC-MS: m/z 454.5 (M + H)⁺. |

| No | Structure and starting material | Deviating reaction conditions/ $^1$H NMR (400 MHz)/LC-MS |
|---|---|---|
| 233 | 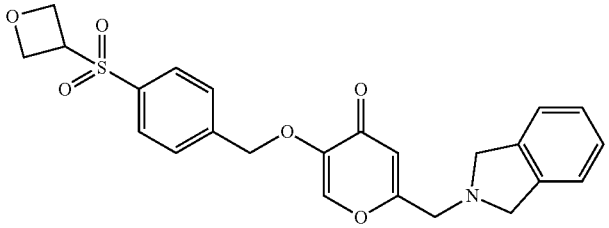 [SMILES: O=c1cc(CN2Cc3ccccc3C2)occ1OCc1ccc(S(=O)(=O)C2COC2)cc1]<br>Starting material: 4-(Oxetan-3yl-sulfonyl)benzyl 4-methylbenzene-sulfonate | Conditions: DMSO, C.<br>$^1$H NMR (Chloroform-d) δ: 7.92 (m, 2H), 7.66 (m, 3 H), 7.21 (m, 4 H), 6.53 (s, 1 H), 5.17 (s, 2 H), 4.97 (dd, 2 H), 4.79 (t, 2 H), 4.45 (tt, 1 H), 4.04 (s, 4 H), 3.78 (s, 2 H); LC-MS: m/z 454.7 (M + 1 )$^+$. |
| 234 | 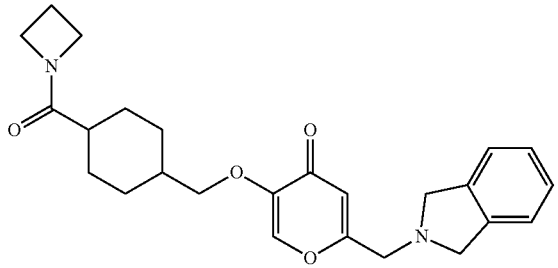 [SMILES: O=C(C1CCC(COc2coc(CN3Cc4ccccc4C3)cc2=O)CC1)N1CCC1]<br>Starting material: (4-(Azetidine-1-carbonyl)cyclohexyl)methyl 4-methyl-benzenesulfonate | 1H NMR (Chloroform-d) δ: 7.59 (s, 1 H), 7.23 (m, 4 H), 6.51 (s, 1 H), 3.97-4.17 (m, 8 H), 3.87 (s, 2 H), 3.67-3.78 (m, 2 H), 1.50-2.35 (m, 10 H), 1.11 (m, 2 H); LC-MS: m/z 423.6 (M + 1)+. |
| 235 | 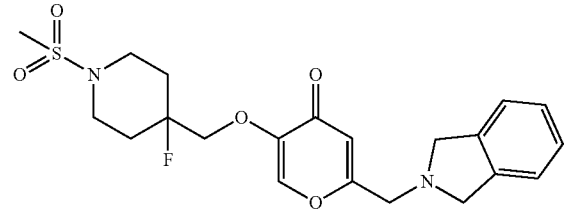 [SMILES: CS(=O)(=O)N1CCC(F)(COc2coc(CN3Cc4ccccc4C3)cc2=O)CC1]<br>Starting material: (4-Fluoro-1-(methyl-sulfonyl)piperidin-4-yl)methyl 4-methylbenzenesulfonate | Conditions: DMSO, Cs$_2$CO$_3$.<br>1H NMR (Chloroform-d) δ: 7.77 (s, 1H), 7.26-7.18 (m, 4H), 6.50 (s, 1H), 4.09 (d, 2H, J = 19.5 Hz), 4.045 (br s, 4H) 3.779 (s, 2H), 3.75-3.71 (m, 2H), 3.06-2.99 (m, 2H), 2.81 (s, 3H), 2.16-2.08 (m, 2H), 1.99-1.83 (m, 2H); LC-MS: m/z 437.8 (M + 1)+. |
| 236 | 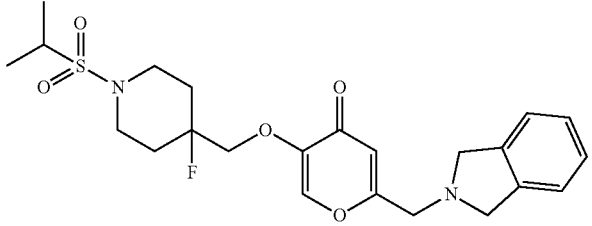 [SMILES: CC(C)S(=O)(=O)N1CCC(F)(COc2coc(CN3Cc4ccccc4C3)cc2=O)CC1]<br>Starting material: (4-Fluoro-1-(iso-propylsulfonyl)piperidin-4-yl)methyl 4-methylbenzenesulfonate | Conditions: DMSO, Cs$_2$CO$_3$.<br>1H NMR (Chloroform-d) δ: 7.77 (s, 1H), 7.21-7.19 (m, 4H), 6.50 (s, 1H), 4.07 (d, 2H, J = 20 Hz), 4.05 (s, 4H), 3.80-3.72 (m, 4H), 3.29-3.16 (m, 3H), 2.09-2.00 (m, 2H), 1.95-1.76 (m, 2H), 1.35 (d, 6H, J = 6.8 Hz); LC-MS: m/z 465.7 (M + 1)+. |

| No | Structure and starting material | Deviating reaction conditions/ $^1$H NMR (400 MHz)/LC-MS |
|---|---|---|
| 237 | 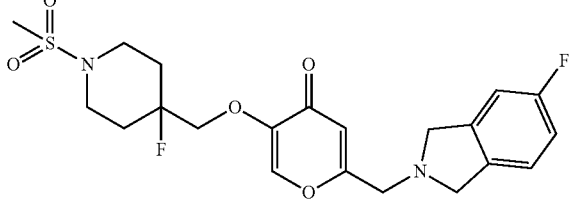<br>Starting material: (4-Fluoro-1-(methyl-sulfonyl)piperidin-4-yl)methyl 4-methylbenzenesulfonate; | Conditions: DMSO, $Cs_2CO_3$.<br>1H NMR (Chloroform-d) δ: 7.77 (s, 1H), 7.16-7.11 (m, 1H), 6.95-9.88 (m, 2H), 6.49 (s, 1H), 4.09 (d, 2H, 20 Hz), 4.04-3.98 (m, 4H), 3.78-3.71 (m, 4H), 3.07-2.99 (m, 2H), 2.82 (s, 3H), 2.17-2.07 (m, 2H), 2.00-1.82 (m, 2H); LC-MS: m/z 455.1 (M + 1)+. |
| 238 | 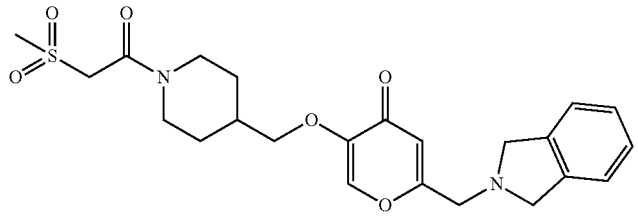 [SMILES: CS(=O)(=O)CC(=O)N1CCC(COc2coc(CN3Cc4ccccc4C3)cc2=O)CC1]<br>(tosylate)<br>Starting material: (1-(2-(Methyl-sulfonyl)acetyl)piperidin-4-yl)methyl 4-methylbenzenesulfonate | Conditions: 70° C.<br>1H NMR (Methanol-d) δ: 8.10 (s, 1 H), 7.69 (d, 2 H), 7.34 (s, 4 H), 7.22 (d, 2 H), 6.65 (s, 1 H), 4.32-4.63 (m, 9 H), 4.10 (br d, 1 H), 3.78 (d, 2 H), 3.21 (m, 1 H), 3.12 (s, 3 H), 2.77 (td, 1 H), 2.36 (s, 3 H), 2.15 (br s, 1 H), 1.95 (m, 2 H), 1.45 (m, 1 H), 1.29 (m, 1 H); LC-MS: m/z 461.8 (M + 1)+. |
| 239 | 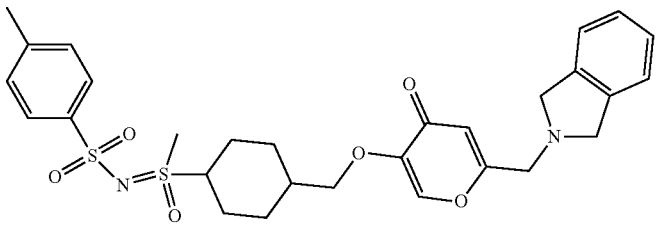 [SMILES: Cc1ccc(S(=O)(=O)N=S(C)(=O)C2CCC(COc3coc(CN4Cc5ccccc5C4)cc3=O)CC2)cc1]<br>(formate)<br>Starting material: (4-(S-Methyl-N-tosylsulfonimidoyl)cyclohexyl)methyl-4-methylbenzenesulfonate | Conditions: 70° C.<br>1H NMR (Chloroform-d) δ: 8.04 (s, 1 H), 7.85 (d, 2 H), 7.61 (m, 1 H), 7.27 (m, 2 H), 7.22 (m, 4 H), 6.50 (m, 1 H), 4.08 (m, 4 H), 3.83 (m, 4 H), 3.33 (m, 4 H), 2.40 (s, 3 H), 1.50-2.30 (m, 9 H); LC-MS: m/z 571.8 (M + 1)+. |
| 240 | 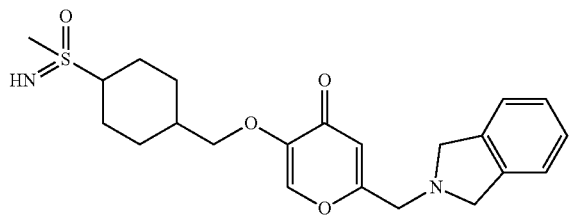 [SMILES: CS(=N)(=O)C1CCC(COc2coc(CN3Cc4ccccc4C3)cc2=O)CC1]<br>(formate)<br>Starting material: (4-(S-Methylsulfon-imidoyl)cyclohexyl)methyl 4-methyl-benzenesulfonate | Conditions: 70° C.<br>1H NMR (Chloroform-d) δ: 8.12 (br, 1 H), 7.62 (d, 1 H), 7.22 (m, 4 H), 6.51 (s, 1 H), 4.07 (d, 4 H), 3.87 (d, 1 H), 3.81 (d, 2 H), 3.72 (d, 1 H), 2.95 (m, 4 H), 1.97-2.38 (m, 5 H), 1.54-1.96 (m, 4 H), 1.22 (m, 1 H); LC-MS: m/z 417.3 (M + 1)+. |
| 241 | 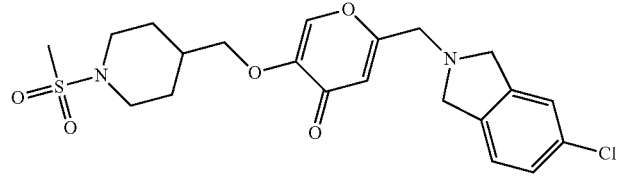 [SMILES: CS(=O)(=O)N1CCC(COc2coc(CN3Cc4ccc(Cl)cc4C3)cc2=O)CC1]<br>Starting material: (1-(Methylsulfonyl)-piperidin-4-yl)methyl 4-methyl-benzenesulfonate | Conditions: 85° C., C.<br>1H NMR (DMSO-d6) δ: 8.15 (s, 1 H), 7.33 (s, 1 H), 7.26 (s, 2 H), 6.39 (s, 1 H), 3.94 (s, 2 H), 3.93 (br s, 2 H), 3.78 (s, 1 H), 3.69-3.75 (m, 2 H), 3.54-3.61 (m, 2 H), 2.85 (s, 3 H), 2.65-2.77 (m, 3 H), 1.78-1.90 (m, 3 H), 1.23-1.33 (m, 2 H); LC-MS: m/z 453.3 |

| No | Structure and starting material | Deviating reaction conditions/ ¹H NMR (400 MHz)/LC-MS |
|---|---|---|
| 242 | 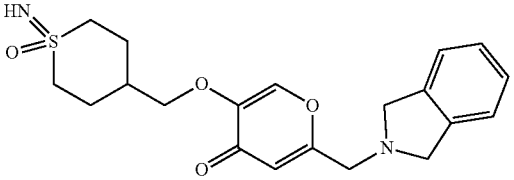 [SMILES: N=S1(=O)CCC(COc2coc(CN3Cc4ccccc4C3)cc2=O)CC1]<br>Starting material: (1-imino-1-oxidotetrahydro-2H-thiopyran-4-yl)methyl 4-methylbenzenesulfonate | Condition: 1,4-dioxane, reflux.<br>1H NMR (DMSO-d6) δ: 8.15 (s, 1 H), 7.17-7.27 (m, 4 H), 6.39 (s, 1 H), 3.95 (s, 4 H), 3.79 (s, 2 H), 3.71-3.77 (m, 2 H), 3.63-3.69 (m, 1 H), 2.96-3.08 (m, 4 H), 2.00-2.09 (m, 3 H), 1.64-1.73 (m, 2 H); LC-MS: m/z 389.3 |
| 243 | 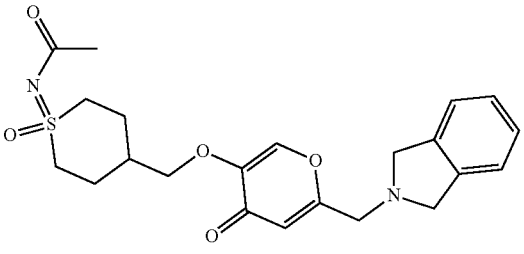 [SMILES: CC(=O)N=S1(=O)CCC(COc2coc(CN3Cc4ccccc4C3)cc2=O)CC1]<br>Starting material: (1-(Acetylimino)-1-oxidotetrahydro-2H-thiopyran-4-yl)-methyl 4-methylbenzenesulfonate | Condition: D.<br>1H NMR (DMSO-d6) δ: 8.12-8.18 (m, 1 H), 7.17-7.27 (m, 4 H), 6.39-6.41 (m, 1 H), 3.95 (s, 4 H), 3.79 (s, 2 H), 3.71-3.77 (m, 2 H), 3.55-3.65 (m, 2 H), 3.39 (s, 2 H), 2.05-2.22 (m, 3 H), 1.97 (s, 1 H), 1.94 (s, 2 H), 1.55-1.84 (m, 2 H); LC-MS: m/z 431.3 |
| 244 | 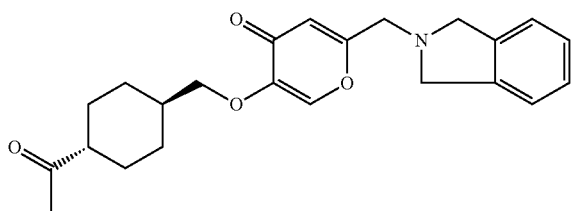 [SMILES: CC(=O)[C@H]1CC[C@H](COc2coc(CN3Cc4ccccc4C3)cc2=O)CC1]<br>Starting material: ((1r,4r)-4-Acetyl-cyclohexyl)methyl 4-methylbenzene-sulfonate | Condition: F and E.<br>1H NMR (DMSO-d6) δ: 8.20 (s, 1 H), 7.33-7.42 (m, 4 H), 6.73 (s, 1 H), 4.58 (br s, 2 H), 3.63-3.68 (m, 1 H), 2.29-2.36 (m, 1 H), 2.06-2.12 (m, 3 H), 1.81-1.95 (m, 4 H), 1.62-1.75 (m, 1 H), 1.17-1.29 (m, 4 H), 1.07-1.11 (m, 2 H), 1.00-1.07 (m, 1 H), 0.83-0.89 (m, 1 H); LC-MS: m/z 382.7 |
| 244a | 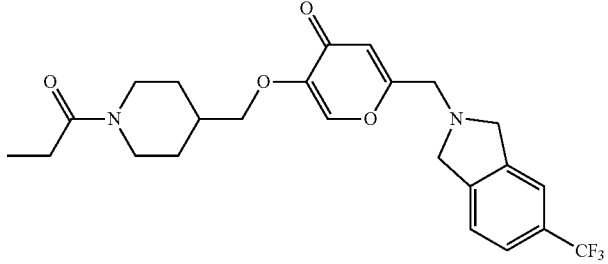 [SMILES: CCC(=O)N1CCC(COc2coc(CN3Cc4ccc(C(F)(F)F)cc4C3)cc2=O)CC1]<br>Starting material: (1-Propionyl-piperidin-4-yl)methyl 4-methyl-benzenesulfonate | Conditions: DMSO, 80° C., B.<br>¹H NMR (Chloroform-d) δ: 7.60 (s, 1H), 7.49 (d, 1H), 7.46 (s, 1H), 7.31 (d, 1H), 6.49 (s, 1H), 4.68 (br d, 1H), 4.09 (s, 3H), 3.89 (br d, 1H), 3.79 (s, 2H), 3.66-3.77 (m, 2H), 3.50-3.62 (m, 1H), 2.96-3.10 (m, 1H), 2.53-2.63 (m, 1H), 2.31-2.39 (m, 2H), 2.06-2.18 (m, 1H), 1.99 (br d, 1H), 1.79-1.89 (m, 1H), 1.18-1.30 (m, 2H), 1.14 (m, 3H); LC-MS: m/z 465.5 (M + H)⁺. |

Example 6

2-((4,5-Difluoroisoindolin-2-yl)methyl)-5-((1-(methylsulfonyl)piperidin-4-yl)methoxy)-4H-pyran-4-one (Compound 245)

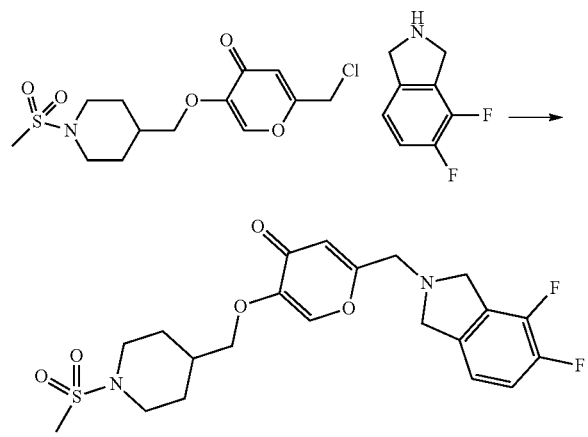

To a solution of 2-(chloromethyl)-5-((1-(methylsulfonyl)piperidin-4-yl)methoxy)-4H-pyran-4-one (0.15 g, 0.45 mmol) in ACN (10 ml) were added 4,5-di-fluoroisoindoline, HCl (0.08 g, 0.45 mmol), K$_2$CO$_3$ (0.15 g, 1.12 mmol) and KI (0.07 g, 0.45 mmol). The reaction mixture was heated at 90° C. for 2 h. The mixture was cooled to RT, water (10 ml) was added and the product was extracted with EtOAc. The combined extracts were washed with water, dried with Na$_2$SO$_4$, filtered and evaporated. The crude product was purified by column chromatography to afford the title product. $^1$H NMR (Chloroform-d) δ: 7.60 (s, 1H), 7.00-7.07 (m, 1H), 6.87-6.92 (m, 1H), 6.48 (s, 1H), 4.11-4.15 (m, 4H), 4.02 (s, 2H), 3.86 (br d, 2H), 3.77 (s, 2H), 3.74 (d, 2H), 2.79 (s, 3H), 2.65-2.73 (m, 1H), 1.97-2.03 (m, 4H).

The following compounds were prepared according to the procedure described for Compound 245 of Example 6 starting from 2-(chloromethyl)-5-((1-(methylsulfonyl)-piperidin-4-yl)methoxy)-4H-pyran-4-one and another appropriate starting material. The characterization data, starting material and possible deviations in reaction conditions (solvent, reaction temperature, reaction time, purification method), if any, are indicated on the table.

Example 7

4-(((6-(Isoindolin-2-ylmethyl)-4-oxo-4H-pyran-3-yl)oxy)methyl)-N,N-dimethylpiperidine-1-carboxamide (Compound 246)

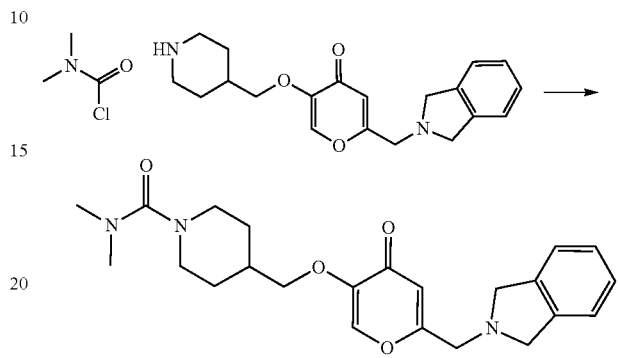

A round-bottomed-flask was charged with 2-(isoindolin-2-ylmethyl)-5-(piperidin-4-ylmethoxy)-4H-pyran-4-one trifluoroacetate (0.36 g), CH$_2$Cl$_2$ (3 mL), dimethylcarbamoyl chloride (0.10 mL, 1.1 mmol) and Et$_3$N (0.4 mL, 2.9 mmol). After 3 h at RT the reaction was not complete (LC-MS), so more of dimethylcarbamyl chloride (0.10 mL, 1.1 mmol) and Et$_3$N (0.4 mL, 2.9 mmol) were added. The solution was concentrated and then saturated NaHCO$_3$ was added. Aqueous layer was extracted with EtOAc. Combined organic layers were dried with anhydrous Na$_2$SO$_4$, filtered and concentrated. Crude material was purified by column chromatography to give the title compound (0.07 g). $^1$H NMR (Chloroform-d) δ: 7.59 (s, 1H), 7.16-7.24 (m, 4H), 6.49 (s, 1H), 4.04 (s, 4H), 3.77 (s, 2H), 3.65-3.75 (m, 4H), 2.82 (s, 6H), 2.73-2.81 (m, 2H), 1.97-2.12 (m, 1H), 1.79-1.93 (m, 2H), 1.30 (m, 2H). LC-MS: m/z 412.6 (M+H)$^+$.

The following compounds were prepared according to the procedure described for Compound 246 of Example 7 starting from 2-(isoindolin-2-ylmethyl)-5-(piperidin-4-ylmethoxy)-4H-pyran-4-one trifluoroacetate and another appropriate starting material.

The characterization data and the starting material are indicated on the table.

| 245a | 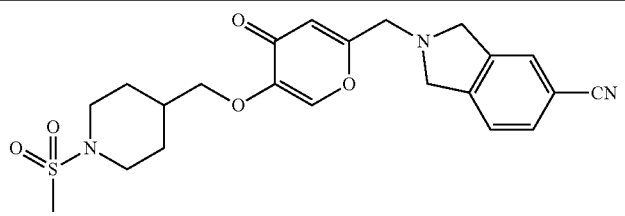 | $^1$H NMR (Chloroform-d) δ: 7.60 (s, 1H), 7.52-7.56 (m, 1H), 7.49 (s, 1H), 7.31 (d, 1H), 6.48 (s, 1H), 4.05-4.13 (br s, 4H), 3.82-3.90 (m, 2H), 3.79 (s, 2H), 3.74 (d, 2H), 2.79 (s, 3H), 2.64-2.74 (m, 2H), 1.96-2.07 (m, 3H), 1.33-1.51 (m, 2H); LC-MS: m/z 444.3 (M + H)$^+$. |
|---|---|---|
| | Starting material: Isoindoline-5-carbonitrile hydrochloride | |

| No | Structure and starting material | ¹H NMR (400 MHz)/LC-MS |
|---|---|---|
| 247 | 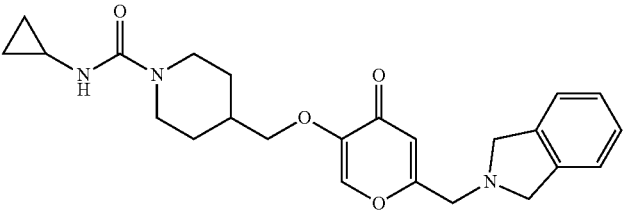 [SMILES: O=C(NC1CC1)N1CCC(COc2coc(CN3Cc4ccccc4C3)cc2=O)CC1]<br>Starting material: Cyclopropyl isocyanate | ¹H NMR (Chloroform-d) δ: 7.59 (s, 1H), 7.17-7.25 (m, 4H), 6.50 (s, 1H), 4.72 (br s, 1H), 4.05 (s, 4H), 3.94 (br d, 2H), 3.78 (s, 2H), 3.70 (d, 2H), 2.79 (br m, 2H), 2.60-2.68 (m, 1H), 1.96-2.17 (m, 1H), 1.87 (br d, 2H), 1.24 (qd, 2H), 0.68-0.75 (m, 2H), 0.42-0.49 (m, 2H). LC-MS: m/z 341.3 (M + H)⁺. |
| 248 | 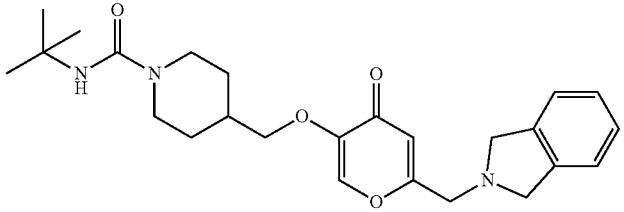 [SMILES: CC(C)(C)NC(=O)N1CCC(COc2coc(CN3Cc4ccccc4C3)cc2=O)CC1]<br>Starting material: tert-Butylisocyanate | ¹H NMR (Chloroform-d) δ: 7.59 (s, 1H), 7.18-7.23 (m, 4H), 6.49 (s, 1H), 4.04 (s, 4H), 3.92 (br d, 2H), 3.77 (s, 2H), 3.71 (d, 2H), 2.76 (m, 2H), 1.97-2.10 (m, 1H), 1.87 (br m, 2H), 1.17-1.31 (m, 2H). LC-MS: m/z 440.3 (M + H)⁺. |
| 249 | 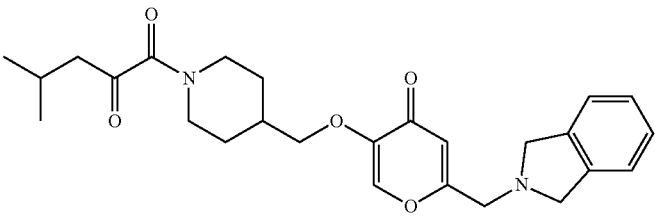 [SMILES: CC(C)CC(=O)C(=O)N1CCC(COc2coc(CN3Cc4ccccc4C3)cc2=O)CC1]<br>Starting material: 4-Methyl-2-oxo-valeric acid | ¹H NMR (Chloroform-d) δ: 7.60 (s, 1H), 7.19-7.23 (m, 4H), 6.49 (s, 1H), 4.04 (s, 4H), 3.77 (s, 2H), 3.72-3.76 (m, 2H), 2.98-3.15 (m, 2H), 2.62-2.66 (m, 2H), 2.15-2.24 (m, 4H), 1.96 (br d, 2H), 1.23-1.38 (m, 2H), 0.97 (d, 6H)<br>LCMS: m/z 453.4 (M + H)⁺. |
| 250 | 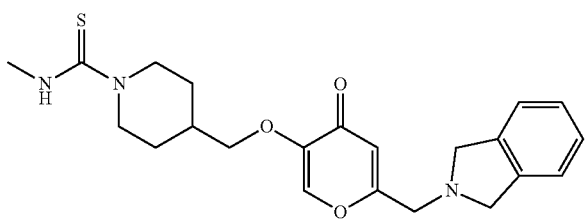 [SMILES: CNC(=S)N1CCC(COc2coc(CN3Cc4ccccc4C3)cc2=O)CC1]<br>Starting material: Methyl isothiocyanate | ¹H NMR (Chloroform-d) δ: 7.63 (s, 1H), 7.14-7.31 (m, 4H), 6.55 (s, 1H), 5.80 (br s, 1H), 4.65 (br d, 2H), 4.09-4.20 (m, 4H), 3.87 (s, 2H), 3.71 (d, 2H), 3.16 (d, 3H), 2.98-3.12 (m, 2H), 2.05-2.23 (m, 1H), 1.79-2.01 (m, 2H), 1.25-1.42 (m, 2H). LCMS: m/z 414.7 (M + H)⁺. |
| 251 | 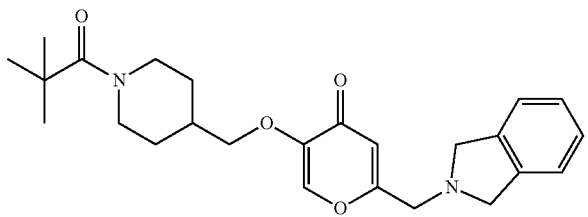 [SMILES: CC(C)(C)C(=O)N1CCC(COc2coc(CN3Cc4ccccc4C3)cc2=O)CC1]<br>Starting material: Trimethylacetyl chloride | ¹H NMR (Chloroform-d) δ: 7.61 (s, 1H), 7.19-7.29 (m, 4H), 6.50-6.62 (m, 1H), 4.47 (br d, 2H), 4.20 (s, 4H), 3.92 (s, 2H), 3.70 (d, 2H), 2.83 (br m, 2H), 2.00-2.21 (m, 1H), 1.92 (br d, 2H), 1.28 (s, 9H), 1.12-1.27 (m, 2H). LCMS: m/z 425.8 (M + H)⁺. |

| No | Structure and starting material | ¹H NMR (400 MHz)/LC-MS |
|---|---|---|
| 252 | 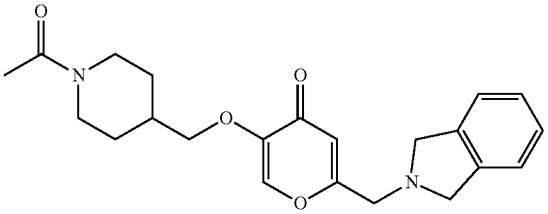 [SMILES: CC(=O)N1CCC(COc2coc(CN3Cc4ccccc4C3)cc2=O)CC1]<br>Starting material: Acetyl chloride | ¹H NMR (Chloroform-d) δ: 7.60 (s, 1H), 7.18-7.23 (m, 4H), 6.49 (s, 1H), 4.61-4.70 (m, 2H), 4.04 (s, 4H), 3.85 (br d, 2H), 3.67-3.79 (m, 2H), 3.02-3.13 (m, 2H), 2.83-2.95 (m, 1H), 2.51-2.63 (m, 2H), 2.10 (s, 3H), 1.78-1.88 (m, 2H). LC-MS: m/z 383.2 (M + H)⁺. |
| 253 | 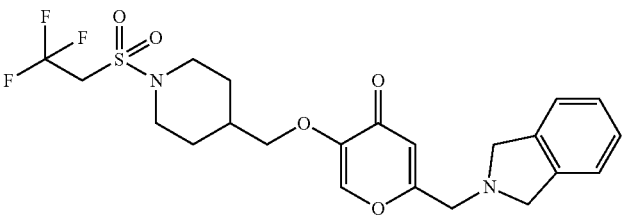 [SMILES: O=c1cc(CN2Cc3ccccc3C2)occ1OCC1CCN(S(=O)(=O)CC(F)(F)F)CC1]<br>Starting material: 2,2,2-Trifluoro-ethanesulfonyl chloride | ¹H NMR (Chloroform-d) δ: 7.61 (s, 1H), 7.21 (d, 4H), 6.49 (s, 1H), 4.04 (s, 4H), 3.91 (br d, 2H), 3.66-3.79 (m, 7H), 2.89 (m, 2H), 1.93-2.11 (m, 3H), 1.41 (qd, 2H). LC-MS: m/z 487.5 (M + H)⁺. |
| 254 | 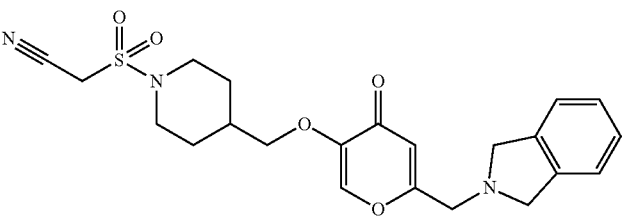 [SMILES: N#CCS(=O)(=O)N1CCC(COc2coc(CN3Cc4ccccc4C3)cc2=O)CC1]<br>Starting material: Cyanomethane-sulfonyl chloride | ¹H NMR (Chloroform-d) δ: 7.61 (s, 1H), 7.19-7.22 (m, 4H), 6.49 (s, 1H), 4.04 (s, 4H), 4.01 (br m, 2H), 3.93-3.95 (m, 2H), 3.75-3.79 (m, 4H), 3.06 (m, 2H), 1.96-2.14 (m, 3H), 1.39-1.52 (m, 2H). LC-MS: m/z 444.5 (M + H)⁺. |
| 255 | 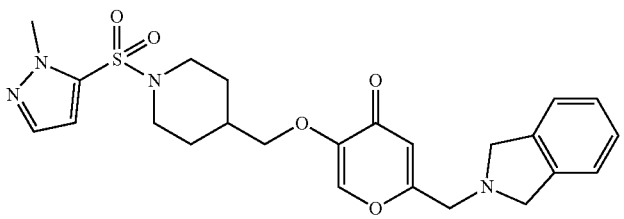 [SMILES: Cn1nccc1S(=O)(=O)N1CCC(COc2coc(CN3Cc4ccccc4C3)cc2=O)CC1]<br>Starting material: 1-Methyl-1H-pyra-zole-5-sulphonyl chloride | ¹H NMR (Chloroform-d) δ: 7.60 (s, 1H), 7.50 (d, 1H), 7.18-7.24 (m, 4H), 6.69 (d, 1H), 6.49 (s, 1H), 4.10 (s, 3H), 4.09 (s, 4H), 3.84-3.91 (m, 2H), 3.80 (s, 2H), 3.74 (d, 2H), 2.55-2.65 (m, 2H), 1.88-2.01 (m, 3H), 1.35-1.49 (m, 2H). LC-MS: m/z 485.5 (M + H)⁺. |
| 256 | 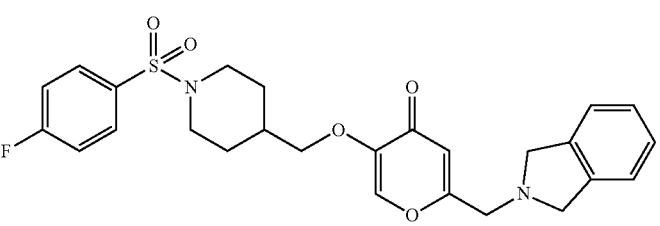 [SMILES: O=c1cc(CN2Cc3ccccc3C2)occ1OCC1CCN(S(=O)(=O)c2ccc(F)cc2)CC1]<br>Starting material: 4-Fluorobenzene-sulfonyl chloride | ¹H NMR (DMSO-d₆) δ: 8.19 (s, 1H), 7.79-7.87 (m, 2H), 7.45-7.55 (m, 2H), 7.32-7.43 (m, 4H), 6.68 (s, 1H), 4.43-4.84 (m, 6H), 3.63-3.71 (m, 4H), 2.23-2.34 (m, 2H), 1.65-1.86 (m, 3H), 1.20-1.39 (m, 2H). LCMS: m/z 499.5 (M + H)⁺. |

| No | Structure and starting material | ¹H NMR (400 MHz)/LC-MS |
|---|---|---|
| 257 | 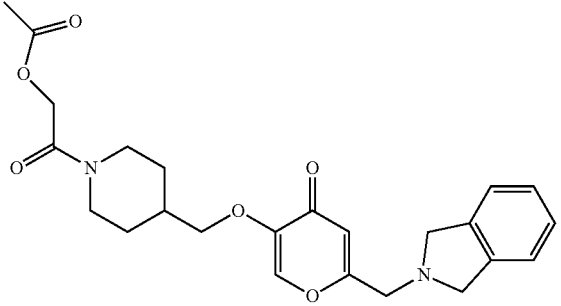 [SMILES: CC(=O)OCC(=O)N1CCC(COc2coc(CN3Cc4ccccc4C3)cc2=O)CC1]<br>Starting material: Acetoxyacetyl chloride | ¹H NMR (Chloroform-d) δ: 7.60 (s, 1H), 7.18-7.26 (m, 4H), 6.49 (s, 1H), 4.73 (d, 2H), 4.04 (s, 4H), 3.77 (s, 2H), 3.65-3.77 (m, 2H), 3.08 (br m, 1H), 2.58-2.71 (m, 1H), 2.11-2.21 (m, 4H), 1.96-2.07 (m, 1H), 1.87 (br d, 1H), 1.17-1.37 (m, 2H). LC-MS: m/z 441.5 (M + H)⁺. |
| 258 | 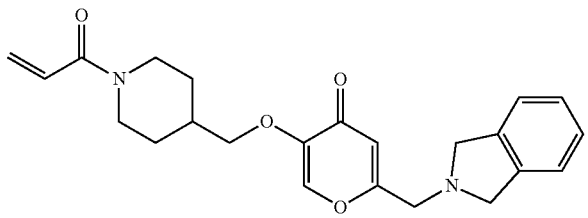<br>Starting material: Acryloyl chloride | ¹H NMR (Chloroform-d) δ: 7.59 (s, 1H), 7.17-7.24 (m, 4H), 6.53-6.64 (m, 1H), 6.49 (s, 1H), 6.22-6.30 (m, 1H), 5.61-5.72 (m, 1H), 4.71 (br d, 1H), 4.04 (s, 4H), 3.77 (s, 2H), 3.73 (br m, 2H), 3.09 (br m, 1H), 2.68 (br m, 1H), 2.08-2.24 (m, 1H), 1.82-2.05 (m, 2H), 1.14-1.37 (m, 2H). LC-MS: m/z 399.5 (M + H)⁺. |
| 259 | 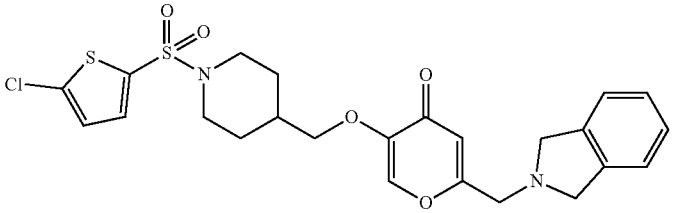 [SMILES: O=c1cc(CN2Cc3ccccc3C2)occ1OCC1CCN(S(=O)(=O)c2ccc(Cl)s2)CC1]<br>Starting material: 5-Chlorothiophene-2-sulfonyl chloride | ¹H NMR (Chloroform-d) δ: 7.60 (s, 1H), 7.31 (d, 1H), 7.18-7.22 (m, 4H), 6.98 (d, 1H), 6.49 (s, 1H), 4.05 (s, 4H), 3.82 (br d, 2H), 3.78 (s, 2H), 3.72 (d, 2H), 2.43 (m, 2H), 1.97 (br d, 2H), 1.83-1.93 (m, 1H), 1.44 (qd, 2H). LCMS: m/z 521.4 (M + H)⁺. |
| 260 | 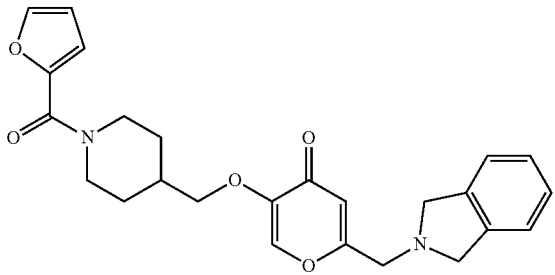 [SMILES: O=C(c1ccco1)N1CCC(COc2coc(CN3Cc4ccccc4C3)cc2=O)CC1]<br>Starting material: 2-Furoyl chloride | ¹H NMR (Chloroform-d) δ: 7.61 (s, 1H), 7.47 (s, 1H), 7.21 (s, 4H), 6.96 (d, 1H), 6.44-6.52 (m, 2H), 4.04 (s, 4H), 3.70-3.83 (m, 4H), 3.05 (br s, 2H), 2.20 (br d, 1H), 1.98 (br d, 2H), 1.35 (qd, 2H). LCMS: m/z 435.5 (M + H)⁺. |
| 261 | 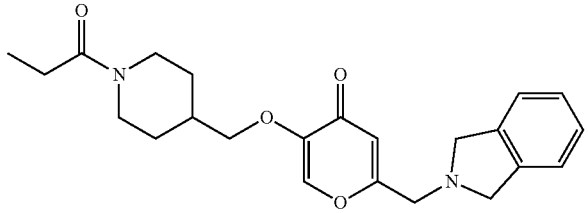 [SMILES: CCC(=O)N1CCC(COc2coc(CN3Cc4ccccc4C3)cc2=O)CC1]<br>Starting material: Propanesulfonyl chloride | ¹H NMR (Chloroform-d) δ: 7.60 (br s, 1H), 7.21 (br s, 4H), 6.50 (br s, 1H), 4.68 (br d, 1H), 4.05 (br s, 4H), 3.62-3.94 (m, 5H), 3.04 (br m, 1H), 2.59 (br m, 1H), 2.35 (br d, 2H), 1.78-2.18 (m, 3H), 1.06-1.32 (m, 5H). LC-MS: m/z 397.6 (M + H)⁺. |

| No | Structure and starting material | $^1$H NMR (400 MHz)/LC-MS |
|---|---|---|
| 262 | 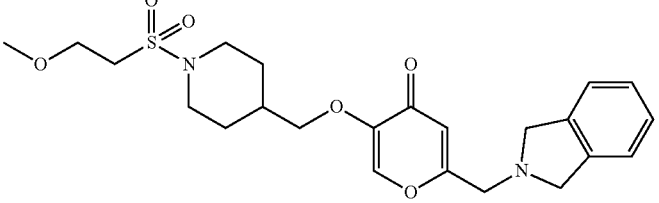<br>Starting material: 2-Methoxyethane-sulfonyl chloride | $^1$H NMR (Chloroform-d) δ: 7.61 (s, 1H), 7.18-7.26 (m, 4H), 6.53 (s, 1H), 4.10 (s, 4H), 3.78-3.86 (m, 4H), 3.69-3.78 (m, 4H), 3.38 (s, 3H), 3.20 (m, 2H), 2.82 (m, 2H), 2.00-2.07 (m, 1H), 1.96 (br d, 2H), 1.32-1.45 (m, 2H). LC-MS: m/z 463.4 (M + H)$^+$. |

Example 8

5-((3-Aminobenzyl)oxy)-2-(isoindolin-2-ylmethyl)-4H-pyran-4-one (Compound 263)

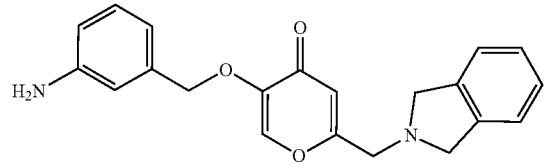 [SMILES: Nc1cccc(COc2coc(CN3Cc4ccccc4C3)cc2=O)c1]

A round-bottomed flask was charged with 2-(isoindolin-2-ylmethyl)-5-((3-nitrobenzyl)oxy)-4H-pyran-4-one (0.640 g, 1.69 mmol), MeOH (17 mL), ammonium chloride (0.226 g, 4.23 mmol) and zinc dust (1.10 g, 16.9 mmol). The mixture was refluxed until the reaction was complete. Filtration through a pad of Celite® was followed by concentration of the aliquots. The residue was partitioned between water and EtOAc. The aqueous layer was extracted with EtOAc. Combined organic layers were dried (Na$_2$SO$_4$), filtered and concentrated to yield the title compound (0.48 g). $^1$H NMR (DMSO-d6) δ: 8.14 (s, 1H), 7.17-7.27 (m, 4H), 7.01 (m, 1H), 6.60 (s, 1H), 6.52 (m, 2H), 6.40 (s, 1H), 5.13 (s, 2H), 4.78 (s, 2H), 3.95 (s, 4H), 3.79 (s, 2H). LC-MS: m/z 349.4 (M+H)$^+$.

Example 9

4/5-(((6-(Isoindolin-2-ylmethyl)-4-oxo-4H-pyran-3-yl)oxy)methyl)-N,N-dimethyl-1H-1,2,3-triazole-1-carboxamide (Compound 264)

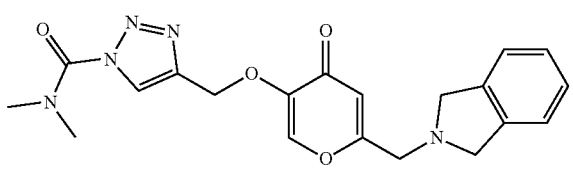

-continued

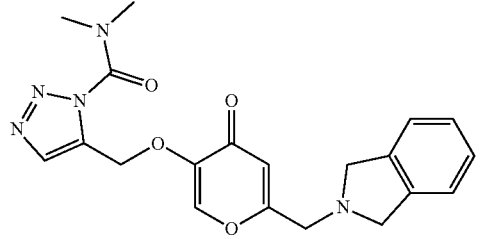

a) 2-(Isoindolin-2-ylmethyl)-5-(prop-2-yn-1-yloxy)-4H-pyran-4-one

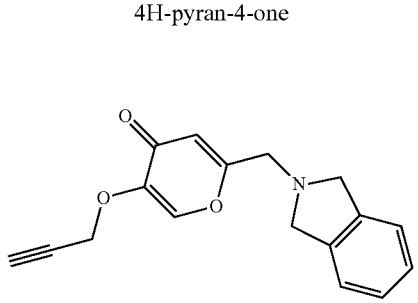

The title compound was prepared from 5-hydroxy-2-(isoindolin-2-ylmethyl)-4H-pyran-4-one (0.487 g, 2.0 mmol), propargyl chloride (0.6 mL, 8.3 mmol) and K$_2$CO$_3$ (0.553 g, 4.0 mmol) in DMF (5 mL) at 50° C. according to the procedure of Example 1, Compound 1. After quenching the reaction with water the aqueous layer was extracted with EtOAc. Combined organic layers were washed with water, dried over anhydrous Na$_2$SO$_4$, filtered and concentrated under vacuum to afford the title compound (350 mg). LC-MS: m/z 282.2 (M+H)$^+$.

b) 5-((1H-1,2,3-Triazol-4-yl)methoxy)-2-(isoindolin-2-ylmethyl)-4H-pyran-4-one

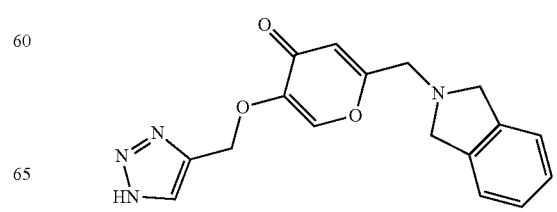

A flask was charged with 2-(isoindolin-2-ylmethyl)-5-(prop-2-yn-1-yloxy)-4H-pyran-4-one (0.35 g, 1.244 mmol) and DMSO (3 mL). Azidotrimethylsilane (0.165 mL, 1.244 mmol), H₂O (3 mL), sodium L-ascorbate (0.049 g, 0.249 mmol) and copper(II) sulfate pentahydrate (0.031 g, 0.124 mmol) were then added. The mixture was heated to 70° C. until the reaction was complete (LC-MS). Mixture was diluted with H₂O and solids were filtered off. The aqueous layer was extracted with EtOAc. Combined organic layers were washed with water, brine, dried over anhydrous Na₂SO₄, filtered and concentrated. Crude material was treated first with EtOAc and then with EtOAc/Et₂O to afford the title compound as a precipitate (0.056 g). LC-MS: m/z 325.3.

c) 4/5-(((6-(Isoindolin-2-ylmethyl)-4-oxo-4H-pyran-3-yl)oxy)methyl)-N,N-dimethyl-1H-1,2,3-triazole-1-carboxamide (Compound 264)

A round-bottomed flask was charged with 5-((1H-1,2,3-triazol-4-yl)methoxy)-2-(isoindolin-2-ylmethyl)-4H-pyran-4-one (0.058 g, 0.179 mmol), acetonitrile (3 mL), Et₃N (0.087 ml, 0.626 mmol), dimethylcarbamyl chloride (0.028 ml, 0.304 mmol) and DMAP (4.37 mg, 0.036 mmol). The solution was allowed to react at RT until complete (LC-MS). Reaction was quenched with saturated NaHCO₃ solution and the aqueous layer was extracted with EtOAc. Combined organic layers were dried with anhydrous Na₂SO₄, filtered and concentrated. Crude material was purified by column chromatography to afford the title compounds (40 mg).

Isomer 1 (Compound 264a): ¹H NMR (Chloroform-d) δ: 7.93 (s, 1H), 7.77 (s, 1H), 7.16-7.24 (m, 4H), 6.51 (s, 1H), 5.27 (s, 2H), 4.04 (s, 4H), 3.77 (s, 2H), 3.22 (br s, 3H), 3.19 (br s, 3H). LC-MS: m/z 396.4 (M+H)⁺.

Isomer 2 (Compound 264b): ¹H NMR (Chloroform-d) δ: 8.26 (s, 1H), 7.84 (s, 1H), 7.16-7.24 (m, 4H), 6.52 (s, 1H), 5.27 (s, 2H), 4.04 (s, 4H), 3.77 (s, 2H), 3.34 (br s, 3H), 3.19 (br s, 3H). LC-MS: m/z 396.4 (M+H)⁺.

Example 10. 4/5-(((6-((3,4-Dihydroisoquinolin-2(1H)-yl)methyl)-4-oxo-4H-pyran-3-yl)oxy)methyl)-N,N-dimethyl-1H-1,2,3-triazole-1-carboxamide (Compound 265)

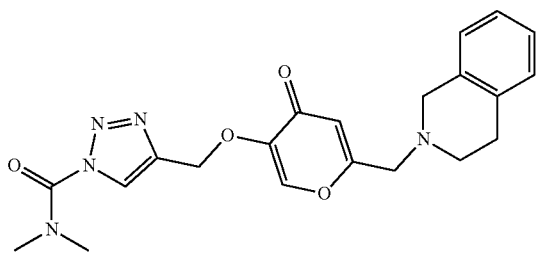

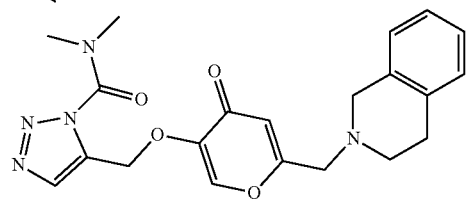

a) 2-((3,4-Dihydroisoquinolin-2(1H)-yl)methyl)-5-(prop-2-yn-1-yloxy)-4H-pyran-4-one

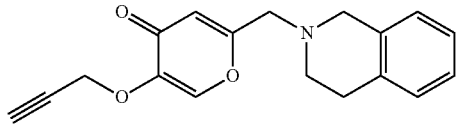 [SMILES: C#CCOc1coc(CN2CCc3ccccc3C2)cc1=O]

Title compound was prepared from 2-{[3,4-dihydroisoquinolin-2(1H)-yl]-methyl}-5-hydroxy-4H-pyran-4-one (0.515 g, 2.0 mmol), propargyl chloride (0.15 mL, 2.07 mmol), K₂CO₃ (0.553 g, 4.0 mmol) in DMF (5 mL) at 50° C. according to the procedure of Example 1, Compound 1. After quenching the reaction with water, the aqueous layer was extracted with EtOAc. Combined organic layers were washed with water, dried over anhydrous Na₂SO₄, filtered and concentrated under vacuum to afford the title compound (0.45 g). LC-MS: m/z 296.3 (M+H)⁺.

b) 5-((1H-1,2,3-Triazol-4-yl)methoxy)-2-((3,4-dihydroisoquinolin-2(1H)-yl)methyl)-4H-pyran-4-one

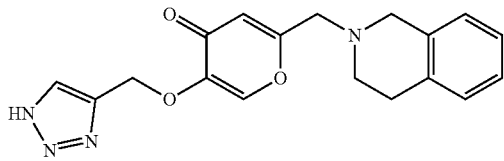 [SMILES: O=c1cc(CN2CCc3ccccc3C2)occ1OCc1c[nH]nn1]

Title compound was prepared from 2-((3,4-dihydroisoquinolin-2(1H)-yl)methyl)-5-(prop-2-yn-1-yloxy)-4H-pyran-4-one (0.15 g, 0.51 mmol), azidotrimethylsilane (0.067 mL, 0.51 mmol), sodium L-ascorbate (0.020 g, 0.10 mmol) and copper (II) sulfate pentahydrate (0.013 g, 0.05 mmol) in DMSO/H₂O (1:1, 4 mL) as described in step (b) of Example 9. The reaction was quenched with water and extracted with EtOAc. The aqueous layer was adjusted to pH 7 and extracted with EtOAc. Combined second extracts were washed with water, dried over anhydrous Na₂SO₄, filtered and concentrated under vacuum to afford the title compound. ¹H NMR (Chloroform-d) δ: 13.35 (br s, 1H), 7.81 (s, 1H), 7.58 (s, 1H), 7.10-7.18 (m, 3H), 7.01 (m, 1H), 6.59 (s, 1H), 5.12 (s, 2H), 3.73 (s, 2H), 3.59 (s, 2H), 2.91-2.97 (m, 2H), 2.80-2.91 (m, 2H). LC-MS: m/z 339.3 (M+H)⁺.

c) 4-(((6-((3,4-Dihydroisoquinolin-2(1H)-yl)methyl)-4-oxo-4H-pyran-3-yl)-oxy)methyl)-N,N-dimethyl-1H-1,2,3-triazole-1-carboxamide (Compound 265)

The title compound was prepared from 5-((1H-1,2,3-triazol-4-yl)methoxy)-2-((3,4-dihydroisoquinolin-2(1H)-yl)methyl)-4H-pyran-4-one (0.08 g, 0.236 mmol), triethylamine (0.1 mL, 0.72 mmol), dimethylcarbamyl chloride (0.033 mL, 0.36 mmol) and DMAP (5.8 mg, 0.05 mmol) in acetonitrile (3 mL) as described in step (c) of Example 9.

Crude material was purified by column chromatography to afford the title compound (0.033 g). Major isomer (Compound 265a): ¹H NMR (Chloroform-d) δ: 7.91-7.94 (m, 1H), 7.77 (s, 1H), 7.08-7.17 (m, 3H), 6.99 (m, 1H), 6.52 (s, 1H), 5.26 (s, 2H), 3.71 (s, 2H), 3.55 (s, 2H), 3.33 (br s, 3H), 3.21 (br s, 3H), 2.90-2.97 (m, 2H), 2.80-2.86 (m, 2H). LC-MS: m/z 410.4 (M+H)⁺.

Example 11

4-(((6-(Isoindolin-2-ylmethyl)-4-oxo-4H-pyran-3-yl)oxy)methyl)-N,N-dimethyl-piperidine-1-carboxamide (Compound 266)

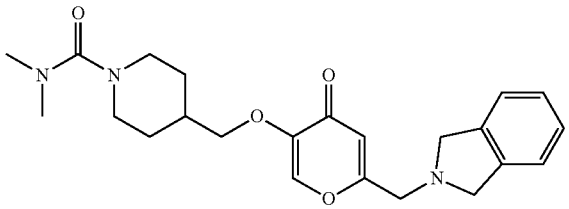 [SMILES: CN(C)C(=O)N1CCC(COc2coc(CN3Cc4ccccc4C3)cc2=O)CC1]

a) tert-Butyl 4-(((6-(isoindolin-2-ylmethyl)-4-oxo-4H-pyran-3-yl)oxy)methyl)-piperidine-1-carboxylate

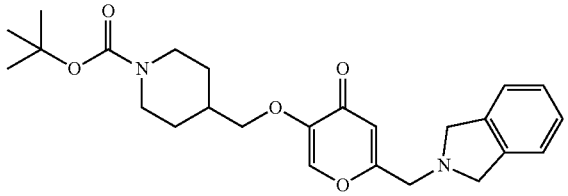 [SMILES: CC(C)(C)OC(=O)N1CCC(COc2coc(CN3Cc4ccccc4C3)cc2=O)CC1]

The compound was prepared from 5-hydroxy-2-(isoindolin-2-ylmethyl)-4H-pyran-4-one (0.73 g, 3.0 mmol), tert-butyl 4-(((methylsulfonyl)oxy)methyl)piperidine-1-carboxylate (1.056 g, 3.6 mmol) and K₂CO₃ (0.871 g, 6.3 mmol) in DMF (6 mL) at 80° C. according to the procedure of Example 1. Crude material was purified by column chromatography to afford the title compound (0.28 g). LC-MS: m/z 441.5 (M+H)⁺.

b) 2-(Isoindolin-2-ylmethyl)-5-(piperidin-4-yl-methoxy)-4H-pyran-4-one hydrogen chloride

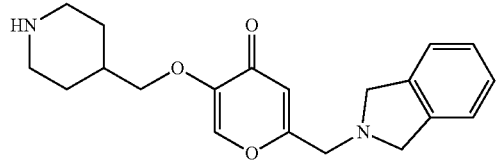 [SMILES: O=c1cc(CN2Cc3ccccc3C2)occ1OCC1CCNCC1]

A round-bottomed-flask was charged with tert-butyl 4-(((6-(isoindolin-2-yl-methyl)-4-oxo-4H-pyran-3-yl)oxy)methyl)piperidine-1-carboxylate (0.28 g, 0.64 mmol), CH₂Cl₂ (4 mL) and trifluoroacetic acid (0.5 mL, 6.7 mmol) at RT. When deprotection had occurred (LC-MS), the solution was concentrated to give the title compound as a TFA salt (0.36 g). LC-MS: m/z 341.4 (M+H)⁺. The HCl salt of title compound can be prepared in a similar manner from tert-butyl 4-(((6-(isoindolin-2-ylmethyl)-4-oxo-4H-pyran-3-yl)oxy)methyl)piperidine-1-carboxylate in premixed solution of acetylchloride (6-7 equivalent) and methanol. Evaporation to dryness afforded the title compound as a HCl salt.

c) 4-(((6-(Isoindolin-2-ylmethyl)-4-oxo-4H-pyran-3-yl)oxy)methyl)-N,N-di-methylpiperidine-1-carboxamide (Compound 267)

A round-bottomed-flask was charged with 2-(isoindolin-2-ylmethyl)-5-(piperidin-4-ylmethoxy)-4H-pyran-4-one trifluoroacetate (0.36 g), DCM (3 mL), dimethylcarbamyl chloride (0.10 mL, 1.1 mmol) and Et₃N (0.4 mL, 2.9 mmol). After 3 h at RT the reaction was not complete (LC-MS), so more of dimethylcarbamyl chloride (0.10 mL, 1.1 mmol) and Et₃N (0.4 mL, 2.9 mmol) were added. The solution was concentrated before saturated NaHCO₃ was added. Aqueous layer was extracted with EtOAc. Combined organic layers were dried with anhydrous Na₂SO₄, filtered and concentrated. Crude material was purified by column chromatography to afford the title compound (0.07 g). ¹H NMR (Chloroform-d) δ: 7.59 (s, 1H), 7.16-7.24 (m, 4H), 6.49 (s, 1H), 4.04 (s, 4H), 3.77 (s, 2H), 3.65-3.75 (m, 4H), 2.82 (s, 6H), 2.73-2.81 (m, 2H), 1.97-2.12 (m, 1H), 1.79-1.93 (m, 2H), 1.30 (m, 2H). LC-MS: m/z 412.6 (M+H)⁺.

The following compounds were prepared according to the procedure of step (c) of Example 11 starting from 2-(isoindolin-2-ylmethyl)-5-(piperidin-4-ylmethoxy)-4H-pyran-4-one hydrogen chloride and another appropriate starting material. The characterization data, starting material and possible deviations in reaction conditions (solvent, reaction temperature, reaction time, purification method), if any, are indicated on the table.

| No | Structure and starting material | Deviating reaction conditions/ ¹H NMR (400 MHz)/LC-MS |
|---|---|---|
| 267 | <br><br>Starting material: Pyrrolidine-1-sulfonyl chloride | Conditions: DMF. ¹H NMR (Chloroform-d) δ: 7.60 (s, 1H), 7.16-7.24 (m, 4H), 6.49 (s, 1H), 4.00-4.09 (m, 4H), 3.68-3.78 (m, 6H), 3.28-3.34 (m, 4H), 2.81 (m, 2H), 1.97-2.04 (m, 1H), 1.87-1.97 (m, 6H), 1.38 (m, 2H). LC-MS: m/z 474.5 (M + H)⁺. |

| No | Structure and starting material | Deviating reaction conditions/ ¹H NMR (400 MHz)/LC-MS |
|---|---|---|
| 268 | 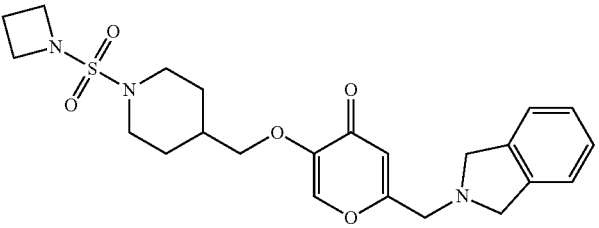 [SMILES: O=c1cc(CN2Cc3ccccc3C2)occ1OCC1CCN(S(=O)(=O)N2CCC2)CC1]<br>Starting material: 1-Azetidine-sulfonyl chloride | Conditions: DMF. ¹H NMR (Chloroform-d) δ: 7.59 (s, 1H), 7.14-7.24 (m, 4H), 6.49 (s, 1H), 4.04 (s, 4H), 3.84-3.93 (m, 4H), 3.77 (s, 2H), 3.75-3.82 (m, 2H), 3.72 (d, 2H), 2.77 (m, 2H), 2.18-2.28 (m, 2H), 1.96-2.04 (m, 1H), 1.92 (m, 2H), 1.36 (m, 2H). LC-MS: m/z 460.5 (M + H)⁺. |
| 269 | 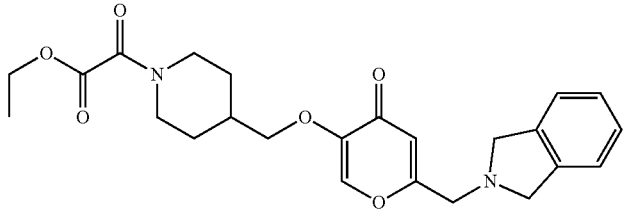 [SMILES: CCOC(=O)C(=O)N1CCC(COc2coc(CN3Cc4ccccc4C3)cc2=O)CC1]<br>Starting material: Ethyl chloro oxoacetate | Conditions: DIPEA.<br>¹H NMR (Chloroform-d) δ: 7.61 (s, 1H), 7.15-7.26 (m, 4H), 6.49 (s, 1H), 4.51-4.59 (m, 1H), 4.33 (q, 2H), 4.04 (s, 4H), 3.77 (s, 2H), 3.66-3.81 (m, 3H), 3.08-3.19 (m, 1H), 2.74 (m, 1H), 2.11-2.25 (m, 1H), 1.88-2.04 (m, 2H), 1.36 (t, 3H), 1.27-1.43 (m, 2H). LC-MS: m/z 441.8 (M + H)⁺. |
| 270 | 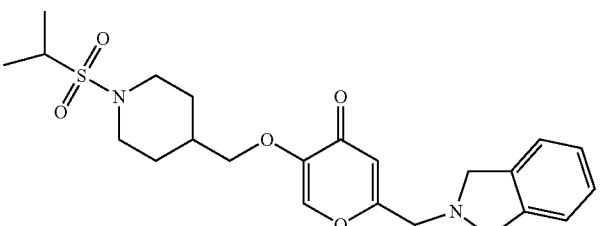<br>Starting material: Isopropylsulfonyl chloride | Conditions: 4 h.<br>1H NMR (Chloroform-d) δ: 7.60 (s, 1 H), 7.21 (m, 4 H), 6.49 (s, 1 H), 4.04 (s, 4 H), 3.87 (m, 2 H), 3.77 (s, 2 H), 3.73 (d, 2 H), 3.18 (m, 1 H), 2.90 (td, 2 H), 2.05 (m, 1 H), 1.94 (br dd, 2 H), 1.34 (m, 8 H); LC-MS: m/z 447.2 (M + 1)+. |
| 271 | 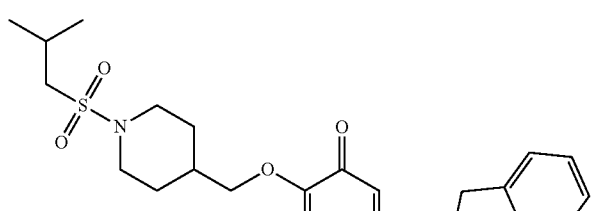<br>Starting material: Isobutanesulfonyl chloride | Conditions: 4 h.<br>1H NMR (Chloroform-d) δ: 7.60 (s, 1 H), 7.21 (m, 4 H), 6.49 (s, 1 H), 4.04 (s, 4 H), 3.84 (m, 2 H), 3.77 (s, 2 H), 3.73 (d, 2 H), 2.74 (m, 4 H), 2.29 (dt, 1 H), 2.00 (m, 3 H), 1.40 (m, 2 H), 1.11 (d, 6 H); LC-MS: m/z 461.2 (M + 1)+. |

Example 12

5-((1-Isobutyrylpiperidin-4-yl)methoxy)-2-(isoindolin-2-ylmethyl)-4H-pyran-4-one (Compound 272) and 2-(Isoindolin-2-ylmethyl)-5-((1-(2,2,2-trifluoroacetyl)piperi-din-4-yl)methoxy)-4H-pyran-4-one (Compound 273)

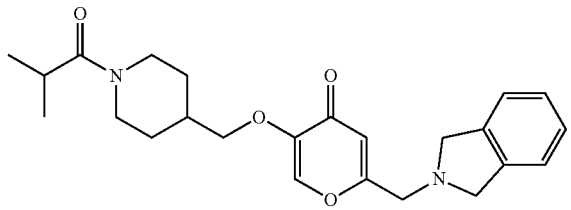

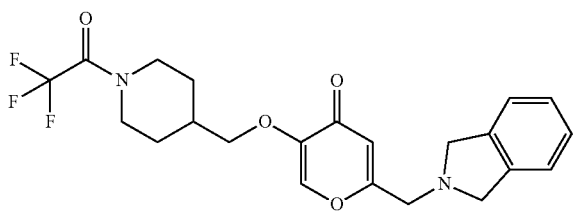

A round-bottomed-flask was charged with tert-butyl 4-(((6-(isoindolin-2-yl-methyl)-4-oxo-4H-pyran-3-yl)oxy)methyl)piperidine-1-carboxylate (0.16 g, 0.36 mmol), $CH_2Cl_2$ (4 mL) and trifluoroacetic acid (0.32 mL, 4.3 mmol). The solution was allowed to react at RT. When the reaction was complete (LC-MS) the solvents were evaporated in vacuo. The residue was dissolved in $CH_2Cl_2$ (4 mL) and $Et_3N$ (0.25 mL, 4.9 mmol). Isobutyryl chloride (0.057 mL, 0.55 mmol) were then added at RT. When the reaction was complete (LC-MS) solvents were evaporated. The residue was partitioned between saturated $NaHCO_3$ and EtOAc. The aqueous layer was extracted with EtOAc. Combined organic layers were dried with anhydrous $Na_2SO_4$, filtered and concentrated to dryness. Crude material was purified by column chromatography followed by semipreparative HPLC to afford the title compounds.

5-((1-Isobutyrylpiperidin-4-yl)methoxy)-2-(isoindolin-2-ylmethyl)-4H-pyran-4-one (Compound 272) (0.004 g): $^1$H NMR (Chloroform-d) δ: 7.60 (s, 1H), 7.16-7.25 (m, 4H), 6.49 (s, 1H), 4.65-4.74 (m, 1H), 4.04 (s, 4H), 3.91-4.01 (m, 1H), 3.77 (s, 2H), 3.64-3.75 (m, 2H), 3.05 (br m, 1H), 2.75-2.85 (m, 1H), 2.50-2.64 (m, 1H), 1.79-1.89 (m, 2H), 1.17-1.25 (m, 2H), 1.08-1.15 (m, 6H). LC-MS: m/z 411.5 (M+H)$^+$.

2-(Isoindolin-2-ylmethyl)-5-((1-(2,2,2-trifluoroacetyl)piperidin-4-yl)methoxy)-4H-pyran-4-one (Compound 273) (0.079 g): $^1$H NMR (Chloroform-d) δ: 7.61 (s, 1H), 7.16-7.24 (m, 4H), 6.49 (s, 1H), 4.54-4.63 (m, 1H), 4.01-4.11 (m, 1H), 4.04 (s, 4H), 3.71-3.81 (m, 4H), 3.09-3.23 (m, 1H), 2.74-2.87 (m, 1H), 2.14-2.30 (m, 1H), 1.95-2.11 (m, 2H), 1.26-1.49 (m, 2H). LC-MS: m/z 437.5 (M+H)$^+$.

Example 13

Cis-N-(4-(((6-(isoindolin-2-ylmethyl)-4-oxo-4H-pyran-3-yl)oxy)methyl)cyclo-pent-2-en-1-yl)cyclopropanesulfonamide, Formate (Compound 274)

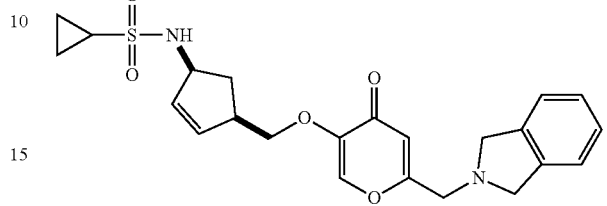

a) cis 5-((4-Aminocyclopent-2-en-1-yl)methoxy)-2-(isoindolin-2-ylmethyl)-4H-pyran-4-one dihydrochloride

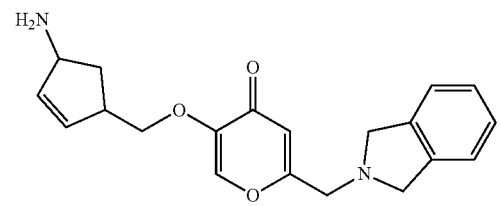 [SMILES: NC1C=CC(COc2coc(CN3Cc4ccccc4C3)cc2=O)C1]

To a suspension of cis-tert-butyl (4-(((6-(isoindolin-2-ylmethyl)-4-oxo-4H-pyran-3-yl)oxy)methyl)cyclopent-2-en-1-yl)carbamate (0.250 g, 0.57 mmol) in 2-propanol (2.5 ml) was added hydrogen chloride (3 M in CPME, 0.653 ml, 1.96 mmol). The mixture was stirred at 50° C. until the reaction reached completion (analysed by LC-MS). The mixture was cooled and the precipitated product was isolated by suction filtration. Drying under vacuum afforded the title compound (0.128 g). $^1$HNMR (400 MHz, DMSO-d6): δ 12.4 (br s, 1H), 8.34 (s, 1H), 8.07 (s, 3H), 7.37 (br, 4H), 6.80 (br s, 1H), 6.07-6.12 (m, 1H), 5.86-5.90 (m, 1H), 4.60 (br, 4H), 4.16-4.27 (br, 1H), 3.84-3.96 (m, 2H), 3.15-3.22 (m, 1H), 2.4-2.54 (m, 3H, partially overlapped by DMSO), 1.67-1.75 (m, 1H).

b) Cis-N-(4-(((6-(isoindolin-2-ylmethyl)-4-oxo-4H-pyran-3-yl)oxy)methyl)-cyclopent-2-en-1-yl)cyclopropanesulfonamide, Formate To a suspension of cis 5-((4-aminocyclopent-2-en-1-yl)methoxy)-2-(isoindolin-2-ylmethyl)-4H-pyran-4-one dihydrochloride (0.128 g, 0.311 mmol) and triethylamine (0.167 ml, 1.195 mmol) in dry DCM (2 ml) was added cyclopropanesulfonyl chloride (35 µl, 0.341 mmol). The mixture was stirred at RT until the reaction reached completion (analysed by LC-MS). The mixture was diluted with DCM and saturated $NaHCO_3$ solution, washed with water and brine, dried over sodium sulphate and concentrated under reduced pressure to afford crude product. Purification by column chromatography and semipreparative HPLC afforded the title compound (18.6 mg). $^1$HNMR (400 MHz, Chloroform-d): δ 7.56 (s, 1H), 7.35-7.39 (m, 2H), 7.29-7.33 (m, 2H), 7.17-

7.24 (m, 4H), 6.49 (m, 1H), 4.11 (t, 2H), 4.04 (s, 4H), 3.76 (d, 2H), 3.15 (t, 2H), 3.10 (br s, 3H), 2.98 (s, 3H); LC-MS: m/z 419.4 (M+H)+

Example 14

Cis-N-(4-(((6-(isoindolin-2-ylmethyl)-4-oxo-4H-pyran-3-yl)oxy)methyl)cyclo-pent-2-en-1-yl)-3-methylbutanamide, Formate (Compound 275)

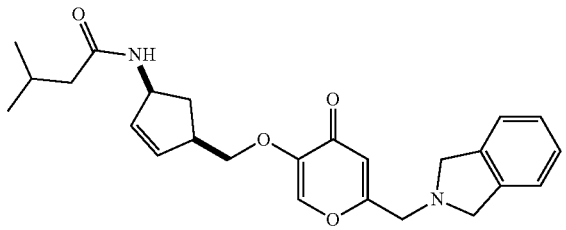

To a suspension of cis 5-((4-aminocyclopent-2-en-1-yl)methoxy)-2-(isoindolin-2-ylmethyl)-4H-pyran-4-one dihydrochloride (0.187 g, 0.455 mmol), triethylamine (0.209 ml, 1.50 mmol), and 4-dimethylaminopyridine (6.1 mg, 0.05 mmol) in dry THF (1.5 ml) was added 3-methylbutyryl chloride (91 µl, 0.75 mmol) in dry THF (0.5 ml). The mixture was stirred at RT until the reaction reached completion (analysed by LC-MS). The mixture was diluted with EtOAc and 5% aqueous Na$_2$CO$_3$ solution and stirred for 10 min. Phases were separated and the organic phase was washed with 5% aqueous NaOH solution, water and brine, dried over sodium sulphate and concentrated under reduced pressure to afford crude product. Purification by column chromatography and semipreparative HPLC afforded the title compound (39.5 mg). $^1$H NMR (Chloroform-d): δ 8.11 (s, 1H), 7.92 (br d, 1H), 7.53 (s, 1H), 7.18-7.25 (m, 4H), 6.51 (s, 1H), 5.81-5.84 (m, 1H), 5.71-5.75 (m, 1H), 5.21-5.29 (m, 1H), 4.08 (s, 4H), 3.81 (s, 2H), 3.81 (dd, 1H), 3.72 (dd, 1H), 3.01-3.08 (m, 1H), 2.49-2.60 (m, 1H), 2.24-2.34 (m, 2H), 2.12 (sept, 1H), 1.55-1.63 (m, 1H), 0.96 (d, 3H), 0.92 (d, 3H); LC-MS: m/z 423.9 (M+H)+

Example 15

Cis-N-(3-(((6-(Isoindolin-2-ylmethyl)-4-oxo-4H-pyran-3-yl)oxy)methyl)-cyclo-pentyl)-methanesulfonamide (Compound 276)

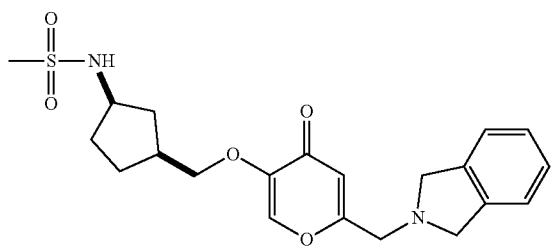

a) cis-tert-Butyl (3-(((6-(isoindolin-2-ylmethyl)-4-oxo-4H-pyran-3-yl)oxy)-methyl)cyclopentyl)carbamate

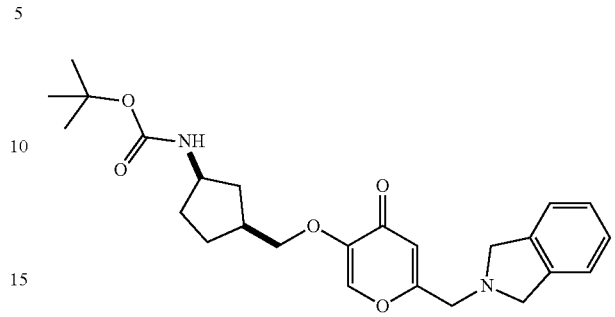

To a mixture of Pd on activated charcoal (10% Pd, 0.102 g, 0.096 mmol) in methanol (15 ml) was added a solution cis-tert-butyl (4-(((6-(isoindolin-2-ylmethyl)-4-oxo-4H-pyran-3-yl)oxy)methyl)cyclopent-2-en-1-yl)carbamate (0.84 g, 1.916 mmol) in methanol (15 ml). The mixture was stirred under hydrogen at RT until the reaction reached completion (analysed by LC-MS). The reaction mixture was filtered through a plug of Celite®, and the filtrate was evaporated to afford crude product. Purification by column chromatography afforded the title compound (0.378 g). $^1$H NMR (Chloroform-d): δ 7.59 (s, 1H), 7.17-7.24 (m, 4H), 6.48 (m, 1H), 5.07 (br, 1H), 3.98-4.08 (m, 1H), 4.04 (s, 4H), 3.82 (d, 2H), 3.77 (d, 2H), 2.36-2.48 (m, 1H), 2.22-2.32 (m, 1H), 1.90-1.99 (m, 1H), 1.78-1.89 (m, 1H), 1.49-1.65 (m, 3H), 1.45 (s, 9H).

b) cis-5-((3-Aminocyclopentyl)methoxy)-2-(isoindolin-2-ylmethyl)-4H-pyran-4-one

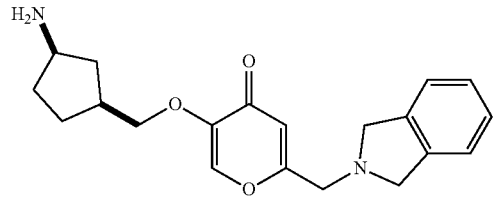 [SMILES: N[C@@H]1CC[C@H](COc2coc(CN3Cc4ccccc4C3)cc2=O)C1]

To a suspension of cis-tert-butyl (3-(((6-(isoindolin-2-ylmethyl)-4-oxo-4H-pyran-3-yl)oxy)methyl)cyclopentyl) carbamate (0.350 g, 0.794 mmol) in 2-propanol (4 ml) was added hydrogen chloride (3 M in CPME, 0.927 ml, 2.78 mmol). The mixture was stirred at 60° C. until the reaction reached completion (analysed by LC-MS). The reaction mixture was diluted with water, basified with saturated aqueous NaHCO$_3$ solution and extracted with EtOAc. Organic phase was washed with brine, dried over sodium sulphate and concentrated under reduced pressure to afford the title compound (0.16 g) which was used as such in the next step. LC-MS: m/z 341.3 (M+H)+ c) Cis-N-(3-(((6-(Isoindolin-2-ylmethyl)-4-oxo-4H-pyran-3-yl)oxy)methyl)-cyclopentyl)-methanesulfonamide To a solution of cis-5-((3-aminocyclopentyl)methoxy)-2-(isoindolin-2-ylmethyl)-4H-pyran-4-one (0.16 g, 0.47 mmol) and triethylamine (0.131 ml, 0.94 mmol) in dry DCM (2.5 ml) was added methanesulfonyl chloride (36 µl, 0.47 mmol). The mixture was stirred at RT until the reaction reached completion (analysed by LC-MS). The mixture was diluted with DCM and saturated NaHCO$_3$ solution, washed with water and brine, dried over sodium sulphate and concentrated under reduced pressure to afford crude product. Purification by column chromatography afforded the title compound (39 mg). $^1$H NMR (Chloroform-d): δ 7.56 (s, 1H), 7.18-7.24 (m, 4H), 6.53 (br d, 1H), 6.52 (s, 1H), 4.05-4.13 (m, 1H), 4.04 (s, 4H), 3.79-3.85 (m, 2H), 3.78 (d, 2H), 3.04 (s, 3H), 2.43-2.52 (m, 1H), 2.23-2.33 (m, 1H), 1.73-2.01 (m, 4H), 1.69 (td, 1H); LC-MS: m/z 463.2 (M−H)$^+$ Example 16

(R)-2-(Isoindolin-2-ylmethyl)-5-((1-(methylsulfonyl) pyrrolidin-3-yl)methoxy)-4H-pyran-4-one (Compound 277)

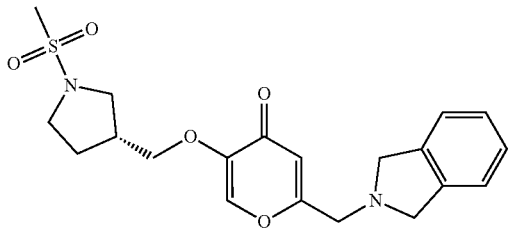 [SMILES: CS(=O)(=O)N1CC[C@@H](COc2coc(CN3Cc4ccccc4C3)cc2=O)C1]

a) (R)-2-(Isoindolin-2-ylmethyl)-5-(pyrrolidin-3-ylmethoxy)-4H-pyran-4-one

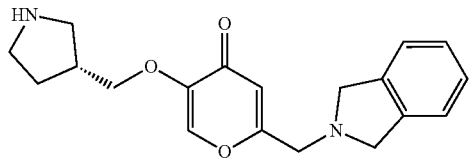 [SMILES: O=c1cc(CN2Cc3ccccc3C2)occ1OC[C@@H]1CCNC1]

The compound was prepared according to the procedure described in step (b) of Example 15 starting from (R)-tert-butyl 3-(((6-(isoindolin-2-ylmethyl)-4-oxo-4H-pyran-3-yl) oxy)methyl)pyrrolidine-1-carboxylate (0.834 g, 1.955 mmol) and hydrogen chloride (3 M in CPME, 2.28 ml, 6.84 mmol) in 2-propanol (10 ml). The title compound (0.175 g) was used as such in the next step. LC-MS: m/z 327.2 (M+H)$^+$ b) (R)-2-(Isoindolin-2-ylmethyl)-5-((1-(methylsulfonyl)pyrrolidin-3-yl)methoxy)-4H-pyran-4-one The compound was prepared according to the procedure described in step (c) of Example 15 starting from (R)-2-(isoindolin-2-ylmethyl)-5-(pyrrolidin-3-ylmethoxy)-4H-pyran-4-one (0.175 g, 0.536 mmol), triethylamine (0.149 ml, 1.072 mmol), and methanesulfonyl chloride (41 µl, 0.536 mmol) in dry DCM (3 ml). Purification by column chromatography afforded the title compound (50 mg). $^1$H NMR (Chloroform-d): δ 7.66 (s, 1H), 7.18-7.24 (m, 4H), 6.49 (m, 1H), 4.06 (s, 4H), 3.95 (dd, 1H), 3.88 (dd, 1H), 3.79 (d, 2H), 3.56 (dd, 1H), 3.45-3.53 (m, 1H), 3.34-3.40 (m, 1H), 3.31 (dd, 1H), 2.88 (s, 3H), 2.74-2.85 (m, 1H), 2.12-2.23 (m, 1H), 1.83-1.94 (m, 1H); LC-MS: m/z 405.2 (M+H)$^+$ Example 17

4-((6-((5-Bromoisoindolin-2-yl)methyl)-4-oxo-4H-pyran-3-yloxy)methyl)benzonitrile (Compound 278)

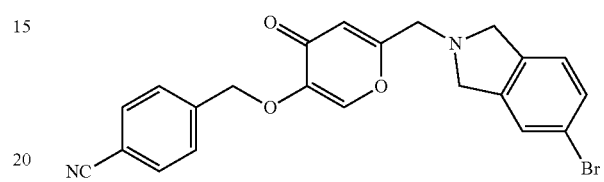

a) 4-((6-(hydroxymethyl)-4-oxo-4H-pyran-3-yloxy) methyl)benzonitrile

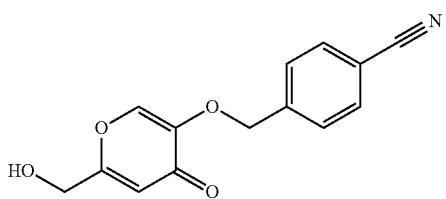 [SMILES: N#Cc1ccc(COc2coc(CO)cc2=O)cc1]

A solution of 5-hydroxy-2-(hydroxymethyl)-4h-pyran-4-one (500 mg, 3.52 mmol), alpha-bromo-p-tolunitrile (690 mg, 3.52 mmol) and potassium carbonate (973 mg, 7.04 mmol) in DMF (10 ml) was heated at 80° C. in a micro-wave reactor for 15 min. The reaction mixture was poured into water. The precipitate was filtered, washed with water, and dried to afford the title compound (0.75 g). $^1$H NMR (400 MHz, DMSO-d$_6$) δ ppm 8.21 (s, 1H), 7.89 (s, 1H), 7.87 (s, 1H), 7.60-7.64 (m, 2H), 6.33-6.35 (m, 1H), 5.07 (s, 2H), 4.30 (s, 2H).

b) (5-(4-Cyanobenzyloxy)-4-oxo-4H-pyran-2-yl) methyl methanesulfonate

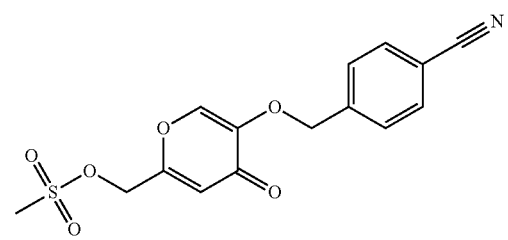 [SMILES: CS(=O)(=O)OCc1cc(=O)c(OCc2ccc(C#N)cc2)co1]

To a solution of 4-((6-(hydroxymethyl)-4-oxo-4H-pyran-3-yloxy)methyl)benzonitrile (0.2 g, 0.777 mmol) and TEA (0.325 ml, 2.332 mmol) in DCM (5 ml) at 0° C. was added dropwise methanesulfonyl chloride (0.075 ml, 0.972 mmol). The reaction mixture was stirred at 20° C. for 3 h, and washed with saturated NaHCO₃, 0.1 M HCl and brine. The organic layer was dried with Na₂SO₄, filtered and evaporated to afford the title compound (0.14 g). ¹H NMR (400 MHz, Chloroform-d) δ ppm 7.66-7.70 (m, 2H), 7.64-7.66 (m, 1H), 7.51-7.56 (m, 2H), 6.43-6.55 (m, 1H), 5.14 (s, 2H), 4.30-5.05 (m, 2H), 3.11-3.15 (m, 3H).

c) 4-((6-((5-Bromoisoindolin-2-yl)methyl)-4-oxo-4H-pyran-3-yloxy)methyl)-benzonitrile A solution of 5-bromoisoindoline (0.07 g, 0.353 mmol) and (5-(4-cyano-benzyloxy)-4-oxo-4H-pyran-2-yl)methyl methanesulfonate (0.119 g, 0.353 mmol) and potassium carbonate (0.098 g, 0.707 mmol) in DMSO (2 ml) was stirred at 60° C. for 30 min. Water was added, and the aqueous layer was extracted with DCM. The organic layers were combined, washed with water and brine, dried with Na₂SO₄, filtered, evaporated, and purified with semipreparative HPLC to afford the title compound (9 mg). 1H NMR (400 MHz, Chloroform-d) δ ppm 7.66-7.70 (m, 1H), 7.63 (s, 1H), 7.52-7.56 (m, 2H), 7.33-7.37 (m, 2H), 7.05-7.17 (m, 1H), 6.50 (s, 1H), 5.13-5.16 (m, 1H), 3.95-4.04 (m, 4H), 3.74-3.76 (m, 2H), 1.54-1.83 (m, 2H); LC-MS: m/z 437.3 (M+H)⁺.

The following compounds were prepared according to the procedure of step (c) of Example 17 starting from isoindoline or derivate thereof and another appropriate starting material. The characterization data, starting material and possible deviations in reaction conditions (solvent, reaction temperature, reaction time, purification method), if any, are indicated on the table.

Purification Methods Used:
A=Crystallization
B=Column chromatography
C=Precipitation in aqueous media
D=Semipreparative HPLC
E=Trituration
F=Salt formation
G=As such

| No | Structure and starting material | Deviating reaction conditions/ ¹H NMR (400 MHz)/LC-MS |
|---|---|---|
| 279 | 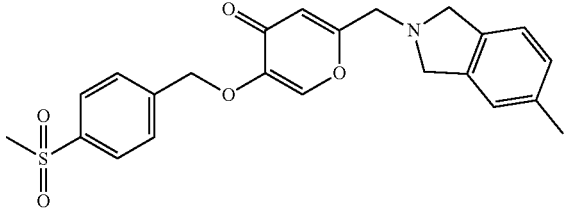<br>Starting material: (5-((4-(Methylsulfonyl)benzyl)oxy)-4-oxo-4H-pyran-2-yl)methyl methanesulfonate; | Conditions: DMF, 85° C., B.<br>1H NMR (DMSO-d6) δ: 8.26 (s, 1 H), 7.94-7.99 (m, 2 H), 7.67-7.72 (m, 2 H), 7.09-7.15 (m, 1 H), 7.05 (s, 1 H), 6.99-7.03 (m, 1 H), 6.43 (s, 1 H), 5.10 (s, 2 H), 3.91 (s, 4 H), 3.78 (s, 2 H), 3.22 (s, 3 H), 2.28 (s, 3 H); LC-MS: m/z 426.3 (M + H)+. |
| 280 | 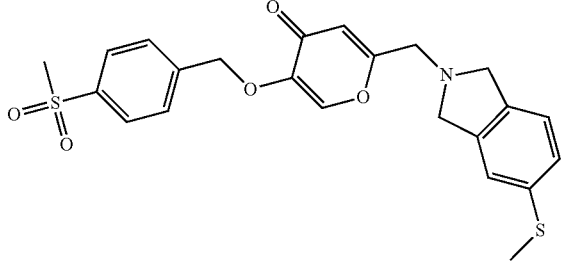 [SMILES: CSc1ccc2c(c1)CN(Cc1cc(=O)c(OCc3ccc(S(C)(=O)=O)cc3)co1)C2]<br>Starting material: (5-((4-(Methylsulfonyl)benzyl)oxy)-4-oxo-4H-pyran-2-yl)methyl methanesulfonate | Conditions: DMF, 80° C.<br>1H NMR (Chloroform-d) δ: 7.94-7.98 (m, 2 H), 7.65 (s, 1 H), 7.61-7.64 (m, 2 H), 7.10-7.15 (m, 3 H), 6.51 (s, 1 H), 5.18 (s, 2 H), 3.98-4.02 (m, 4 H), 3.76 (s, 2 H), 3.06 (s, 3 H), 2.47 (s, 3 H); LC-MS: m/z 458.6 |
| 281 | 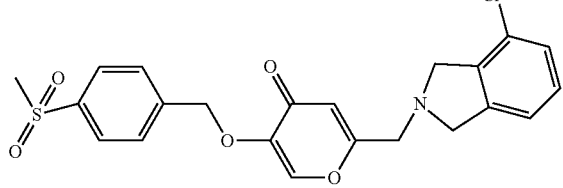<br>Starting material: 2-(Chloromethyl)-5-((4-(methylsulfonyl)benzyl)oxy)-4H-pyran-4-one | Conditions: DMF, 70° C., C and D.<br>1H NMR (DMSO-d6) δ: 8.28 (s, 1 H), 7.95-7.99 (m, 2 H), 7.68-7.72 (m, 2 H), 7.22-7.30 (m, 3 H), 6.46 (s, 1 H), 5.10 (s, 2 H), 3.99-4.10 (m, 4 H), 3.84 (s, 2 H), 3.23 (s, 3 H); LC-MS: m/z 446.6 |

Example 18

N-(3-Hydroxypropyl)-4-(((6-(isoindolin-2-ylmethyl)-4-oxo-4H-pyran-3-yl)oxy)methyl)benzamide (Compound 282)

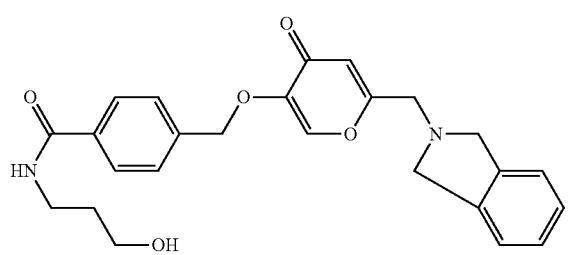 [SMILES: O=C(NCCCO)c1ccc(COc2coc(CN3Cc4ccccc4C3)cc2=O)cc1]

a) 4-(Chloromethyl)-N-(3-hydroxypropyl)benzamide

To a solution of 4-(chloromethyl)benzoyl chloride (2.97 g, 15.71 mmol) in DCM (10 ml) was added 3-amino-1-propanol (1.180 g, 15.71 mmol) in DCM (20 ml) followed by dropwise addition of TEA (2.409 ml, 17.28 mmol) at 0° C. The reaction mixture was stirred at 0° C. for 45 min. Water was added to the mixture, the layers were separated, and the aqueous layer was extracted with DCM. The organic layers were combined, washed with 1 M NaOH, 1 M HCl and brine, dried with $Na_2SO_4$, filtered, and evaporated. The crude product was purified by column chromatography followed by trituration with diethyl ether to afford the title compound. LC-MS: m/z 228.2 $(M+H)^+$.

c) 3-(4-(Chloromethyl)benzamido)propyl acetate

To a solution of 4-(chloromethyl)-N-(3-hydroxypropyl)benzamide (1.79 g, 7.86 mmol) in pyridine (15 ml) was added acetic anhydride (1.115 ml, 11.79 mmol) at 0° C. The reaction mixture was stirred at 0° C. for 15 min and at 20° C. for 30 min. The solvent was evaporated, and water was added to the residue. The aqueous layer was extracted with EtOAc. The organic layers were combined, washed with 1 M HCl, water, 5% $NaHCO_3$ and brine, dried with $Na_2SO_4$, filtered, and evaporated to afford the title compound. LC-MS: m/z 270.2 $(M+H)^+$.

c) 3-(4-(((6-(Isoindolin-2-ylmethyl)-4-oxo-4H-pyran-3-yl)oxy)methyl)-benzamido)propyl acetate The suspension of 5-hydroxy-2-(isoindolin-2-ylmethyl)-4H-pyran-4-one (0.2 g, 0.822 mmol), 3-(4-(chloromethyl)benzamido)propyl acetate (0.222 g, 0.822 mmol) and $K_2CO_3$ (0.199 g, 1.439 mmol) in DMF (2 ml) was heated at 80° C. for 30 min. Water was added to the mixture, and the aqueous layer was extracted with DCM. The organic layers were combined, washed with water and brine, dried with $Na_2SO_4$, filtered, and evaporated. The crude product was purified by column chromatography to afford the title compound. LC-MS: m/z 477.5 $(M+H)^+$.

d) N-(3-Hydroxypropyl)-4-(((6-(isoindolin-2-ylmethyl)-4-oxo-4H-pyran-3-yl)-oxy)methyl)benzamide A suspension of 3-(4-(((6-(isoindolin-2-ylmethyl)-4-oxo-4H-pyran-3-yl)oxy)-methyl)benzamido)propyl acetate (0.195 g, 0.409 mmol), $K_2CO_3$ (0.071 g, 0.512 mmol) and methanol (5 ml) in DCM (5 ml) was stirred at 20° C. for 1 h followed by filtration. The filtrate was evaporated to dryness, and the residue was purified by column chromatography followed by trituration with a mixture of heptane and diethyl ether to afford the title compound (0.04 g). 1H NMR (400 MHz, Chloroform-d) δ ppm 7.74-7.79 (m, 2H), 7.58 (s, 1H), 7.42-7.47 (m, 2H), 7.18-7.24 (m, 4H), 6.91-6.98 (m, 1H), 6.51 (s, 1H), 5.09 (s, 2H), 4.03 (s, 4H), 3.75 (s, 2H), 3.70-3.73 (m, 2H), 3.58-3.64 (m, 3H), 1.75-1.83 (m, 3H), 1.21 (t, J=7.0 Hz, 1H); LC-MS: m/z 435.5 (M+H)+.

Example 19

N-(1-hydroxy-2-methylpropan-2-yl)-4-(((6-(isoindolin-2-ylmethyl)-4-oxo-4H-pyran-3-yl)oxy)methyl)benzamide (Compound 283)

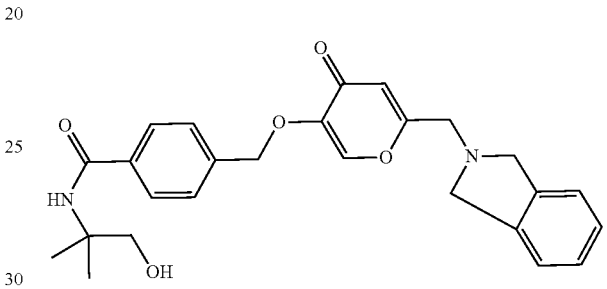

A suspension of 2-(4-(((6-(isoindolin-2-ylmethyl)-4-oxo-4H-pyran-3-yl)oxy)-methyl)benzamido)-2-methylpropyl acetate (0.284 g, 0.579 mmol)] $K_2CO_3$ (0.100 g, 0.724 mmol) and methanol (5 ml) in DCM (5 ml) was stirred at 20° C. for 1 h followed by filtration. The filtrate was evaporated to dryness, and the residue was purified by column chromatography to afford the title compound (0.12 g). 1H NMR (400 MHz, DMSO-d6) δ ppm 8.21 (s, 1H), 7.78-7.84 (m, 2H), 7.51-7.58 (m, 1H), 7.48 (s, 2H), 7.17-7.26 (m, 4H), 6.42 (s, 1H), 5.02 (s, 2H), 4.91 (t, J=6.0 Hz, 1H), 3.95 (s, 4H), 3.79 (s, 2H), 3.50 (d, J=6.0 Hz, 2H), 1.31 (s, 6H); LC-MS: m/z 449.5 $(M+H)^+$.

Example 20

4-(((6-(Isoindolin-2-ylmethyl)-4-oxo-4H-pyran-3-yl)oxy)methyl)piperidine-1-carbaldehyde, HCl (Compound 284)

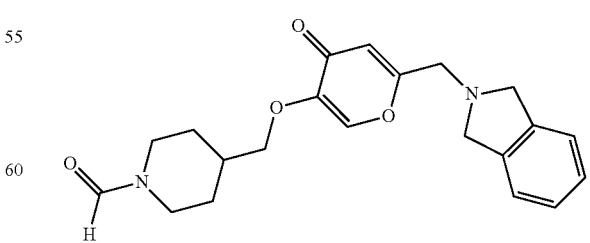

A solution of 2-(isoindolin-2-ylmethyl)-5-(piperidin-4-ylmethoxy)-4H-pyran-4-one (0.13 g, 0.382 mmol) and methyl formate (0.030 ml, 0.496 mmol) was stirred for 30 min 0° C. Then the mixture was allowed to reach 20° C. and stirred for 90 min. Sodium hydroxide (0.04 g, 0.095 mmol) was added to the mixture. The mixture was stirred for 16 h. 10 ml of DCM was added, and the solids were removed by filtration. 1 M HCl in diethyl ether (1 ml) was added to the mixture. The mixture was filtered through Celite® and the solvent was removed under reduced pressure. The residue was treated with diethyl ether, filtered, and dried to afford the title compound (0.1 g). 1H NMR (400 MHz, DMSO-d6) δ ppm 8.22 (s, 1H), 7.99 (s, 1H), 7.34-7.44 (m, 5H), 6.75 (s, 1H), 6.75 (s, 1H), 4.72-4.85 (m, 2H), 4.61 (s, 2H), 4.15-4.23 (m, 1H), 3.70-3.74 (m, 3H), 3.01-3.11 (m, 1H), 2.59-2.72 (m, 1H), 1.95-2.09 (m, 1H), 1.72-1.85 (m, 2H), 1.01-1.22 (m, 3H); LC-MS: m/z 369.2.

Example 21

5-((4-(S-Methylsulfonimidoyl)benzyl)oxy)-2-((5-(trifluoromethyl)isoindolin-2-yl)methyl)-4H-pyran-4-one (Compound 285) and 5-((4-(R-Methylsulfonimidoyl)-benzyl)oxy)-2-((5-(trifluoromethyl)isoindolin-2-yl)methyl)-4H-pyran-4-one (Compound 286)

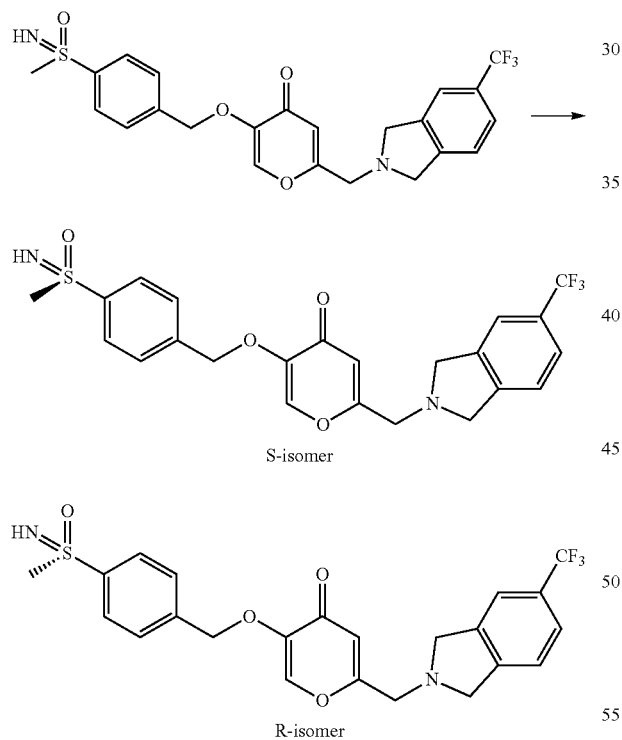

Racemic resolution of 5-((4-(R,S-methylsulfonimidoyl)benzyl)oxy)-2-((5-(trifluoromethyl)isoindolin-2-yl)methyl)-4H-pyran-4-one (0.1 g, 0.21 mmol) was conducted using Chiralpak IF, 5 μm, 20*250 mm column and n-hexane, EtOH and DEA as eluent.

S-isomer (39.3 mg): ¹H NMR (Chloroform-d) δ: 8.02 (d, 2H), 7.64 (s, 1H), 7.61 (d, 2H), 7.50 (d, 1H), 7.46 (s, 1H), 7.31 (d, 1H), 6.52 (s, 1H), 5.17 (s, 2H), 4.09 (s, 4H), 3.79 (s, 2H), 3.11 (s, 3H).

R-isomer (43.9 mg): ¹H NMR (Chloroform-d) δ: 7.99-8.08 (m, 1H), 7.99-8.08 (m, 1H), 7.64 (s, 1H), 7.61 (d, 2H), 7.50 (d, 1H), 7.46 (s, 1H), 7.31 (d, 1H), 7.27 (s, 1H), 7.26-7.27 (m, 1H), 6.52 (s, 1H), 5.17 (s, 2H), 4.09 (s, 4H), 3.79 (s, 2H), 3.11 (s, 3H).

Example 22

5-((1-(Methylsulfonyl)piperidin-4-yl)methoxy)-2-((5-(trifluoromethyl)-2H-isoindol-2-yl)methyl)-4H-pyran-4-one (Compound 287)

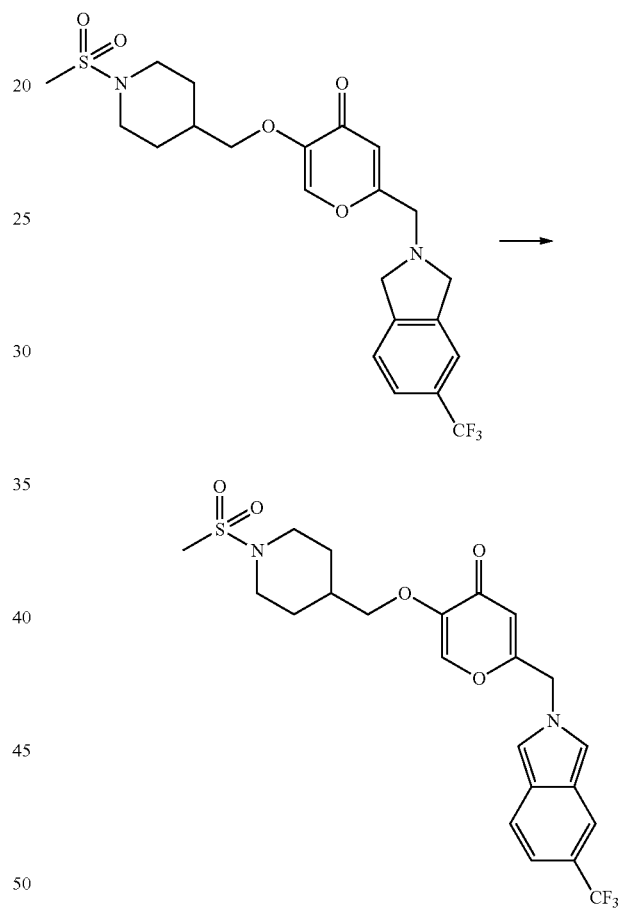

To a solution of 5-((1-(methylsulfonyl)piperidin-4-yl)methoxy)-2-((5-(tri-fluoromethyl)isoindolin-2-yl)methyl)-4H-pyran-4-one (0.40 g, 0.82 mmol) in dry dioxane (10 ml) were added palladium (II) acetate (0.18 g, 0.82 mmol) and cyclohexene (0.41 ml, 4.11 mmol). The reaction mixture was heated at 130° C. for 4 h. The catalyst was filtered off. The solvent was evaporated. The crude product was purified by column chromatography to afford 0.35 g of the title compound. ¹H NMR (Methanol-d₄) δ: 8.01 (s, 1H), 7.87 (s, 1H), 7.62 (m, 1H), 7.50 (d, 1H), 7.37-7.41 (m, 1H), 7.00 (m, 1H), 6.24 (s, 1H), 5.45 (s, 2H), 3.68-3.78 (m, 4H), 2.81 (s, 3H), 2.71-2.80 (m, 2H), 1.88-2.01 (m, 3H), 1.24-1.49 (m, 2H). LC-MS: m/z 487.3 (M+H)⁺.

Example 23

2-((2H-Isoindol-2-yl)methyl)-5-((1-(methylsulfonyl)piperidin-4-yl)methoxy)-4H-pyran-4-one (Compound 288)

Example 24

2-((5-((1-(Methylsulfonyl)piperidin-4-yl)methoxy)-4-oxo-4H-pyran-2-yl)-methyl)isoindoline 2-oxide (Compound 289)

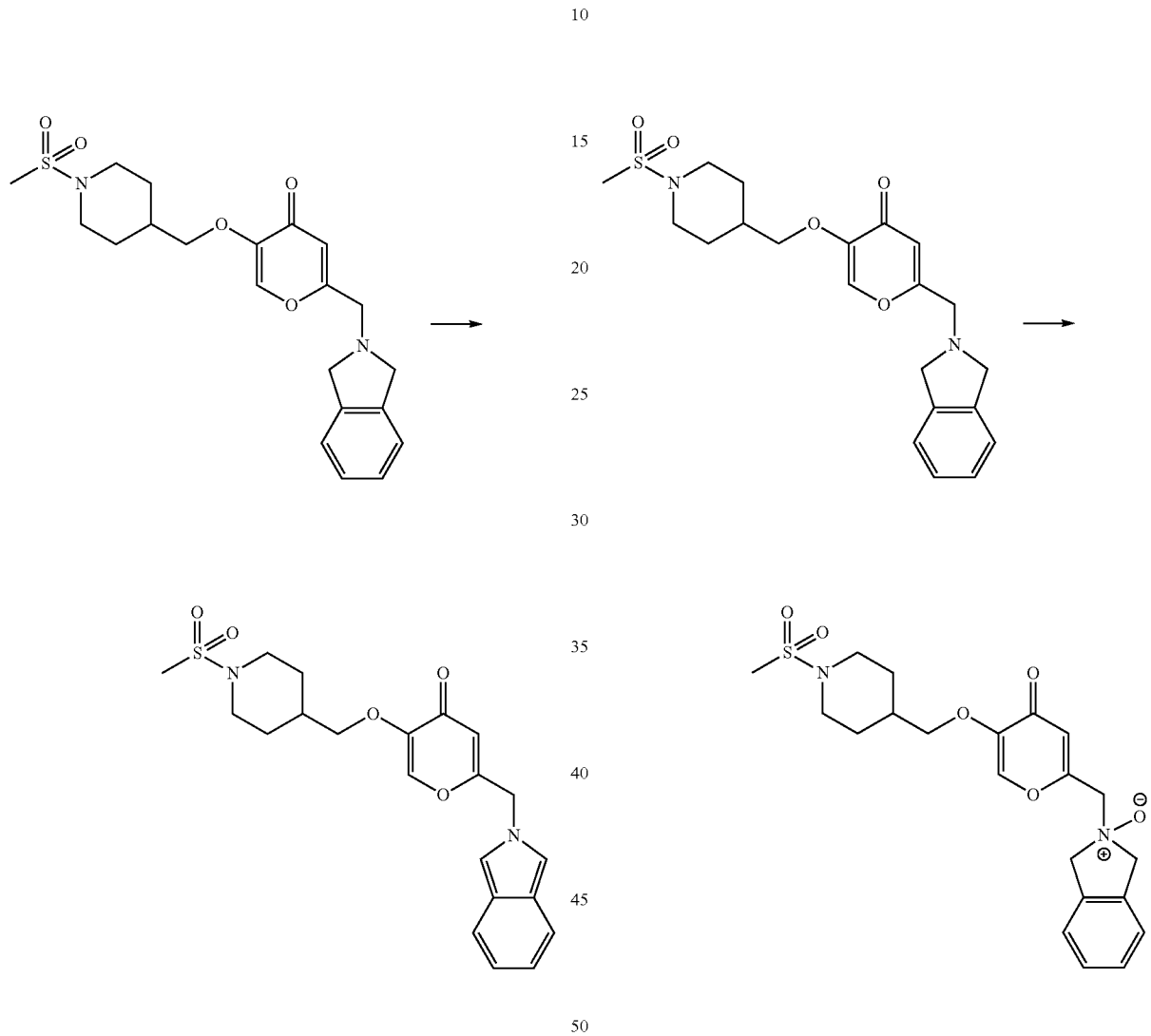

To a solution of 2-(isoindolin-2-ylmethyl)-5-((1-(methylsulfonyl)piperidin-4-yl)methoxy)-4H-pyran-4-one (0.20 g, 0.48 mmol) in dry dioxane (15 ml) were added palladium (II) acetate (107 mg, 0.48 mmol) and cyclohexene (0.48 ml, 4.78 mmol). The reaction mixture was heated at 130° C. for 4 h. The catalyst was filtered off. The solvent was evaporated. The crude product was purified by column chromatography to afford 24.7 mg of the title compound. $^1$H NMR (DMSO-d$_6$) δ: 8.12-8.17 (m, 1H), 7.47 (d, 2H), 6.84 (d, 2H), 6.22 (s, 1H), 5.42 (s, 2H), 3.68 (d, 2H), 3.55 (br d, 3H), 2.84 (s, 3H), 2.65-2.74 (m, 2H), 1.75-1.85 (m, 3H), 1.20-1.30 (m, 2H). LC-MS: m/z 416.5 (M+H)$^+$.

To a solution of 2-(isoindolin-2-ylmethyl)-5-((1-(methylsulfonyl)piperidin-4-yl)methoxy)-4H-pyran-4-one (0.10 g, 0.24 mmol) in methanol (1 ml) were added formic acid (11.0 mg, 0.24 mmol) and hydrogen peroxide 35% solution in water (8.13 mg, 0.24 mmol). The mixture was stirred at RT for 6 h. The solvent was evaporated. The crude product was purified by column chromatography to afford 70 mg of the title compound. $^1$H NMR (DMSO-d$_6$) δ: 10.44 (s, 1H), 7.96 (d, 1H), 7.85 (d, 2H), 7.61 (d, 2H), 7.41 (m, 1H), 7.20 (d, 1H), 6.95 (m, 1H), 6.84 (d, 1H), 6.59 (d, 1H), 3.36 (s, 1H), 3.27 (m, 2H), 2.77 (m, 1H), 2.14 (s, 3H), 1.05-1.13 (m, 8H). LC-MS: m/z 435.2 (M+H)$^+$.

Example 25

2-((5-((1-(Methylsulfonyl)piperidin-4-yl)methoxy)-4-oxo-4H-pyran-2-yl)methyl)-5-(trifluoromethyl)isoindoline 2-oxide (Compound 290)

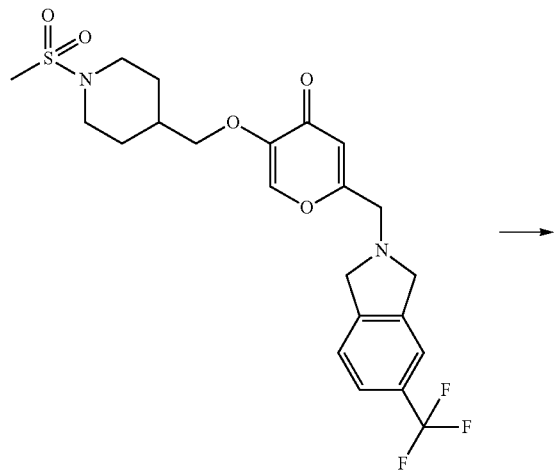

To a solution of 5-((1-(methylsulfonyl)piperidin-4-yl)methoxy)-2-((5-(trifluoro-methyl)isoindolin-2-yl)methyl)-4H-pyran-4-one (0.10 g, 0.20 mmol) in methanol (2 ml) were added formic acid (47.0 mg, 1.02 mmol) and hydrogen peroxide 35% solution in water (0.20 g, 2.05 mmol). The mixture was stirred at RT for 6 h. The solvent was evaporated. The crude product was purified by column chromatography to afford 43 mg of the title compound. $^1$H NMR (DMSO-$d_6$) δ: 8.24 (br s, 1H), 7.77 (br s, 1H), 7.70 (br d, 1H), 7.59 (br d, 1H), 6.68 (s, 1H), 5.15-5.27 (m, 2H), 4.76 (br s, 2H), 4.62 (br d, 2H), 3.75 (br d, 2H), 3.38 (m, 2H), 2.86 (s, 3H), 2.73 (br m, 2H), 1.86 (br d, 3H), 1.24-1.36 (m, 2H). LC-MS: m/z 435.2 (M+H)$^+$.

Example 26

5-((1-(Methylsulfonyl)-1,2,3,4-tetrahydropyridin-4-yl)methoxy)-2-((5-(trifluoro-methyl)isoindolin-2-yl)methyl)-4H-pyran-4-one (Compound 291)

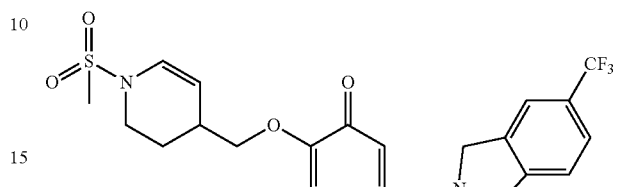

a) Ethyl piperidine-4-carboxylate trifluoroacetate

To a solution of 1-(tert-butyl)-4-ethyl-piperidine-1,4-dicarboxylate (20 g, 77.8 mmol) in DCM (400 ml) was added TFA (200 ml) dropwise at 0° C. followed by stirring at RT for 2 h. The mixture was concentrated under reduced pressure to give 44 g of crude title compound as brown oil. This was used directly in the next reaction step without further purification.

b) Ethyl-1-(methylsulfonyl)piperidine-4-carboxylate

To a solution of ethyl piperidine-4-carboxylate trifluoroacetate (44 g, 162.3 mmol) in ACN (400 ml) was added DIPEA (106 ml, 649.4 mmol) and MsCl (25 ml, 327.4 mmol) at 0° C. followed by stirring at RT for 2-3 h. The reaction mixture was quenched with water (500 ml) and extracted with EtOAc (3×500 ml). The organic layer was washed with brine, dried (anhydrous Na$_2$SO$_4$), filtered and concentrated under reduced pressure. The crude residue was purified by column chromatography over silica gel using 25% EtOAc in hexane as an eluent to give 5.6 g of the title compound as a white solid. MS: m/z 158 [M+H]$^+$.

c) Ethyl-1-(methylsulfonyl)-2-oxopiperidine-4-carboxylate

To a solution of ethyl-1-(methylsulfonyl)piperidine-4-carboxylate (3.6 g, 15.3 mmol) in ACN:H$_2$O (2:5) (14 mL) was added Ruthenium(IV) oxide hydrate (0.2 g, 1.5 mmol) under water bath. After 5 min, sodium periodate (6.8 g, 32.1 mmol) was added portionwise at temperature between 18° C. to 22° C. (temperature should not be more than 30° C. during addition). The mixture was stirred at RT for 7 h. The reaction mixture was quenched with water followed by addition of DCM (50 mL). The mixture was filtered through Celite® bed. The organic layer was separated, dried (anhydrous Na$_2$SO$_4$) and concentrated under reduced pressure. The crude residue was purified by column chromatography over silica gel using 20-40% EtOAc in hexane as an eluent to give 2.3 g of the title compound as a light yellow solid. MS: m/z 250 [M+H]$^+$.

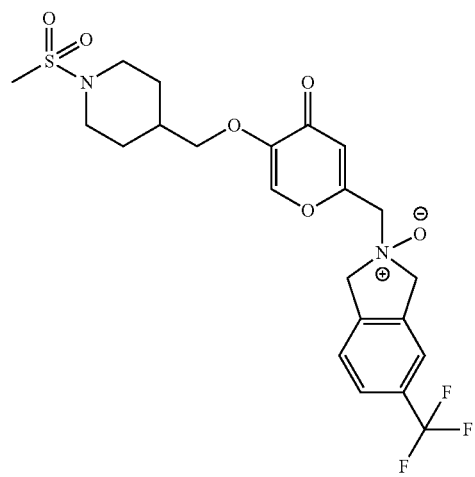

d) Ethyl-2-hydroxy-1-(methylsulfonyl)piperidine-4-carboxylate

To a solution ethyl-1-(methylsulfonyl)-2-oxopiperidine-4-carboxylate (2.26 g, 9.0 mmol) in dry THF (100 ml) was added DIBAL-H in toluene (1.5 M in toluene, 15.1 ml, 22.6 mmol) dropwise at −78° C. followed by stirring for 5 h. The mixture was cooled to RT, quenched with saturated $NH_4Cl$ solution and extracted with EtOAc (3×50 mL). The organic layer was dried (anhydrous $Na_2SO_4$), filtered and concentrated under reduced pressure to give 2.1 g of crude title compound as pale yellow oil. This was used directly in the next reaction step without further purification.

e) Ethyl-1-(methylsulfonyl)-1,2,3,4-tetrahydropyridine-4-carboxylate

To a solution of ethyl-2-hydroxy-1-(methylsulfonyl)piperidine-4-carboxylate (2.1 g, 8.3 mmol) in DCM (40 ml) was added TFAA (2.9 ml, 20.9 mmol) dropwise at −78° C. and followed by stirring for 6 h. Thereafter TEA (24 ml, 167.3 mmol) was added at −78° C. followed by stirring at RT for 2.5 h. The reaction mixture was quenched with aqueous $NaHCO_3$ solution and extracted with DCM (3×50 mL). The organic layer was washed with water, dried (anhydrous $Na_2SO_4$), filtered and concentrated under reduced pressure. The crude residue was purified by column chromatography over silica gel using 10-20% EtOAc in hexane as an eluent to give 1.1 g of the title compound as light yellow solid. MS: m/z 234 $[M+H]^+$.

f) (1-(Methylsulfonyl)-1,2,3,4-tetrahydropyridin-4-yl)methanol

To a solution ethyl 1-(methylsulfonyl)-1,2,3,4-tetrahydropyridine-4-carboxylate (0.95 g, 4.0 mmol) in dry THF (100 ml) was added $LiBH_4$ (3.0 M in THF, 2.7 ml, 8.1 mmol) dropwise at −40° C. followed by stirring at RT for 16 h. The reaction mixture was quenched with ice and extracted with EtOAc (3×50 mL). The organic layer was dried (anhydrous $Na_2SO_4$), filtered and concentrated under reduced pressure to give 0.77 g of the title compound as transparent oil. MS: m/z 192 $[M+H]^+$.

g) (1-(Methylsulfonyl)-1,2,3,4-tetrahydropyridin-4-yl)methyl methanesulfonate To a solution of (1-(methylsulfonyl)-1,2,3,4-tetrahydropyridin-4-yl)methanol (0.76 g, 3.97 mmol) in ACN (10 ml) was added DIPEA (2.9 ml, 15.91 mmol) and MsCl (0.6 ml, 7.95 mmol) at 0° C. followed by stirring for 10 min. The reaction mixture was quenched with brine (50 ml) and extracted with EtOAc (3×25 mL). The organic layer was dried (anhydrous $Na_2SO_4$), filtered and concentrated under reduced pressure to give 1.2 g of crude title compound. This was used directly in the next reaction step without further purification. MS: m/z 270 $[M+H]^+$.

h) 5-((1-(Methylsulfonyl)-1,2,3,4-tetrahydropyridin-4-yl)methoxy)-2-((5-(tri-fluoromethyl)isoindolin-2-yl)methyl)-4H-pyran-4-one To a solution of 5-hydroxy-2-((5-(trifluoromethyl)isoindolin-2-yl)methyl)-4H-pyran-4-one (0.5 g, 1.6 mmol) and (1-(methylsulfonyl)-1,2,3,4-tetrahydropyridin-4-yl)methyl methanesulfonate (0.4 g, 1.6 mmol) in ACN (10 ml) was added $Cs_2CO_3$ (1.3 g, 4.0 mmol) followed by stirring at 70° C. for 16 h. The mixture was diluted with EtOAc (50 ml), filtered and concentrated under reduced pressure. The crude was purified by reverse phase preparative HPLC using Agilent, X Select Hexyl Phenyl (19×250) mm, 5 μm, gradient 30% to 70% ACN in water containing 5 mM of Ammonium acetate in water, RT, 13.5 min to give 13.7 mg of the title compound as brown solid. $^1$H-NMR (400 MHz; DMSO-$d_6$): δ 8.17 (s, 1H), 7.63 (s, 1H), 7.57 (d, 1H), 7.47 (d, 1H), 6.52 (d, 1H), 6.41 (s, 1H), 4.96 (q, 1H), 4.07 (s, 4H), 3.81 (s, 2H), 3.63-3.66 (m, 2H), 3.53-3.57 (m, 1H), 3.40-3.45 (m, 1H), 2.99 (s, 3H), 2.59-2.68 (m, 2H), 1.90-1.95 (m, 1H), 1.71-1.72 (m, 1H); MS: m/z 485 $[M+H]^+$.

EXPERIMENTS

CYP11A1 Inhibition

The ability of the test compounds to inhibit conversion of cholesterole to pregnenolone and isocaproic acid was measured by modification of isocaproic acid release assay (IARA) described by Ruangwises et. al. (Biology of Reproduction 1991; 45(1):143-50) except that human H295R adrenocortical carcinoma cell line was used as source of enzyme and extraction was done with dextran-coated charcoal suspension (Isomaa, V. et al., Endocrinology 1982; 111(3):833-843). The H295R cell line has been shown to express all the key steroidogenic enzymes. To determine the half maximal inhibitory concentration ($IC_{50}$) of the test compounds on CYP11A1 inhibition, the cells were treated for three days with increasing concentrations of the test compounds in the presence of 3 nM [24,25-3H]-labelled cholesterol (American Radiolabelled Chemicals). The final DMSO concentration was 1%. Cell culture medium was extracted with dextran-coated charcoal suspension and the radiolabelled isocaproic acid was determined by mixing 100 μl of supernatant fraction in 200 μl of scintillation fluid (OptiPhase SuperMix, Perkin Elmer). Radioactivity was measured using a Microbeta scintillation counter (1450 MicroBeta Trilux, Wallac). All the test compounds were studied at 10 concentrations in duplicates.

The compounds of the invention were screened in the above mentioned assay and the $IC_{50}$ values of the compounds are set forth in Table 1 below wherein "A" refers to an $IC_{50}$ value of less than 150 nM, "B" refers to $IC_{50}$ value in range of 150 to 300 nM and "C" refers to $IC_{50}$ value in range of 301 nM to 2000 nM.

TABLE 1

| Group | Compound No. |
|---|---|
| A | 2, 5, 8, 10, 11, 12, 15, 21, 22, 23, 36, 37, 44, 47, 49, 65, 69a, 70, 71, 72, 73, 74, 83, 84, 89, 90, 91, 92, 93, 95, 103, 104, 109, 111, 113, 114, 115, 116, 122, 129, 130, 131, 134, 137, 138, 139, 146, 162, 172, 173, 176, 184, 185, 186, 187, 188, 189, 190, 192, 195, 196, 205, 211, 213, 215, 216, 217, 219, 221, 222, 224, 225, 226, 229, 230, 232, 234, 238, 244, 244a, 249, 251, 254, 255, 257, 261, 262, 271, 272, 278, 285 and 286 |

TABLE 1-continued

| Group | Compound No. |
|---|---|
| B | 1, 4, 6, 7, 9, 20, 24, 25, 26, 28, 29, 30, 31, 34, 39, 46, 53, 56, 61, 63, 64, 67, 68, 69, 81, 82, 82a, 85, 86, 88, 94, 97, 98, 99, 100, 101, 102, 107, 108, 120, 121, 124, 126, 127, 128, 135, 136, 140, 142, 143, 147, 158, 161, 163, 164, 165, 168, 169, 174, 177, 180, 181, 191, 194, 198, 199, 200, 208, 209, 210, 214, 218, 220, 223, 227, 228, 231, 233, 235, 236, 237, 239, 241, 247, 248, 250, 252, 256, 258, 260, 267, 268, 269, 270, 273, 276, 279, 280, 283, 284 and 291 |
| C | 3, 13, 14, 16, 17, 18, 19, 27, 32, 33, 35, 38, 40, 41, 42, 43, 45, 48, 50, 51, 52, 55, 57, 58, 59, 60, 62, 66, 75, 76, 77, 78, 79, 80, 87, 96, 105, 106, 110, 112, 117, 118, 119, 123, 125, 132, 133, 141, 144, 145, 148, 149, 150, 151, 152, 153, 154, 155, 156, 157, 159, 160, 166, 170, 171, 178, 179, 182, 183, 193, 197, 201, 202, 203, 206, 207, 212, 240, 242, 243, 245, 245a, 253, 263, 264, 265, 274, 275, 277, 281, 282, 287, 289 and 290 |

ABBREVIATIONS

ACN—Acetonitrile
DAST—Diethylaminosulfur trifluoride
DCE—1,2-Dichloroethane
DCM—Dichloromethane
DEA—Diethanolamine
DIBAL-H—Diisobutylaluminum hydride solution
DIPEA—N,N-diisopropylethylamine
DMF—N,N-Dimethylformamide
DMSO—Dimethylsulfoxide
DPPA—Diphenylphosphoryl azide
DBU—1,8-Diazabicyclo[5.4.0]undec-7-ene
EtOAc—Ethyl acetate
EtOH—Ethanol
IPA—Isopropyl Alcohol
LAH—Lithium aluminium hydride
LiHMDS—Hexamethyldisilazane lithium salt TAI Lithium bis(trimethylsilyl)amide
m-CPBA—3-Chloroperoxybenzoic acid
MeOH—Methanol
Ms—Methanesulfonyl
MTBE—Methyl Tertiary Butyl Ether
PPh$_3$—Triphenylphosphine
Pd$_2$(dba)$_3$-Tris(dibenzylideneacetone)dipalladium(0)
Pd(PPh$_3$)$_4$—Tetrakis(triphenylphosphine)palladium(0)
PPTS—Pyridinium p-toluenesulfonate
rac-BINAP—rac-2,2'-bis(diphenylphosphino)-1,1'-binaphthyl
RT—Room temperature
rt—Retention time
TBABr—Tetrabutylammonium bromide
TBAF—Tetrabutylammonium fluoride
TBME—Methyl tert-butyl ether
TBSCl-tert-Butyldimethylsilyl chloride
TEA—Triethylamine
TFA—Trifluoroacetic acid
TFAA—Trifluoroacetic anhydride
THF—Tetrahydrofuran
TMEDA—Tetramethylethylenediamine
Tf—trifluoromethanesulfonyl
Ts—p-Toluenesulfonyl

The invention claimed is:

1. A compound of formula (ID):

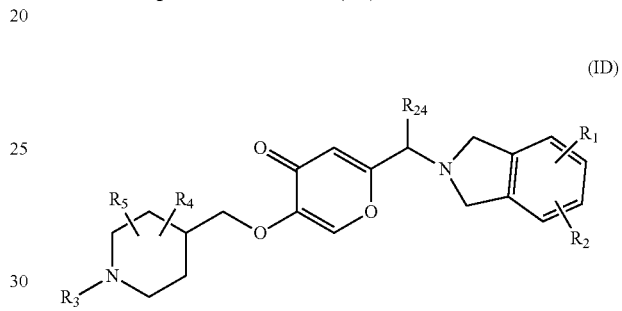

(ID)

wherein R1 is hydrogen, halogen, halo $C_{1-7}$ alkyl or halo $C_{1-7}$ alkoxy;
$R_2$, $R_4$ and $R_5$ are hydrogen;
$R_3$ is -D-C(O)—$NR_6R_7$, —C(O)$R_8$ or —SO$_2R_{11}$;
D is absent;
$R_6$ is $C_{1-7}$ alkyl;
$R_7$ is hydrogen;
$R_8$ is $C_{1-7}$ alkyl or halo $C_{1-7}$ alkyl;
$R_{11}$ is $C_{1-7}$ alkyl, $C_{3-7}$ cycloalkyl, $C_{1-7}$ alkoxy $C_{1-7}$ alkyl, —$NR_{12}R_{13}$ or oxetanyl;
$R_{12}$, and $R_{13}$ are $C_{1-7}$ alkyl;
$R_{24}$ is hydrogen or $C_{1-7}$ alkyl;
or a tautomer, or a pharmaceutically acceptable salt thereof.

2. The compound according to claim 1, which is selected from:
   5-((1-(Oxetan-3-ylsulfonyl)piperidin-4-yl)methoxy)-2-((5-(trifluoromethyl)isoindolin-2-yl)methyl)-4H-pyran-4-one;
   5-((1-(Methylsulfonyl)piperidin-4-yl)methoxy)-2-((5-(trifluoromethyl)isoindolin-2-yl)methyl)-4H-pyran-4-one;
   2-(Isoindolin-2-ylmethyl)-5-((1-(methylsulfonyl)piperidin-4-yl)methoxy)-4H-pyran-4-one;
   2-((5-Fluoroisoindolin-2-yl)methyl)-5-((1-(methylsulfonyl)piperidin-4-yl)methoxy)-4H-pyran-4-one;
   5-((1-(Cyclopropylsulfonyl)piperidin-4-yl)methoxy)-2-(isoindolin-2-ylmethyl)-4H-pyran-4-one;
   5-((1-(Ethylsulfonyl)piperidin-4-yl)methoxy)-2-(isoindolin-2-ylmethyl)-4H-pyran-4-one;
   5-((1-(Ethylsulfonyl)piperidin-4-yl)methoxy)-2-((5-fluoroisoindolin-2-yl)methyl)-4H-pyran-4-one;
   5-((1-(Cyclopropylsulfonyl)piperidin-4-yl)methoxy)-2-((5-fluoroisoindolin-2-yl)methyl)-4H-pyran-4-one;

5-((1-(Ethylsulfonyl)-4-methylpiperidin-4-yl)methoxy)-2-(isoindolin-2-ylmethyl)-4H-pyran-4-one;
2-(1-Isoindolin-2-yl)ethyl)-5-((1-(methylsulfonyl)piperidin-4-yl)methoxy)-4H-pyran-4-one;
5-((1-(Methylsulfonyl)piperidin-4-yl)methoxy)-2-((5-(trifluoromethoxy)isoindolin-2-yl)methyl)-4H-pyran-4-one;
2-(Isoindolin-2-ylmethyl)-5-((1-(pyrrolidine-1-carbonyl)piperidin-4-yl)methoxy)-4H-pyran-4-one;
5-((1-Butyrylpiperidin-4-yl)methoxy)-2-(isoindolin-2-ylmethyl)-4H-pyran-4-one;
5-((1-(2,2-Difluoropropanoyl)piperidin-4-yl)methoxy)-2-(isoindolin-2-ylmethyl)-4H-pyran-4-one;
5-((1-(2,2-Difluoropropanoyl)piperidin-4-yl)methoxy)-2-((5-fluoroisoindolin-2-yl)methyl)-4H-pyran-4-one;
2-((5-Fluoroisoindolin-2-yl)methyl)-5-((1-propionylpiperidin-4-yl)methoxy)-4H-pyran-4-one;
4-(((6-(Isoindolin-2-ylmethyl)-4-oxo-4H-pyran-3-yl)oxy)methyl)-N,N-di-methylpiperidine-1-sulfonamide;
4-(((6-(Isoindolin-2-ylmethyl)-4-oxo-4H-pyran-3-yl)oxy)methyl)-N-methyl-piperidine-1-carboxamide;
4-(((6-(Isoindolin-2-ylmethyl)-4-oxo-4H-pyran-3-yl)oxy)methyl)-N-iso-propylpiperidine-1-carboxamide;
4-(((6-((5-Fluoroisoindolin-2-yl)methyl)-4-oxo-4H-pyran-3-yl)oxy)methyl)-N,N-dimethylpiperidine-1-sulfonamide;
2-(Isoindolin-2-ylmethyl)-5-((4-(oxetan-3-ylsulfonyl)benzyl)oxy)-4H-pyran-4-one;
2-((5-Chloroisoindolin-2-yl)methyl)-5-((1-(methylsulfonyl)piperidin-4-yl)methoxy)-4H-pyran-4-one;
5-((1-Propionylpiperidin-4-yl)methoxy)-2-((5-(trifluoromethyl)isoindolin-2-yl)methyl)-4H-pyran-4-one;
N-(tert-Butyl)-4-(((6-(isoindolin-2-ylmethyl)-4-oxo-4H-pyran-3-yl)oxy)-methyl)piperidine-1-carboxamide;
2-(Isoindolin-2-ylmethyl)-5-((1-pivaloylpiperidin-4-yl)methoxy)-4H-pyran-4-one;
5-((1-Acetylpiperidin-4-yl)methoxy)-2-(isoindolin-2-ylmethyl)-4H-pyran-4-one;
2-(Isoindolin-2-ylmethyl)-5-((1-propionylpiperidin-4-yl)methoxy)-4H-pyran-4-one;
2-(Isoindolin-2-ylmethyl)-5-((1-((2-methoxyethyl)sulfonyl)piperidin-4-yl)methoxy)-4H-pyran-4-one;
2-(Isoindolin-2-ylmethyl)-5-((1-(isopropylsulfonyl)piperidin-4-yl)methoxy)-4H-pyran-4-one;
5-((1-(Isobutylsulfonyl)piperidin-4-yl)methoxy)-2-(isoindolin-2-ylmethyl)-4H-pyran-4-one;
5-((1-Isobutyrylpiperidin-4-yl)methoxy)-2-(isoindolin-2-ylmethyl)-4H-pyran-4-one;
2-(Isoindolin-2-ylmethyl)-5-((1-(2,2,2-trifluoroacetyl)piperidin-4-yl)methoxy)-4H-pyran-4-one;
or a tautomer, or a pharmaceutically acceptable salt thereof.

3. A method for treating a steroid receptor dependent condition or disease in a subject comprising administering to the subject in need thereof a therapeutically effective amount of a compound according to claim 1.

4. The method according to claim 3, wherein the steroid receptor dependent disease is cancer.

5. The method according to claim 4, wherein the cancer is prostate cancer.

6. The method according to claim 5, wherein the prostate cancer is castration-resistant prostate cancer (CRPC).

7. The method according to claim 3, wherein a therapeutically effective amount of the compound of formula (ID) is administered in addition to a glucocorticoid and/or a mineralocorticoid and, optionally, one or more anti-cancer agents.

8. The method according to claim 3, wherein a therapeutically effective amount of the compound of formula (ID) is administered in addition to one or more anti-cancer agents selected from the group consisting of:
  non-steroidal androgen receptor antagonists;
  steroidogenesis inhibitors;
  chemotherapeutic agents;
  antiestrogens;
  epigenetic modulators;
  mTOR inhibitors;
  AKT inhibitors;
  radiopharmaceuticals;
  GnRH/LHRH analogues;
  PI3K inhibitors; and
  CDK4/6 inhibitors.

9. The method according to claim 7, wherein the one or more anti-cancer agents is selected from the group consisting of:
  non-steroidal androgen receptor antagonists;
  steroidogenesis inhibitors;
  chemotherapeutic agents;
  antiestrogens;
  epigenetic modulators;
  mTOR inhibitors;
  AKT inhibitors;
  radiopharmaceuticals;
  GnRH/LHRH analogues;
  PI3K inhibitors; and
  CDK4/6 inhibitors.

10. A pharmaceutical composition comprising a compound according to claim 1 and a pharmaceutically acceptable carrier.

11. A pharmaceutical combination comprising a compound according to claim 1 and at least one additional active ingredient selected from the group consisting of:
  glucocorticoids;
  mineralocorticoids;
  non-steroidal androgen receptor antagonists;
  steroidogenesis inhibitors;
  chemotherapeutic agents;
  antiestrogens;
  epigenetic modulators;
  mTOR inhibitors;
  AKT inhibitors;
  radiopharmaceuticals;
  GnRH/LHRH analogues;
  PI3K inhibitors; and
  CDK4/6 inhibitors.

* * * * *